(12) United States Patent
Thorson et al.

(10) Patent No.: US 7,906,460 B2
(45) Date of Patent: *Mar. 15, 2011

(54) ACTIVE-SITE ENGINEERING OF NUCLEOTIDYLYLTRANSFERASES AND GENERAL ENZYMATIC METHODS FOR THE SYNTHESIS OF NATURAL AND "UNNATURAL" UDP- AND TDP-NUCLEOTIDE SUGARS

(75) Inventors: Jon Thorson, Madison, WI (US); Dimitar B. Nikilov, New York, NY (US)

(73) Assignee: Sloan-Kettering Institute for Cancer, New York, NY (US)

( * ) Notice: Subject to any disclaimer, the term of this patent is extended or adjusted under 35 U.S.C. 154(b) by 1072 days.

This patent is subject to a terminal disclaimer.

(21) Appl. No.: 11/536,208

(22) Filed: Sep. 28, 2006

(65) Prior Publication Data

US 2007/0178487 A1 Aug. 2, 2007

Related U.S. Application Data

(62) Division of application No. 10/013,542, filed on Dec. 13, 2001, now Pat. No. 7,122,359.

(60) Provisional application No. 60/254,927, filed on Dec. 13, 2000.

(51) Int. Cl.
*C40B 40/06* (2006.01)
*C12N 9/10* (2006.01)

(52) U.S. Cl. .......................................... 506/16; 435/193

(58) Field of Classification Search .................. None
See application file for complete search history.

(56) References Cited

OTHER PUBLICATIONS

Witkowski, A. et al., "conversion of a β-Ketoacyl Synthase to a Malonyl Decarboxylase by Replacement of the Active-Site Cysteine with Glutamine", Biochemistry (1990) 38:11643-11650.
Chang, H. Y. et al., "The important of conserved residues in human liver UDPglucose pyrophosphorylase", Eur J. Biochem (1996) 236:723-728, abstract only.
Anisuzzaman, A. K. M. et al., "Selective Replacement of Primary Hydroxyl Groups in Carbohydrates: Preparation of Some Carbohydrate Derivatives Containing Halomethyl Groups," Carbohyr. Res. (1978) 61, 511-518.
Becthhold, A. et al., "Hight lights and New Aspects of Bioorganic Chemistry," Wiley-VCH, Weinheim (Editors: Diederichsen et al.) (1999) 313.
Branden, C. et al. "Introduction to Protein Structure," New York: Garlan Publishing, Inc. (1991).
Brown, K. et al., "Crystal Structure of the Bifunctional N-Acetylglucosamine 1-phosphate uridylytransferase from *Escherichia coli*: A Paradigm for the Related Pyrophosphorylase Superfamily," The EMBO Journal (1999) 18, 4096-4107.

Brungher A. T., "Free R Value: A Novel Statistical Quantity for Assessing the Accuracy of Crystal Structures," Nature (1992) 355, 472-475.
Brungher A. T., "A System for X-Ray Crystallography and NMR," X-PLOR v. 3.1 Manual (1993) New Haven: Yale University.
Bulik D. A. et al., "UDP-N-acetyglucosamine Pyrophosphorylase, a Key Enzyme in Encysting Giardia, Is Allosterically Regulated," Journal of Biol. Chem. (2000) 275, 14722-14728.
Charnock, S. J. et al., "Structure of the Nucleotide-Diphospho-Sugar Transferase, SpsA from *Bacillus subtilis*, in Native and Nucleotide-Complexed Forms," Biochem. (1999) 38, 6380-6385.
Collaborative Computational Project, No. 4, SERC Daresbury Laboratory, Warrington WA4 4AD, England, "The CCP4 Suite: Programs for Protein Cystallography," Acta Crystallographics Section D, Biological Crystallography (1994) D, 50, 760-763.
Elhalabi, J. M. et al., "Synthesis and Applications for Unnatural Sugar Nucleotides," Cur. Med. Chem. (1999) 6, 93-116.
Fraser, C. M. et al., "The Minimal Gene Complement of Mycoplasma Genitalium," Science (1995) 270, 397-403.
Gallo, M. A. et al, "The dnrM gene in Streptomyces peucetius contains a naturally occurring frameshift mutation that is suppressed by another locus outside of the daunorubicin-production gene cluster," Micobiol. (1996) 142, 269-275.
Garegg, P. J. et al., "Partial Substitution of Thioglycosides by Phase Transfer Catalyzed Benzoylation and Benzylation," Journal of Carbohydr. Chem. (1993) 12, 933-953.
Gastinel, L. N. Carmillau et al., "Crystal Structure of the Bovine β4Galatosyltransferase Catalytic Domain and Its Complex with Uridine Diphosphogalactose," The EMBO Journal, (1999) 18, 3546-3557.
Greenberg. W. A. et al., "Design and Synthesis of New Aminogycoside Antibiotics Containing Neamine as an Opitimal Core Structure: Correlation of Antibiotic Activity with in Vitro Inhibition of Translation," J. Am. Chem. Soc. (1999) 121, 6527-6541.
Ha, S. et al., "The 1.9 A Crystal Structure of *Escherichia coli* MurG, a Membrane-Associated Glycosyltransferase Involved in Peptidoglycan Biosynthesis," Protein Science (2000) 9, 1045-1052.
Hallis, T. M. et al, "Learning Nature's Strategies for Making Deoxy Sugars: Pathways, Mechanisms and Combinatorial Applications," Acc. Chem. Res. (1999) 32, 579-588.
Hendrickson, W. A., "Determination of Macromolecular Structures from Anomalous Diffraction of Synchrotron Radiation," Science (1991) 254, 51-58.
Hutchinson, C. R., "Combinatorial Biosynthesis for New Drug Discovery," Curr. Opin. Microbiol. (1998) 1, 319-329.
Jiang, J. et al, "A General Enzymatic Method for the Synthesis of Natural and 'Unnatural' UDP- and TDP-Nucleotide Sugars," J. Am. Chem. Soc. (2000) 122, 6803-6804.
Jiang, X. M. et al., "Structure and Sequence of the rfb (O anitgen) gene cluster of *Salmonella serovar* typhimurium (strain LT2)," Mol. Microbiol. (1991) 5, 695-713.

(Continued)

*Primary Examiner* — Traviss C McIntosh, III
(74) *Attorney, Agent, or Firm* — Quarles & Brady, LLP

(57) ABSTRACT

The present invention provides mutant nucleotidylyl-transferases, such as $E_p$, having altered substrate specificity; methods for their production; and methods of producing nucleotide sugars, which utilize these nucleotidylyl-transferases. The present invention also provides methods of synthesizing desired nucleotide sugars using natural and/or modified $E_p$ or other nucleotidyltransferases; and nucleotide sugars synthesized by the present methods. The present invention further provides new glycosyl phosphates, and methods for making them.

4 Claims, 32 Drawing Sheets

OTHER PUBLICATIONS

Johnson, D. A. et al., Comprehensive Chemistry of Natural Product Chemistry (Editors: Barton, et al.) Elsevier Science, Oxford, (1991) 311.

Johnson, D. A. et al., "Mechanisms and Pathways from Recent Deoxysugar Biosynthesis Research," Curr. Opin. Biol. (1998) 2, 642-649.

Jones, T. A. et al., "Improved Methods for Building Protein Models in Electron Density Mpas and the Location of Errors in these Models," Acta Crystallogr. (1991) A47, 110-119.

Kanie, O. et al, "Acceptor—substrate recognition by N-acetylglucosaminyltransferase-V: Critical role of the 4-hydroxyl group in β-D-GlepNAc(1->2)-DMan p9(1->6)-β-D-GlepOR," Carbohydr. Research (1993) 243, 139-164.

Kiel, J. A. et al., "Glycogen in *Bacillus subtilis*: Molecular Characterization of an Operon Encoding Enzymes Involved in Glycogen Biosynthesis and Degradation," Mol. Microbiol. (1994) 11, 203-318.

Kirschning, A. et al., "Chemical and Biochemical Aspects of Deoxysugars and Deoxysugar Oligasaccharides," Top. Curr. Chem. (1997) 188, 1-84.

Kornfeld, S. et al., "The Enzymatic Synthesis of Thymidine-linked Sugars," Journal of Biological Chemistry (1961) 236, 1791-1794.

Lindquist, L. et al., "Purification Characterization and HPLC Assay of *Salmonella* Glucose-1-Phosphate Thymidylylphospherase from the cloned rfbA Gene," Eur. J. Biochem (1993) 211, 763-770.

Liu, H., Thorson, J. S., "Pathways and Mechanisms in the Biogenesis of Novel Deoxysugars by Bacteria," Ann. Rev. Microbiol. (1994) 48, 223-256.

Madduri, K. et al., "Production of the Antitumor Drug Epirubicin (4'-epidoxorubicin) and its Precursor by a Genetically Engineered Strain of Streptomyces Peucetius," Nat. Biotech. (1998) 16, 69-74.

Maunier, P. Boullanger et al., "Synthesis and surface-active properties of amphiphilic 6-aminocarbonyl derivatives of D-glucose," Carbohydr. Res. (1997), 299, 49-57.

Mollerach, M. et al., "Characterization of the galU of *Streptococcus pneumoniae* Encoding a Uridine Diphosphoglucose Pyrophosphorylase: A Gene Essential for Capsular Polysaccharide Biosynthesis," J. Exp. Med. (1998) 188, 2047-2056.

Nelson, K. E. et al., "Evidence for lateral gene transfer between Archaea and Bacteria from genome sequence of Thermotoga maritima," Nature (1999) 399, 323-329.

Nilsson D. et al., "Primary Structure of the tms and prs Genes of *Bacillus subrilis*," Mol. Genet. (1989) 218, 565-571.

Omura, Microlide Antibiotics, Chemistry, Biology and Practice, 2nd Edition, Academic Press: New York (1984).

Ramachandran, G. N. et al., "Stereochemistry of Polypeptide Chain Configurations," J. Molec. Biol. (1963) 7, 95-99.

Reeves et al., "Bacterial polysaccharide synthesis and gene nomenclature," Trends Microbiology (1996) 4, 495-502.

Rossmann, M. G. et al., "Evolutionary and structural relationship among dehydrogenases," The Enzymes (Editor: I.P.D. Boyyer, Academic Press: New York (1975) 61-102.

Sambrook et al., "Studies of the Biosynthesis of 3,6-Dideoxyhexoses: Molecular Cloning and Characterization of the asc (Ascarylose) Region from Yersinia pseudotubercolosis Serogroup VA," A Laboratory Manual, 2nd Edition, Cold Spring Harbor Laboratory Press (1989).

Sheu, K.-F. R. et al., "Stereochemical Courses of Nucleotidyltransferase and Phosphortransferase Action. Uridine Disphosphate Bluccose Pyrophosphorylase, Galactose-1-Phosphate Uridylyltranferase, Adenylate Kinase, and Nucleoside Diphosphate Kinase," Biochem. (1979) 18, 5548-5556.

Solenburg, P. J. et al., "Production of Hybrid Glycopeptide Antibiotics in vitro and in *Streptomyces toyocaensis*," Chem. & Biol. (1997) 4, 195-202.

Stover, C. K. et al., "Complete genome sequence of *Pseudomonas neruginosa* PA01, an opportunist pathogen," Nature 406, 959-964, Aug. 2000.

Thorson, J. S. et al., "Understanding and Exploiting Nature's Chemical Arsenal: The Past, Present and Future of Calicheamicin Research," Cur. Pharm. Des. (2000) 6:1841-1879.

Thorson, J. S. et al., "Enediune Biosynthesis and Self-Resistance: A Progress Report," Bioorg. Chem. (1999) 27, 172-188.

Thorson, J. S. et al., "Glc-1-P Cytitdylytransferase," Journal of Bacteriology (1994) 176, 5483-5493.

Thorson, J. S. et al., "Nature's Carbohydrate Chemists: The Enzymatic Glycosylation of Bioactive Bacterial Metabolites," Curr. Org. Chem. (2001) 5:139-167.

Trefzer, A. et al., "Genes and Enzymes Involved in Deoxysugar Biosynthesis in Bacteria," Nat. Prod. Rep. (1999) 16, 283-299.

Vrielink, A. et al., "Crystal Structure of the DNA Modifying Enzyme β- Glucosyltransferase in the Presence and Absence . . . ," The EMBO Journal (1994) 13:3413-3422.

Weymouth-Wilson, A. C., "The Role of Carbohydrates in Biologically Active Natural Products," Nat. Prod. Rep. (1997) 14:99-110.

Whitwam, R. E. et al., "The Gene calC Encodes for a Non-Heme Iron Matalloprotein Responsible for Calicheamicin Self-Resistance . . . ," Am. Chem. Soc. (2000) 122:1556-1557.

Wu, M. X. et al., "The N-Terminal Region is Important for the Allosteric Activation and Inhibition of the *Escheria coli* . . . ," Archives Biochem. Biophys. (1998) 358:182-188.

Zhao, L. et al. "Engineering a Methymycin/Pikromycin-Calicheamicin Hybrid: Construction of Two New Macrolides Carrying a Designed . . . ," J. Am. Chem. Soc. (1999) 121:9881-9882.

Zhao, Y. et al. "A Methodological Comparison: The Advantage of Phosphorimidates in Expanding the Sugar Nucleotide Repertoire," J. Org. Chem. (1998) 63:7568-7572.

Zhiyuan, A. et al., "Synthesis of double-chain bis-sulfone neoglycolipds of the 2"-, 3"-, 4"-, and 6"-deoxyglobotrioses ," Carbohydr. Res. (1994) 262:79-101.

Barton, W.A. et al., "Structure, Mechanism and Engineering of a Nucleotidylyltransferase as a First Step . . . ," Nature Structural Biology, (2001) 8:545-551.

Bulter, T. et al., "Enzymatic Synthesis of Nucleotide sugars," Glycoconjugate Journal, (1999) 16:147-159.

Holm, L. et al., "Touring Protein Fold Space with Dali/FSSP", Nucleic Acids Res., (1998) 26:316-319.

FIG. 2
| Substrate | | TTP Conv. (%)[a] | Reten. (min)[b] | UTP Conv. (%)[a] | Reten. (min)[b] |
|---|---|---|---|---|---|
| 2[c] | 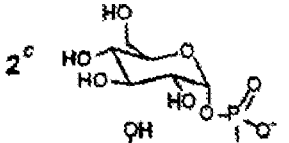 | 99.3 ± 0.1 | 4.1[d] | 99.5 ± 0.7 | 3.7[d] |
| 43 | 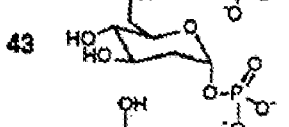 | 25.5 ± 0.4[e] | 4.2 | 22.3 ± 0.4[e] | 3.7 |
| 28 | 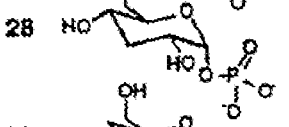 | 96.2 ± 0.9[f] | 4.3 | 6.5 ± 0.3[f] | 3.7 |
| 20 | 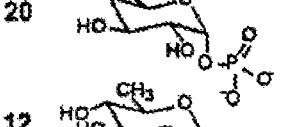 | 98.3 ± 1.6 | 4.4 | 99.3 ± 0.4 | 3.9 |
| 12 | 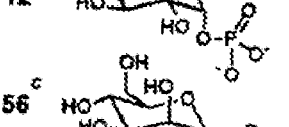 | 98.2 ± 1.7 | 4.3 | 99.1 ± 0.8 | 3.9 |
| 56[c] | 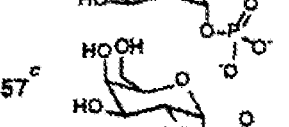 | 99.5 ± 0.1[g] | 4.1 | 17.9 ± 1.7[g] | 3.7 |
| 57[c] | 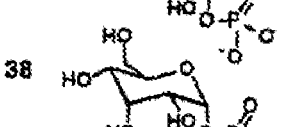 | 56.8 ± 0.4[g] | 4.2 | 32.7 ± 2.7[g] | 3.7[d] |
| 38 | 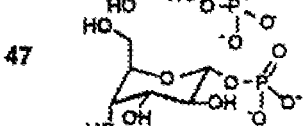 | 14.8 ± 0.1 | 4.0 | -[h] | -[h] |
| 47 | 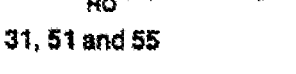 | 5.4 ± 0.4 | 4.0 | -[h] | -[h] |
| 31, 51 and 55 | | -[h] | -[h] | -[h] | -[h] |

*FIG. 7*
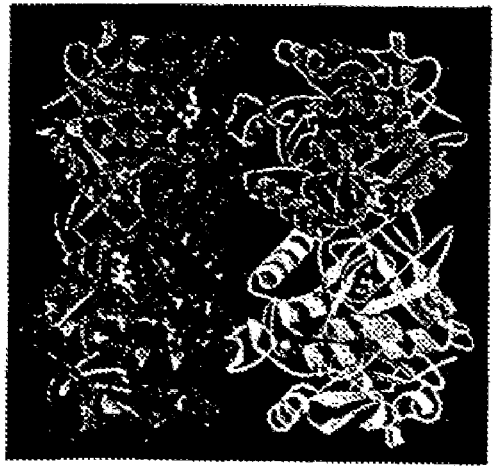

*FIG. 8(b)*
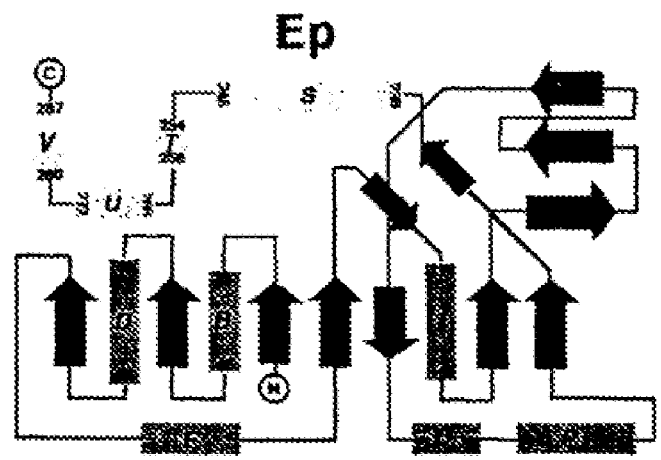
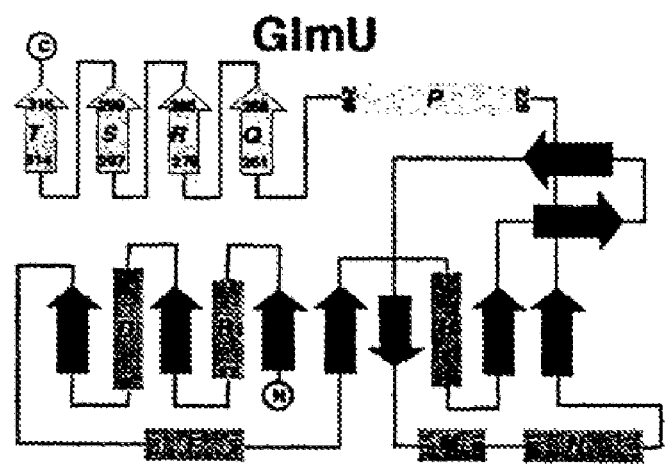
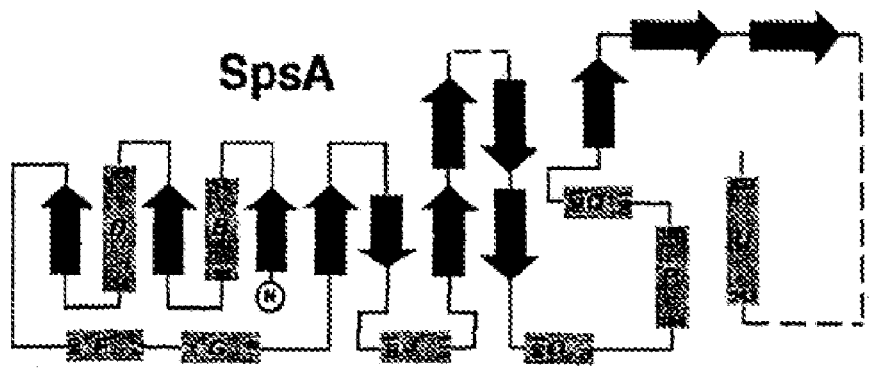

FIG. 11

| Substrate | Wild-Type $E_p$ % Conv. | Mutant Pool % Conv. | Trp224His % Conv. | Thr201Ala % Conv. |
|---|---|---|---|---|
| 1 | 99.3 ± 0.8 | 90.7 ± 2.8 | 98.6 ± 1.1 | 99.3 ± 0.1 |
| 2 | 48.5 ± 0.4 | 18.3 ± 1.4 | 16.9 ± 3.1 | 99.5 ± 1.6 |
| 3 | § | 10.7 ± 3.8 | 35.9 ± 0.5 | § |
| 4 | 97.2 ± 2.9 | 48.0 ± 0.9 | 72.3 ± 0.5 | 23.5 ± 2.6 |
| 5 | 14.8 ± 0.1 | § | § | § |
| 6 | § | 97.9 ± 2.1 | 65.9 ± 1.1 | § |

```
                                                         Smallest Sum
                                                   High  Probability
        Sequences producing high-scoring segment pairs:  Score   P(N)        N 1. gi|1710100    GLUCOSE-1-PHOSPHATE THYMIDYLYLTRANSFERAS...   1510   0        1
 2. gi|9957817    Glucose-1-phosphate thymidylyltransferas...   1507   0        1
 3. gi|9957822    Glucose-1-phosphate thymidylyltransferas...   1499   0        1
 4. gi|9957847    Glucose-1-phosphate thymidylyltransferas...   1497   0        1
 5. gi|9957866    Glucose-1-phosphate thymidylyltransferas...   1496   0        1
 6. gi|9957852    Glucose-1-phosphate thymidylyltransferas...   1488   0        1
 7. gi|9957857    Glucose-1-phosphate thymidylyltransferas...   1450   0        1
 8. gi|9957836    Glucose-1-phosphate thymidylyltransferas...   1444   0        1
 9. gi|1073702    RfbA protein - Shigella flexneri (strain..    1440   0        1
10. gi|141362     GLUCOSE-1-PHOSPHATE THYMIDYLYLTRANSFERAS...   1437   0        1
11. gi|9957831    Glucose-1-phosphate thymidylyltransferas...   1429   0        1
12. gi|9957841    Glucose-1-phosphate thymidylyltransferas...   1424   0        1
13. gi|2507297    GLUCOSE-1-PHOSPHATE THYMIDYLYLTRANSFERAS...   1411   0        1
14. gi|2121141    Glucose-1-phosphate thymidylyltransferas...   1408   0        1
15. gi|9957862    Glucose-1-phosphate thymidylyltransferas...   1359   2.7e-178  1
16. gi|9957827    Glucose-1-phosphate thymidylyltransferas...   1356   7.1e-178  1
17. gi|585826     GLUCOSE-1-PHOSPHATE THYMIDYLYLTRANSFERAS...   1067   2.2e-171  3
18. gi|11348597   Glucose-1-phosphate thymidylyltransferas...   1185   2.8e-154  1
19. gi|3135675    Putative glucose-1-phosphate thymidyltra...   1139   6.3e-148  1
20. gi|3608394    Putative glucose-1-phosphate thymidyl tr...   1113   3.4e-144  1
21. gi|1666808    RfbA [Leptospira interrogans]                  1103   5.9e-143  1
22. gi|4234804    RmlA [Leptospira borgpetersenii]               1092   1.9e-141  1
23. gi|1881544    Glucose-1-phosphate thymidyl transferase..    1073   8.1e-139  1
24. gi|2500162    GLUCOSE-1-PHOSPHATE THYMIDYLYLTRANSFERAS...   1070   2.1e-138  1
25. gi|7471939    Glucose-1-phosphate thymidylyltransferas...   1069   2.9e-138  1
26. gi|7434861    Glucose-1-phosphate thymidylyltransferas...   1064   1.4e-137  1
27. gi|4200433    Cps2L [Streptococcus pneumoniae]               1056   1.8e-136  1
28. gi|3320399    Glucose-1-phosphate thymidyl transferase..    1055   2.5e-136  1
29. gi|7592816    D-glucose-1-phosphate thymidylyltransfer...   1051   6.8e-136  1
30. gi|5545318    Glucose-1-phosphate thymidylyltransferas...   1045   5.9e-135  1
31. gi|1944160    Glucose-1-phosphate-thymidylyltransferas...   1045   5.9e-135  1
32. gi|4406249    Glucose-1-phosphate thymidylyl transfera..    1039   4e-134    1
33. gi|3832506    Glucose-1-phosphate thymidylyl transfera..    1039   4e-134    1
34. gi|1710101    GLUCOSE-1-PHOSPHATE THYMIDYLYLTRANSFERAS...   1035   1e-133    1
35. gi|3907610    Glucose-1-phosphate thimidylyl transfera...   1033   2.7e-133  1
36. gi|9977936    GLUCOSE-1-PHOSPHATE THYMIDYLYLTRANSFERAS...   1031   5.1e-133  1
37. gi|1098479    Glucose-1-phosphate thymidylyl transferase.   1029   9.6e-133  1
38. gi|7434867    Probable glucose-1-phosphate thymidylylt...   1023   6.5e-132  1
39. gi|9978667    GLUCOSE-1-PHOSPHATE THYMIDYLYLTRANSFERAS...   1019   2.3e-131  1
40. gi|585825     GLUCOSE-1-PHOSPHATE THYMIDYLYLTRANSFERAS...   1010   4e-130    1
41. gi|2500161    PROBABLE GLUCOSE-1-PHOSPHATE THYMIDYLYLT...   1007   1e-129    1
42. gi|2507298    GLUCOSE-1-PHOSPHATE THYMIDYLYLTRANSFERAS...    998   1.8e-128  1
```

FIG. 19(B)

| | | | | | |
|---|---|---|---|---|---|
| 43. | gi\|1710102 | GLUCOSE-1-PHOSPHATE THYMIDYLXLTRANSFERAS... | 998 | 1.8e-128 | 1 |
| 44. | gi\|5931969 | Glucose-1-phosphate thymidyltransferase ... | 549 | 6.2e-128 | 2 |
| 45. | gi\|11261716 | Glucose-1-phosphate thymidylyltransferas... | 984 | 1.6e-126 | 1 |
| 46. | gi\|5199111 | Glucose-1-phosphate thymidyl transferase... | 540 | 6.5e-125 | 2 |
| 47. | gi\|7434866 | Glucose-1-phosphate thymidyltransferas... | 966 | 4.8e-124 | 1 |
| 48. | gi\|1710029 | GLUCOSE-1-PHOSPHATE THYMIDYLXLTRANSFERAS... | 948 | 1.5e-121 | 2 |
| 49. | gi\|1314579 | Glucose-1-phosphate thymidylyltransferas... | 466 | 3.5e-120 | 3 |
| 50. | gi\|1890601 | ExpA7 [Sinorhizobium meliloti] | 551 | 5.9e-120 | 2 |
| 51. | gi\|6677602 | Putative glucose-1-phosphate thymidyl tr... | 933 | 1.7e-119 | 1 |
| 52. | gi\|6688395 | RmlA protein [Legionella pneumophila] | 933 | 1.7e-119 | 1 |
| 53. | gi\|148192 | Similar to Streptomyces griseus StrD pro... | 543 | 1e-118 | 2 |
| 54. | gi\|421098 | Hypothetical protein o292 - Escherichia ... | 536 | 9.3e-118 | 2 |
| 55. | gi\|7434863 | Glucose-1-phosphate thymidylyltransferas... | 518 | 6.2e-117 | 2 |
| 56. | gi\|8133016 | Putative dTDP-1-glucose synthase; AknY [... | 907 | 6.6e-116 | 1 |
| 57. | gi\|9714064 | Glucose-1-phosphate thymidyltransferase ... | 511 | 6.6e-114 | 2 |
| 58. | gi\|6018314 | Putative STDP-glucose synthase [Streptom... | 883 | 1.4e-112 | 1 |
| 59. | gi\|3789899 | Alpha-D-glucose-1-phosphate thymidylyltr... | 882 | 1.9e-112 | 1 |
| 60. | gi\|7688728 | NovV [Streptomyces spheroides] | 504 | 1.4e-111 | 2 |
| 61. | gi\|11095238 | DTDP-glucose synthase; glucose-1-phospha... | 499 | 9.6e-111 | 2 |
| 62. | gi\|10808782 | Glucose-1-phosphate thymidyltransferase ... | 865 | 4.1e-110 | 1 |
| 63. | gi\|4884772 | TDP-glucose synthase homolog [Streptomyc... | 863 | 7.8e-110 | 1 |
| 64. | gi\|5921158 | Glucose-1-phosphate thymidyltransferase ... | 859 | 2.8e-109 | 1 |
| 65. | gi\|4884768 | TDP-glucose synthase [Streptomyces spect... | 483 | 2.6e-107 | 2 |
| 66. | gi\|5579435 | SpcK [Streptomyces flavopersicus] | 470 | 3e-105 | 2 |
| 67. | gi\|4033331 | DTDP-glucose synthase [Actinoplanes sp. ... | 452 | 4.4e-103 | 2 |
| 68. | gi\|580709 | OAC3 [Azorhizobium caulinodans] | 798 | 7.3e-101 | 1 |
| 69. | gi\|1072851 | Probable glucose-1-phosphate thymidylylt... | 798 | 7.3e-101 | 1 |
| 70. | gi\|2804683 | Glucose-1-phosphate thymidyltransferase ... | 758 | 2.4e-95 | 1 |
| 71. | gi\|2804721 | Glucose-1-phosphate thymidyl transferase... | 737 | 1.9e-92 | 1 |
| 72. | gi\|2127533 | Glucose-1-phosphate thymidylyltransferas... | 466 | 1.7e-89 | 3 |
| 73. | gi\|1944620 | Glucose-1-phosphate thymidylyltransferas... | 652 | 1e-80 | 2 |
| 74. | gi\|4574181 | Glucose-1-phosphate thymidyl transferase... | 651 | 1.4e-80 | 1 |
| 75. | gi\|730618 | SPORE COAT POLYSACCHARIDE BIOSYNTHESIS P... | 268 | 1.3e-50 | 4 |
| 76. | gi\|10178986 | Spore coat polysaccharide synthesis [glu... | 261 | 6.1e-44 | 4 |
| 77. | gi\|11279395 | Glucose-1-phosphate thymidylyltransferas... | 279 | 4.8e-42 | 3 |
| 78. | gi\|7329194 | DTDP-D-glucose synthase [Streptomyces an... | 279 | 4.8e-42 | 3 |
| 79. | gi\|4731596 | BlmD [Streptomyces bluensis] | 175 | 1e-41 | 4 |
| 80. | gi\|4406265 | Glucose-1-phosphate thymidylyl transfera... | 365 | 4.2e-41 | 1 |
| 81. | gi\|7448174 | Glucose-1-phosphate thymidylyltransferas... | 250 | 5.9e-39 | 3 |
| 82. | gi\|7448197 | Hypothetical protein - Synechocystis sp.... | 220 | 8.6e-39 | 3 |
| 83. | gi\|11279397 | Probable dTDP-1-glucose synthase [import... | 181 | 1.7e-38 | 4 |
| 84. | gi\|280334 | StrD protein - Streptomyces griseus | 156 | 1.1e-37 | 4 |
| 85. | gi\|134991 | GLUCOSE-1-PHOSPHATE THYMIDYLYLTRANSFERAS... | 156 | 1.1e-37 | 4 |
| 86. | gi\|11279396 | Glucose-1-phosphate thymidylyltransferas... | 153 | 2e-37 | 4 |
| 87. | gi\|3256058 | StrD [Streptomyces glaucescens] | 153 | 8.1e-36 | 4 |
| 88. | gi\|11497938 | Glucose-1-phosphate thymidylyltransferas... | 209 | 7.1e-35 | 4 |
| 89. | gi\|975621 | Glucose-1-phosphate thymidylyltransferas... | 160 | 7.1e-35 | 4 |
| 90. | gi\|7481814 | DTDP-glucose synthase - Streptomyces vir... | 158 | 3.3e-34 | 4 |
| 91. | gi\|7448156 | Glucose-1-phosphate thymidylyltransferas... | 181 | 4.5e-34 | 4 |
| 92. | gi\|6002933 | DNDP-glucose synthetase [Streptomyces fr... | 163 | 8.3e-34 | 4 |
| 93. | gi\|7448164 | Glucose-1-phosphate thymidylyltransferas... | 131 | 1.1e-33 | 5 |
| 94. | gi\|7448155 | Probable glucose-1-phosphate thymidylylt... | 134 | 1.2e-32 | 5 |
| 95. | gi\|4240414 | NDP-hexose synthetase homolog [Streptomy... | 156 | 1.8e-32 | 4 |
| 96. | gi\|2209217 | Glucose-1-phosphate thymidyl transferase... | 267 | 1.4e-27 | 1 |
| 97. | gi\|6015646 | Glucose-1-phosphate thymidylyltransferas... | 156 | 5.4e-27 | 4 |
| 98. | gi\|6933896 | Putative TDP-glucose synthase [Streptomy... | 228 | 1.8e-26 | 3 |
| 99. | gi\|4884858 | Glucose-1-phosphate thymidylyltransferas... | 343 | 2.6e-25 | 2 |

FIG. 19(C)

| | | | | | |
|---|---|---|---|---|---|
| 100. | gi\|7473590 | Probable glucose-1-phosphate thymidylyt... | 117 | 8.6e-23 | 5 |
| 101. | gi\|1346094 | UTP--GLUCOSE-1-PHOSPHATE URIDYLYLTRANSFE... | 124 | 3.3e-19 | 3 |
| 102. | gi\|10956341 | PXO1-94 (Bacillus anthracis) | 138 | 3.4e-19 | 3 |
| 103. | gi\|10176276 | UTP-glucose-1-phosphate uridylyltransfer... | 126 | 6.5e-19 | 3 |
| 104. | gi\|7521440 | Probable sugar-phosphate nucleotidyl tra... | 139 | 1e-18 | 3 |
| 105. | gi\|7521719 | Sugar-phosphate nucleotidyl transferase ... | 140 | 2.5e-18 | 3 |
| 106. | gi\|6138856 | UTP-glucose-1-phosphate uridylyltransfer... | 121 | 4.9e-18 | 3 |
| 107. | gi\|2501471 | PUTATIVE UTP--GLUCOSE-1-PHOSPHATE URIDYL... | 130 | 9.2e-18 | 3 |
| 108. | gi\|10580603 | Glucose-1-phosphate thymidylyltransferas... | 119 | 1.9e-17 | 4 |
| 109. | gi\|6360274 | 96% identity with amino acids 1-24 of E... | 130 | 3.1e-17 | 2 |
| 110. | gi\|7434850 | UTP--glucose-1-phosphate uridylyltransfe... | 130 | 3.5e-17 | 3 |
| 111. | gi\|2501469 | UTP--GLUCOSE-1-PHOSPHATE URIDYLYLTRANSFE... | 132 | 3.8e-17 | 3 |
| 112. | gi\|7434856 | UTP--glucose-1-phosphate uridylyltransfe... | 139 | 4.6e-17 | 3 |
| 113. | gi\|2501467 | UTP--GLUCOSE-1-PHOSPHATE URIDYLYLTRANSFE... | 131 | 4.6e-17 | 3 |
| 114. | gi\|10892706 | Glucose-1-P thymidylyltransferase (Carbo... | 154 | 6.4e-17 | 4 |
| 115. | gi\|10892777 | Glucose-1-phosphate thymidylyltransferas... | 150 | 8.7e-17 | 4 |
| 116. | gi\|7739964 | Putative UDP-glucose pyrophosphorylase [... | 130 | 1.7e-16 | 3 |
| 117. | gi\|555064 | Glucose-1-phosphate uridylyltransferase ... | 132 | 1.7e-16 | 3 |
| 118. | gi\|7434852 | UTP--glucose-1-phosphate uridylyltransfe... | 109 | 1.8e-16 | 3 |
| 119. | gi\|3132048 | Glucose-1-phosphate uridylyltransferase ... | 133 | 2.4e-16 | 3 |
| 120. | gi\|3550619 | UTP-glucose-1-phosphate uridylyltransfer... | 133 | 3.1e-16 | 3 |
| 121. | gi\|1177038 | PUTATIVE UTP--GLUCOSE-1-PHOSPHATE URIDYL... | 123 | 3.3e-16 | 3 |
| 122. | gi\|10174923 | UTP-glucose-1-phosphate uridylyltransfer... | 111 | 3.4e-16 | 3 |
| 123. | gi\|3777501 | Putative GDP-mannose pyrophosphorylase [... | 150 | 6.5e-16 | 3 |
| 124. | gi\|3970693 | GDP-mannose pyrophosphorylase (Candida a... | 150 | 6.5e-16 | 3 |
| 125. | gi\|3777503 | Putative GDP-mannose pyrophosphorylase [... | 150 | 6.5e-16 | 3 |
| 126. | gi\|7296813 | CG1129 gene product [alt 1] (Drosophila ... | 115 | 8.3e-16 | 2 |
| 127. | gi\|4340429 | NDP-hexose synthetase homolog (Streptomy... | 112 | 8.3e-16 | 2 |
| 128. | gi\|7448166 | Probable glucose-1-phosphate thymidylylt... | 116 | 1e-15 | 5 |
| 129. | gi\|2127932 | Glucose-1-phosphate thymidylyltransferas... | 143 | 1.3e-15 | 4 |
| 130. | gi\|3323397 | Mannose-1-phosphate guanylyltransferase ... | 152 | 1.7e-15 | 4 |
| 131. | gi\|585225 | UTP--GLUCOSE-1-PHOSPHATE URIDYLYLTRANSFE... | 137 | 1.8e-15 | 3 |
| 132. | gi\|7434851 | UTP--glucose-1-phosphate uridylyltransfe... | 109 | 2.1e-15 | 3 |
| 133. | gi\|10176341 | UTP-glucose-1-phosphate uridylyltransfer... | 133 | 3.4e-15 | 3 |
| 134. | gi\|2501470 | UTP--GLUCOSE-1-PHOSPHATE URIDYLYLTRANSFE... | 139 | 3.7e-15 | 3 |
| 135. | gi\|7497318 | Hypothetical protein C43C1.5 - Caenorhab... | 171 | 5.4e-15 | 2 |
| 136. | gi\|10174033 | Mannose-1-phosphate guanyltransferase (S... | 129 | 1.1e-14 | 4 |
| 137. | gi\|7331158 | GDP-mannose pyrophosphorylase (Pichia su... | 135 | 1.9e-14 | 3 |
| 138. | gi\|6320148 | Mannose-1-phosphate guanyltransferase, G... | 150 | 4.8e-14 | 3 |
| 139. | gi\|10579718 | Glucose-1-phosphate thymidylyltransferas... | 105 | 6e-14 | 3 |
| 140. | gi\|7448165 | Mannose-1-phosphate guanyltransferase PA... | 113 | 6.3e-14 | 4 |
| 141. | gi\|2121148 | Glucose-1-phosphate thymidyltransferase ... | 168 | 6.6e-14 | 1 |
| 142. | gi\|10640826 | Mannose-1-phosphate guanyltransferase re... | 132 | 7e-14 | 2 |
| 143. | gi\|894204 | Mannose-1-phosphate guanyltransferase [S... | 148 | 8.3e-14 | 3 |
| 144. | gi\|9055395 | dTDP-glucose synthase (Streptomyces rime... | 167 | 9e-14 | 1 |
| 145. | gi\|10579656 | Glucose-1-phosphate thymidylyltransferas... | 148 | 1.1e-13 | 2 |
| 146. | gi\|4760690 | GDP-mannose pyrophosphorylase (Candida g... | 144 | 3e-13 | 3 |
| 147. | gi\|7649503 | Putative nucleotide phosphorylase (Strep... | 86 | 5.5e-13 | 3 |
| 148. | gi\|7448158 | Glucose-1-phosphate thymidylyltransferas... | 106 | 6.5e-13 | 5 |
| 149. | gi\|7448170 | Probable rmlA2 protein - Mycobacterium t... | 102 | 8.4e-13 | 2 |
| 150. | gi\|10880965 | Putative UTP-glucose-1-phosphate uridyly... | 113 | 8.4e-13 | 3 |
| 151. | gi\|6015731 | Glucose-1-phosphate thymidylyltransferas... | 115 | 9.4e-13 | 3 |
| 152. | gi\|7434855 | UTP--glucose-1-phosphate uridylyltransfe... | 107 | 1.2e-12 | 3 |
| 153. | gi\|11352828 | UTP--glucose-1-phosphate uridylyltransfe... | 106 | 1.4e-12 | 3 |
| 154. | gi\|4884956 | Glucose-1-phosphate thymidylyltransferas... | 157 | 2.2e-12 | 1 |
| 155. | gi\|4378170 | UTP-glucose-1-phosphate uridylyltransfer... | 116 | 2.8e-12 | 2 |
| 156. | gi\|7451544 | Mannose-1-phosphate guanyltransferase - ... | 120 | 3.3e-12 | 3 |

FIG. 19(D)

| | | | | | |
|---|---|---|---|---|---|
| 157. | gi\|2501468 | UTP--GLUCOSE-1-PHOSPHATE URIDYLYLTRANSFE.. | 107 | 6.2e-13 | 3 |
| 158. | gi\|7492163 | Mannose-1-phosphate guanyltransferase - .. | 136 | 1.6e-11 | 3 |
| 159. | gi\|11261675 | UTP--glucose-1-phosphate uridylyltransfe.. | 101 | 1.7e-11 | 3 |
| 160. | gi\|7448173 | Probable glucose-1-phosphate thymidylylt.. | 83 | 1.8e-11 | 4 |
| 161. | gi\|7434849 | UTP--glucose-1-phosphate uridylyltransfe.. | 126 | 2e-11 | 2 |
| 162. | gi\|11261677 | UTP-glucose-1-phosphate uridylyltransfer.. | 109 | 4.4e-11 | 3 |
| 163. | gi\|11261687 | Probable UTP--glucose-1-phosphate uridyl.. | 107 | 5.7e-11 | 3 |
| 164. | gi\|7381245 | UDPG-pyrophosphorylase [Acetobacter xyli.. | 103 | 5.7e-11 | 3 |
| 165. | gi\|3372537 | UTP-glucose-1-phosphate uridylyltransfer.. | 115 | 6e-11 | 3 |
| 166. | gi\|6015664 | UDP-glucose pyrophosphorylase [Sulfolobu.. | 122 | 9.4e-11 | 4 |
| 167. | gi\|10579698 | Glucose-1-phosphate thymidylyltransferas.. | 128 | 9.9e-11 | 3 |
| 168. | gi\|7448161 | Probable mannose-1-phosphate guanylyltra.. | 136 | 1.3e-10 | 3 |
| 169. | gi\|11261681 | UTP--glucose-1-phosphate uridylyltransfe.. | 107 | 1.4e-10 | 3 |
| 170. | gi\|7448163 | Glucose-1-phosphate thymidylyltransferas.. | 79 | 1.5e-10 | 4 |
| 171. | gi\|3559951 | UDP-glucose pyrophosphorylase [Pseudomon.. | 106 | 2.4e-10 | 3 |
| 172. | gi\|1169833 | UTP--GLUCOSE-1-PHOSPHATE URIDYLYLTRANSFE.. | 117 | 2.7e-10 | 3 |
| 173. | gi\|2117938 | UTP--glucose-1-phosphate uridylyltransfe.. | 108 | 3.4e-10 | 3 |
| 174. | gi\|120929 | UTP--GLUCOSE-1-PHOSPHATE URIDYLYLTRANSFE.. | 125 | 4.7e-10 | 2 |
| 175. | gi\|541065 | ExoN protein - Rhizobium meliloti | 112 | 7.1e-10 | 3 |
| 176. | gi\|7448599 | Putative mannose-1-phosphate guanyltrans.. | 108 | 7.2e-10 | 3 |
| 177. | gi\|6066425 | Mannose-1-phosphate guanyltransferase [L.. | 130 | 8e-10 | 3 |
| 178. | gi\|462035 | UTP--GLUCOSE-1-PHOSPHATE URIDYLYLTRANSFE.. | 112 | 8.1e-10 | 3 |
| 179. | gi\|7434854 | Probable UTP--glucose-1-phosphate uridyl.. | 138 | 9.1e-10 | 1 |
| 180. | gi\|10579655 | Glucose-1-phosphate thymidylyltransferas.. | 90 | 2e-09 | 3 |
| 181. | gi\|4103324 | GDP-mannose pyrophosphorylase [Solanum t.. | 115 | 2e-09 | 3 |
| 182. | gi\|423784 | Unknown [Leptospira borgpetersenii] | 93 | 2e-09 | 3 |
| 183. | gi\|5814381 | Unknown [Leptospira interrogans] | 95 | 2e-09 | 3 |
| 184. | gi\|7448169 | Probable mannose-1-phosphate guanyltrans.. | 115 | 3.7e-09 | 2 |
| 185. | gi\|3183569 | UTP--GLUCOSE-1-PHOSPHATE URIDYLYLTRANSFE.. | 125 | 5.7e-09 | 3 |
| 186. | gi\|7448154 | Mannose-1-phosphate guanylyltransferase .. | 104 | 6.5e-09 | 3 |
| 187. | gi\|11261685 | UTP--glucose-1-phosphate uridylyltransfe.. | 93 | 7.3e-09 | 3 |
| 188. | gi\|3319929 | GalU protein [Pectobacterium carotovorum.. | 131 | 8.4e-09 | 1 |
| 189. | gi\|116099 | UTP--GLUCOSE-1-PHOSPHATE URIDYLYLTRANSFE.. | 103 | 9.4e-09 | 3 |
| 190. | gi\|7521439 | Probable sugar phosphate transferase APE.. | 129 | 1.6e-08 | 1 |
| 191. | gi\|7269958 | GDP-mannose pyrophosphorylase like prote.. | 107 | 3.1e-08 | 2 |
| 192. | gi\|7448168 | Mannose-1-phosphate guanylyltransferase - .. | 89 | 4.7e-08 | 2 |
| 193. | gi\|7447202 | Probable glucose-1-phosphate thymidylylt.. | 84 | 7.6e-08 | 2 |
| 194. | gi\|1360733 | UTP--glucose-1-phosphate uridylyltransfe.. | 122 | 8.7e-08 | 2 |
| 195. | gi\|138826 | UTP--GLUCOSE-1-PHOSPHATE URIDYLYLTRANSFE.. | 122 | 8.8e-08 | 2 |
| 196. | gi\|96762 | UTP--glucose-1-phosphate uridylyltransfe.. | 123 | 8.8e-08 | 2 |
| 197. | gi\|2501466 | UTP--GLUCOSE-1-PHOSPHATE URIDYLYLTRANSFE.. | 123 | 9.8e-08 | 2 |
| 198. | gi\|10803043 | UDP-glucose pyrophosphorylase [Haemophil.. | 113 | 1.6e-07 | 2 |
| 199. | gi\|7448172 | Probable glucose-1 phosphate transferase.. | 80 | 1.9e-07 | 3 |
| 200. | gi\|7434875 | Glucose-1-phosphate adenylyltransferase .. | 93 | 2.1e-07 | 2 |
| 201. | gi\|985168 | UTP--GLUCOSE-1-PHOSPHATE URIDYLYLTRANSFE.. | 113 | 2.2e-07 | 2 |
| 202. | gi\|2133677 | Pyrophosphorylase ppp-1 homolog - Caenor.. | 120 | 2.8e-07 | 1 |
| 203. | gi\|3041873 | PUTATIVE TRANSLATION INITIATION FACTOR E.. | 120 | 2.8e-07 | 1 |
| 204. | gi\|7206597 | C. elegans (PPP-1) putative translation .. | 120 | 2.8e-07 | 1 |
| 205. | gi\|11354079 | Probable sugar-phosphate nucleotidyl tra.. | 95 | 3.6e-07 | 2 |
| 206. | gi\|10436247 | Unnamed protein product [Homo sapiens] | 118 | 5.2e-07 | 1 |
| 207. | gi\|2494312 | TRANSLATION INITIATION FACTOR EIF-2B GAM.. | 118 | 5.2e-07 | 1 |
| 208. | gi\|9966779 | Eukaryotic translation initiation factor.. | 118 | 5.2e-07 | 1 |
| 209. | gi\|7434857 | UTP--glucose-1-phosphate uridylyltransfe.. | 88 | 7.3e-07 | 2 |
| 210. | gi\|11261689 | UTP--glucose-1-phosphate uridylyltransfe.. | 93 | 9.4e-07 | 2 |
| 211. | gi\|1978827 | Pyrophosphorylase 1 - Caenorhabditis bri.. | 118 | 9.8e-07 | 1 |
| 212. | gi\|11353798 | Mannose-1-phosphate guanyltransferase-re.. | 91 | 1.2e-06 | 2 |
| 213. | gi\|629265 | lmbO protein - Streptomyces lincolnensis | 84 | 1.2e-06 | 2 |

FIG. 19(E)

| | | | | | |
|---|---|---|---|---|---|
| 214. | gi\|11347154 | Probable sugar-phosphate nucleotidyltran... | 92 | 1.3e-06 | 2 |
| 215. | gi\|7451542 | Hypothetical protein - Synechocystis sp.... | 85 | 1.4e-06 | 3 |
| 216. | gi\|11261683 | UTP--glucose-1-phosphate uridylyltransfe... | 88 | 1.5e-06 | 2 |
| 217. | gi\|11498742 | Glucose-1-phosphate cytidylyltransferase... | 114 | 1.9e-06 | 1 |
| 218. | gi\|11279398 | Mannose-1-phosphate guanylyltransferase-... | 105 | 2.4e-06 | 2 |
| 219. | gi\|10436672 | Unnamed protein product [Homo sapiens] | 108 | 4.1e-06 | 2 |
| 220. | gi\|7019387 | GDP-mannose pyrophosphorylase B [Homo sa... | 108 | 4.1e-06 | 3 |
| 221. | gi\|11431464 | GDP-mannose pyrophosphorylase B [Homo sa... | 108 | 4.1e-06 | 3 |
| 222. | gi\|265795 | Glucose-1-phosphate thymidylyl-transfera... | 111 | 4.8e-06 | 1 |
| 223. | gi\|348416 | Glucose-1-phosphate thymidylyltransferas... | 111 | 4.8e-06 | 1 |
| 224. | gi\|7448171 | Hypothetical protein - Synechocystis sp.... | 99 | 1.2e-05 | 2 |
| 225. | gi\|586920 | HYPOTHETICAL PROTEIN IN SOD 3'REGION | 92 | 1.6e-05 | 2 |
| 226. | gi\|3320397 | Putative glycerol-2-phosphate [Streptoco... | 106 | 1.7e-05 | 2 |
| 227. | gi\|3818694 | Cps23fM [Streptococcus pneumoniae] | 109 | 1.7e-05 | 3 |
| 228. | gi\|7424852 | Glucose-1-phosphate adenylyltransferase ... | 88 | 1.8e-05 | 3 |
| 229. | gi\|729582 | GLUCOSE-1-PHOSPHATE ADENYLYLTRANSFERASE ... | 82 | 2.7e-05 | 4 |
| 230. | gi\|232171 | GLUCOSE-1-PHOSPHATE ADENYLYLTRANSFERASE ... | 76 | 3.1e-05 | 3 |
| 231. | gi\|7434848 | UTP--glucose-1-phosphate uridylyltransfe... | 64 | 3.2e-05 | 4 |
| 232. | gi\|10560009 | Glucose-1-phosphate thymidylyltransferas... | 79 | 3.4e-05 | 3 |
| 233. | gi\|11362831 | Virulence factor XF0591 [imported] - Xyl... | 76 | 5.1e-05 | 3 |
| 234. | gi\|11351850 | Probable nucleotidyl transferase PA0597 ... | 77 | 5.8e-05 | 3 |
| 235. | gi\|4845244 | Unknown [Pseudomonas aeruginosa] | 77 | 5.8e-05 | 3 |
| 236. | gi\|11261781 | Glucose-1-phosphate adenylyltransferase ... | 77 | 7.9e-05 | 2 |
| 237. | gi\|2811060 | GLUCOSE-1-PHOSPHATE ADENYLYLTRANSFERASE ... | 77 | 8.1e-05 | 3 |
| 238. | gi\|7473559 | Probable mannose-1-phosphate guanyltrans... | 77 | 0.00018 | 3 |
| 239. | gi\|7448162 | Glucose-1-phosphate thymidylyltransferas... | 76 | 0.00019 | 3 |
| 240. | gi\|2731775 | ADP-glucose pyrophosphorylase [Thermus c... | 74 | 0.00041 | 3 |
| 241. | gi\|7429848 | Glucose-1-phosphate thymidylyltransferas... | 94 | 0.00052 | 2 |
| 242. | gi\|10638193 | UTP-glucose-1-phosphate uridylyltransfer... | 70 | 0.00054 | 2 |
| 243. | gi\|10638206 | UTP-glucose-1-phosphate uridylyltransfer... | 70 | 0.00054 | 2 |
| 244. | gi\|11359596 | Eukaryotic initiation factor eIF2B gamma... | 95 | 0.00057 | 1 |
| 245. | gi\|7303057 | CG8190 gene product [Drosophila melanoga... | 95 | 0.00078 | 2 |
| 246. | gi\|7488395 | Translation regulator GCD6 homolog F1913... | 94 | 0.0011 | 1 |
| 247. | gi\|8051798 | Putative transferase [Amycolatopsis orie... | 87 | 0.0018 | 2 |
| 248. | gi\|10638087 | UTP-glucose-1-phosphate uridylyltransfer... | 75 | 0.0018 | 2 |
| 249. | gi\|7469529 | Hypothetical protein - Synechocystis sp.... | 70 | 0.002 | 3 |
| 250. | gi\|11497858 | Glucose-1-phosphate thymidylyltransferas... | 81 | 0.002 | 3 |
| 251. | gi\|132501 | GLUCOSE-1-PHOSPHATE CYTIDYLYLTRANSFERASE... | 92 | 0.003 | 1 |
| 252. | gi\|10638183 | UTP-glucose-1-phosphate uridylyltransfer... | 71 | 0.0025 | 2 |
| 253. | gi\|10638186 | UTP-glucose-1-phosphate uridylyltransfer... | 71 | 0.0025 | 2 |
| 254. | gi\|10638209 | UTP-glucose-1-phosphate uridylyltransfer... | 70 | 0.0025 | 2 |
| 255. | gi\|10638144 | UTP-glucose-1-phosphate uridylyltransfer... | 70 | 0.0025 | 2 |
| 256. | gi\|6041791 | Putative translation initiation factor E... | 91 | 0.0028 | 1 |
| 257. | gi\|10173702 | Glucose-1-phosphate adenylyltransferase ... | 86 | 0.0029 | 2 |
| 258. | gi\|3834671 | ADP-glucose pyrophosphorylase [Rhodospir... | 57 | 0.0031 | 4 |
| 259. | gi\|10638189 | UTP-glucose-1-phosphate uridylyltransfer... | 75 | 0.0034 | 2 |
| 260. | gi\|6515114 | ADP-glucose pyrophosphorylase small subu... | 85 | 0.0053 | 2 |
| 261. | gi\|232170 | GLUCOSE-1-PHOSPHATE ADENYLYLTRANSFERASE ... | 81 | 0.006 | 2 |
| 262. | gi\|10640388 | Glucose-1-phosphate thymidylyltransferas... | 57 | 0.0061 | 3 |
| 263. | gi\|10638171 | UTP-glucose-1-phosphate uridylyltransfer... | 70 | 0.0062 | 2 |
| 264. | gi\|10638177 | UTP-glucose-1-phosphate uridylyltransfer... | 70 | 0.0062 | 2 |
| 265. | gi\|10638180 | UTP-glucose-1-phosphate uridylyltransfer... | 70 | 0.0062 | 2 |
| 266. | gi\|10638195 | UTP-glucose-1-phosphate uridylyltransfer... | 70 | 0.0062 | 2 |
| 267. | gi\|10638165 | UTP-glucose-1-phosphate uridylyltransfer... | 70 | 0.0062 | 2 |
| 268. | gi\|10638203 | UTP-glucose-1-phosphate uridylyltransfer... | 84 | 0.0062 | 2 |
| 269. | gi\|2811033 | GLUCOSE-1-PHOSPHATE ADENYLYLTRANSFERASE ... | 73 | 0.0076 | 2 |
| 270. | gi\|8895696 | Mannose-1-phosphate-guanyltransferase-li... | 86 | 0.0086 | 2 |

FIG. 19(F)

| # | gi | Description | Score | E-value | N |
|---|---|---|---|---|---|
| 271. | gi\|406922 | Homology to UDP pyrophosphorylase N76548... | 87 | 0.0099 | 1 |
| 272. | gi\|11261806 | Probable glucose-1-phosphate adenylyltra... | 73 | 0.011 | 2 |
| 273. | gi\|7671532 | Glucose-1-phosphate adenylyltransferase ... | 79 | 0.011 | 2 |
| 274. | gi\|633874 | Alpha-D-glucose cytidylyltransferase; Ep... | 86 | 0.014 | 1 |
| 275. | gi\|485384 | Alpha-D-glucose-1-phosphate cytidylyltra... | 86 | 0.014 | 1 |
| 276. | gi\|421276 | Glucose-1-phosphate cytidylyltransferase... | 86 | 0.014 | 1 |
| 277. | gi\|10638192 | UTP-glucose-1-phosphate uridylyltransfer... | 70 | 0.015 | 2 |
| 278. | gi\|10638156 | UTP-glucose-1-phosphate uridylyltransfer... | 64 | 0.015 | 2 |
| 279. | gi\|10638153 | UTP-glucose-1-phosphate uridylyltransfer... | 64 | 0.015 | 2 |
| 280. | gi\|10638168 | UTP-glucose-1-phosphate uridylyltransfer... | 64 | 0.015 | 2 |
| 281. | gi\|2146023 | LnbO protein - Streptomyces lincolnensis... | 73 | 0.015 | 2 |
| 282. | gi\|2568972 | DdhA [Vibrio anguillarum] | 83 | 0.017 | 2 |
| 283. | gi\|1237080 | ADP-glucose pyrophosphorylase [Pisum sat... | 80 | 0.018 | 2 |
| 284. | gi\|7447201 | Glucose-1-phosphate cytidylyltransferase... | 85 | 0.019 | 1 |
| 285. | gi\|7531163 | Probable licC protein (licC) - syphilis ... | 83 | 0.019 | 1 |
| 286. | gi\|121283 | GLUCOSE-1-PHOSPHATE ADENYLYLTRANSFERASE ... | 80 | 0.023 | 2 |
| 287. | gi\|100675 | Glucose-1-phosphate adenylyltransferase ... | 80 | 0.023 | 2 |
| 288. | gi\|5917789 | ADP-glucose pyrophosphorylase small subu... | 80 | 0.024 | 2 |
| 289. | gi\|8683019 | T22C5.13 [Arabidopsis thaliana] | 73 | 0.024 | 2 |
| 290. | gi\|1575754 | ADP glucose pyrophosphorylase small subu... | 80 | 0.024 | 2 |
| 291. | gi\|11347147 | Probable sugar nucleotidyltransferase Cj... | 84 | 0.025 | 1 |
| 292. | gi\|21403 | ADP-glucose pyrophosphorylase; glucose-1... | 80 | 0.028 | 2 |
| 293. | gi\|100426 | Glucose-1-phosphate adenylyltransferase ... | 80 | 0.028 | 2 |
| 294. | gi\|633678 | ADP-glucose pyrophosphorylase [Spinacia ... | 80 | 0.028 | 2 |
| 295. | gi\|10638150 | UTP-glucose-1-phosphate uridylyltransfer... | 70 | 0.03 | 2 |
| 296. | gi\|2130035 | Glucose-1-phosphate adenylyltransferase ... | 80 | 0.03 | 2 |
| 297. | gi\|232172 | GLUCOSE-1-PHOSPHATE ADENYLYLTRANSFERASE ... | 80 | 0.03 | 2 |
| 298. | gi\|7340287 | Small subunit ADP glucose pyrophosphoryl... | 80 | 0.03 | 2 |
| 299. | gi\|1707939 | GLUCOSE-1-PHOSPHATE ADENYLYLTRANSFERASE ... | 80 | 0.031 | 2 |
| 300. | gi\|1237062 | ADP-glucose pyrophosphorylase [Pisum sat... | 80 | 0.032 | 2 |
| 301. | gi\|1707943 | GLUCOSE-1-PHOSPHATE ADENYLYLTRANSFERASE ... | 80 | 0.032 | 2 |
| 302. | gi\|1707940 | GLUCOSE-1-PHOSPHATE ADENYLYLTRANSFERASE ... | 80 | 0.032 | 2 |
| 303. | gi\|3015514 | ADPG pyrophosphorylase small subunit [Ar... | 80 | 0.033 | 2 |
| 304. | gi\|1071859 | Glucose-1-phosphate adenylyltransferase ... | 80 | 0.033 | 2 |
| 305. | gi\|1325984 | ADP-glucose pyrophosphorylase small subu... | 80 | 0.033 | 2 |
| 306. | gi\|232164 | GLUCOSE-1-PHOSPHATE ADENYLYLTRANSFERASE ... | 85 | 0.033 | 2 |
| 307. | gi\|7434881 | Glucose-1-phosphate adenylyltransferase ... | 80 | 0.033 | 2 |
| 308. | gi\|1707930 | GLUCOSE-1-PHOSPHATE ADENYLYLTRANSFERASE ... | 62 | 0.033 | 2 |
| 309. | gi\|7434879 | Glucose-1-phosphate adenylyltransferase ... | 80 | 0.033 | 2 |
| 310. | gi\|2625084 | ADP-glucose pyrophosphorylase small subu... | 80 | 0.033 | 2 |
| 311. | gi\|7434871 | Glucose-1-phosphate adenylyltransferase ... | 80 | 0.033 | 2 |
| 312. | gi\|7434891 | Glucose-1-phosphate adenylyltransferase ... | 62 | 0.044 | 2 |
| 313. | gi\|1707928 | GLUCOSE-1-PHOSPHATE ADENYLYLTRANSFERASE ... | 62 | 0.044 | 2 |
| 314. | gi\|2149021 | ADPG pyrophosphorylase large subunit [Ar... | 75 | 0.044 | 2 |
| 315. | gi\|4586350 | Glucose-1-phosphate adenylyltransferase ... | 75 | 0.044 | 2 |
| 316. | gi\|1707923 | GLUCOSE-1-PHOSPHATE ADENYLYLTRANSFERASE ... | 62 | 0.044 | 2 |
| 317. | gi\|100580 | Glucose-1-phosphate adenylyltransferase ... | 62 | 0.045 | 2 |
| 318. | gi\|5091608 | Identical to gb\|D50317 ADP glucose pyrop... | 62 | 0.045 | 2 |
| 319. | gi\|7434885 | Glucose-1-phosphate adenylyltransferase ... | 73 | 0.057 | 2 |
| 320. | gi\|7488095 | ADP-glucose pyrophosphorylase small subu... | 80 | 0.059 | 2 |
| 321. | gi\|7434886 | Glucose-1-phosphate adenylyltransferase ... | 64 | 0.064 | 3 |
| 322. | gi\|7488396 | Translation regulator GCD6 homolog T9A21... | 81 | 0.065 | 1 |
| 323. | gi\|6320417 | Translation initiation factor eIF-2B eps... | 81 | 0.065 | 1 |
| 324. | gi\|7521184 | Probable mannose-1-phosphate guanyltrans... | 64 | 0.065 | 3 |
| 325. | gi\|1197640 | DdhA [Yersinia enterocolitica (type O:8)] | 80 | 0.088 | 1 |
| 326. | gi\|134448 | ADP-glucose pyrophosphorylase [Synechocy... | 80 | 0.088 | 1 |
| 327. | gi\|7447199 | Glucose-1-phosphate cytidylyltransferase... | 80 | 0.088 | 1 |

FIG. 19(G)

| | | | | | |
|---|---|---|---|---|---|
| 328. | gi\|1707944 | GLUCOSE-1-PHOSPHATE ADENYLYLTRANSFERASE ... | 80 | 0.088 | 1 |
| 329. | gi\|3023677 | PROBABLE TRANSLATION INITIATION FACTOR E... | 77 | 0.09 | 2 |
| 330. | gi\|121293 | GLUCOSE-1-PHOSPHATE ADENYLYLTRANSFERASE ... | 62 | 0.1 | 2 |
| 331. | gi\|7434883 | Glucose-1-phosphate adenylyltransferase ... | 75 | 0.1 | 2 |
| 332. | gi\|97163 | Lic-1 protein C - Haemophilus influenzae... | 75 | 0.12 | 1 |
| 333. | gi\|7464390 | LICC PROTEIN | 73 | 0.12 | 1 |
| 334. | gi\|9787341 | Probable mannose-1-phosphate guanyltrans... | 66 | 0.13 | 2 |
| 335. | gi\|7434873 | Glucose-1-phosphate adenylyltransferase ... | 72 | 0.14 | 2 |
| 336. | gi\|1707922 | GLUCOSE-1-PHOSPHATE ADENYLYLTRANSFERASE ... | 72 | 0.14 | 2 |
| 337. | gi\|3023676 | PROBABLE TRANSLATION INITIATION FACTOR E... | 78 | 0.16 | 1 |
| 338. | gi\|1707932 | GLUCOSE-1-PHOSPHATE ADENYLYLTRANSFERASE ... | 71 | 0.17 | 2 |
| 339. | gi\|1707929 | GLUCOSE-1-PHOSPHATE ADENYLYLTRANSFERASE ... | 69 | 0.18 | 2 |
| 340. | gi\|7671230 | ADP-glucose pyrophosphorylase catalytic ... | 69 | 0.19 | 2 |
| 341. | gi\|7448160 | Glucose-1-phosphate adenylyltransferase ... | 62 | 0.21 | 2 |
| 342. | gi\|11023507 | Putative glucose-1-P-cytidylyltransferas... | 77 | 0.21 | 1 |
| 343. | gi\|1840114 | ADP-glucose pyrophosphorylase large subu... | 65 | 0.24 | 2 |
| 344. | gi\|57594C1 | GalF [Escherichia coli] | 64 | 0.27 | 2 |
| 345. | gi\|2506458 | GLUCOSE-1-PHOSPHATE ADENYLYLTRANSFERASE ... | 76 | 0.28 | 1 |
| 346. | gi\|7434878 | Glucose-1-phosphate adenylyltransferase ... | 72 | 0.29 | 2 |
| 347. | gi\|1778236 | ADP-glucose pyrophosphorylase large subu... | 69 | 0.31 | 2 |
| 348. | gi\|7448167 | Probable glucose-1-phosphate thymidylylt... | 75 | 0.36 | 1 |
| 349. | gi\|7434893 | Glucose-1-phosphate adenylyltransferase ... | 80 | 0.39 | 2 |
| 350. | gi\|5882732 | Similar to gb\|AF135432 GDP-mannose pyrop... | 74 | 0.46 | 1 |
| 351. | gi\|8646773 | Putative GDP-mannose pyrophosphorylase; ... | 74 | 0.46 | 1 |
| 352. | gi\|7434866 | Glucose-1-phosphate adenylyltransferase ... | 57 | 0.48 | 2 |
| 353. | gi\|7434889 | Glucose-1-phosphate adenylyltransferase ... | 57 | 0.49 | 2 |
| 354. | gi\|5817791 | ADP-glucose pyrophosphorylase large subu... | 69 | 0.5 | 2 |
| 355. | gi\|7471938 | Glucose-1-phosphate adenylyltransferase ... | 71 | 0.53 | 2 |
| 356. | gi\|7471937 | Glucose-1-phosphate adenylyltransferase ... | 63 | 0.59 | 3 |
| 357. | gi\|11386853 | PROBABLE GLUCOSE-1-PHOSPHATE ADENYLYLTRA... | 66 | 0.6 | 2 |
| 358. | gi\|7434869 | Glucose-1-phosphate adenylyltransferase ... | 62 | 0.6 | 2 |
| 359. | gi\|7492700 | Probable mannose-1-phosphate guanyl tran... | 57 | 0.62 | 2 |
| 360. | gi\|2139037 | Glucose-1-phosphate adenylyltransferase ... | 72 | 0.69 | 1 |
| 361. | gi\|2146810 | Glucose-1-phosphate adenylyltransferase ... | 72 | 0.69 | 1 |
| 362. | gi\|7448100 | UDP-N-acetylglucosamine pyrophosphorylas... | 48 | 0.75 | 4 |
| 363. | gi\|135927 | UDP-N-ACETYLGLUCOSAMINE PYROPHOSPHORYLAS... | 43 | 0.79 | 5 |
| 364. | gi\|7522214 | Glucose-1-phosphate adenylyltransferase ... | 66 | 0.84 | 2 |
| 365. | gi\|4544432 | Putative GDP-mannose pyrophosphorylase ... | 70 | 0.89 | 1 |
| 366. | gi\|10629507 | Mannose-1-phosphate guanyltransferase re... | 70 | 0.89 | 1 |
| 367. | gi\|7447208 | Glucose-1-phosphate cytidylyltransferase... | 70 | 0.89 | 1 |
| 368. | gi\|232186 | GLUCOSE-1-PHOSPHATE ADENYLYLTRANSFERASE ... | 63 | 0.93 | 2 |
| 369. | gi\|2981299 | Ribosomal protein S4 homolog [Trypanosom... | 54 | 0.94 | 3 |
| 370. | gi\|5923897 | ADP-glucose pyrophosphorylase large subu... | 63 | 0.95 | 2 |
| 371. | gi\|7434884 | Glucose-1-phosphate adenylyltransferase ... | 63 | 0.95 | 2 |
| 372. | gi\|6626364 | GalF-like [Bradyrhizobium japonicum] | 69 | 0.95 | 1 |
| 373. | gi\|11353789 | Type 2C Protein Phosphatase related prot... | 69 | 0.95 | 1 |
| 374. | gi\|7434874 | Glucose-1-phosphate adenylyltransferase ... | 59 | 0.96 | 2 |
| 375. | gi\|7563759 | Hypothetical protein; 64083-64412 [Arabi... | 68 | 0.98 | 1 |
| 376. | gi\|5701881 | ADP-glucose pyrophosphorylase [Ipomoea b... | 63 | 0.99 | 2 |
| 377. | gi\|5852076 | ADP-glucose pyrophosphorylase [Ipomoea b... | 62 | 1 | 2 |
| 378. | gi\|7331939 | Contains similarity to Pfam families PFO... | 54 | 1 | 3 |
| 379. | gi\|479426 | Fibronectin-binding protein - Streptococ... | 66 | 1 | 1 |
| 380. | gi\|476970 | Mannose-1-phosphate guanylyltransferase ... | 66 | 1 | 1 |
| 381. | gi\|3211569 | ADP-glucose pyrophosphorylase large subu... | 61 | 1 | 2 |
| 382. | gi\|7671236 | ADP-glucose pyrophosphorylase large subu... | 56 | 1 | 2 |

SEQUENCE LISTING

<160> NUMBER OF SEQ ID NOS: 12

<210> SEQ ID NO 1
<211> LENGTH: 292
<212> TYPE: PRT
<213> ORGANISM: Salmonella enterica

<400> SEQUENCE: 1

Met Lys Thr Arg Lys Gly Ile Ile Leu Ala Gly Gly Ser Gly Thr Arg
1               5                   10                  15

Leu Tyr Pro Val Thr Met Ala Val Ser Lys Gln Leu Leu Pro Ile Tyr
            20                  25                  30

Asp Lys Pro Met Ile Tyr Tyr Pro Leu Ser Thr Leu Met Leu Ala Gly
        35                  40                  45

Ile Arg Asp Ile Leu Ile Ile Ser Thr Pro Gln Asp Thr Pro Arg Phe
    50                  55                  60

Gln Gln Leu Leu Gly Asp Gly Ser Gln Trp Gly Leu Asn Leu Gln Tyr
65                  70                  75                  80

Lys Val Gln Pro Ser Pro Asp Gly Leu Ala Gln Ala Phe Ile Ile Gly
                85                  90                  95

Glu Glu Phe Ile Gly Asn Asp Asp Cys Ala Leu Val Leu Gly Asp Asn
            100                 105                 110

Ile Phe Tyr Gly His Asp Leu Pro Lys Leu Met Glu Ala Ala Val Asn
        115                 120                 125

Lys Glu Ser Gly Ala Thr Val Phe Ala Tyr His Val Asn Asp Pro Glu
    130                 135                 140

Arg Tyr Gly Val Val Glu Phe Asp Gln Ser Gly Thr Ala Val Ser Leu
145                 150                 155                 160

Glu Glu Lys Pro Leu Gln Pro Lys Ser Asn Tyr Ala Val Thr Gly Leu
                165                 170                 175

Tyr Phe Tyr Asp Asn Ser Val Val Glu Met Ala Lys Asn Leu Lys Pro
            180                 185                 190

Ser Ala Arg Gly Glu Leu Glu Ile Thr Asp Ile Asn Arg Ile Tyr Met
        195                 200                 205

-continued

Glu Gln Gly Arg Leu Ser Val Ala Met Met Gly Arg Gly Tyr Ala Trp
    210                 215                 220

Leu Asp Thr Gly Thr His Gln Ser Leu Ile Glu Ala Ser Asn Phe Ile
225                 230                 235                 240

Ala Thr Ile Glu Glu Arg Gln Gly Leu Lys Val Ser Cys Pro Glu Glu
                245                 250                 255

Ile Ala Tyr Arg Lys Gly Phe Ile Asp Ala Glu Gln Ile Lys Asn Leu
            260                 265                 270

Ala Lys Pro Leu Ser Lys Asn Ala Tyr Gly Gln Tyr Leu Leu Asn Met
        275                 280                 285

Ile Lys Gly Tyr
        290

<210> SEQ ID NO 2
<211> LENGTH: 293
<212> TYPE: PRT
<213> ORGANISM: Pseudomonas aeruginosa

<400> SEQUENCE: 2

Met Lys Arg Lys Gly Ile Ile Leu Ala Gly Gly Ser Gly Thr Arg Leu
1               5                   10                  15

His Pro Ala Thr Leu Ala Ile Ser Lys Gln Leu Leu Pro Val Tyr Asp
                20                  25                  30

Lys Pro Met Ile Tyr Tyr Pro Leu Ser Thr Leu Met Leu Ala Gly Ile
            35                  40                  45

Arg Glu Ile Leu Ile Ile Ser Thr Pro Gln Asp Thr Pro Arg Phe Gln
    50                  55                  60

Gln Leu Leu Gly Asp Gly Ser Asn Trp Gly Leu Asp Leu Gln Tyr Ala
65                  70                  75                  80

Val Gln Pro Ser Pro Asp Gly Leu Ala Gln Ala Phe Leu Ile Gly Glu
                85                  90                  95

Ser Phe Ile Gly Asn Asp Leu Ser Ala Leu Val Leu Gly Asp Asn Leu
            100                 105                 110

Tyr Tyr Gly His Asp Phe His Glu Leu Leu Gly Ser Ala Ser Gln Arg
        115                 120                 125

Gln Thr Gly Ala Ser Val Phe Ala Tyr His Val Leu Asp Pro Glu Arg
    130                 135                 140

Val Gly Val Val Glu Phe Asp Gln Gly Gly Lys Ala Ile Ser Leu Glu
145                 150                 155                 160

Glu Lys Pro Leu Glu Pro Lys Ser Asn Tyr Ala Val Thr Gly Leu Tyr
                165                 170                 175

Phe Tyr Asp Gln Gln Val Val Asp Ile Ala Arg Asp Leu Lys Pro Ser
            180                 185                 190

Pro Arg Gly Glu Leu Glu Ile Thr Asp Val Asn Arg Ala Tyr Leu Glu
        195                 200                 205

Arg Gly Gln Leu Ser Val Glu Ile Met Gly Arg Gly Tyr Ala Trp Leu
    210                 215                 220

Asp Thr Gly Thr His Asp Ser Leu Leu Glu Ala Gly Gln Phe Ile Ala
225                 230                 235                 240

Thr Leu Glu Asn Arg Gln Gly Leu Lys Val Ala Cys Pro Glu Glu Ile
                245                 250                 255

Ala Tyr Arg Gln Lys Trp Ile Asp Ala Ala Gln Leu Glu Lys Leu Ala
            260                 265                 270

Ala Pro Leu Ala Lys Asn Gly Tyr Gly Gln Tyr Leu Lys Arg Leu Leu
        275                 280                 285

```
Thr Glu Thr Val Tyr
        290

<210> SEQ ID NO 3
<211> LENGTH: 292
<212> TYPE: PRT
<213> ORGANISM: Mycoplasma genitalium

<400> SEQUENCE: 3

Met Lys Thr Lys Ile Arg Lys Ala Val Ile Pro Ala Ala Gly Leu Gly
1               5                   10                  15

Val Arg Leu Leu Pro Ala Thr Lys Ala Ile Pro Lys Glu Met Leu Pro
            20                  25                  30

Leu Val Asn Lys Pro Thr Ile Gln Tyr Ile Val Glu Glu Ala Val Lys
        35                  40                  45

Ser Gly Ile Glu Gln Ile Leu Val Ile Val Ser Ser Lys Lys Thr Ala
    50                  55                  60

Ile Leu Asp His Phe Asp Tyr Asp Leu Ile Leu Glu Asn Ala Leu Ile
65                  70                  75                  80

Gln Lys Asn Lys Leu Gln Glu His Lys Glu Ile Glu Asp Ile Ala Asn
                85                  90                  95

Leu Ala His Ile Phe Phe Val Arg Gln Lys Asn Gln Asp Gly Leu Gly
            100                 105                 110

Asp Ala Ile Leu Phe Ala Glu Ser Phe Val Gly Asn Glu Asp Phe Ala
        115                 120                 125

Val Leu Leu Gly Asp Asp Val Val Phe Ser Lys Glu Pro Ala Leu Lys
    130                 135                 140

Gln Cys Leu Glu Ala Tyr Tyr Glu Thr Asn Cys Gln Thr Ile Gly Val
145                 150                 155                 160

Gln Glu Val Asp Pro Cys His Val Asp Lys Tyr Gly Ile Ile Thr Pro
                165                 170                 175

Glu Gly Asp Tyr Lys Asn Lys Asp Leu Ile Lys Val Leu Ala Met Thr
            180                 185                 190

Glu Lys Pro Lys Pro Lys Asp Ala Lys Ser Asn Leu Ala Ile Leu Gly
        195                 200                 205

Arg Tyr Val Leu Lys Pro Ser Ile Phe Lys Ala Leu Arg Ser Val Pro
    210                 215                 220

Tyr Gly Val Gly Gly Glu Leu Gln Leu Thr Asp Gly Leu Asn Phe Cys
225                 230                 235                 240

Leu Lys Asn Glu Asn Phe Tyr Ala Arg Lys Phe Thr Gly Thr Arg Phe
                245                 250                 255

Asp Val Gly Thr Lys Ser Gly Phe Ile Lys Ala Asn Leu Phe Thr Ala
            260                 265                 270

Leu Asn Asn Lys Asp Ile Ser Lys Glu Val Leu Glu Leu Leu Asn
        275                 280                 285

Leu Val Lys Ala
    290

<210> SEQ ID NO 4
<211> LENGTH: 298
<212> TYPE: PRT
<213> ORGANISM: Streptococcus pneumoniae

<400> SEQUENCE: 4

Met Thr Ser Lys Val Arg Lys Ala Val Ile Pro Ala Ala Gly Leu Gly
1               5                   10                  15

Thr Arg Phe Leu Pro Ala Thr Lys Ala Leu Ala Lys Glu Met Leu Pro
```

```
                    20                  25                  30
Ile Val Asp Lys Pro Thr Ile Gln Phe Ile Val Glu Glu Ala Leu Lys
                35                  40                  45

Ser Gly Ile Glu Asp Ile Leu Val Thr Gly Lys Ser Lys Arg Ser Ile
     50                  55                  60

Glu Asp His Phe Asp Ser Asn Phe Glu Leu Glu Tyr Asn Leu Lys Glu
 65                  70                  75                  80

Lys Gly Lys Thr Asp Leu Leu Lys Leu Val Asp Glu Thr Thr Gly Met
                 85                  90                  95

Arg Leu His Phe Ile Arg Gln Thr His Pro Arg Gly Leu Gly Asp Ala
                100                 105                 110

Val Leu Gln Ala Lys Ala Phe Val Gly Asn Glu Pro Phe Val Val Met
            115                 120                 125

Leu Gly Asp Asp Leu Met Asp Ile Thr Asp Glu Lys Ala Val Pro Leu
        130                 135                 140

Thr Lys Gln Leu Met Asn Asp Tyr Glu Lys Thr His Ala Ser Thr Ile
145                 150                 155                 160

Ala Val Met Pro Val Pro His Glu Asp Val Ser Ser Tyr Gly Val Ile
                165                 170                 175

Ala Pro Gln Gly Glu Gly Ser Asn Gly Leu Tyr Ser Val Glu Thr Phe
            180                 185                 190

Val Glu Lys Pro Ala Pro Glu Thr Pro Ser Asp Leu Ala Ile Ile
        195                 200                 205

Gly Arg Tyr Leu Leu Thr Pro Glu Ile Phe Glu Ile Leu Glu Lys Gln
    210                 215                 220

Ala Pro Gly Ala Gly Asn Glu Ile Gln Leu Thr Asp Ala Ile Asp Thr
225                 230                 235                 240

Leu Asn Lys Thr Gln Arg Val Phe Ala Arg Glu Phe Thr Gly Thr Arg
                245                 250                 255

Tyr Asp Val Gly Asp Lys Phe Gly Phe Met Lys Thr Ser Ile Asp Tyr
            260                 265                 270

Ala Leu Lys His Pro Gln Val Lys Asp Asp Leu Lys Asn Tyr Leu Ile
        275                 280                 285

Gln Leu Gly Lys Glu Leu Thr Glu Lys Glu
    290                 295

<210> SEQ ID NO 5
<211> LENGTH: 380
<212> TYPE: PRT
<213> ORGANISM: Bacillus subtilis

<400> SEQUENCE: 5

Met Lys Lys Gln Cys Val Ala Met Leu Leu Ala Gly Gly Lys Gly Ser
1                5                  10                  15

Arg Leu Ser Gly Leu Thr Lys Asn Met Ala Lys Pro Ala Val Ser Phe
                20                  25                  30

Gly Gly Lys Tyr Arg Ile Ile Asp Phe Thr Leu Ser Asn Cys Ser Asn
            35                  40                  45

Ser Gly Ile Asp Thr Val Gly Ile Leu Thr Gln Tyr Gln Pro Leu Glu
        50                  55                  60

Leu Asn Ser Tyr Ile Gly Ile Gly Ser Ala Trp Asp Leu Asp Arg Tyr
 65                  70                  75                  80

Asn Gly Gly Val Thr Val Leu Pro Pro Tyr Ala Glu Ser Ser Glu Val
                 85                  90                  95

Lys Trp Tyr Lys Gly Thr Ala Ser Ser Thr Tyr Glu Asn Leu Asn Tyr
```

```
            100                 105                 110
Leu Asn Gln Tyr Asp Pro Glu Tyr Val Leu Ile Leu Ser Gly Asp His
        115                 120                 125
Ile Tyr Lys Met Asp Tyr Gly Lys Met Leu Asp Tyr His Ile Glu Lys
    130                 135                 140
Lys Ala Asp Val Thr Ile Ser Val Ile Glu Val Gly Trp Glu Glu Ala
145                 150                 155                 160
Ser Arg Phe Gly Ile Met Lys Ala Asn Pro Asp Gly Thr Ile Thr His
                165                 170                 175
Phe Asp Glu Lys Pro Lys Phe Pro Lys Ser Asn Leu Ala Ser Met Gly
            180                 185                 190
Ile Tyr Ile Phe Asn Trp Pro Leu Leu Lys Gln Tyr Leu Glu Met Asp
        195                 200                 205
Asp Gln Asn Pro Tyr Ser Ser His Asp Phe Gly Lys Asp Ile Ile Pro
    210                 215                 220
Leu Leu Leu Glu Glu Lys Lys Leu Ser Ala Tyr Pro Phe Lys Gly
225                 230                 235                 240
Tyr Trp Lys Asp Val Gly Thr Val Gln Ser Leu Trp Glu Ala Asn Met
                245                 250                 255
Asp Leu Leu Lys Glu Asp Ser Glu Leu Lys Leu Phe Glu Arg Lys Trp
            260                 265                 270
Lys Ile Tyr Ser Val Asn Pro Asn Gln Pro Gln Phe Ile Ser Ser
        275                 280                 285
Asp Ala Gln Val Gln Asp Ser Leu Val Asn Glu Gly Cys Val Val Tyr
    290                 295                 300
Gly Asn Val Ser His Ser Val Leu Phe Gln Gly Val Thr Val Gly Lys
305                 310                 315                 320
His Thr Thr Val Thr Ser Ser Val Ile Met Pro Asp Val Thr Ile Gly
                325                 330                 335
Glu His Val Val Ile Glu Asn Ala Ile Val Pro Asn Gly Met Val Leu
            340                 345                 350
Pro Asp Gly Ala Val Ile Arg Ser Glu Lys Asp Ile Glu Glu Val Leu
        355                 360                 365
Leu Val Ser Glu Glu Phe Val Glu Lys Glu Leu Ile
    370                 375                 380

<210> SEQ ID NO 6
<211> LENGTH: 423
<212> TYPE: PRT
<213> ORGANISM: Thermotoga maritima

<400> SEQUENCE: 6

Met Gly Asn Thr Val Ala Met Ile Leu Ala Gly Gly Gln Gly Thr Arg
1               5                   10                  15
Leu Gly Val Leu Thr Glu Arg Ile Ala Lys Pro Ala Val Pro Phe Gly
            20                  25                  30
Gly Lys Tyr Arg Leu Ile Asp Phe Thr Leu Ser Asn Cys Val Asn Ser
        35                  40                  45
Gly Ile Tyr Arg Val Gly Val Leu Thr Gln Tyr Arg Pro His Val Leu
    50                  55                  60
Ser Lys His Ile Gly Ile Gly Arg Pro Trp Asp Leu Asp Arg Lys Asp
65                  70                  75                  80
Gly Gly Val Glu Ile Leu Pro Pro Tyr Val Gly Arg His Glu Ser Asp
                85                  90                  95
Trp Tyr Lys Gly Thr Ala Asn Ala Val Tyr Gln Asn Leu Glu Phe Leu
```

```
                100                 105                 110
Glu Glu Asn Asp Ala Glu Leu Val Leu Ile Leu Ser Gly Asp His Val
            115                 120                 125
Tyr Ala Met Asn Tyr Asn Asp Leu Ile Asp Tyr His Leu Leu Lys Glu
        130                 135                 140
Ala Asp Gly Thr Ile Ala Cys Met Glu Val Pro Ile Glu Glu Ala Ser
145                 150                 155                 160
Arg Phe Gly Ile Met Ile Thr Asp Val Asp Gly Arg Ile Val Asp Phe
                165                 170                 175
Glu Glu Lys Pro Ala Lys Pro Arg Ser Asn Leu Ala Ser Leu Gly Ile
            180                 185                 190
Tyr Val Phe Asn Tyr Glu Phe Leu Lys Lys Val Leu Ile Glu Asp Glu
        195                 200                 205
Asn Asp Pro Asn Ser Ser His Asp Phe Gly Lys Asp Val Ile Pro Arg
210                 215                 220
Ile Leu Arg Glu Asn Leu Gly Ser Leu Tyr Ala Phe Arg Phe Asp Gly
225                 230                 235                 240
Tyr Trp Arg Asp Val Gly Thr Leu Arg Ser Tyr Trp Glu Ala Asn Leu
                245                 250                 255
Glu Leu Val Leu Pro Val Pro Pro Phe Asn Leu Tyr Asp Pro Asn Trp
            260                 265                 270
Arg Phe Phe Thr His Thr Glu Glu Met Pro Pro Ala Tyr Val Ala Pro
        275                 280                 285
Gly Ser Lys Val Ser Thr Ser Leu Val Ser Glu Gly Ala Glu Val Tyr
290                 295                 300
Gly Asn Val Phe Asn Ser Val Ile Phe Gln Gly Val Lys Ile Gly Arg
305                 310                 315                 320
Gly Thr Val Val Lys Asn Ser Val Ile Met Thr Arg Thr Glu Ile Gly
                325                 330                 335
Glu Asn Cys Tyr Leu Glu Asn Val Ile Ala Glu Asn Val Lys Ile
            340                 345                 350
Gly Ser Asn Val Arg Met Gly Val Gly Glu Asp Ala Glu Ser Lys Leu
        355                 360                 365
Asp Pro Lys Val Tyr Ser Gly Leu Leu Thr Val Val Gly Met Asn Ser
370                 375                 380
Val Ile Pro Asp Asp Met Val Ile Gly Lys Asn Cys Val Ile Gly Ile
385                 390                 395                 400
Gly Val Arg Pro Glu Asp Phe Lys Ser Lys Thr Leu Glu Ser Gly Asp
                405                 410                 415
Tyr Val Ile Val Arg Glu Glu
            420

<210> SEQ ID NO 7
<211> LENGTH: 364
<212> TYPE: PRT
<213> ORGANISM: Hypocrea jecorina

<400> SEQUENCE: 7

Met Lys Gly Leu Ile Leu Val Gly Gly Phe Gly Thr Arg Leu Arg Pro
1               5                   10                  15
Leu Thr Leu Thr Leu Pro Lys Pro Leu Val Glu Phe Cys Asn Lys Pro
            20                  25                  30
Met Ile Val His Gln Ile Glu Ala Leu Val Ala Ala Gly Val Thr Asp
        35                  40                  45
Ile Val Leu Ala Val Asn Tyr Arg Pro Glu Ile Met Glu Lys Phe Leu
```

```
                50                  55                  60
Ala Glu Tyr Glu Glu Lys Tyr Asn Ile Asn Ile Glu Phe Ser Val Glu
 65                  70                  75                  80

Ser Glu Pro Leu Asp Thr Ala Gly Pro Leu Lys Leu Ala Glu Arg Ile
                 85                  90                  95

Leu Gly Lys Asp Asp Ser Pro Phe Phe Val Leu Asn Ser Asp Val Ile
                100                 105                 110

Cys Asp Tyr Pro Phe Lys Glu Leu Leu Glu Phe His Lys Ala His Gly
                115                 120                 125

Asp Glu Gly Thr Ile Val Val Thr Lys Val Glu Glu Pro Ser Lys Tyr
            130                 135                 140

Gly Val Val His Lys Pro Asn His Pro Ser Arg Ile Asp Arg Phe
145                 150                 155                 160

Val Glu Lys Pro Val Glu Phe Val Gly Asn Arg Ile Asn Ala Gly Met
                165                 170                 175

Tyr Ile Phe Asn Pro Ser Val Leu Lys Arg Ile Glu Leu Arg Pro Thr
                180                 185                 190

Ser Ile Glu Lys Glu Thr Phe Pro Ala Met Val Ala Asp Asn Gln Leu
            195                 200                 205

His Ser Phe Asp Leu Glu Gly Phe Trp Met Asp Val Gly Gln Pro Lys
210                 215                 220

Asp Phe Leu Ser Gly Thr Cys Leu Tyr Leu Ser Leu Thr Lys Lys
225                 230                 235                 240

Gly Ser Lys Glu Leu Thr Pro Pro Thr Glu Pro Tyr Val His Gly Gly
                245                 250                 255

Asn Val Met Ile His Pro Ser Ala Lys Ile Gly Lys Asn Cys Arg Ile
                260                 265                 270

Gly Pro Asn Val Thr Ile Gly Pro Asp Val Val Gly Asp Gly Val
            275                 280                 285

Arg Leu Gln Arg Cys Val Leu Leu Lys Gly Ser Lys Val Lys Asp His
                290                 295                 300

Ala Trp Val Lys Ser Thr Ile Val Gly Trp Asn Ser Thr Val Gly Arg
305                 310                 315                 320

Trp Ala Arg Leu Glu Asn Val Thr Val Leu Gly Asp Asp Val Thr Ile
                325                 330                 335

Gly Asp Glu Ile Tyr Val Asn Gly Gly Ser Val Leu Pro His Lys Ser
                340                 345                 350

Ile Lys Ala Asn Val Asp Val Pro Ala Ile Ile Met
            355                 360

<210> SEQ ID NO 8
<211> LENGTH: 362
<212> TYPE: PRT
<213> ORGANISM: Candida albicans

<400> SEQUENCE: 8

Met Lys Gly Leu Ile Leu Val Gly Gly Tyr Gly Thr Arg Leu Arg Pro
 1               5                  10                  15

Leu Thr Leu Thr Leu Pro Lys Pro Leu Val Glu Phe Gly Asn Arg Pro
                20                  25                  30

Met Ile Leu His Gln Ile Glu Ala Leu Ala Ala Ala Gly Val Thr Asp
                35                  40                  45

Ile Val Leu Ala Val Asn Tyr Arg Pro Glu Val Met Val Ser Thr Leu
            50                  55                  60

Lys Lys Tyr Glu Glu Glu Tyr Gly Val Ser Ile Thr Phe Ser Val Glu
```

```
                65                  70                  75                  80
Glu Glu Pro Leu Gly Thr Ala Gly Pro Leu Lys Leu Ala Glu Glu Val
                    85                  90                  95

Leu Lys Lys Asp Asp Ser Pro Phe Phe Val Leu Asn Ser Asp Val Ile
                    100                 105                 110

Cys Asp Tyr Pro Phe Lys Glu Leu Ala Asp Phe His Lys Ala His Gly
                    115                 120                 125

Ala Ala Gly Thr Ile Val Ala Thr Lys Val Asp Glu Pro Ser Lys Tyr
                130                 135                 140

Gly Val Ile Val His Asp Arg Asp Thr Pro Asn Leu Ile Asp Arg Phe
145                 150                 155                 160

Val Glu Lys Pro Val Glu Phe Val Gly Asn Arg Ile Asn Ala Gly Leu
                    165                 170                 175

Tyr Ile Leu Asn Pro Ser Val Ile Asp Leu Ile Glu Met Arg Pro Thr
                    180                 185                 190

Ser Ile Glu Lys Glu Thr Phe Pro Ile Leu Val Glu Gln Lys Gln Leu
                    195                 200                 205

Tyr Ser Phe Asp Leu Glu Gly Tyr Trp Met Asp Val Gly Gln Pro Lys
                210                 215                 220

Asp Phe Leu Ser Gly Thr Cys Leu Tyr Leu Thr Ser Leu Ser Lys Lys
225                 230                 235                 240

His Pro Glu Lys Leu Cys Lys Glu Lys Tyr Val His Gly Gly Asn Val
                    245                 250                 255

Leu Ile Asp Pro Thr Ala Lys Ile His Pro Ser Ala Leu Ile Gly Pro
                    260                 265                 270

Asn Val Thr Ile Gly Pro Asn Val Val Gly Glu Gly Ala Arg Ile
                    275                 280                 285

Gln Arg Ser Val Leu Leu Ala Asn Ser Gln Val Lys Asp His Ala Trp
                290                 295                 300

Val Lys Ser Thr Ile Val Gly Trp Asn Ser Arg Ile Gly Lys Trp Ala
305                 310                 315                 320

Arg Thr Glu Gly Val Thr Val Leu Gly Asp Asp Val Glu Val Lys Asn
                    325                 330                 335

Glu Ile Tyr Val Asn Gly Ala Lys Val Leu Pro His Lys Ser Ile Ser
                340                 345                 350

Ser Asn Val Glu Lys Glu Ser Ile Ile Met
                355                 360

<210> SEQ ID NO 9
<211> LENGTH: 445
<212> TYPE: PRT
<213> ORGANISM: Thermotoga maritima

<400> SEQUENCE: 9

Met Arg Ala Leu Val Leu Ala Ala Gly Lys Gly Thr Arg Met Lys Ser
1               5                   10                  15

Lys Ile Pro Lys Val Leu His Pro Leu Ser Gly Arg Pro Met Ile Glu
                    20                  25                  30

Trp Val Ile Glu Thr Ala Gly Lys Val Ala Gln Lys Val Gly Val Val
                35                  40                  45

Leu Gly Phe Glu Ala Glu Leu Val Arg Lys Ala Leu Pro Glu Trp Val
            50                  55                  60

Asp Val Phe Val Gln Gly Glu Gln Leu Gly Thr Ala His Ala Val Met
65                  70                  75                  80

Cys Ala Lys Asp Phe Ile Glu Pro Gly Asp Asp Val Leu Ile Leu Tyr
```

```
                85                  90                  95
Gly Asp Val Pro Leu Ile Ser Glu Asn Thr Leu Lys Arg Met Ile Glu
            100                 105                 110
Glu His Arg Lys Gly Ala Asp Val Thr Ile Leu Val Ala Asp Leu Glu
        115                 120                 125
Asp Pro Ser Gly Tyr Gly Arg Val Ile Gln Asp Gly Asp Lys Tyr Arg
    130                 135                 140
Ile Ile Glu Asp Thr Asp Leu Pro Glu Glu Leu Lys Ser Val Thr Thr
145                 150                 155                 160
Ile Asn Thr Gly Phe Tyr Val Phe Ser Gly Asp Phe Leu Leu Arg Ala
                165                 170                 175
Leu Pro Glu Ile Lys Asn Glu Asn Ala Lys Gly Glu Tyr Tyr Leu Thr
            180                 185                 190
Asp Ala Val Asn Phe Ala Glu Lys Val Arg Val Arg Thr Asp Asp
        195                 200                 205
Leu Leu Glu Ile Thr Gly Val Asn Thr Arg Lys Thr Leu Val Trp Leu
    210                 215                 220
Glu Glu Gln Leu Arg Met Arg Lys Ile Glu Glu Leu Leu Glu Asn Gly
225                 230                 235                 240
Val Thr Ile Leu Asp Pro Ala Thr Thr Tyr Ile His Tyr Ser Val Glu
                245                 250                 255
Ile Gly Met Asp Thr Val Ile Tyr Pro Met Thr Phe Ile Glu Gly Lys
            260                 265                 270
Ser Arg Val Gly Glu Asn Cys Glu Ile Gly Pro Met Thr Arg Ile Val
        275                 280                 285
Asp Cys Glu Ile Gly Asn Asn Val Lys Ile Thr Arg Ser Glu Cys Phe
    290                 295                 300
Lys Ser Val Ile Glu Asp Asp Val Ser Val Gly Pro Phe Ala Arg Leu
305                 310                 315                 320
Arg Glu Gly Thr Ile Leu Lys Lys Ser Lys Ile Gly Asn Phe Val
                325                 330                 335
Glu Ile Lys Lys Ser Thr Ile Gly Glu Gly Thr Lys Ala Gln His Leu
            340                 345                 350
Ser Tyr Ile Gly Asp Ala Phe Val Gly Lys Asn Val Asn Val Gly Ala
        355                 360                 365
Gly Thr Ile Thr Cys Asn Tyr Asp Gly Lys Lys Lys Asn Pro Thr Phe
    370                 375                 380
Ile Glu Asp Gly Ala Phe Ile Gly Ser Asn Ser Ser Leu Val Ala Pro
385                 390                 395                 400
Val Arg Ile Gly Lys Gly Ala Leu Ile Gly Ala Gly Ser Val Ile Thr
                405                 410                 415
Glu Asp Val Pro Pro Tyr Ser Leu Gly Leu Gly Arg Ala Arg Gln Val
            420                 425                 430
Val Lys Glu Gly Trp Val Leu Lys Lys Arg Lys Glu Glu
        435                 440                 445

<210> SEQ ID NO 10
<211> LENGTH: 456
<212> TYPE: PRT
<213> ORGANISM: Bacillus subtilis

<400> SEQUENCE: 10

Met Asp Lys Arg Phe Ala Val Val Leu Ala Ala Gly Gln Gly Thr Arg
1               5                   10                  15

Met Lys Ser Lys Leu Tyr Lys Val Leu His Pro Val Cys Gly Lys Pro
```

```
                     20                  25                  30
Met Val Glu His Val Val Asp Glu Ala Leu Lys Leu Ser Leu Ser Lys
                 35                  40                  45

Leu Val Thr Ile Val Gly His Gly Ala Glu Glu Val Lys Lys Gln Leu
             50                  55                  60

Gly Asp Lys Ser Glu Tyr Arg Val Gln Ala Lys Gln Leu Gly Thr Ala
65                  70                  75                  80

His Ala Val Lys Gln Ala Gln Pro Phe Leu Ala Asp Glu Lys Gly Val
                 85                  90                  95

Thr Ile Val Ile Cys Gly Asp Thr Pro Leu Leu Thr Ala Glu Thr Met
            100                 105                 110

Glu Gln Met Leu Lys Glu His Thr Gln Arg Glu Ala Lys Arg Thr Ile
        115                 120                 125

Leu Thr Ala Val Ala Glu Asp Pro Thr Gly Tyr Gly Arg Ile Ile Arg
    130                 135                 140

Ser Glu Asn Gly Ala Val Gln Lys Ile Val Glu His Lys Asp Ala Ser
145                 150                 155                 160

Glu Glu Glu Arg Leu Val Thr Glu Ile Asn Thr Gly Thr Tyr Cys Phe
                165                 170                 175

Asp Asn Glu Ala Leu Phe Arg Ala Ile Asp Gln Val Ser Asn Asp Asn
            180                 185                 190

Ala Gln Gly Glu Tyr Tyr Leu Pro Asp Val Ile Glu Ile Leu Lys Asn
        195                 200                 205

Glu Gly Glu Thr Val Ala Ala Tyr Gln Thr Gly Asn Phe Gln Glu Thr
    210                 215                 220

Leu Gly Val Asn Asp Arg Val Ala Leu Ser Gln Ala Glu Gln Phe Met
225                 230                 235                 240

Lys Glu Arg Ile Asn Lys Arg His Met Gln Asn Gly Val Thr Leu Ile
                245                 250                 255

Asp Pro Met Asn Thr Tyr Ile Ser Pro Asp Ala Val Ile Gly Ser Asp
            260                 265                 270

Thr Val Ile Tyr Pro Gly Thr Val Ile Lys Gly Glu Val Gln Ile Gly
        275                 280                 285

Glu Asp Thr Ile Ile Gly Pro His Thr Glu Ile Met Asn Ser Ala Ile
    290                 295                 300

Gly Ser Arg Thr Val Ile Lys Gln Ser Val Val Asn His Ser Lys Val
305                 310                 315                 320

Gly Asn Asp Val Asn Ile Gly Pro Phe Ala His Ile Arg Pro Asp Ser
                325                 330                 335

Val Ile Gly Asn Glu Val Lys Ile Gly Asn Phe Val Glu Ile Lys Lys
            340                 345                 350

Thr Gln Phe Gly Asp Arg Ser Lys Ala Ser His Leu Ser Tyr Val Gly
        355                 360                 365

Asp Ala Glu Val Gly Thr Asp Val Asn Leu Gly Cys Gly Ser Ile Thr
    370                 375                 380

Val Asn Tyr Asp Gly Lys Asn Lys Tyr Leu Thr Lys Ile Glu Asp Gly
385                 390                 395                 400

Ala Phe Ile Gly Cys Asn Ser Asn Leu Val Ala Pro Val Thr Val Gly
                405                 410                 415

Glu Gly Ala Tyr Val Ala Ala Gly Ser Thr Val Thr Glu Asp Val Pro
            420                 425                 430

Gly Lys Ala Leu Ala Ile Ala Arg Ala Arg Gln Val Asn Lys Asp Asp
        435                 440                 445
```

Tyr Val Lys Asn Ile His Lys Lys
        450                 455

<210> SEQ ID NO 11
<211> LENGTH: 257
<212> TYPE: PRT
<213> ORGANISM: Yersinia pseudotuberculosis

<400> SEQUENCE: 11

Val Lys Ala Val Ile Leu Ala Gly Gly Leu Gly Thr Arg Leu Ser Glu
1               5                   10                  15

Glu Thr Val Val Lys Pro Lys Pro Met Val Glu Ile Gly Gly Lys Pro
            20                  25                  30

Ile Leu Trp His Ile Met Lys Leu Tyr Ser Ser Tyr Gly Ile Asn Asp
        35                  40                  45

Phe Val Ile Cys Cys Gly Tyr Lys Gly Tyr Val Ile Lys Glu Tyr Phe
    50                  55                  60

Ala Asn Tyr Phe Met His Met Ser Asp Ile Thr Phe Cys Met Arg Asp
65                  70                  75                  80

Asn Glu Met Val Val His Gln Lys Arg Val Glu Pro Trp Asn Val Thr
                85                  90                  95

Leu Val Asp Thr Gly Glu Asp Ser Met Thr Gly Gly Arg Leu Arg Arg
            100                 105                 110

Val Lys Asp Tyr Val Lys Asp Asp Glu Ala Phe Cys Phe Thr Tyr Gly
        115                 120                 125

Asp Gly Val Ser Asp Val Asn Ile Ala Glu Leu Ile Ala Phe His Lys
    130                 135                 140

Ser His Gly Lys Gln Ala Thr Leu Thr Ala Thr Tyr Pro Pro Gly Arg
145                 150                 155                 160

Phe Gly Ala Leu Asp Ile Lys Asp Lys Gln Val Arg Ser Phe Lys Glu
                165                 170                 175

Lys Phe Lys Gly Asp Gly Ala Leu Ile Asn Gly Gly Tyr Phe Val Leu
            180                 185                 190

Ser Pro Lys Val Ile Asp Leu Ile Asp Gly Asp Lys Ser Thr Trp Glu
        195                 200                 205

Gln Glu Pro Leu Met Thr Leu Ala Ala Gln Gly Glu Leu Met Ala Phe
    210                 215                 220

Glu His Ala Gly Phe Trp Gln Pro Met Asp Thr Leu Arg Asp Lys Ile
225                 230                 235                 240

Tyr Leu His Glu Leu Trp Glu Glu Gly Arg Ala Pro Trp Lys Val Trp
                245                 250                 255

Glu

<210> SEQ ID NO 12
<211> LENGTH: 257
<212> TYPE: PRT
<213> ORGANISM: Salmonella typhimurium

<400> SEQUENCE: 12

Met Lys Ala Val Ile Leu Ala Gly Gly Leu Gly Thr Arg Leu Ser Glu
1               5                   10                  15

Glu Thr Ile Val Lys Pro Lys Pro Met Val Glu Ile Gly Gly Lys Pro
            20                  25                  30

Ile Leu Trp His Ile Met Lys Met Tyr Ser Val His Gly Ile Lys Asp
        35                  40                  45

Phe Ile Ile Cys Cys Gly Tyr Lys Gly Tyr Val Ile Lys Glu Tyr Phe
    50                  55                  60

```
Ala Asn Tyr Phe Leu His Met Ser Asp Val Thr Phe His Met Ala Glu
65                  70                  75                  80

Asn Arg Met Glu Val His His Lys Arg Val Glu Pro Trp Asn Val Thr
                85                  90                  95

Leu Val Asp Thr Gly Asp Ser Ser Met Thr Gly Gly Arg Leu Lys Arg
            100                 105                 110

Val Ala Glu Tyr Val Lys Asp Asp Glu Ala Phe Leu Phe Thr Tyr Gly
        115                 120                 125

Asp Asp Val Ala Asp Leu Asp Ile Lys Ala Thr Ile Asp Phe His Lys
    130                 135                 140

Ala His Gly Lys Lys Ala Thr Leu Thr Ala Thr Phe Pro Pro Gly Arg
145                 150                 155                 160

Phe Gly Ala Leu Asp Ile Arg Ala Gly Gln Val Arg Ser Phe Gln Glu
            165                 170                 175

Lys Pro Lys Gly Asp Gly Ala Met Ile Asn Gly Gly Phe Phe Val Leu
            180                 185                 190

Asn Pro Ser Val Ile Asp Leu Ile Asp Asn Asp Ala Thr Thr Trp Glu
            195                 200                 205

Gln Glu Pro Leu Met Thr Leu Ala Gln Gln Gly Glu Leu Met Ala Phe
    210                 215                 220

Glu His Pro Gly Phe Trp Gln Pro Met Asp Thr Leu Arg Asp Lys Val
225                 230                 235                 240

Tyr Leu Glu Gly Leu Trp Glu Lys Gly Lys Ala Pro Trp Lys Thr Trp
            245                 250                 255

Glu
```

US 7,906,460 B2

ACTIVE-SITE ENGINEERING OF NUCLEOTIDYLYLTRANSFERASES AND GENERAL ENZYMATIC METHODS FOR THE SYNTHESIS OF NATURAL AND "UNNATURAL" UDP- AND TDP-NUCLEOTIDE SUGARS

This application is a divisional application of U.S. patent application Ser. No. 10/013,542, filed Dec. 13, 2001, now U.S. Pat. No. 7,122,359, which claims the benefit of U.S. Application Ser. No. 60/254,927, filed Dec. 13, 2000 each of which are incorporated herein in there entirety.

FIELD OF THE INVENTION

The present invention is directed to nucleotidylyl-transferases and mutant nucleotidylyltransferases having altered substrate specificity and methods for their production.

The present invention is also directed to methods of synthesizing desired nucleotide sugars using natural and/or mutant $E_p$ or other nucleotidyltransferases, preferably $E_p$ or other nucleotidylyltransferases modified by the present methods. Additionally, the present invention is directed to nucleotide sugars synthesized by the present methods.

The present invention is further directed to new glycosyl phosphates, and methods for making them.

BACKGROUND OF THE INVENTION

Many bioactive metabolites possess unusual carbohydrates required for molecular recognition. (See for example, Liu, H.-w.; Thorson, J. S. Ann. Rev. Microbiol., 1994, 48, 223-256; Weymouth-Wilson, A. C. Nat. Prod. Rep. 1997, 14, 99-110; In Macrolide Antibiotics, Chemistry, Biology and Practice; Omura, S. Ed., Academic Press: New York; 1984; Johnson, D. A.; Liu, H.-w. Curr. Opin. Chem. Biol. 1998, 2, 642-649; and Trefzer, A.; Salas, J. A.; Bechthold, A. Nat. Prod. Rep. 1999, 16, 283-299.) In fact, roughly 70% of current lead compounds in modern drug discovery derive directly from natural products, many of which are glycosylated metabolites. (See Thorson, J. S. et al. Nature's Carbohydrate Chemists: The Enzymatic Glycosylation of Bioactive Bacterial Metabolites. Curr. Org. Chem. manuscript in press, (2000); and references therein and Weymouth-Wilson, A. C. The Role of Carbohydrates in Biologically Active Natural Products. Nat. Prod. Rep. 14, 99-110 (1997)). Examples of pharmaceutically important glycosylated metabolites include, for example, amphotericin, megalomicin/erythromycin, mithramycin, doxorubicin, vancomycin and calicheamicin, as shown in FIG. 5. While it is known that the sugar moieties of these pharmaceutically important metabolites often define their corresponding biological activity, (see Weymouth-Wilson, A. C., The Role of Carbohydrates in Biologically Active Natural Products, Nat. Prod. Rep. 14, 99-110 (1997)), efficient methods to systematically alter these essential carbohydrate ligands are still lacking.

In metabolite biosynthesis, glycosylation begins with the nucleotidylyltransferase-catalyzed activation of a sugar phosphate as a nucleotide diphosphosugar (NDP-sugar) donor. After activation, a number of enzymatic processing reactions often occur (e.g., deoxygenation, transamination, oxidation/reduction, epimerization, alkylation, and decarboxylation) prior to the culminating glycosyltransferase-catalyzed attachment to the aglycon. (Liu, H.-w. & Thorson, J. S. Pathways and Mechanisms in the Biogenesis of Novel Deoxysugars by Bacteria. Ann. Rev. Microbiol. 48, 223-256 (1994); Kirschning, A., Bechtold, A. F-W. & Rohr, J. Chemical and Biochemical Aspects of Deoxysugars and Deoxysugar Oligosaccharides. Top. Curr. Chem. 188, 1-84 (1997); Johnson, D. A. & Liu, H.-w. Mechanisms and Pathways from Recent Deoxysugar Biosynthesis Research. Curr. Opin. Chem. Biol. 2, 642-649 (1998); Hallis, T. M. & Liu, H.-w. Learning Nature's Strategies for Making Deoxy Sugars: Pathways, Mechanisms, and Combinatorial Applications. Acc. Chem. Res. 32, 579-588 (1999); Johnson, D. A. & Liu, H.-w. In Comprehensive Chemistry of Natural Product Chemistry (Barton, D.; Nakanishi; K.; Meth-Cohn, O. eds), Elsevier Science, Oxford, 311, (1999); Trefzer, A., Salas, J. & Bechthold, A. Genes and Enzymes Involved in Deoxysugar Biosynthesis in Bacteria. Nat. Prod. Rep. 16, 283-299 (1999); and Bechthold, A. & Rohr, J. In New Aspects of Bioorganic Chemistry (Diederichsen, U.; Lindhorst, T. K.; Wessjohann, L.; Westerman, B., eds.) Wiley-VCH, Weinheim, 313, (1999)).

The glycosyltransferases that incorporate these essential ligands are thought to rely almost exclusively upon UDP- and TDP-nucleotide sugars; however some have demonstrated promiscuity towards the sugar donor, (e.g., Gal, D-galactose; Glc, D-glucose; Man, D-mannose; NTP, nucleotide triphosphate; pFPTC, pentafluorophenoxythiocarbonyl; TDP, thymidine diphosphate; TMP, thymidine monophosphate; TTP, thymidine triphosphate; UDP, uridine diphosphate.) Genetic experiments suggest that downstream glycosyltransferases in secondary metabolism are promiscuous with respect to their NDP-sugar donor, setting the stage for the expansion of "combinatorial biosynthesis" approaches to change metabolite glycosylation. (See Madduri, K. et al., Production of the antitumor drug epirubicin (4'-epidoxorubicin) and its precursor by a genetically engineered strain of Streptomyces peucetius Nat. Biotech. 16, 69-74 (1998); and Hutchinson, C. R. Combinatorial Biosynthesis for New Drug Discovery. Curr. Opin. Microbiol. 1, 319-329 (1998).) This information has led to the exploitation of the carbohydrate biosynthetic machinery to manipulate metabolite glycosylation, (Madduri, K.; Kennedy, J.; Rivola, G.; Inventi-Solari, A.; Filppini, S.; Sanuso, G.; Colombo, A. L.; Gewain, K. M.; Occi, J. L.; MacNeil, D. J.; Hutchinson, C. R. Nature Biotech. 1998, 16, 69-74; and Zhao, L.; Ahlert, J.; Xue, Y.; Thorson, J. S.; Sherman, D. H.; Liu, H.-w. J. Am. Chem. Soc., 1999, 121, 9881-9882 and references therein), revitalizing interest in methods to expand the repertoire of available UDP- and TDP-sugar nucleotides. (See Zhao, Y.; Thorson, J. S. J. Org. Chem. 1998, 63, 7568-7572; and Elhalabi, J. M.; Rice, K. G. Cur. Med. Chem. 1999, 6, 93-116.)

These in vivo methods are limited by both a particular host's biosynthetic machinery and the specific host's tolerance to each newly constructed metabolite. Further, in vitro progress in this area is limited by the availability of the required NDP-sugar substrates. (Solenberg, P. J. et al., Production of Hybrid Glycopeptide Antibiotics in vitro and in Streptomyces toyocaensis. Chem. & Biol. 4, 195-202 (1997).)

Thus, there is a need for a greater variety of available NDP-sugar substrates.

Salmonella enterica LT2 α-D-glucopyranosyl phosphate thymidylyltransferase ($E_p$) is a member of the prevalent nucleotidylyltransferase family responsible for the reversible conversion of α-D-hexopyranosyl phosphate and NTP to the corresponding NDP-sugar nucleotide and pyrophosphate. Of the many nucleotidylyl-transferases studied, the NDP-sugar nucleotide-forming thymidylyltransferases have received the least attention in prior work. (See Lindquist, L.; Kaiser, R.; Reeves, P. R.; Lindberg, A. A. Eur. J. Biochem. 1993, 211, 763-770, and Gallo, M. A.; Ward J.; Hutchinson, C. R. Microbiol. 1996, 142, 269-275.) Even in $E_p$, substrate specificity studies prior to the work of the present inventors were limited to only a few available hexopyranosyl phosphates. (See Lindquist, L.; Kaiser, R.; Reeves, P. R.; Lindberg, A. A. Eur. J. Biochem. 1993, 211, 763-770.)

SUMMARY OF THE INVENTION

The present invention is directed to methods of engineering or mutating nucleotidylyltransferases, such as $E_p$, to vary their specificity in a directed manner. The invention is also directed to nucleotidylyl-transferases and mutated nucleotidyltransferases, preferably $E_p$ or other nucleotidyltransferases modified by the present methods. The present invention is further directed to mutant $E_p$ and other nucleotidyltransferases with altered substrate specificity, methods for their production, and methods of producing nucleotide sugars, which utilize these nucleotidyl-transferases.

The present invention is also directed to methods of synthesizing desired nucleotide sugars using natural and/or mutated $E_p$ or other nucleotidylyltransferases, preferably $E_p$ or other nucleotidyltransferases mutated by the present methods. Additionally, the present invention is directed to nucleotide sugars synthesized by the present methods.

Examples of nucleotide sugars produced the present methods (that is, via the exploitation of the promiscuity of $E_p$) include, but are not limited to Thymidine 5'-(α-D-glucopyranosyl diphosphate) (58); Uridine 5'-(α-D-glucopyranosyl diphosphate) (59); Thymidine 5'-(2-deoxy-α-D-glucopyranosyl diphosphate) (60); Uridine 5'-(2-deoxy-α-D-glucopyranosyl diphosphate) (61); Thymidine 5'-(3-deoxy-α-D-glucopyranosyl diphosphate) (62); Uridine 5'-(3-deoxy-α-D-glucopyranosyl diphosphate) (63); Thymidine 5'-(4-deoxy-α-D-glucopyranosyl diphosphate) (64); Uridine 5'-(4-deoxy-α-D-glucopyranosyl diphosphate) (65); Thymidine 5'-(6-deoxy-α-D-glucopyranosyl diphosphate) (66); Uridine 5'-(6-deoxy-α-D-glucopyranosyl diphosphate) (67); Thymidine 5'-(α-D-mannopyranosyl diphosphate) (68); Uridine 5'-(α-D-mannopyranosyl diphosphate) (69); Thymidine 5'-(α-D-galactopyranosyl diphosphate) (70); Uridine 5'-(α-D-galactopyranosyl diphosphate) (71); Thymidine 5'-(α-D-allopyranosyl diphosphate) (72); Uridine 5'-(α-D-allopyranosyl diphosphate) (73); Thymidine 5'-(α-D-altropyranosyl diphosphate) (74); Uridine 5'-(α-D-altropyranosyl diphosphate) (75); Thymidine 5'-(α-D-gulopyranosyl diphosphate) (76); Uridine 5'-(α-D-gulopyranosyl diphosphate) (77); Thymidine 5'-(α-D-idopyranosyl diphosphate) (78); Uridine 5'-(α-D-idopyranosyl diphosphate) (79); Thymidine 5'-(α-D-talopyranosyl diphosphate) (80); Uridine 5'-(α-D-talopyranosyl diphosphate) (81); Thymidine 5'-(6-amino-6-deoxy-α-D-glucopyranosyl diphosphate) (109); Uridine 5'-(6-amino-6-deoxy-α-D-glucopyranosyl diphosphate) (110); Thymidine 5'-(4-amino-4-deoxy-α-D-lucopyranosyl diphosphate) (111); Uridine 5'(4-amino-4-deoxy-α-D-glucopyranosyl diphosphate) (112); Thymidine 5'-(3-amino-3-deoxy-α-D-glucopyranosyl diphosphate) (113); Uridine 5'-(3-amino-3-deoxy-α-D-glucopyranosyl diphosphate) (114); Thymidine 5'-(2-amino-2-deoxy-α-D-glucopyranosyl diphosphate) (115); Uridine 5'-(2-amino-2-deoxy-α-D-glucopyranosyl diphosphate) (116); Thymidine 5'-(6-acetamido-6-deoxy-α-D-glucopyranosyl diphosphate) (117); Uridine 5'-(6-acetamido-6-deoxy-α-D-glucopyranosyl diphosphate) (118); Thymidine 5'-(4-acetamido-4-deoxy-α-D-glucopyranosyl diphosphate) (119); Uridine 5'-(4-acetamido-4-deoxy-α-D-glucopyranosyl diphosphate) (120); Thymidine 5'-(3-acetamido-3-deoxy-α-D-glucopyranosyl diphosphate) (121); Uridine 5'-(3-acetamido-3-deoxy-α-D-glucopyranosyl diphosphate) (122); Thymidine 5'-(2-acetamido-2-deoxy-α-D-glucopyranosyl diphosphate) (123); Uridine 5'-(2-acetamido-2-deoxy-α-D-glucopyranosyl diphosphate) (124); Thymidine 5'-(4-amino-4,6-dideoxy-α-D-glucopyranosyl diphosphate) (125); and Uridine 5'-(4-amino-4,6-dideoxy-α-D-glucopyranosyl diphosphate) (126). Nucleotide sugars such as these, and methods for making them, are provided by the present invention.

Examples of nucleotide sugars according to the present invention, which may be produced by designed mutants of $E_p$ include, but are not limited to, Thymidine 5'-(6-acetamido-6-deoxy-α-D-glucopyranosyl diphosphate) (117); Uridine 5'-(6-acetamido-6-deoxy-α-D-glucopyranosyl diphosphate) (118); Thymidine 5'-(α-D-glucopyran-6-uronic acid diphosphate) (130); Uridine 5'-(α-D-glucopyran-6-uronic acid diphosphate) (131); Thymidine 5'-(2-acetamido-2-deoxy-α-D-glucopyranosyl diphosphate) (123); Uridine 5'-(2-acetamido-2-deoxy-α-D-glucopyranosyl diphosphate) (124); Thymidine 5'-(4-amino-4,6-dideoxy-α-D-glucopyranosyl diphosphate) (125); Uridine 5'-(4-amino-4,6-dideoxy-α-D-glucopyranosyl diphosphate) (126); Thymidine 5'-(α-D-arabinopyranosyl diphosphate) (128); and Uridine 5'-(α-D-arabinopyranosyl diphosphate) (129). These nucleotide sugars, and methods for making them, are provided by the present invention.

The present invention is also directed to new glycosyl phosphates, and methods for making them. Examples of these new glycosyl phosphates and methods for synthesizing them are represented for example in FIG. 1(b).

The present inventors have discovered that $E_p$ is pliable in terms of its substrate specificity. The present inventors have also discovered the three dimensional structure of $E_p$ and the molecular details of $E_p$ substrate recognition.

In general, the present invention provides a very rapid method of converting sugar phosphates to nucleotide diphosphosugars.

The present invention will broadly impact efforts to understand and exploit the biosynthesis of glycosylated bioactive natural products, many of which are pharmacologically useful. (See Thorson, J. S.; Shen, B.; Whitwam, R. E.; Liu, W.; Li, Y.; Ahlert, J. Bioorg. Chem., 1999, 27, 172-188; Whitwam, R. E.; Ahlert, J.; Holman, T. R.; Ruppen, M.; Thorson, J. S. J. Am. Chem. Soc., 2000, 122, 1556-1557; Thorson, J. S.; Sievers, E. L.; Ahlert, J.; Shepard, E.; Whitwam, R. E.; Onwueme, K. C.; Ruppen, M. Cur. Pharm. Des., 2000, manuscript in press; and J. S. Thorson, T. J. Hosted Jr., J. Jiang, J. B. Biggins, J. Ahlert, M. Ruppen, Curr. Org. Chem. 2000.)

BRIEF DESCRIPTION OF THE DRAWINGS

FIG. 1(a) depicts a reaction according to the present invention, catalyzed by $E_p$. In this reaction, the enzyme catalyzes the reversible conversion of an α-D-hexopyranosyl phosphate (such as an α-D-glucopyranosyl phosphate)(2) and NTP, such as TTP (1) to the corresponding NDP-sugar nucleotide (for example a TDP-sugar nucleotide, such as TDP-Glc)(3) and pyrophosphate (4). Glc1P (2) depicted in the reaction of FIG. 1(a) is a commercially available α-D-hexopyranosyl phosphate (although other α-D-hexopyranosyl phosphates that may be used in accordance with the present invention may include those synthesized from free sugars.)

FIG. 1(b) depicts the synthesis of α-D-hexopyranosyl phosphates.

FIG. 2. $E_p$-Catalyzed Conversion of Substrates (a) Percent conversion=$[A_P/(A_P+A_T)]\times 100$, where $A_P$ is the NDP-sugar product peak integration and $A_T$ represents the NTP peak integration. HRMS for all observed products reported in the supporting information. (b) Standard retention times: TDP, 4.5 min; TTP, 7.2 min; UDP, 4.0 min; UTP, 6.1 min. (c) Commercially available. (d) Coelutes with commercially available standard. (e) Product hydrolysis observed (43, 7.6% TDP and 10.2% UDP). (f) Adjusted for the 2:1 α/β-28. (g) In contrast to previously published studies (See Lindquist, L; Kaiser, R.; Reeves, P. R.; Lindberg, A. A., Eur J. Biochem, 1993, 211, 763-770). (h) No products observed.

FIG. 3(a) sets forth a reaction according to the present invention, catalyzed by $E_p$. FIG. 3(b) shows an overview of the key steps in the described syntheses of $E_p$ substrates analogs. The box highlights the point from which the aminodeoxy-α-D-glucose phosphate series and N-acetyl-aminodeoxy-α-D-glucose phosphate series diverge. The reaction conditions of the steps are as follows: (a) TMSSEt, $ZnI_2$ (84.2% overall yield); (b) i) MeONa, ii) NaH, BnBr (77.3% average overall yield, two steps) (c) i) $SnCl_2$, PhSH, $Et_3N$, ii) $Ac_2O$, pyr (84.0% average overall yield, two steps); (d) i) $Tf_2O$, pyr, ii) $NaN_3$ (87.7% average overall yield, two steps); (e) i) NaOMe, ii) $CH_3CH(OCH_3)_2CH_3$, TsOH, iii) NaH, BnBr, iv) HCl/MeOH, v) BzCl, DMAP, $Et_3N$ (87.3% average overall yield, five steps); final steps (not shown): i) phosphorylation, ii) reductive deprotection, iii) cation exchange to give the $Na^+$ salt (44.4% average overall yield).

FIG. 7 Quaternary structure of $E_p$ bound to UDP-Glc or dTTP. (a) Two 90 degree views of the $E_p$ tetramer bound to four molecules of UDP-Glc. (b) The $E_p$ tetramer bound to eight molecules of dTTP.

FIG. 11. Percent conversion of sugar phosphates according to the present invention by wild-type and mutant enzymes. The alterations from native substrate (Glc-1-P, 1) are highlighted in red. For the mutant pool, mutants Asp41Asn, Glu62Asp, Thr201A and Trp224His were pooled, concentrated and an aliquote constituting 60 μg of each mutant (corresponding to 3.5 U $E_p$) was utilized for the assay.

Percent conversion was determined as described in Jiang, J., Biggins, J. B. & Thorson, J. S. A General Enzymatic Method for the Synthesis of Natural and "Unnatural" UDP- and TDP-Nucleotide Sugars. J. Am. Chem. Soc. 122, 6803-6804 (2000).

§Represents less than 5% conversion to product.

Figure 12:

FIG. 12. Shows alignment of the Thymidylyltransferase sequence.

Figure 13:
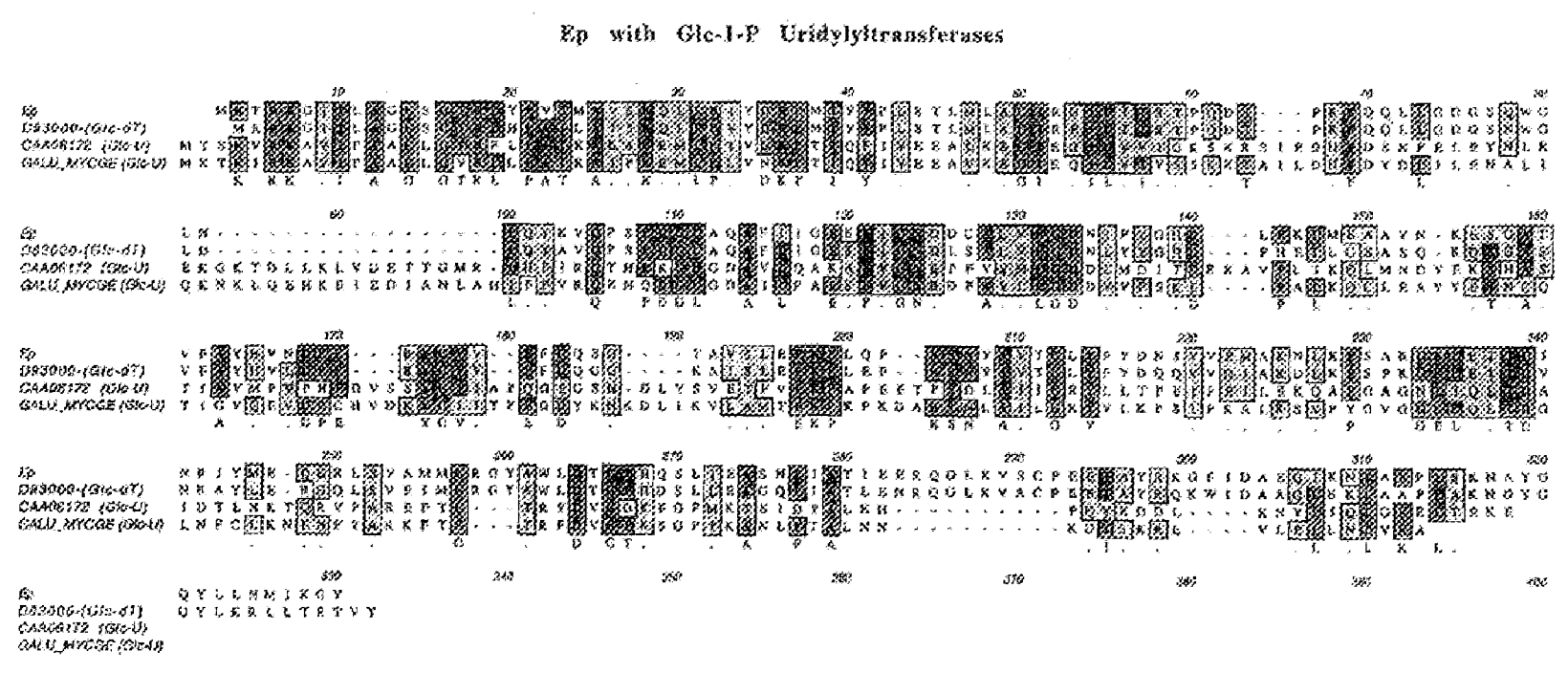

FIG. 13. Shows alignment of the $E_p$ sequence with Glc-1-P Uridylyltransferases.

Figure 14:
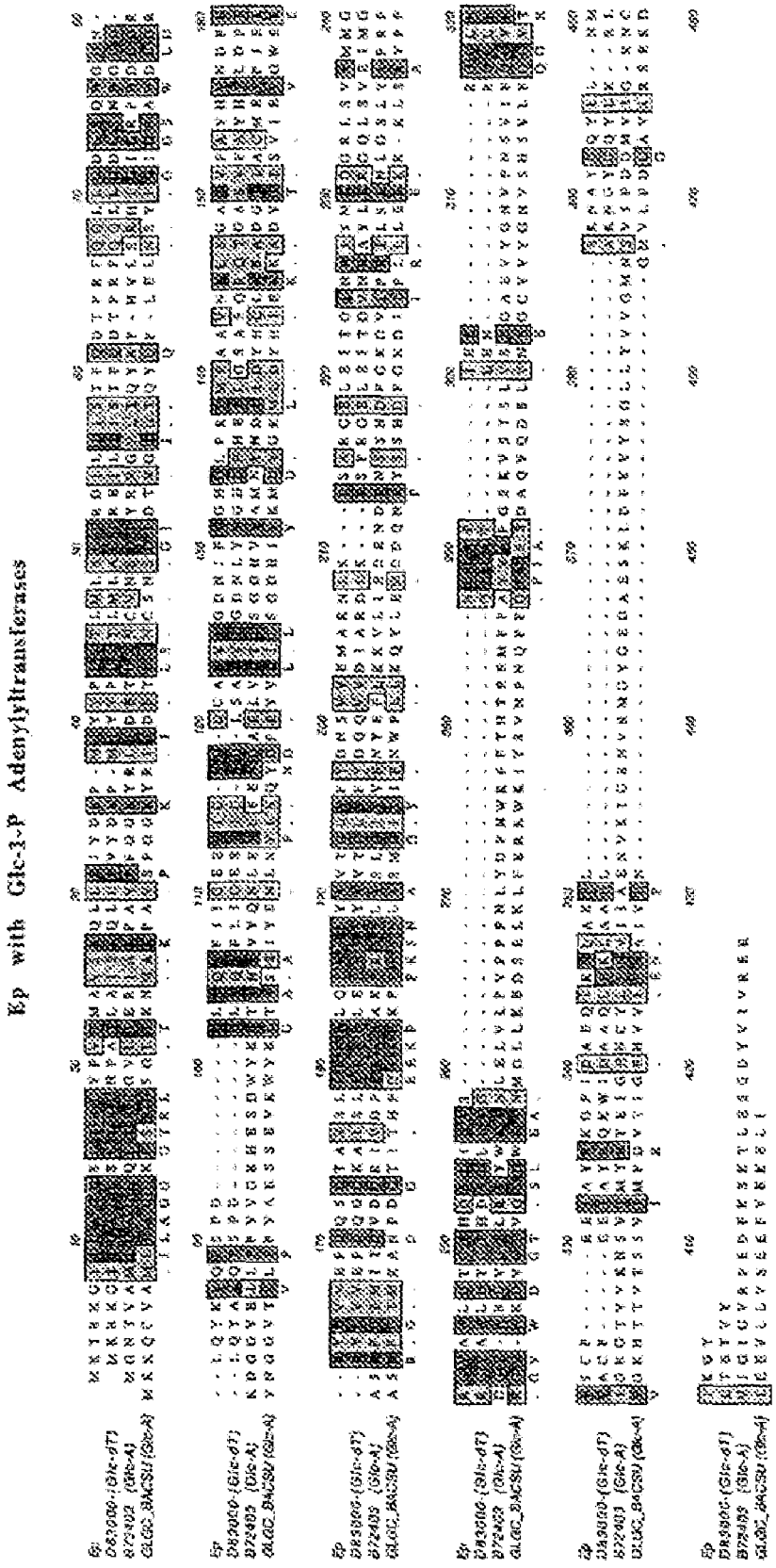

FIG. 14. Shows alignment of the $E_p$ sequence with Glc-1-P Adenylyltransferases.

Figure 15:
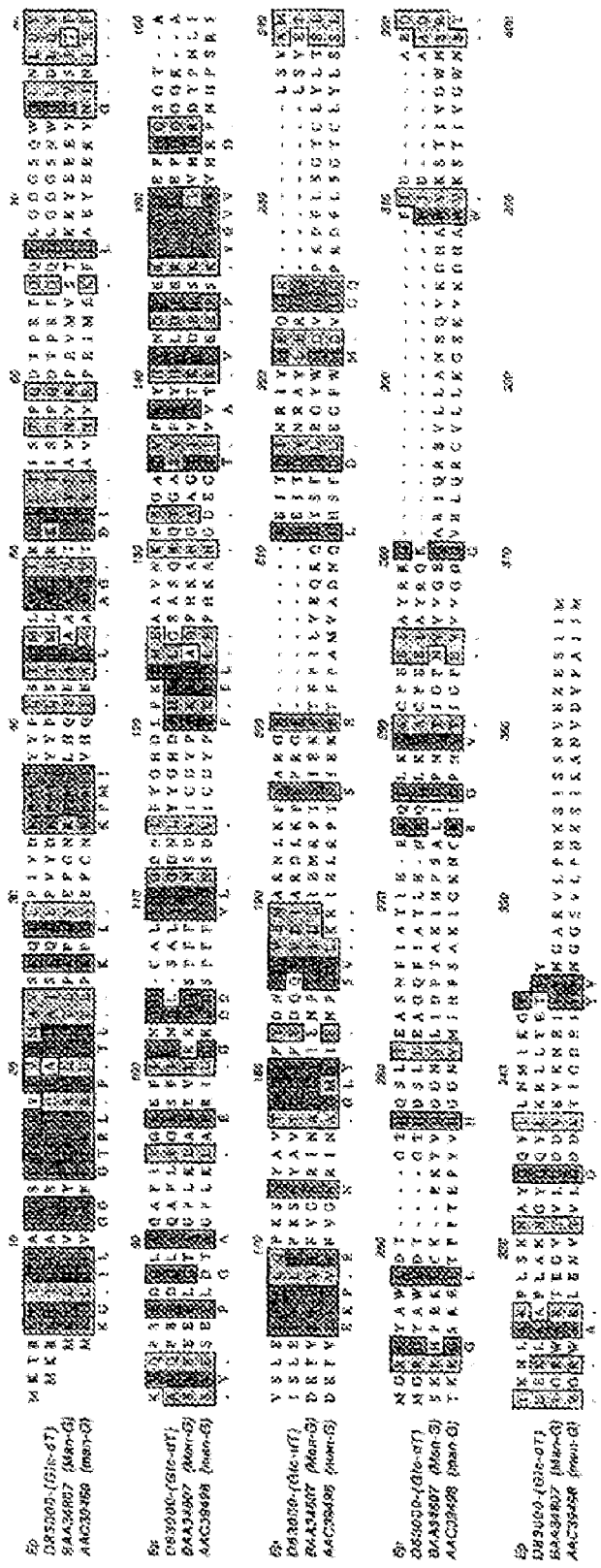

FIG. 15. Shows alignment of the $E_p$ sequence with Man-1-P Guanylyltransferases.

Figure 16:
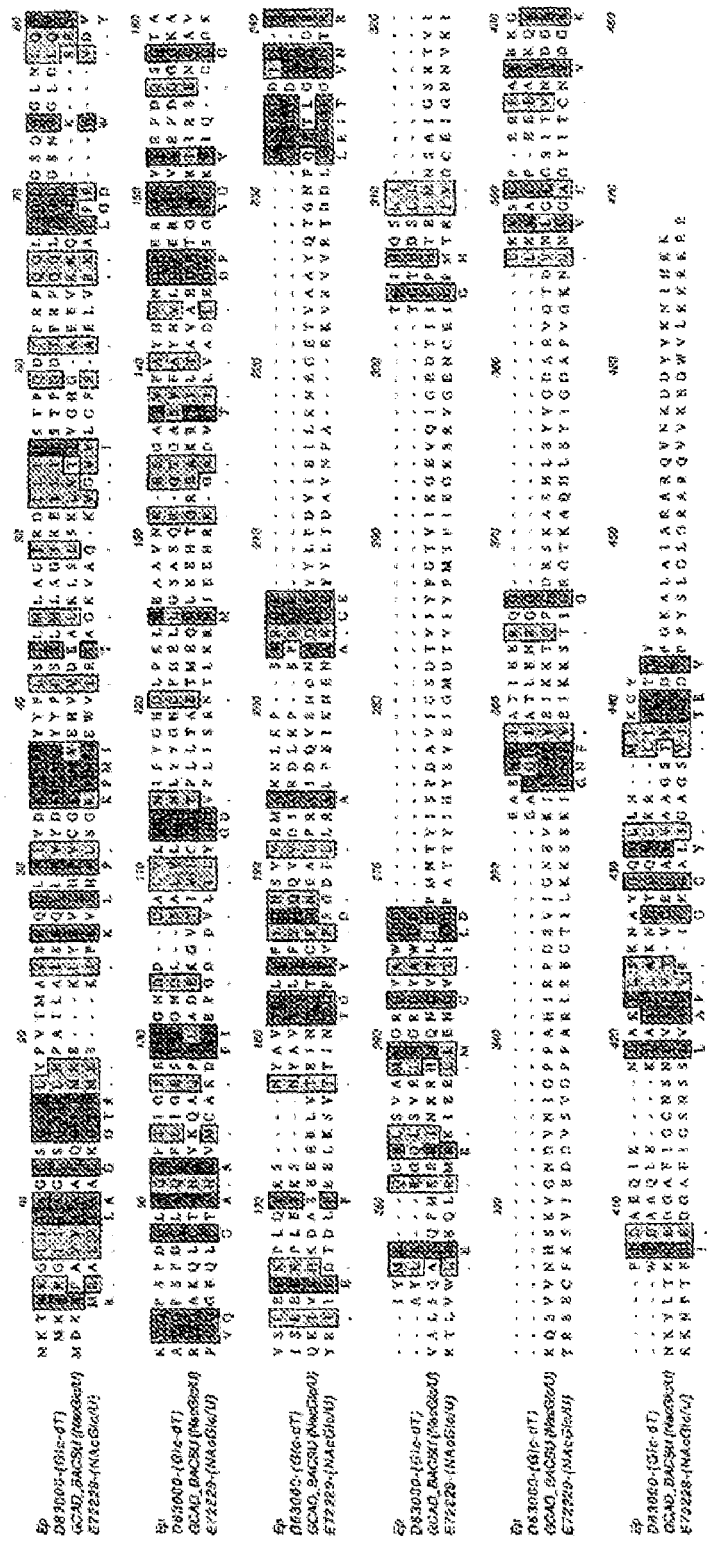

FIG. 16. Shows alignment of the $E_p$ sequence with NAcGlc-1-P Uridylyltransferases.

Figure 17:
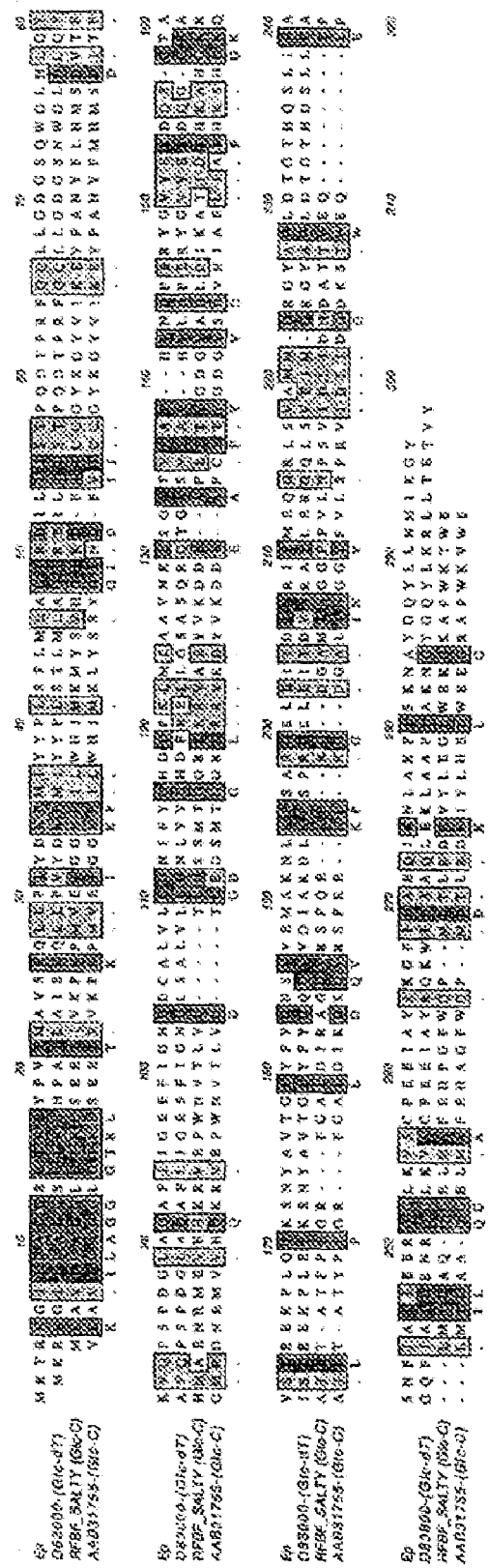

FIG. 17. Shows alignment of the $E_p$ sequence with Glc-1-P Cytidylyltransferases.

Figure 18:
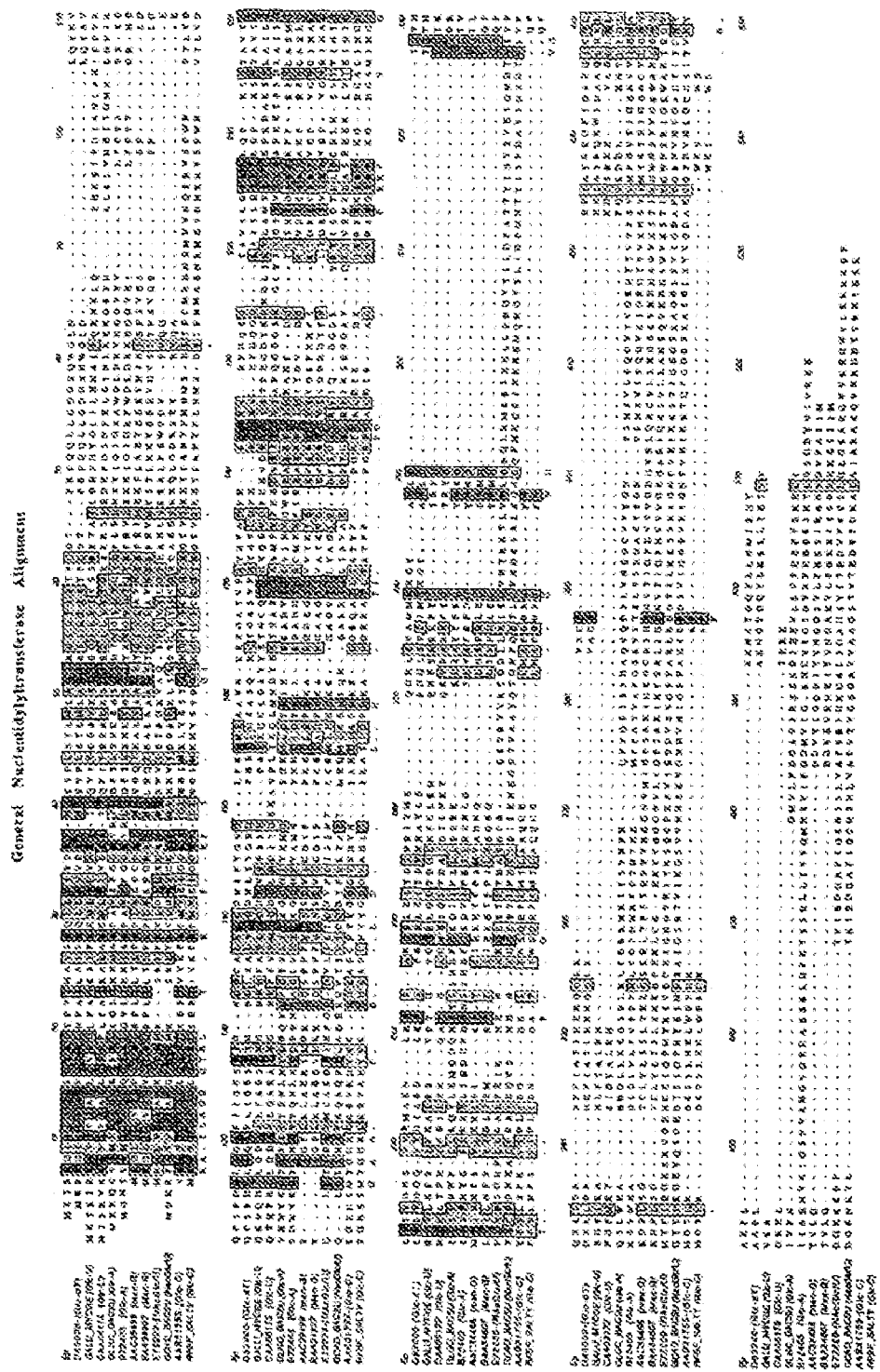

FIG. 18. Shows general Nucleotidylyltransferase Alignment.

FIG. 19. FIG. 19 is a BLASR analysis for $E_p$ sequences, showing sequences producing high-scoring segment pairs.

Figure 20A:
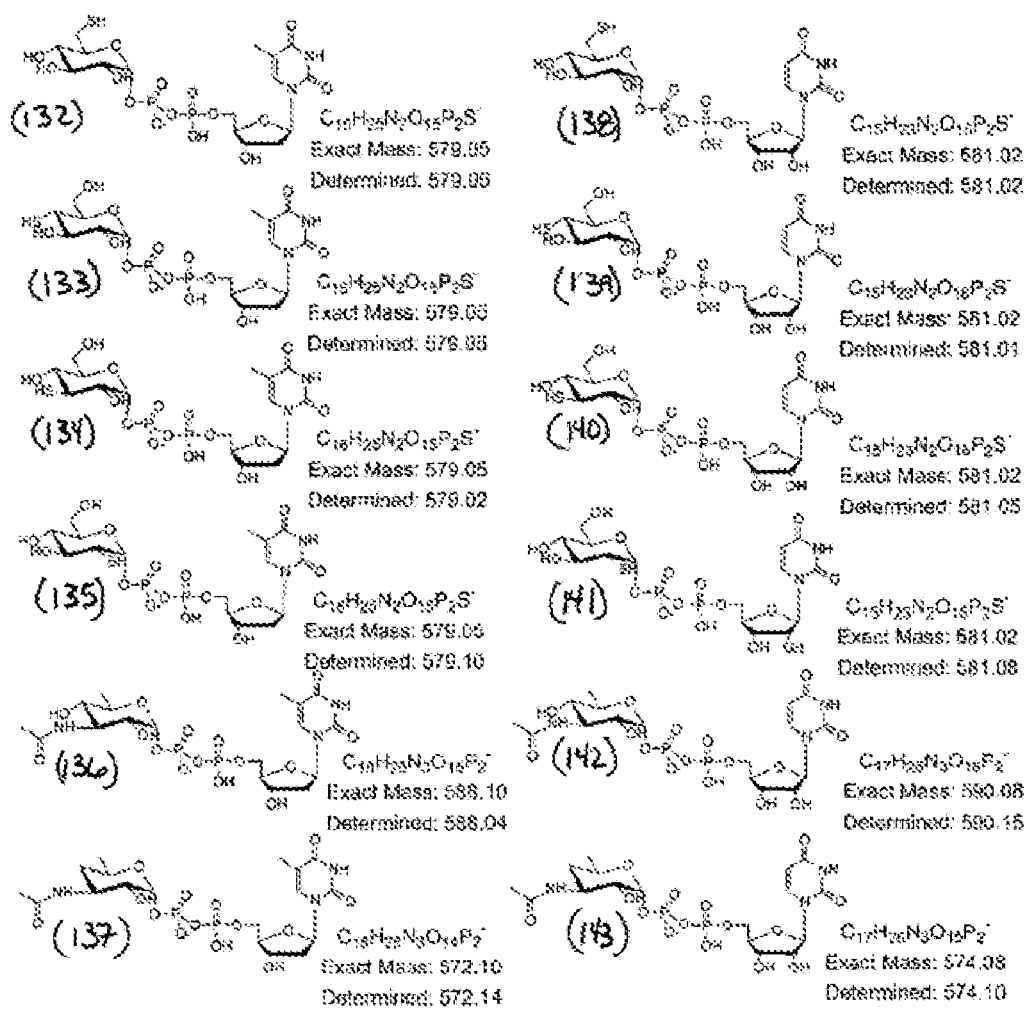
Figure 20B:
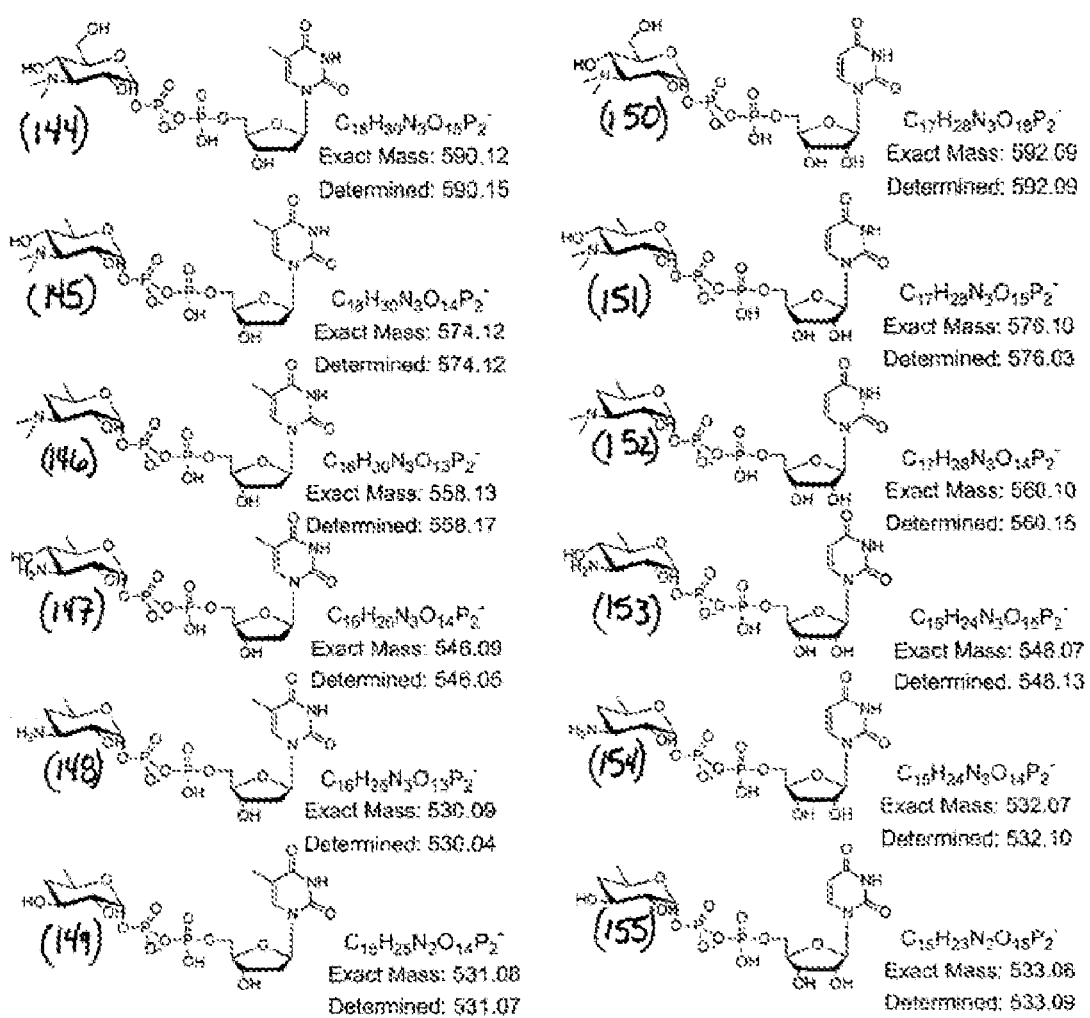

FIG. 20. FIGS. 20(a) and 20(b) depict NDP-sugar nucleotides that may be prepared using nucleotydylyl-transferases as enzymes in accordance with the present invention.

Figure 21:
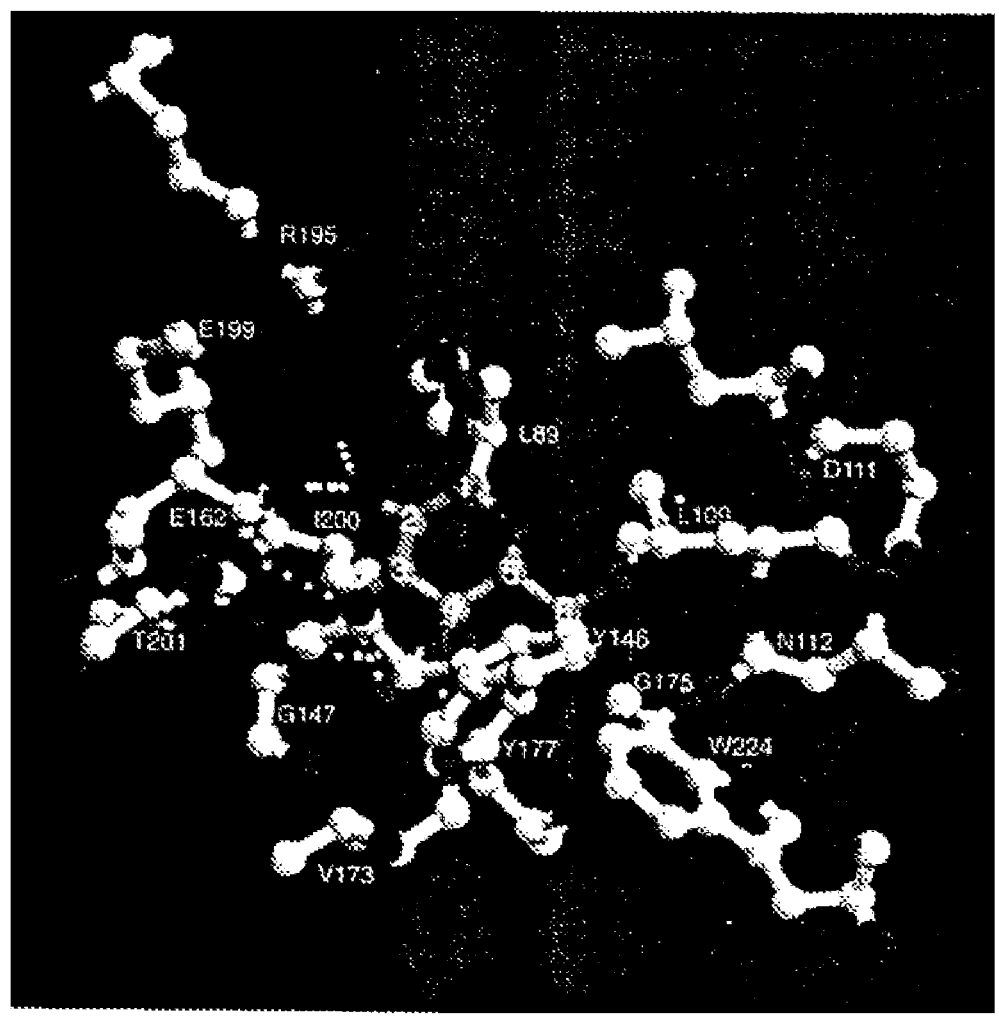

FIG. 21. Interaction between $E_p$ and the glucose moiety in the sugar binding pocket.

Figure 22:
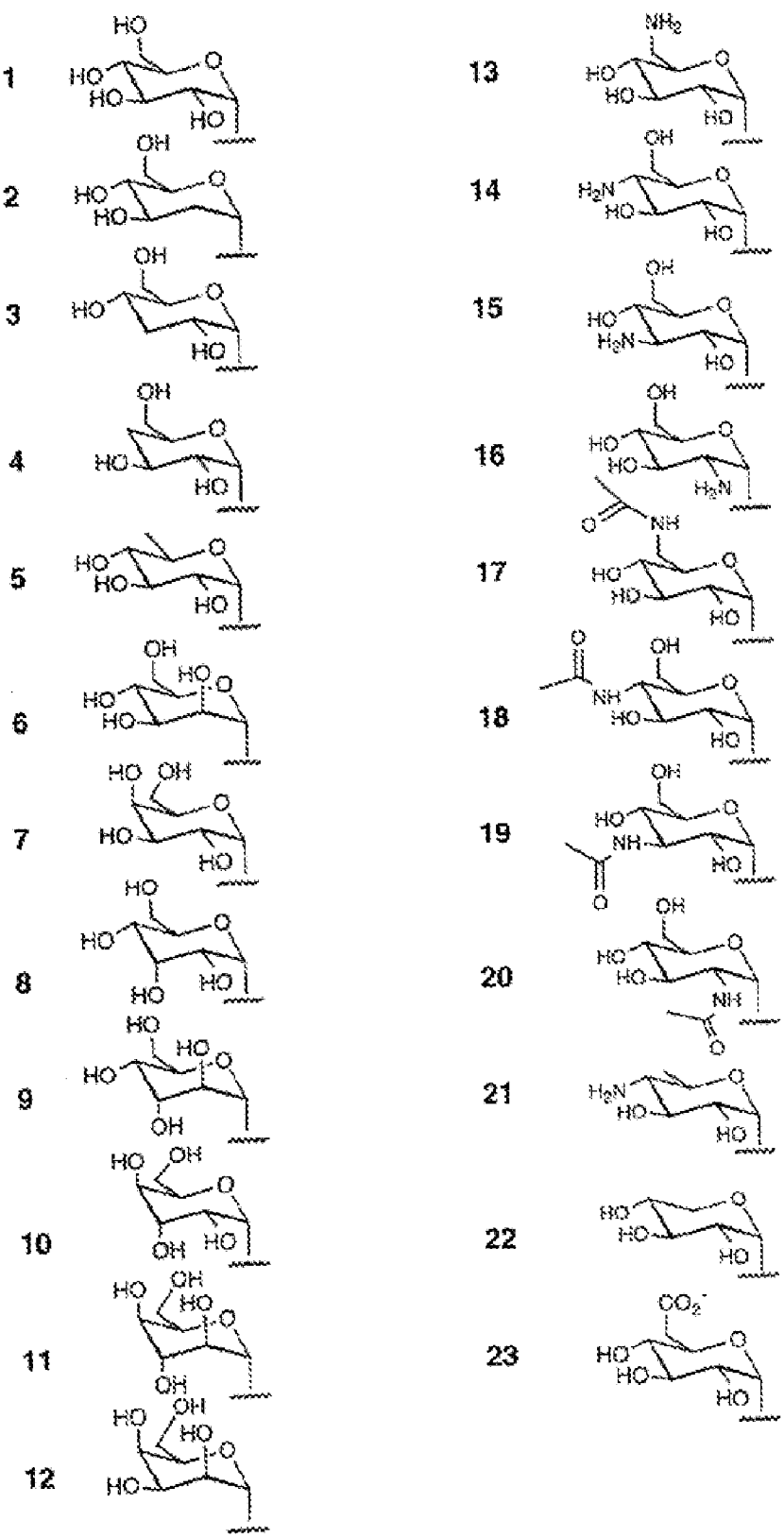

FIG. 22. Summary of sugar phosphate accepted by $E_p$ and mutants

Figure 23:
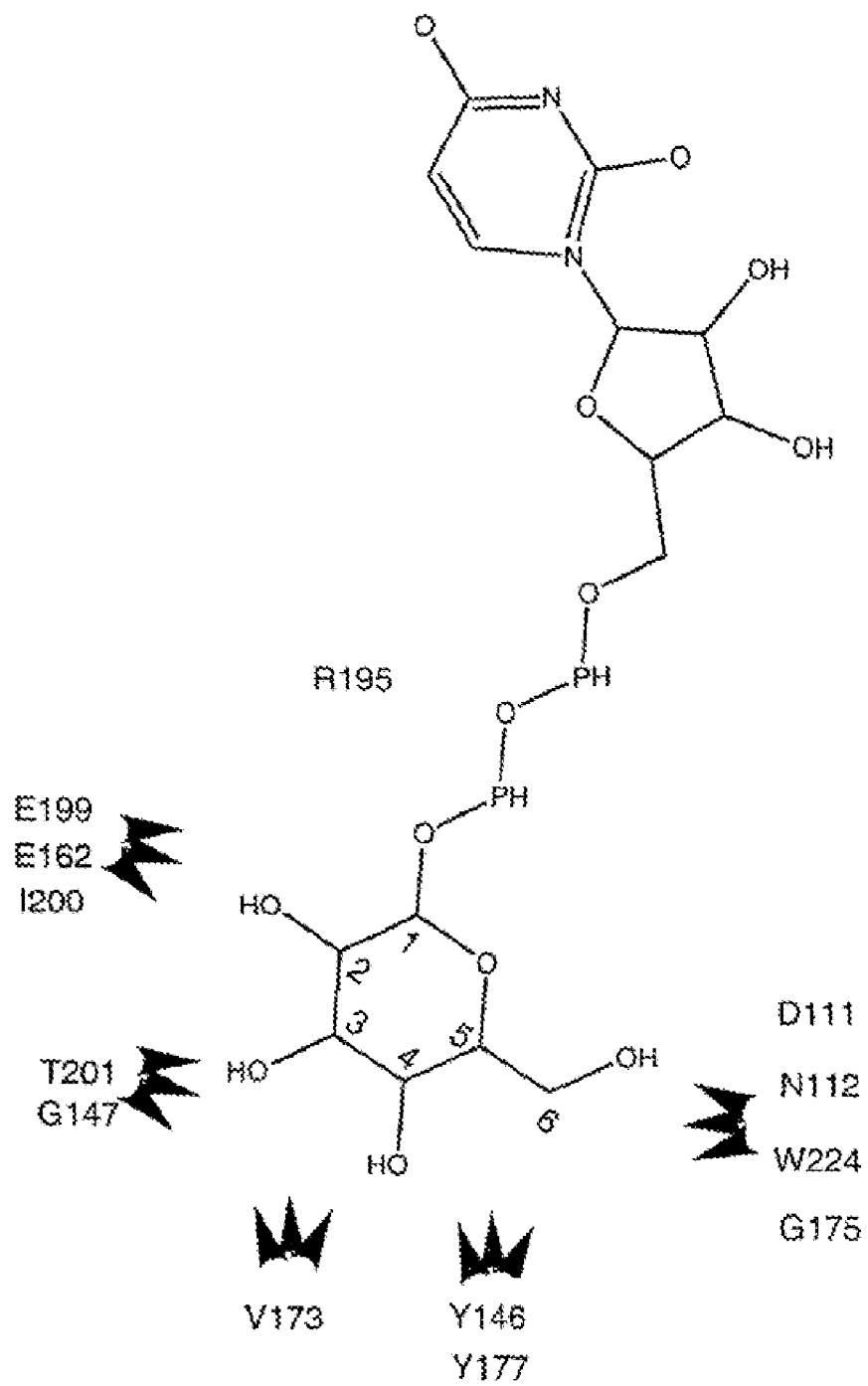

FIG. 23. One dimensional representation of FIG. 21 illustrating some of the important contacts and potential sites for engineering promiscuity of nucleotidyly-transferases.

DETAILED DESCRIPTION OF THE EXEMPLARY EMBODIMENTS

The present inventors discovered that the *Salmonella enterica* LT2 rmlA-encoded α-D-glucopyranosyl phosphate thymidylyltransferase ($E_p$), (also referred to as dTDP-glucose synthase, dTDP-glucose pyrophosphorylase, thymidine diphosphoglucose pyrophosphorylase and thymidine diphosphate glucose pyrophosphorylase), which catalyzes the conversion of α-D-glucopyranosyl phosphate (Glc-1-P) and dTTP to dTDP-α-D-glucose (TDP-Glc) and pyrophosphate ($PP_i$), displays unexpected promiscuity toward both its nucleotide triphosphate (NTP) and its sugar phosphate substrates.

Through a substrate specificity reevaluation of *Salmonella enterica* LT2 α-D-glucopyranosyl phosphate thymidylyl-transferase ($E_p$), the present inventors made the surprising discovery that this enzyme can convert a wide variety of phosphates, including for example, α-D-hexopyranosyl phosphates, including, but not limited to, deoxy-α-D-glucopyranosyl, aminodeoxy-α-D-hexopyranosyl and acetamidodeoxy-α-D-hexopyranosyl phosphates to their corresponding dTDP- and UDP-nucleotide sugars.

This discovery led to the invention by the present inventors of general chemo-enzymatic methods of rapidly generating nucleotide diphosphosugar reagents. These methods allow for the provision of a substrate set for developing in vitro glycosylation systems, which are useful for, inter alia, in vitro production of known bioactive metabolites and of new bioactive metabolites.

α-D-Hexopyranosyl Phosphates and Methods of Making the Same

An embodiment of the invention includes α-D-hexopyranosyl phosphates, methods including combining these phosphates with NTP in the presence of nucleotidylyl-transferase, which may be wild type or mutated, and nucleotide sugars produced by converting such hexopyranosyl phosphates using nucleotidylyl-transferases, such as $E_p$.

$E_p$ is encoded by rmlA, which was previously known as rfbA (Reeves et al. Trends Microbiol. 1996, 4, 495-502). The rmlA-encoded $E_p$ was overexpressed in *E. coli* to provide the desired $E_p$ as >5% of the total soluble protein. The corresponding $E_p$ was purified to near homogeniety with a specific activity of 110 U mg$^{-1}$, a 2-fold improvement over the previously reported values. (See Lindquist, L.; Kaiser, R.; Reeves, P. R.; Lindberg, A. A. Eur. J. Biochem., 1993, 211, 763-770.) An $(NH_4)_2SO_4$ precipitate of *E. coli*-prfbA-C crude extracts was dialyzed against buffer B (20 mM Tris.HCl, 1 mM EDTA, pH 7.5) The dialysate was resolved by anion exchange (DE52, 3×15 cm, 50 mL buffer B wash followed by a linear gradient of 0-500 mM NaCl, 1.0 mL min$^{-1}$) and the $E_p$ fractions combined, concentrated and further resolved by FPLC gel filtration (S-200, 2×70 cm, 50 mM Tris.HCl, 200 mM NaCl, pH 7.5). The purified $E_p$ was stored in aliquots (−80° C.) until used.

Although α-D-glucopyranosyl phosphate (2) (FIG. 2), α-D-mannopyranosyl phosphate (compound 56) (FIG. 2) and α-D-galactopyranosyl phosphate (57) (FIG. 2) were commercially available for examination as potential substrates for $E_p$, most of the α-D-hexopyranosyl phosphates examined were synthesized from free sugars.

For synthetically derived α-D-hexopyranosyl phosphates, particularly glycosyl phosphates, a general phosphorylation strategy from the appropriately protected precursor relied upon i) anomeric activation via the ethy 1-thio-β-D-pyranoside [to form e.g., Ethyl 2,3,4-tri-O-benzoyl-6-deoxy-1-thio-β-D-glucopyranoside (9), Ethyl 2,3,6-tri-O-benzoyl-4-deoxy-1-thio-β-D-glucopyranoside (17), Ethyl 2,4,6-tri-O-benzoyl-3-deoxy-1-thio-β-D-glucopyranoside (25), Ethyl 2,3,4,6-tetra-O-benzoyl-1-thio-β-D-gulopyranoside (30), Ethyl 2,3,4,6-tetra-O-benzoyl-1-thio-β-D-allopyranoside (35) and Ethyl 3,4,6-tri-O-benzoyl-2-deoxy-1-thio-β-D-glucopyranoside (40) (The α/β-40 mixture (1:1.5) was chromatographically resolved.) (FIG. 1(*b*))], ii) deprotection/reprotection [to form e.g., thyl 2,3,4-tri-O-benzyl-6-deoxy-1-thio-β-D-glucopyranoside (10), Ethyl 2,3, 6-tri-O-benzyl-4-deoxy-1-thio-β-D-glucopyranoside (18), Ethyl 2,4,6-tri-O-benzyl-3-deoxy-1-thio-β-D-glucopyranoside (26), Ethyl 2,3,4,6-tetra-O-benzyl-1-thio-β-D-gulopyranoside (31), and Ethyl 2,3,4,6-tetra-O-benzyl-1-thio-β-D-allopyranoside (36) (FIG. 1(*b*))], iii) phosphorylation [to form e.g., Dibenzyl-(2,3,4-tri-O-benzyl-6-deoxy-α-D-glucopyranosyl) phosphate (11), Dibenzyl-(2,3,6-tri-O-benzyl-4-deoxy-α-D-glucopyranosyl) phosphate (19), Dibenzyl-(2,4,6-tri-O-benzyl-3-deoxy-α-D-glucopyranosyl) phosphate (27), Dibenzyl-(2,3,4,6-tetra-O-benzyl-α-D-gulopyranosyl) phosphate (32), Dibenzyl-(2,3,4,6-tetra-O-benzyl-α-D-allopyranosyl) phosphate (37), and Dibenzyl-(3,4,6-tri-O-benzoyl-2-deoxy-α-D-glucopyranosyl) phosphate (41) (FIG. 1(*b*)), and iv) complete deprotection [to form e.g., Disodium 6-deoxy-α-D-glucopyranosyl phosphate (12), Disodium 4-deoxy-α-D-glucopyranosyl phosphate (20), Disodium 3-deoxy-α-D-glucopyranosyl phosphate (28), Disodium α-D-gulopyranosyl phosphate (33), Disodium α-D-allopyranosyl phosphate (38) and Disodium 2-deoxy-α-D-glucopyranosyl phosphate (43) (FIG. 1(*b*))].

Figure 1:
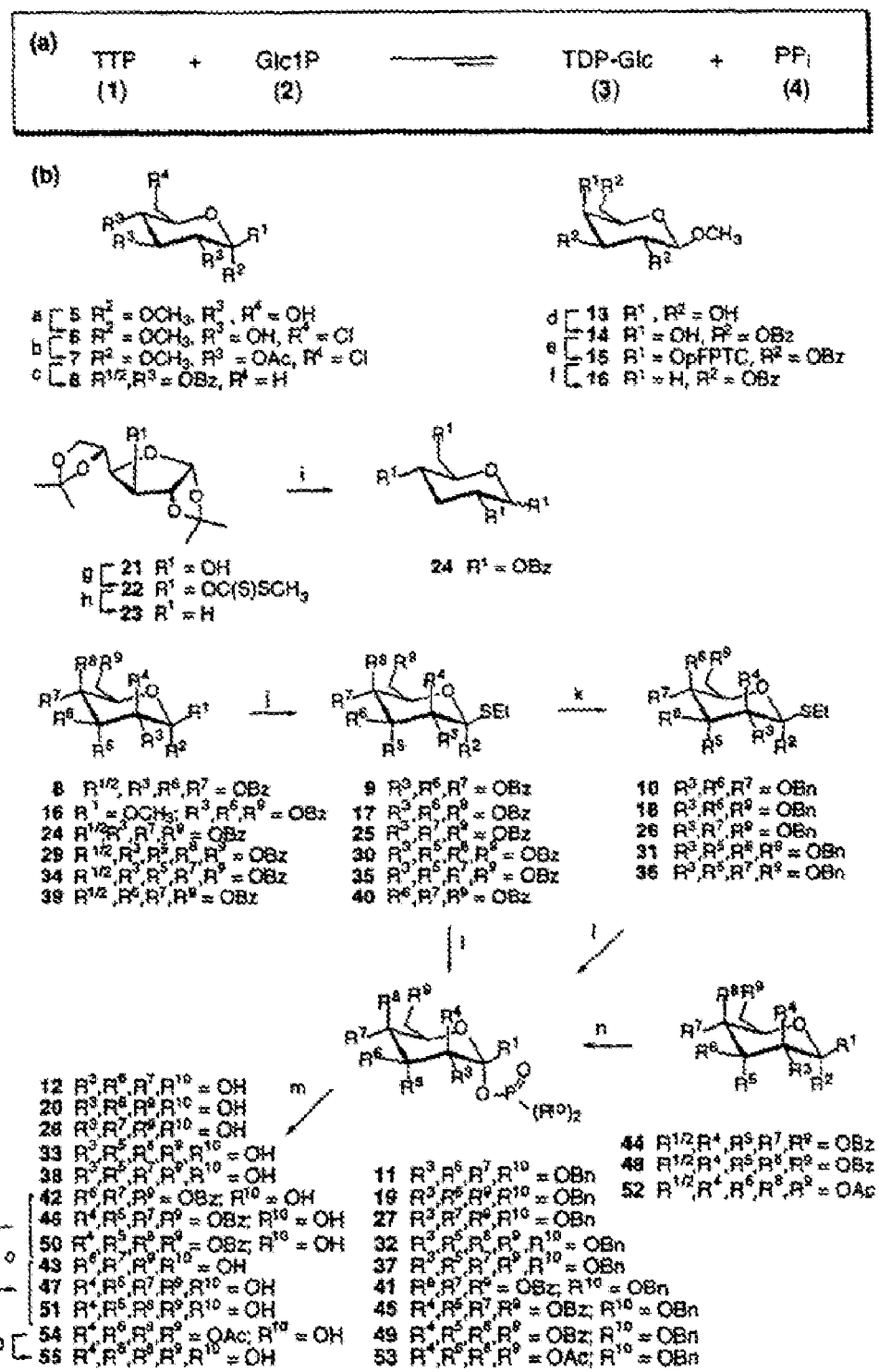
FIG. 1.

In FIG. 1(*b*): (a) $Ph_3P$, $CCl_4$; (b) $Ac_2O$, pyr; (c) (i) $LiAlH_4$, (ii) AcOH/HCl, (iii) BzCl, pyr; (d) BzCl, pyr; (e) pFPTC-Cl, DMAP; (f) (n-Bu)3SnH; (g)(i) NaH, imidazole; (ii) $CS_2$; (iii) $CH_3I$; (h) AIBN, (n-Bu)$_3$SnH; (i) (i) $CF_3CO_2H$, (ii) BzCl, pyr; (j) EtS-TMS, $ZnI_2$; (k) (i) NaOMe; (ii) NaH; (iii) BnBr; (l) (i) (BnO)2P(O)OH, NIS; (m) $H_2$, Pd/C; (n) (i) HBr; (ii) (BnO)2P(O)OH, silver triflate, 2,4,6-collidine; (O) NaOH; (p) AcOH/HCl. In each case, cation exchange provided the Na+ salt.

The overall yield of this four-step phosphorylation strategy ranged from 19%-28% including the final ion exchange. FIG. 1(*b*) shows these glycosyl phosphates and methods for synthesizing them. These glycosyl phosphates, and methods for making them, are provided by the present invention.

The present method includes anomerically activating an ethyl 1-thio-β-D-pyranoside to form a compound having the formula 1

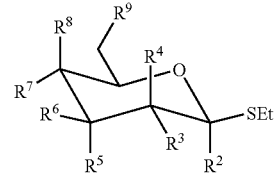

wherein $R^2$ is $OCH_3$, OBz, or OH,
$R^3$ is OH, OAc, or OBz,
$R^4$ is H, OH, or a halogen atom, and
$R^5$, $R^6$, $R^7$, $R^8$, and $R^9$ are each OBz,
and three or more of $R^3$, $R^5$, $R^6$, $R^7$, $R^8$, and $R^9$ are OBz substituents; deprotecting the OBz substituents to convert at least one such substituent to a OBn substituent; phosphorylating to form a compound of the formula 2,

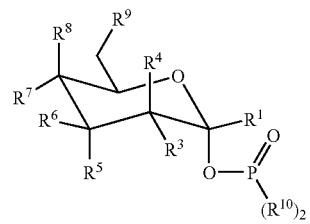

wherein $R^1$ is $OCH_3$, OBz, OAc or OH,
$R^2$ is $OCH_3$, OBz, OAc or OH,

R³ is OH, OAc, or OBz,
R⁴ is H, OH, OBz, OAc or a halogen atom,
R⁵, R⁶, R⁷, R⁸, and R⁹ are each OBz or OAc, and R¹⁰ is OH, or OBn,
wherein at least four of R³, R⁴, R⁵, R⁶, R⁷, R⁸, R⁹, and R¹⁰ are independently OBn or OBz substituents; and
deprotecting to convert any OBn substituents to OH substituents.

Preferably, the α-D-hexopyranosyl phosphate is a glycosyl phosphate. Also included are α-D-hexopyranosyl phosphates, preferably glycosyl phosphates synthesized by these methods. Preferably these α-D-hexopyranosyl phosphates are selected from the group consisting of deoxy-α-D-glucopyranosyl, aminodeoxy-α-D-hexopyranosyl and acetamidodeoxy-α-D-hexopyranosyl phosphates.

The present invention also includes a method that includes providing isolated $E_p$ having the formula 3

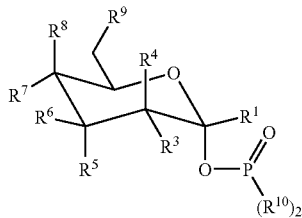

wherein R¹ is OCH₃, OBz, OAc or OH,
R² is OCH₃, OBz, OAc or OH,
R³ is OH, OAc, or OBz,
R⁴ is H, OH, OBz, OAc or a halogen atom,
R⁵, R, R⁷, R⁸, and R⁹ are each OBz or OAc, and
R¹⁰ is OH, or OBn,
wherein at least four of R³, R⁴, R⁵, R⁶, R⁷, R⁸, R⁹, and R¹⁰ are independently OH or OBz substituents.

Alternatively, phosphorylation of Dibenzyl-(2,3,4,6-tetra-O-benzoyl-α-D-altropyranosyl) phosphate (45), Dibenzyl-(2,3,4,6-tetra-O-benzoyl-α-D-idopyranosyl) phosphate (49) and Dibenzyl-(2,3,4,6-tetra-O-acetyl-α-D-talopyranosyl) phosphate (53) (FIG. 1(b)) via the glycosyl halide followed by complete deprotection gave the glycosyl phosphates Disodium α-D-altropyranosyl phosphate (47), Disodium α-D-idopyranosyl phosphate (51) and Disodium α-D-talopyranosyl phosphate (55) as depicted in FIG. 1(b) in an overall yield ranging from 37%-47%. The 6-deoxy precursor 1,2,3,4-tetra-O-benzoyl-6-deoxy-α,β-D-glucopyranose (8) may be synthesized by LiAlH₄ reduction and subsequent benzoylation of the halide Methyl 2,3,4-tri-O-acetyl-6-chloro-6-deoxy-α-D-glucopyranoside (7). (See Anisuzzaman, A. K. M.; Whistler, R. L. Carbohydr. Res. 1978, 61, 511-518.). For the 4-deoxy progenitor, deoxygenation at C-4 may be accomplished by selective benzoylation of methyl β-D-galactopyranoside Methyl β-D-galactopyranoside (13) (as depicted in FIG. 1(b)) to provide the desired tribenzolated Methyl 2,3,6-tri-O-benzoyl-β-D-galactopyranoside (14) (54%) as well as the tetrabenzolated derivative (19%). Subsequent C-4 activation Methyl 2,3,6-tri-O-benzoyl-4-O-pentafluorophenoxythiocarbonyl-β-D-galactopyranoside (15) and (n-Bu)₃SnH reductive 4-deoxygenation were accomplished as described in Kanie, O.; Crawley, S. C.; Palcic, M. M.; Hindsgaul, O. Carbohydr. Res. 1993, 243, 139-164 to give the desired 4-deoxy precursor Methyl 2,3,6-tri-O-benzoyl-4-deoxy-β-D-galactopyranoside (16). The 3-deoxy predecessor 1,2,4,6-tetra-O-benzoyl-3-deoxy-α-D-glucofuranose (24) (FIG. 1(b)) was synthesized from 1,2:5,6-di-O-isopropylidene-α-D-glucofuranose (21) by reduction of the previously reported furanose 1,2:5,6-Di-O-isopropylidene-3-O-(methylthio)thiocarbonyl-α-D-glucofuranose (22) (See Zhiyuan, Z.; Magnusson, G. Carbohydr. Res. 1994, 262, 79-101), while the 2-deoxy precursor (39) derived from a commercial source.

Thus, another embodiment of the present invention includes methods of making α-D-hexopyranosyl phosphates, which include, but are not limited to, phosphorylating a phosphate selected from the group consisting of Dibenzyl-(2,3,4,6-tetra-O-benzyol-α-D-altropyranosyl) phosphate, Dibenzyl-(2,3,4,6-tetra-O-benzyl-α-D-idopyranoxyl)phosphate, and Dibenzyl-(2,3,4,6-tetra-O-acetyl-α-D-talopyranosyl) phosphate via a glycosyl halide; and deprotecting to form a glycosyl phosphate selected from the group consisting of Disodium α-D-altropyranosyl phosphate, Disodium α-D-idopyranosyl phosphate and Disodium α-D-talopyranosyl phosphate. The present invention also includes α-D-hexopyranosyl phosphates prepared according to this method.

Nucleotide Sugars and Methods of Synthesizing the Same
The present invention includes methods of making nucleotide sugars, which include combining α-D-hexopyranosyl phosphate and NTP in the presence of at least one mutated nucleotidylyltransferase. Other methods according to the present invention include combining α-D-hexopyranosyl phosphate and NTP other than TTP in the presence of at least one nucleotidylyltransferase, and combining NTP and α-D-hexopyranosyl phosphate other than Glc1P in the presence of at least one nucleotidylyltransferase.

The present invention includes a method of synthesizing nucleotide sugars that includes combining a nucleotidylyltransferase, α-D-glucopyranosyl phosphate, Mg⁺2, NTP and inorganic pyrophosphatase, and incubating. Preferably, the incubating is at a temperature of from about 30° C. to about 45° C., preferably about 33° C. to about 42° C., even more preferably about 37° C. for about 20 to about 40 minutes, preferably about 25 to about 35 minutes, and even more preferably about 30 minutes. The nucleotydylyltransferase according to these methods may include one or more natural and/or mutated nucleotidylyltransferases, such as natural and/or mutated $E_p$.

The present invention further includes nucleotide sugars made by the methods described herein.

Nucleotide sugars of the present invention may be selected from the group consisting of TDP-sugar, GDP-sugar, CDP-sugar, UDP-sugar, and ADP-sugar and combinations thereof.

In embodiments utilizing or including mutated nucleotidylyltransferases, a preferred mutated nucleotidylyltransferase is $E_p$ mutated at one or more amino acids selected from the group consisting of V173, G147, W224, N112, G175, D111, E162, T201, I200, E199, R195, L89, L89T, L109, Y146 and Y177.

In embodiments utilizing or including mutated nucleotidylyl transferases, a preferred mutated nucleotidylyl transferases is $E_p$ mutated at one or more amino acids in its active site, its divalent cation binding site, and/or its auxiliary site.

Likewise, other preferred mutated nucleotidylyl transferases include nucleotidylyl transferases mutated at one or more amino acids in their active sites, divalent cation binding sites, and/or their auxiliary sites.

To evaluate the synthetic utility of purified thymidylyltransferase, $E_p$, α-D-hexopyranosyl phosphate, Mg⁺2 and NTP were incubated at about 37° C. for about 30 min and the extent of product formation determined by HPLC. The results of these assays are illustrated in FIG. 2. Confirmation of product formation was based upon HPLC co-elution with commercially available standards and/or HPLC isolation and high resolution mass spectroscopy of the product. (For select compounds, product peaks were lyophilized and submitted directly for HRMS (FAB) analysis.) As controls, little or no product formation was observed in the absence of $E_p$, glycosyl phosphate, $Mg^{+2}$, or NTP. A reaction containing 5 mM NTP, 10 mM sugar phosphate and 5.5 mM $MgCl_2$ in a total volume of 50 μL 50 mM potassium phosphate buffer, pH 7.5 at 37° C. was initiated by the addition of 3.52 U $E_p$ (1 U=the amount of protein needed to produce 1 μmol TDP-D-glucose $min^{-1}$). The reaction was incubated with slow agitation for 30 min at 37° C., quenched with MeOH (50 μL), centrifuged (5 min, 14,000×g) and the supernatant was stored at −20° C. until analysis by HPLC. Samples (20 μL) were resolved on a Sphereclone 5u SAX column (250×4.6 mm) fitted with a guard column (30×4.6 mm) using a linear gradient (20-60 mM potassium phosphate buffer, pH 5.0, 1.5 mL $min^{-1}$, $A_2$ 75 nm).

The following nucleotide sugars are non-limiting examples of nucleotide sugars according to the present invention, which may preferably be produced in accordance with one or more of the methods described herein, and in particular the reactions of FIG. 2: (58) Thymidine 5'-(α-D-glucopyranosyl diphosphate) (HRMS (FAB) calc for $C_{16}H_{25}O_{16}N_2P_2$ 563.0705. found m/z 563.0679 (M+H)). (59) Uridine 5'-(α-D-glucopyranosyl diphosphate) (HRMS (FAB): calc for $C_{14}H_{23}O_{17}N_2P_2$ 565.0507. found m/z 565.0472 (M+H)). (60) Thymidine 5'-(2-deoxy-α-D-glucopyranosyl diphosphate) (HRMS (FAB) calc for $C_{16}H_{25}O_{15}N_2P_2$ 547.0704. found m/z 547.0714 (M+H)). (61) Uridine 5'-(2-deoxy-α-D-glucopyranosyl diphosphate) (HRMS (FAB): calc $C_{14}H_{23}O_{16}N_2P_2$ 549.0506. found m/z 549.0510 (M+H)). (62) Thymidine 5'-(3-deoxy-α-D-glucopyranosyl diphosphate) (HRMS (FAB) calc for $C_{16}H_{25}O_{15}N_2P_2$ 547.0704. found m/z 547.0720 (M+H)). (63) Uridine 5'-(3-deoxy-α-D-glucopyranosyl diphosphate) (HRMS (FAB): calc $C_{14}H_{23}O_{16}N_2P_2$ 549.0506. found m/z 549.0485 (M+H)). (64) Thymidine 5'-(4-deoxy-α-D-glucopyranosyl diphosphate) (HRMS (FAB) calc for $C_{16}H_{25}O_{15}N_2P_2$ 547.0704. found m/z 547.0693 (M+H)). (65) Uridine 5'-(4-deoxy-α-D-glucopyranosyl diphosphate) (HRMS (FAB): calc $C_{14}H_{23}O_{16}N_2P_2$ 549.0506. found m/z 549.0500 (M+H)). (66) Thymidine 5'-(6-deoxy-α-D-glucopyranosyl diphosphate) (HRMS (FAB) calc for $C_{16}H_{25}O_{15}N_2P_2$ 547.0704. found m/z 547.0730 (M+H)). (67) Uridine 5'-(6-deoxy-α-D-glucopyranosyl diphosphate) (HRMS (FAB): calc $C_{14}H_{23}O_{16}N_2P_2$ 549.0506. found m/z 549.0492 (M+H)). (68) Thymidine 5'-(α-D-mannopyranosyl diphosphate) (HRMS (FAB) calc 563.0705. found m/z 563.0701 (M+H)). (69) Uridine 5'-(α-D-mannopyranosyl diphosphate) (HRMS (FAB): calc 565.0507. found m/z 565.0503 (M+H)). (70) Thymidine 5'-(α-D-galactopyranosyl diphosphate) (HRMS (FAB) calc 563.0705. found m/z 563.0710 (M+H)). (71) Uridine 5'-(α-D-galactopyranosyl diphosphate) (HRMS (FAB): calc 565.0507. found m/z 565.0508 (M+H)). (72) Thymidine 5'-(α-D-allopyranosyl diphosphate) (HRMS (FAB) calc 563.0705. found m/z 563.0715 (M+H)). (73) Uridine 5'-(α-D-allopyranosyl diphosphate) (HRMS (FAB): calc 565.0507. found m/z 565.0507 (M+H)). (74) Thymidine 5'-(α-D-altropyranosyl diphosphate) (HRMS (FAB) calc 563.0705. found m/z 563.0699 (M+H)). (75) Uridine 5'-(α-D-altropyranosyl diphosphate) (HRMS (FAB): calc 565.0507. found m/z 565.0511 (M+H)). (76) Thymidine 5'-(α-D-gulopyranosyl diphosphate) (HRMS (FAB) calc 563.0705. found m/z 563.00712 (M+H)). (77) Uridine 5'-(α-D-gulopyranosyl diphosphate) (HRMS (FAB): calc 565.0507. found m/z 565.0512 (M+H)). (78) Thymidine 5'-(α-D-idopyranosyl diphosphate) (HRMS (FAB) calc 563.0705. found m/z 563.0708 (M+H)). (79) Uridine 5'-(α-D-idopyranosyl diphosphate) (HRMS (FAB): calc 565.0507. found m/z 565.0507 (M+H)). (80) Thymidine 5'-(α-D-talopyranosyl diphosphate) (HRMS (FAB) calc 563.0705. found m/z 563.0710 (M+H)). and (81) Uridine 5'-(α-D-talopyranosyl diphosphate) (HRMS (FAB): calc 565.0507. found m/z 565.0499 (M+H)). although data is not depicted for all products.

Other nucleotide sugars in accordance with the present invention include, but are not limited to, the following: (109) Thymidine 5'-(6-amino-6-deoxy-α-D-glucopyranosyl diphosphate) (HRMS (FAB): calc for $C_{16}H_{26}O_{15}N_3P_2$ 562.0839. found m/z 562.0837 (M+H)). (110) Uridine 5'-(6-amino-6-deoxy-α-D-glucopyranosyl diphosphate) (HRMS (FAB): calc for $C_{15}H_{24}O_{16}N_3P_2$ 564.0632. found m/z 564.0640 (M+H)). (111) Thymidine 5'-(4-amino-4-deoxy-α-D-glucopyranosyl diphosphate) (HRMS (FAB): calc for $C_{16}H_{26}O_{15}N_3P_2$ 562.0839. found m/z 562.0848 (M+H)). (112) Uridine 5'-(4-amino-4-deoxy-α-D-glucopyranosyl diphosphate) (HRMS (FAB): calc for $C_{15}H_{24}O_{16}N_3P_2$ 564.0632. found m/z 564.0638 (M+H)). (113) Thymidine 5'-(3-amino-3-deoxy-α-D-glucopyranosyl diphosphate) (HRMS (FAB): calc for $C_{16}H_{26}O_{15}N_3P_2$ 562.0839. found m/z 562.0835 (M+H)). (114) Uridine 5'-(3-amino-3-deoxy-α-D-glucopyranosyl diphosphate) (HRMS (FAB): calc for $C_{15}H_{24}O_{16}N_3P_2$ 564.0632. found m/z 564.0622 (M+H)). (115) Thymidine 5'-(2-amino-2-deoxy-α-D-glucopyranosyl diphosphate) (HRMS (FAB): calc for $C_{16}H_{26}O_{15}N_3P_2$ 562.0839. found m/z 562.0842 (M+H)). (116) Uridine 5'-(2-amino-2-deoxy-α-D-glucopyranosyl diphosphate) (HRMS (FAB): calc for $C_{15}H_{24}O_{16}N_3P_2$ 564.0632. found m/z 564.0630 (M+H)). (117) Thymidine 5'-(6-acetamido-6-deoxy-α-D-glucopyranosyl diphosphate) (HRMS (FAB): calc for $C_{18}H_{28}O_{16}N_3P_2$ 604.0945. found m/z 604.0953 (M+H)). (118) Uridine 5'-(6-acetamido-6-deoxy-α-D-glucopyranosyl diphosphate) (HRMS (FAB): calc for $C_{17}H_{26}O_{17}N_3P_2$ 606.0737. found m/z 606.0732 (M+H)). (119) Thymidine 5'-(4-acetamido-4-deoxy-α-D-glucopyranosyl diphosphate) (HRMS (FAB): calc for $C_{18}H_{28}O_{16}N_3P_2$ 604.0945. found m/z 604.0940 (M+H)). (120) Uridine 5'-(4-acetamido-4-deoxy-α-D-glucopyranosyl diphosphate). HRMS (FAB): calc for $C_{17}H_{26}O_{17}N_3P_2$ 606.0737. found m/z 606.0730 (M+H)). (121) Thymidine 5'-(3-acetamido-3-deoxy-α-D-glucopyranosyl diphosphate) (HRMS (FAB): calc for $C_{18}H_{28}O_{16}N_3P_2$ 604.0945. found m/z 604.0947 (M+H)). (122) Uridine 5'-(3-acetamido-3-deoxy-α-D-glucopyranosyl diphosphate) (HRMS (FAB): calc for $C_{17}H_{26}O_{17}N_3P_2$ 606.0737. found m/z 606.0735 (M+H)). (123) Thymidine 5'-(2-acetamido-2-deoxy-α-D-glucopyranosyl diphosphate) (HRMS (FAB): calc for $C_{18}H_{28}O_{16}N_3P_2$ 604.0945. found m/z 604.0951 (M+H)). (124) Uridine 5'-(2-acetamido-2-deoxy-α-D-glucopyranosyl diphosphate) (HRMS (FAB): calc for $C_{17}H_{26}O_{17}N_3P_2$ 606.0737. found m/z 606.0738 (M+H)). (125) Thymidine 5'-(4-amino-4,6-dideoxy-α-D-glucopyranosyl diphosphate) (HRMS (FAB): calc for $C_{16}H_{26}O_{14}N_3P_2$ 546.0889. found m/z 546.0895 (M+H)). and (126) Uridine 5'-(4-amino-4,6-dideoxy-α-D-glucopyranosyl diphosphate) (HRMS (FAB): calc for $C_{15}H_{24}O_{15}N_3P_2$ 548.0682. found m/z 548.0673 (M+H)).

Further nucleotide sugars in accordance with the present invention include, but are not limited to, the following:
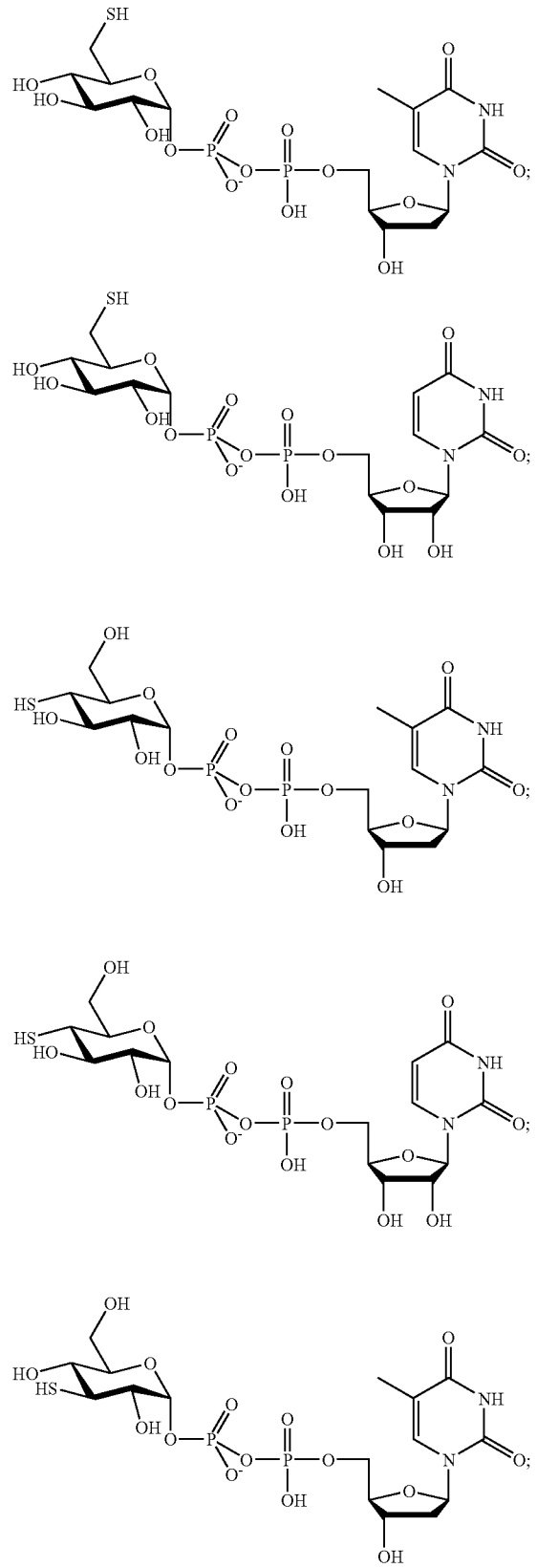
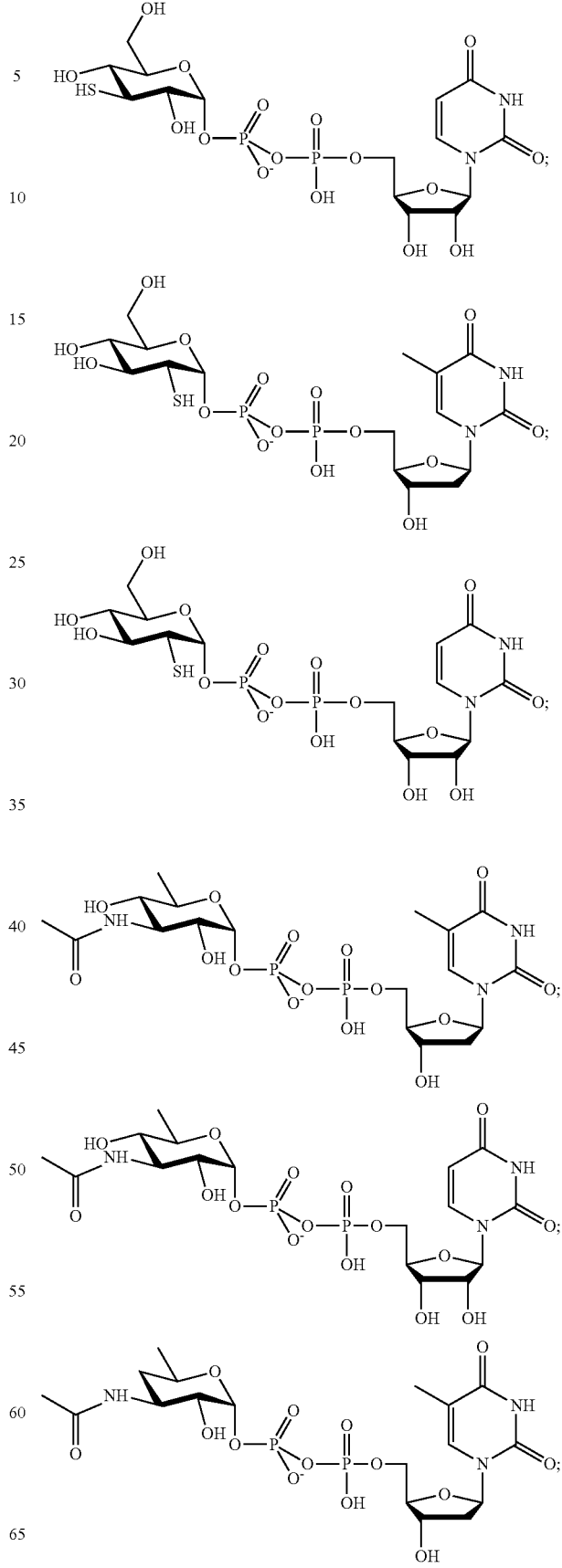

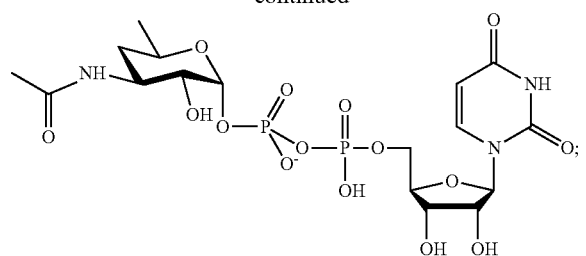
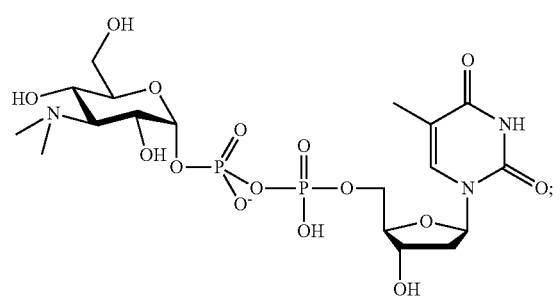
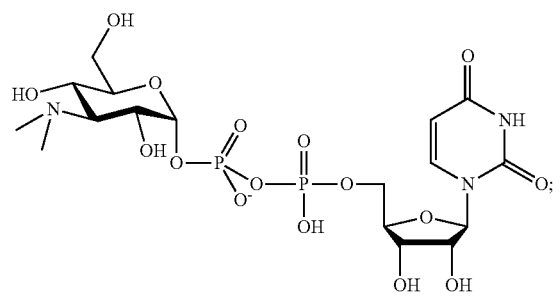
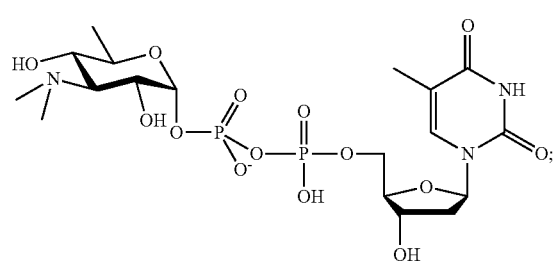
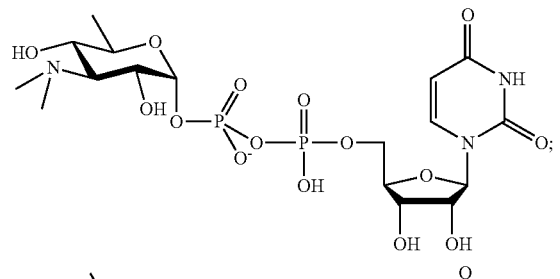
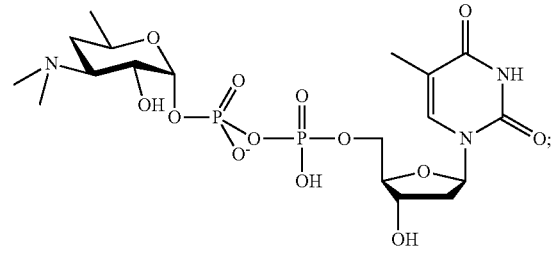
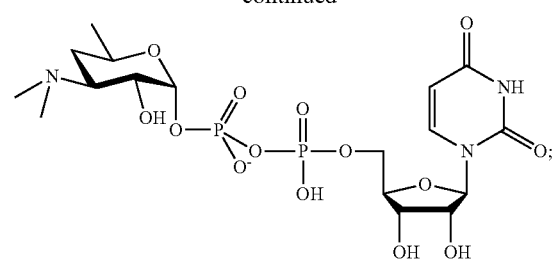
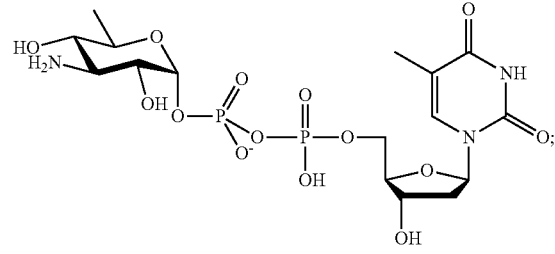
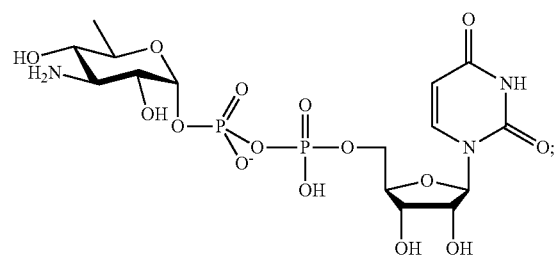
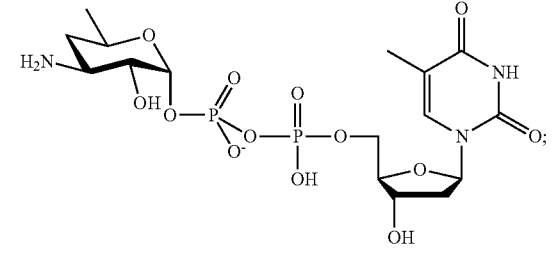
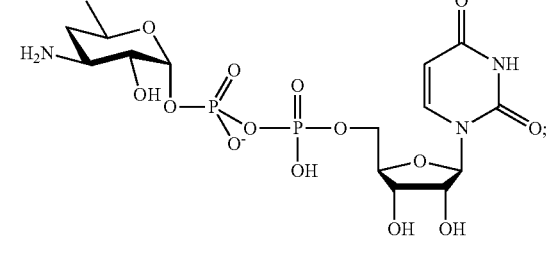
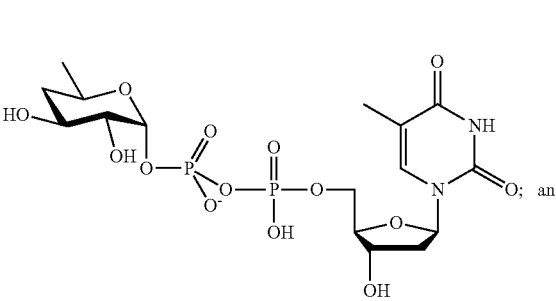

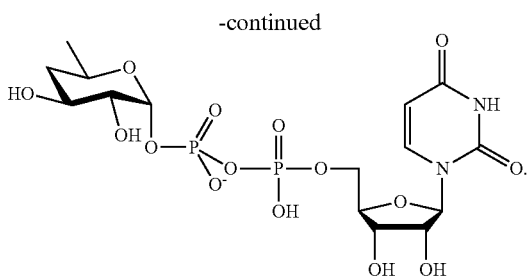

FIG. 2 illustrates the utility of $E_p$ as a catalyst/reagent to simplify the synthesis of useful nuleotide sugars—of the twelve glycosyl phosphate tested (which include all possible α-D-hexoses and monodeoxy α-D-glucoses), all produce product with both TTP and UTP under the conditions described. These yield might be further improved by using pryophosphatase to drive the equilibrium of the reaction. An examination of accepted α-D-hexopyranosyl phosphates to with TTP suggests that $E_p$ prefers pyranosyl phosphates, which are predicted to exist predominately as $^4C_1$ conformers [e.g., (12), (20), (28), (43), α-D-glucopyranosyl phosphate (2), α-D-mannopyranosyl phosphate (56), and α-D-galactopyranosyl phosphate (57) (FIGS. 1 and 2)], while those predicted to not adopt the $^4C_1$ conformation [e.g., Ethyl 2,3,4,6-tetra-O-benzyl-1-thio-β-D-gulopyranoside (31), α-D-allopyranosyl phosphate (38), α-D-altropyranosyl phosphate (47), α-D-idopyranosyl phosphate (51) and α-D-talopyranosyl phosphate (55) (FIGS. 1 and 2)] show less activity.

Regarding specific interactions required for conversion, analysis of the corresponding deoxy series [(12), (20), (28) and (43) (FIGS. 1 and 2)] implicates only a single required hydroxyl (C-2), the removal of which impairs the yield by >70%. A similar trend is observed in the UTP series with two exceptions, glycosides (28) and α-D-mannopyranosyl phosphate (56) (FIGS. 1 and 2). Cumulatively, these results suggest that, while the C-2 hydroxyl is important for turnover, alterations at C-3 in the context of UTP result in adverse cooperativity.

Aminodeoxy-α-D-hexapyranosyl phosphates and acetamidodeoxy-α-D-hexapyranosyl phosphates are each examples of α-D-hexapyranosyl phosphates that may be used in accordance with the present invention. A direct comparison of the aminodeoxy-α-D-glucopyranosyl phosphate series to their corresponding acetamidodeoxy analogs provides insight pertaining to the ability of the $E_p$ active site to accommodate additional steric bulk.

Of the aminodeoxy-α-D-glucopyranosyl phosphates examined, only two, 2-amino-2-deoxy-α-D-glucopyranosyl phosphate (107) (FIG. 4) and 2-acetamido-2-deoxy-α-D-glucopyranosyl phosphate (108) (FIG. 4), were commercially available. The syntheses of the remaining analogs diverged from the key intermediates Ethyl 6-azide-2,3',4-tri-O-benzyl-6-deoxy-1-thio-β-D-glucopyranoside (89), Ethyl 4-azide-2,3,6-tri-O-benzyl-4-deoxy-1-thio-β-D-glucopyranoside (94) and Ethyl 3-azide-2,4,6-tri-O-benzyl-3-deoxy-1-thio-β-D-glucopyranoside (100) (FIG. 3(b)).

Thus, the present invention includes a method of making aminodeoxy-α-D-glucopyranosyl phosphates comprising converting an intermediate selected from the group consisting of ethyl 6-azide-2,3,4-tri-O-benzyl-6-deoxy-1-thio-β-D-glucopyranoside (89), ethyl 4-azide-2,3,6 tri-O-benzyl-4-deoxy-1-thio-β-D-glucopyranoside (94), and ethyl 3-azide-2,4,6-tri-O-benzyl-3-deoxy-1-thio-β-D-glucopyranoside (100) to a corresponding amide.

Figure 3:
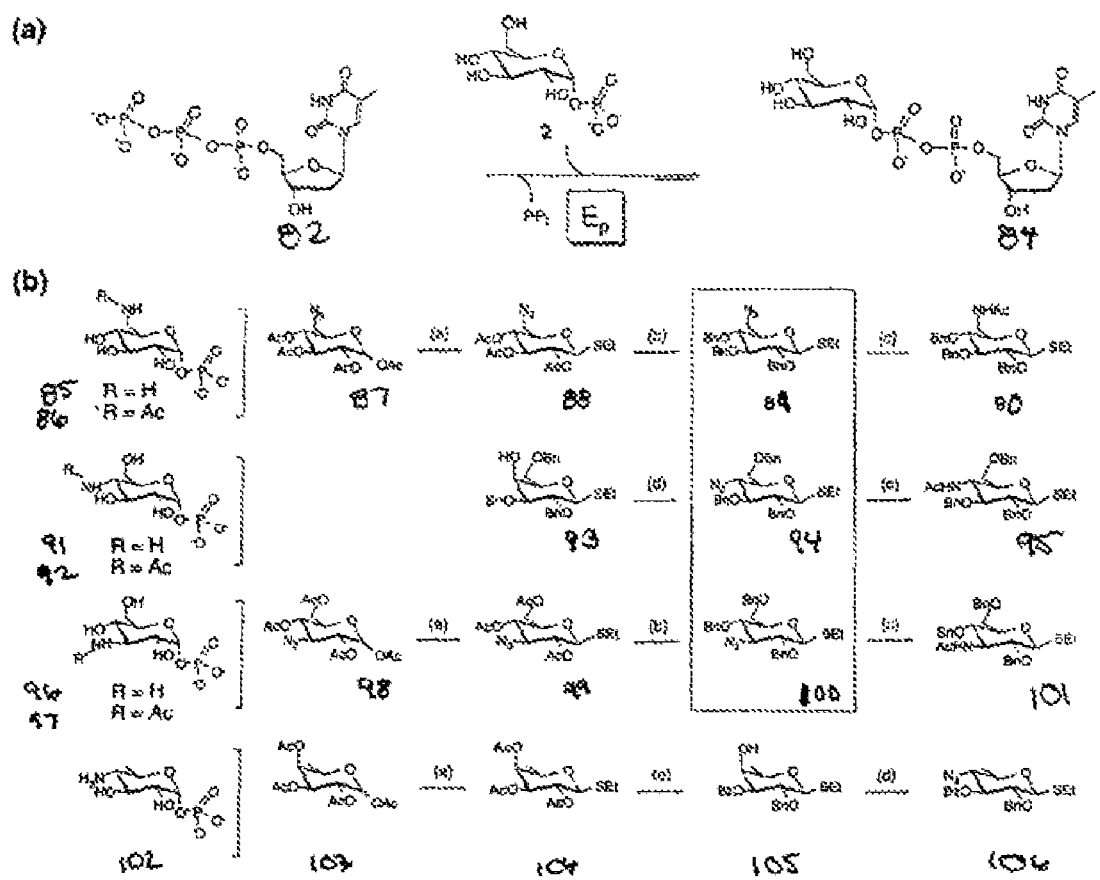
FIG. 3.

Ethyl 1-thio-β-D-pyranosides (89) and (100) derived from previously reported glycosides (FIG. 3(b)(87)) (see V. Maunier, P. Boullanger, D. Lafont, Y. Chevalier, Carbohydr. Res. 1997, 299, 49-57) and FIG. 3(b)(98) (W. A. Greenberg, E. S. Priestley, P. S. Sears, P. B. Alper, C. Rosenbohm, M. Hendrix, S.-C. Hung, C.-H. Wong, J. Am. Chem. Soc. 1999, 121, 6527-6541), respectively), while (94) was synthesized, from the previously reported compound (93) (FIG. 3(b)) (P. J. Garegg, I. Kvarnstrom, A. Niklasson, G. Niklasson, S. C. T. Svensson, J. Carbohydr. Chem. 1993, 12, 933-953) in a manner similar to that of the deoxy-α-D-glucopyranosyl phosphate syntheses described herein. Specifically, this strategy invoked a protection scheme to selectively expose the position of substitution followed by activation (via TsCl or $Tf_2O$) and $SN^2$ displacement by sodium azide. From the divergent point (FIG. 3 (89), (94) and (100)), an efficient azide selective $SnCl_2$ reduction followed by acetylation gave the desired ethyl 1-thio-β-D-pyranoside precursors (90), (95), and (101). Finally, the subsequent phosphorylation of FIG. 3(b) (89), (90), (94), (95), (100), and (101) was accomplished by reaction with dibenzyl phosphate as previously described where the culminating reductive deprotection also led to the conversion of the FIG. 3(b) (89), (94), and (100) azides to the desired amines. As an aminodideoxy sugar representative, 4-amino-4,6-dideoxy-α-D-glucopyranosyl phosphate (FIG. 3(b) (102)) was also synthesized from peracetylated D-fucose (FIG. 3(b) (103)) as illustrated in FIG. 3 using a similar strategy.

To evaluate the synthetic utility of thymidylyl-transferase, purified $E_p$, α-D-glucopyranosyl phosphate, $Mg^{+2}$, NTP and inorganic pyrophosphatase were incubated at 37° C. for 30 min and the extent of product formation determined by HPLC. The inorganic pyrophosphatase was included to drive the reaction forward. A reaction containing 2.5 mM NTP, 5.0 mM sugar phosphate, 5.5 mM $MgCl_2$ and 10 U inorganic pyrophosphatase in a total volume of 50 μL 50 mM potassium phosphate buffer, pH 7.5 at 37° C. was initiated by the addition of 3.52 U $E_p$ (1 U=the amount of protein needed to produce 1 mol TDP-D-glucose $min^{-1}$). The reaction was incubated with slow agitation for 30 min at 37° C., quenched with MeOH (50 μL), centrifuged (5 min, 14,000×g) and the supernatant was stored at −20° C. until analysis by HPLC. Samples (30 μL) were resolved on a Sphereclone 5 u SAX column (150×4.6 mm) fitted with a SecurityGuard™ cartridge (Phenomenex; Torrance, Calif.) using a linear gradient (50-200 mM potassium phosphate buffer, pH 5.0, 1.5 mL $min^{-1}$, $A_2$ 75 nm).

Figure 4:
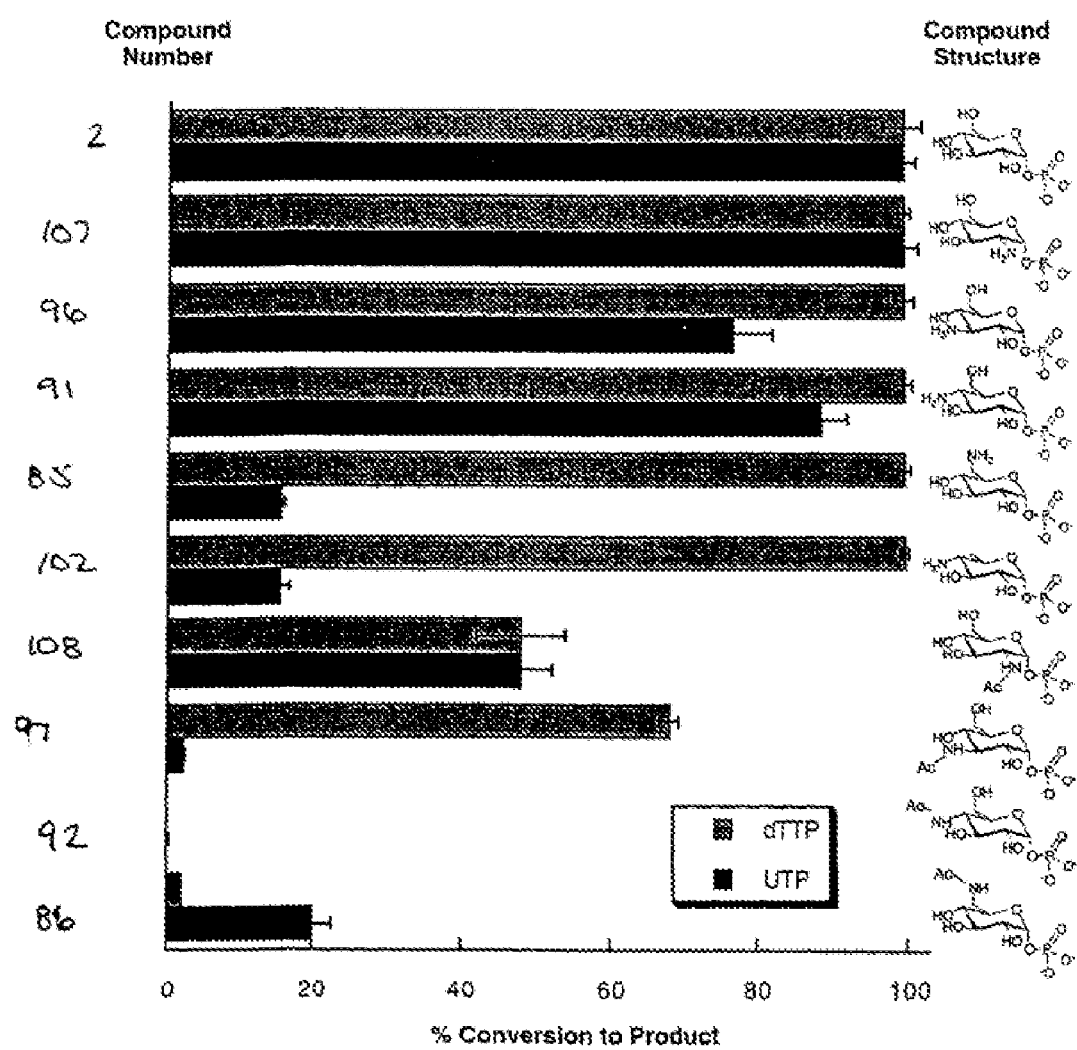
FIG. 4. Percent conversion to product using substrates according to the present invention.

The results of these assays are illustrated in FIG. 4. For each assay, confirmation of product formation was based upon high resolution mass spectroscopy of HPLC-isolated products and, also in some cases, HPLC co-elution with commercially available standards. (Allosteric activation is common for the nucleotidylyltransferase family (for examples see: M. X. Wu, J. Preiss, Arch. Biochem. Biophys. 1998, 358, 182-188; and D. A. Bulik, P. van Ophem, J. M. Manning, Z. Shen, D. S. Newburg, E. L. Jarroll, J. Biol. Chem. 2000, 275, 14722-14728) although data is not yet available pertaining to the allosteric effectors of $E_p$.) As controls, no product formation was observed in the absence of $E_p$, glucopyranosyl phosphate, $Mg^{+2}$, or NTP.

The nucleotide sugars (109)-(126) set forth above are examples of nucleotide sugars of the present invention, which may be produced in accordance with the methods described herein, and in particular the reactions diagramed in FIG. 4. A comparison of the aminodeoxy-α-D-glucopyranosyl phosphate/dTTP assay results (FIG. 4 (85), (91), (96), and (107)) to the $E_p$ native reaction (FIG. 4, (2)/dTTP) reveals that amino substitution has little or no effect on product formation, and, with the exception of compound (85) (FIG. 4), a similar phenomenon is observed in presence of UTP.

The divergence of compound (85) from this trend is consistent with UTP-dependent $E_p$ "adverse cooperativity" in the presence of certain hexopyranosyl phosphates, as described herein. This phenomenon is perhaps attributable to allosteric activation by dTTP. Evaluation of the acetamidodeoxy-α-D-glucopyranosyl phosphate/dTTP assays (FIG. 4 compounds (86), (92), (97) and (108)), in comparison to their non-acetylated counterparts (FIG. 4 (85), (91), (96) and (107)), reveal that a bulky N-acetyl group at C-2 or C-3 (FIG. 4 (97) and (108)) is well-tolerated while the identical C-4 or C-6 substitution (FIG. 4 (92)) and (86)) results in less activity. Given that these effects most likely derive from unfavored steric interactions, it follows that the $E_p$ active site is able to accommodate additional C-2/C-3 bulk while sterics limit the allowed C-4/C-6 substitutions.

Surprisingly, product formation from FIG. 4 (86)/UTP was markedly increased (8-fold) in comparison to (86)/dTTP. This is the first example to contradict the typical adverse UTP-dependent effect upon yields observed, as illustrated by FIG. 4 compounds (85) and (97). Finally, a comparison of aminodideoxy-α-D-glucopyranosyl phosphate (FIG. 4 (102) (The product of this reaction, thymidine 5'-(4-amino-4,6-dideoxy-α-D-glucopyranosyl diphosphate), is an important critical intermediate in the formation of the calicheamicin aryltetrasaccharide to that of (FIG. 4 (96)) reveals C-6 deoxygenation does not effect dTTP-dependent $E_p$ catalysis but greatly diminishes UTP-dependent conversion. However, given independent deoxygenation at C-6 or amino substitution at C-4 (FIG. 4 (91)) each has no effect on product yield, data from independent substitutions may not be reliable in predicting the effects of multiple substitutions on product yield.

FIG. 4 illustrates the utility of $E_p$ as a catalyst/reagent to simplify the synthesis of useful nucleotide sugar pools—of the nine substrate analogs tested, all provide product with dTTP and with dUTP under the conditions described. Further, seven with dTTP and four with UTP provide appreciable product (>50% conversion) under the conditions described.

Nucleotide sugars produced via the exploitation of the promiscuity of $E_p$ include, but are not limited to, compounds (58)-(81), (109)-(126) and those set forth in FIGS. 20(a) and 20(b).

Nucleotidylyltransferases
Structure-Based Engineering of $E_p$

Figure 6:
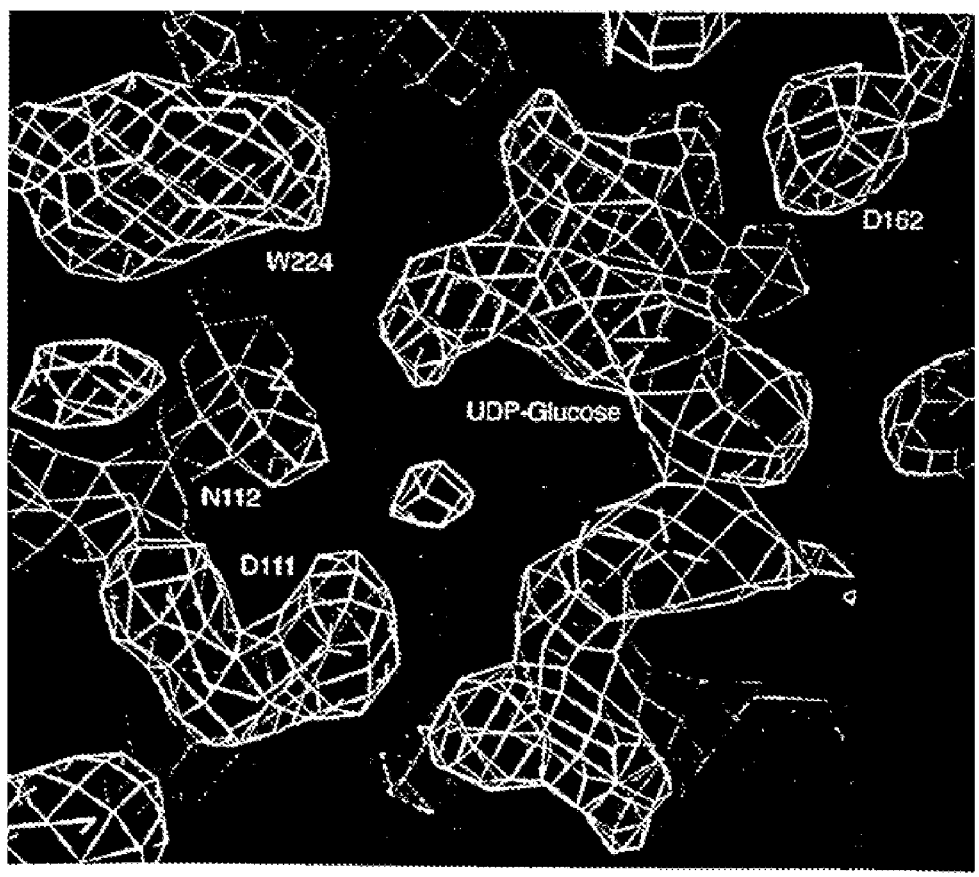
FIG. 6. Representative region of the density-modified experimental electron density map showing the substrate binding pocket in the $E_p$ UDP-Glc structure configured at 1.2.sigma.

The present inventors have determined the first three dimensional structures of this unique enzyme in complex with the product UDP-α-D-glucose (UDP-Glc) and with the substrate dTTP at 1.9 Å and 2.0 Å resolution, respectively. A three dimensional structure of $E_p$ is depicted in FIG. 6. This discovery has facilitated the elucidation of the molecular details of $E_p$ substrate recognition. The structures reveal the catalytic mechanism of thymidylyltransferases, which is further supported by new kinetic data. The present inventors have also used structure-based engineering or mutations of $E_p$ to produce modified enzymes. These inventive enzymes are capable of utilizing "unnatural" sugars previously not accepted by wild-type $E_p$.

Structure Determination

The $E_p$-UDP-Glc structure was determined using selenomethionine-labeled protein crystals and a data-set collected at a wavelength corresponding to the selenium absorption peak. A representative portion of the experimental electron density is shown in FIG. 6. The $E_p$-dTTP structure was subsequently determined by molecular replacement using the $E_p$-UDP-Glc monomer structure as a search model.

Overview of the $E_p$ Structure

The structure of the biologically active $E_p$ tetramer is illustrated in FIG. 7. The present model is refined at 2.0 Å resolution to an R factor of 18.3% with restrained temperature factors and good stereochemistry. FIG. 7a shows $E_p$ in complex with UDP-Glc and FIG. 7b displays the $E_p$-dTTP complex. The two tetrameric structures are very similar with r.m.s.d. for equivalent $C_\alpha$ positions=1.0 Å. The enzyme has overall dimensions of about 80 Å×80 Å×60 Å and a compact tertiary structure generated by four monomers packing tightly against each other along two two-fold axes of symmetry drawn on the leftmost panel of FIG. 7. The overall surface area buried during tetramer formation is approximately 10,000 Å, equivalent to the surface of one monomer. The monomer interactions are dominated by helix-helix packing of the four large helices in the center of the $E_p$ tetramer and surrounding extensive loop-loop interactions involving multiple van der Waals contacts, hydrogen bonds, and salt bridges. The active site pockets of the monomers are located close to, but not overlapping with, the monomer interface.

The $E_p$ monomer (FIG. 8) is a two-domain molecule with overall size of approximately 50 Å×50 Å×50 Å. The domain containing the active site is dominated by a large seven-stranded mixed central β-sheet, with an unusual left-handed twist, packed against three α-helices on one side and another three α-helices on the other. Its extensive hydrophobic core contains no cavities and is dominated by aromatic side chains.

This domain has overall resemblance, including the location of the active site in a large pocket on the top of the β-sheet, to other nucleotide binding proteins (see Vrielink, A., Ruger, W., Dreissen, H. P. C. & Freemont, P. S. Crystal Structure of the DNA Modifying Enzyme β-Glucosyltransferase in the Presence and Absence of the Substrate Uridine Diphosphoglucose, EMBO J. 13, 3413-3422 (1994); Charnock, S. J. & Davies, G. J. Structure of the Nucleotide-Diphospho-Sugar Transferase, SpsA from *Bacillus subtilis*, in Native and Nucleotide-Complexed Forms. Biochem. 38, 6380-6385 (1999); Gastinel, L. N. Cambillau, C. & Bourne, Y. Crystal Structures of the Bovine 4Galatosyltransferase Catalytic Domain and Its Complex with Uridine Diphosphogalactose, EMBO J. 18, 3546-3557 (1999); Ha, S., Walker, D., Shi, Y. & Walker, S. The 1.9 Å Crystal Structure of *Escherichia coli* MurG, a Membrane-Associated Glycosyltransferase Involved in Peptidoglycan Biosynthesis. Prot. Sci. 9, 1045-1052 (2000); and Brown, K., Pompeo, F., Dixon, S., Mengin-Lecreulx, D., Cambillau, C. & Bourne, Y. Crystal Structure of the Bifunctional N-Acetylglucosamine 1-phosphate uridylyltransferase from *Escherichia coli*: A Paradigm for the Related Pyrophosphorylase Superfamily. EMBO J. 18, 4096-4107 (1999)), containing the α/β open-sheet Rossmann fold. (Rossmann, M. G., et al., Evolutionary and structural relationship among dehydrogenases, in The Enzymes, I. P. D. Boyyer, Editor. Academic Press: New York. p. 61-102 (1975); and Branden, C. & Tooze, J. Introduction to Protein Structure. New York: Garlan Publishing, Inc. (1991).) The second $E_p$ domain (represented by yellow in (FIG. 8), packing tightly to the side of the active-site domain, contains four α-helices and a two-stranded β-sheet and is involved in the inter-monomer packing interactions forming the $E_p$ tetramer.

Structural Homology to Glycosyltransferases and Uridylyltransferases

Figure 8A:
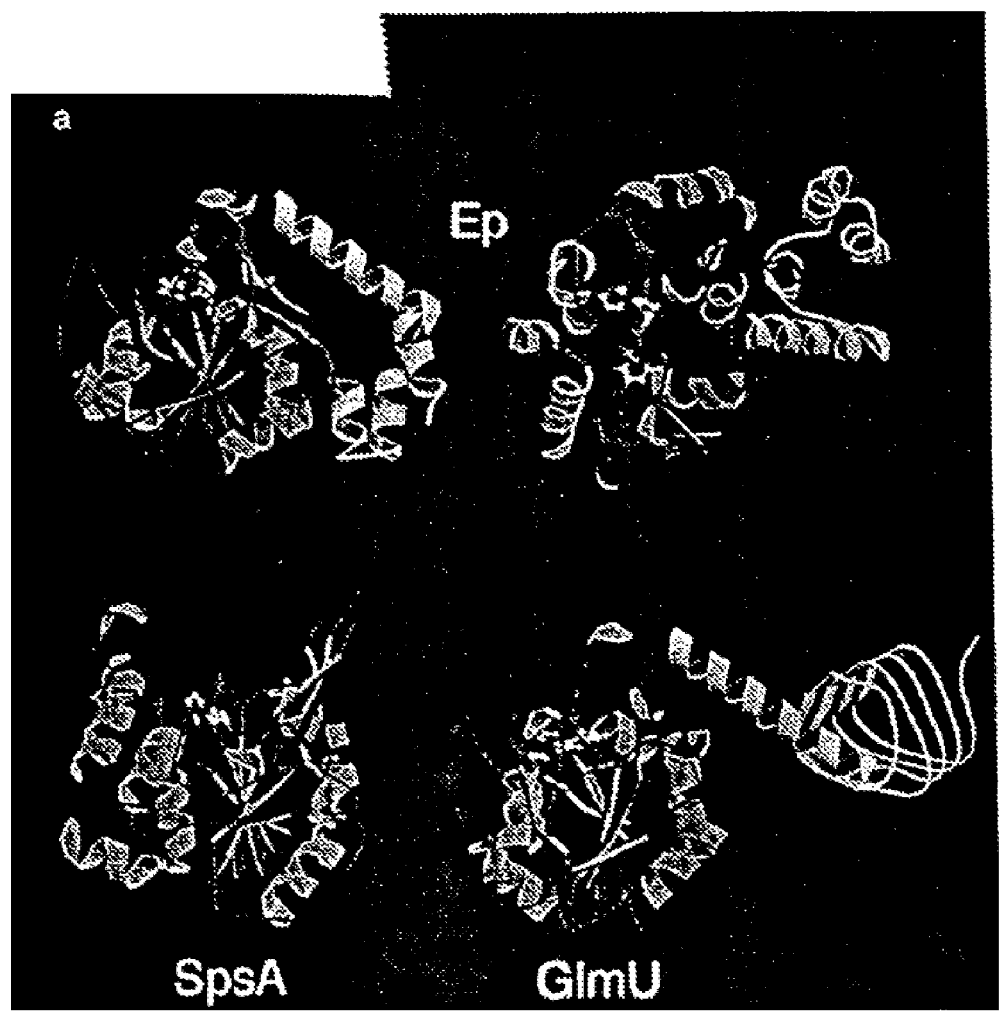
FIG. 8. Structures of the $E_p$ monomer and structural homologs SpsA and GlmU. The β strands and α helices of the α/β open sheet Rossmann fold are shown in red and green respectively, while variable regions are shown in yellow. (a) Two 90 degree views of the $E_p$ monomer (upper) and the corresponding structures of SpsA (lower left) and GlmU (lower right). (b) The folding topology of $E_p$, SpsA, and GlmU.

The present inventors' elucidation of the structure of $E_p$ represents the first such elucidation of a structure of a thymidylyltransferase. Comparison of the structure with the contents of the FSSP database, (Holm, L. & Sander, C. Touring Protein Fold Space with Dali/FSSP. Nucleic Acids Res., 26, 316-319 (1998)) revealed that the overall $E_p$ fold is different from other previously determined structures. The closest structural homologs of $E_p$ are the SpsA glycosyltransferase from *Bacillus subtilis* and the functionally related *E. coli* enzyme GlmU. GlmU is a bifunctional enzyme containing acetyltransferase and uridylyltransferase domains, respectively. FIG. 8 illustrates these three proteins, highlighting the structurally similar regions. As expected, the structural homology lies within the nucleotide-sugar binding domains. The active sites of the enzymes are located in pockets on top of the large β-sheet, although the precise positioning differs between glycosyltransferases and nucleotidyltransferases and involves secondary structure elements, which are not structurally equivalent. The three-dimensional structures of two other sugar-phosphate transferring enzymes, α-D-galactopyranosyl phosphate (Gal-1-P) uridylyltransferase and kanamycin nucleotidyltransferase are known, but do not activate sugars and both differ structurally and functionally from $E_p$.

Active Site Interactions: Substrate and Product Binding

Figure 9:
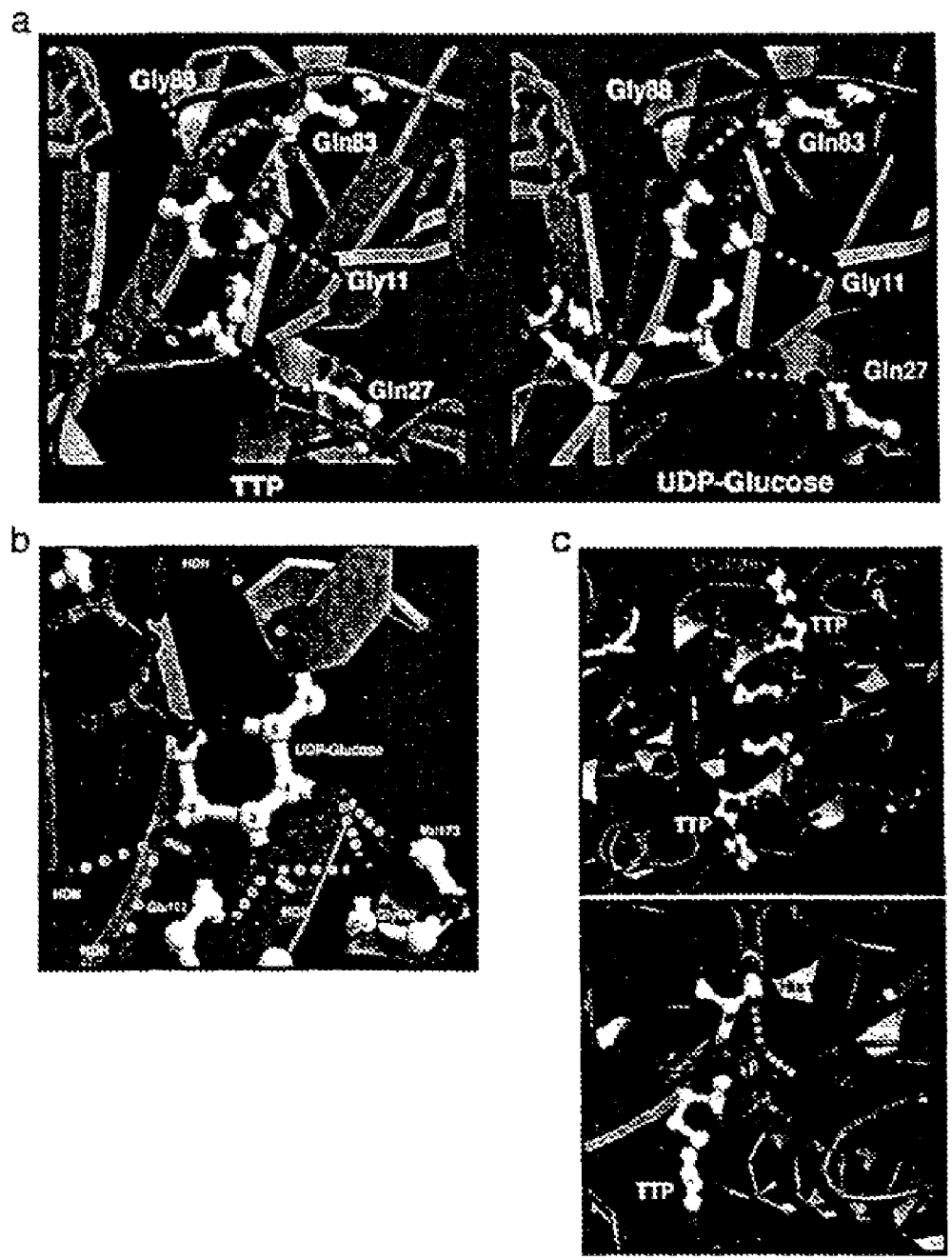
FIG. 9. Close up views of the $E_p$ active site. Hydrogen bonds are depicted by green dashed lines. (a) Interactions between $E_p$ and the dTTP substrate (left) and the UDP-Glc product (right). (b) Interactions between $E_p$ and the glucose moiety in the sugar binding pocket. (c) Two different views of dTTP bound in the 'accessory' site at the monomer interface. The different chains of the tetramer are labeled either in blue (chain-A) or red (chain-B). The β-phosphate of dTTP hydrogen bonds with both His117 of chain-A and Gly221 of chain-B.

FIG. 8 shows two 90° views of the $E_p$ active site pocket. In both of the $E_p$-dTTP and $E_p$-UDP-Glc structures, the experimental electron density for the dTTP and UDP-Glc is excellent. $E_p$ utilizes both dTTP and UTP, but not CTP, and FIG. 9a illustrates the structural basis for this substrate specificity. Specifically, the exocyclic N3 and O4 ring atoms of both dT and U are hydrogen bonded to Gln83. In addition, O4 hydrogen bonds to the main chain N of Gly88 while O2 is bound to the main chain N of Gly11. Finally, the 3'-hydroxyl group of the pentose forms a hydrogen bond with Gln27. The substrate dTTP also makes extensive van der Waals contacts with Leu9, Leu89 and Leu109, which form a hydrophobic bed for the nucleoside, and position 5 of the pyrimidine base is far enough from any protein atom to allow an easy fit for the methyl group of dT in the pocket. The phosphate groups of dTTP lie in an extended position firmly held in place by multiple interactions with the main chain nitrogen atoms of Ser13, Gly14, and Thr15, and with the catalytically important $Mg^{+2}$ (see below). The γ-phosphate also makes a hydrogen bond with Thr15 and both the α- and γ-phosphates bind Arg16. The nearby Arg145, Lys163, and Arg195 create a favorable electrostatic environment, but do not interact directly with dTTP.

Figure 5:
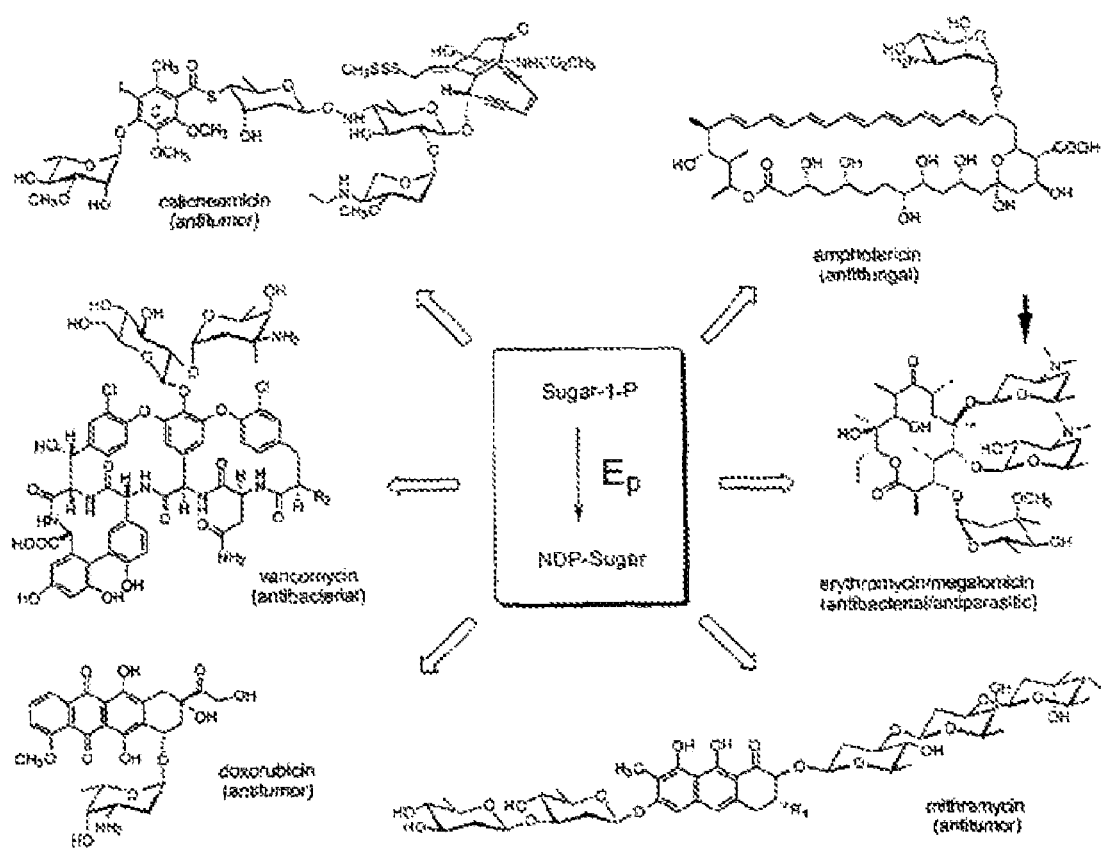
FIG. 5. Examples of pharmacologically important glycosylated metabolites. The general nucleotidylyl-transferase-catalyzed formation of NDP-sugars is highlighted in the box while the carbohydrate ligands of each metabolite are accentuated in red. Note the difference between erythromycin from *S. erythrea* and megalomicin from *M. megalomicea* is the addition of a third sugar megosamine (highlighted by the arrow).
Figure 10:
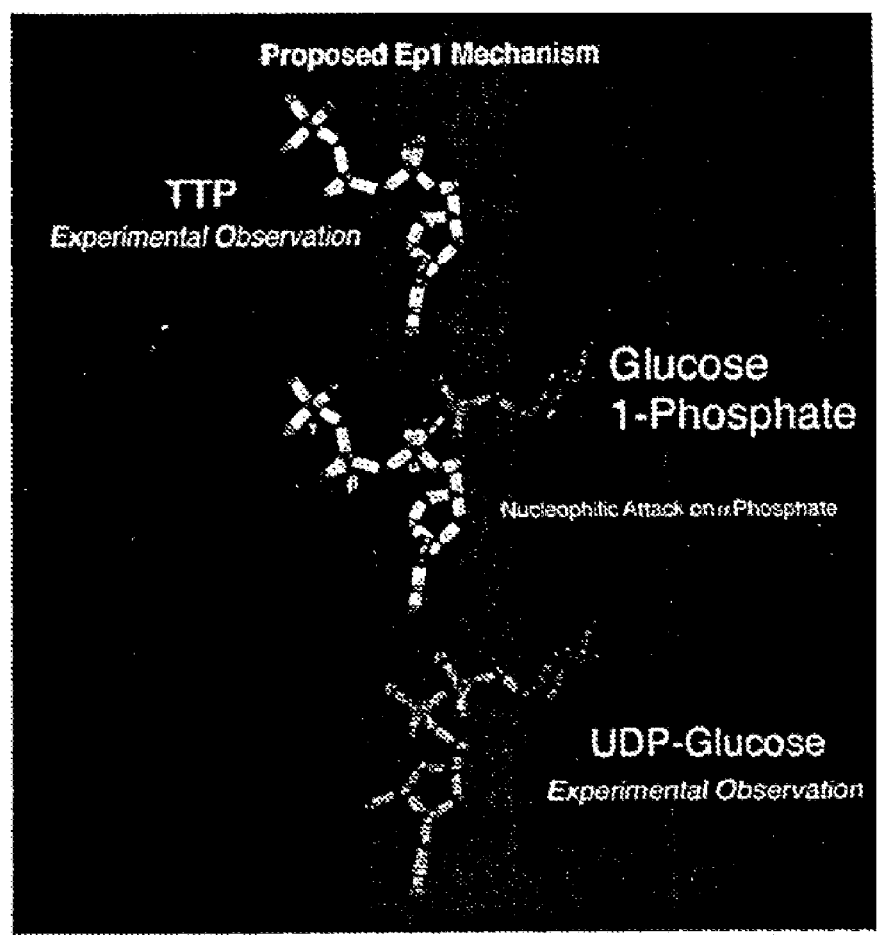
FIG. 10. (a) The proposed enzymatic mechanism based on the structures of substrate- and product-bound $E_p$. (b) The determination of $E_p$ steady state kinetic parameters. The conditions for the $E_p$ assay conditions and HPLC resolution of reactants and products were similar to those described in Jiang, J., Biggins, J. B. & Thorson, J. S. A General Enzymatic Method for the Synthesis of Natural and "Unnatural" UDP- and TDP-Nucleotide Sugars. J. Am. Chem. Soc. 122, 6803-6804 (2000). The Lineweaver-Burke plots of from assays (done in triplicate) varying dTTP concentration as a function of α-D-glucose-1-phosphate concentration (mM): 0.5 (□), 0.3 nM (○), 0.2 (◇), 0.1 (Δ) and 0.05 (■). (c) Secondary plot from FIG. 6b (dTTP $K_m$=0.7±0.2; $V_{max}$=0.03±0.01 mM min⁻¹). (d) The Lineweaver-Burke plots of assays (done in triplicate) varying α-D-glucose-1-phosphate concentration as a function of dTTP concentration (mM): 0.25 (□), 0.15 nM (○), 0.1 (◇), 0.05 (Δ) and 0.02 (■). (e) Secondary plot from FIG. 6d (α-D-glucose-1-phosphate $K_m$=0.3±0.1; $V_{max}$=0.03±0.02 mM min⁻¹).
Figure 10:
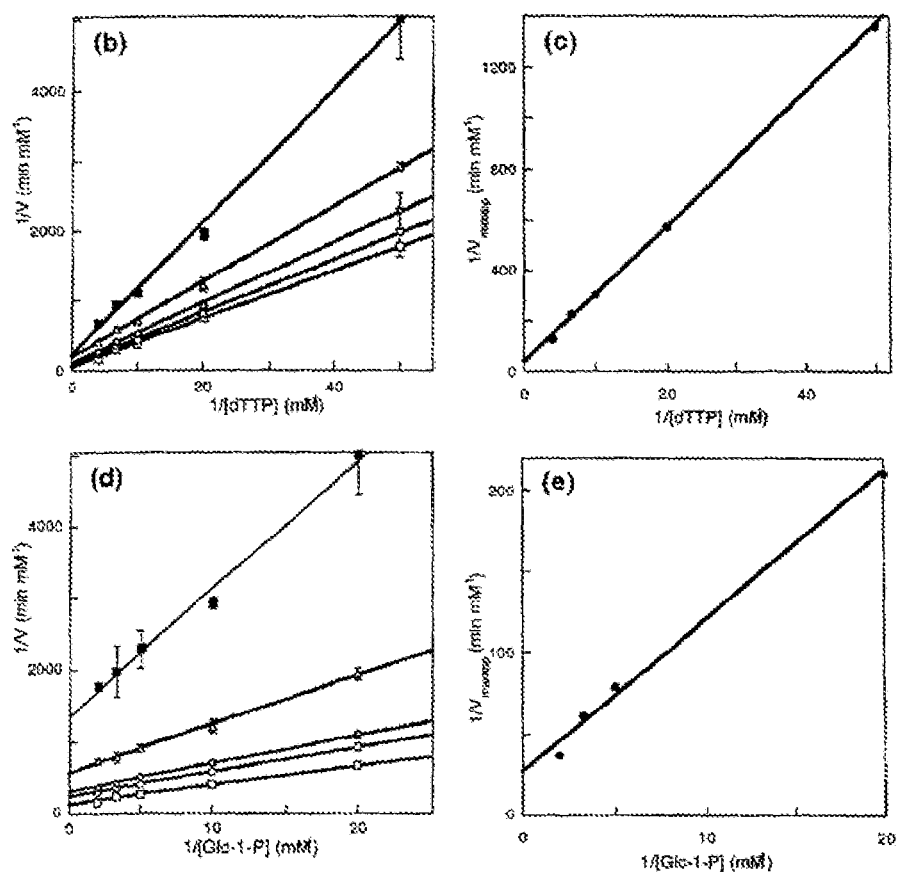

The $E_p$ product, UDP-Glc, is bound along the diameter of the surface pocket. The nucleoside sits in the active site in virtually the same conformation as the substrate dTTP, with the addition of a hydrogen bond between the 2'-hydroxyl of the ribose and the main chain O of Gly11. In the glucose-binding pocket, as illustrated on (NAT) FIG. 5b, the hydroxyl groups O2, O3 and O4 of the glucose moiety are directly hydrogen-bonded to protein residues, while O6 is bound to $E_p$ via a water molecule. Gln162 binds both O2 and O3, the main chain N of Gly147 binds both O3 and O4, and the main chain O of Val173 binds O4. The side chain of ThR201 is also close to both O2 and O3. In addition, four well-ordered water molecules, shown on FIG. 5b, bridge $E_p$ and the glucose moiety. Leu109, Leu89, and Ile200 make van der Waals contacts with the underside of the hexose ring and Trp224 and Tyr146 close the glucose binding pocket which would prevent bulkier sugars, for example disaccharides, from binding. In the $E_p$-UDP-Glc structure, the phosphate groups are now twisted away from their straight conformation in dTTP so that they can connect the nucleoside with the hexose—see also FIG. 10. The phosphates are also much more solvent exposed and do not interact with any main chain atoms, but instead, with the side chains of the positively charged Arg16, Lys163, and Arg195, as well as with water molecules.

Divalent Cation Binding Site

The activity of nucleotidyltransferases is strictly dependent on a divalent cation involved in catalysis via stabilizing the leaving $PP_i$ (See Kornfeld, S. & Glaser, L. J. Biol. Chem. 236, 1791-1794 (1961)). Crystallographic data generated by the present inventors allow for the identification of the location of this cofactor and, in this region, a $Mg^{+2}$ electron density feature, larger than a water molecule and chemically ideal for a metal location, was modeled. Indeed the $Mg^{+2}$ is 2.6 Å away from the β-phosphate oxygen and is also coordinated by the side chain of Gln26, main chain O of Gly11, main chain nitrogens of Ser13 and Gly14, and a water molecule. This region (particularly Gly10 to Gly15) is mostly disordered in the $E_p$-UDP-Glc structure, indicating that the $Mg^{+2}$, in addition to electrostatically stabilizing the leaving group, also plays a structural role in folding the substrate-binding region of $E_p$ around itself to fix the NTP at an optimal position for the catalytic event.

A Secondary dTTP-Binding Site and Possible Allosteric Control

The structure of $E_p$-dTTP, disclosed herein (FIG. 7), indicates that the $E_p$ tetramer binds eight molecules of dTTP—four in the active site pockets on top of the β-sheet, and four in an auxiliary sites at the interface between the subunits. FIG. 9c shows a close-up of a dTTP molecule in the auxiliary site. There are fewer contacts between $E_p$ and dTTP here than in the active site. As a result, CTP, which is not accepted by $E_p$, could easily fit in the auxiliary site. The dTTP base and the ribose in the secondary site interact with one $E_p$ monomer, including hydrogen bonds to the main chain N of Gly116 and Ser152, and van der Waals contacts with Leu46, Tyr115 and Ile249. The dTTP phosphates, on the other hand, interact primarily with residues of an adjacent $E_p$ monomer, including Arg220 and Gly221.

Several other nucleotidylyltransferases are under allosteric control by metabolites distinct from their products or substrates. The presence of an auxilary site strongly suggests that $E_p$ is also under allosteric control. Indeed, binding of an effector in this hydrophobic pocket at the monomer interface could alter the relative orientation of the $E_p$ monomers, thus altering the conformation or the access to the active site. Given the non-specific nature of the observed interactions, and the fact that nucleotidylyl-transferase effectors are generally not substrates, the putative $E_p$ allosteric effector is most likely not dTTP.

The $E_p$ Catalytic Mechanism

Before the present experiments, two conflicting hypotheses for nucleotidylyltransferase catalysis were suggested. Lindquist and co-workers proposed a ping-pong bi-bi mechanism for $E_p$, the necessary prerequisite for which is the formation of an enzyme-substrate covalent intermediate. (See Lindquist, L., Kaiser, R., Reeves, P. R. and Lindberg, A. A., Purification, Characterization and HPLC Assay of Salmonella Glucose-1-Phosphate Thymidylylphospherase from the cloned rfbA Gene, Eur. J. Biochem, 211, 763-770 (1993). Alternatively, in a related enzyme, Frey and co-workers had previously presented evidence for inverted geometry about the α-phosphate upon attack by Glc-1-P which led the authors to propose a single displacement mechanism for the entire nucleotidylyltransferase family. (Sheu, K.-F. R., Richard, J. P. & Frey, P. A. Stereochemical Courses of Nucleotidyl-transferase and Phosphotransferase Action. Uridine Diphosphate Glucose Pyrophosphorylase, Galactose-1-Phosphate Uridylyltransferase, Adenylate Kinase, and Nucleoside Diphosphate Kinase Biochem. 18, 5548-5556 (1979)).

In the present invention, a comparison of the topology of the $E_p$-bound substrate (dTTP) to the $E_p$-bound product (UDP-Glc) (FIG. 10a) suggests that the Glc-1-P oxygen nucleophile must directly attack the α-phosphate of dTTP. In this reaction, the formation of a phosphodiester bond on one side of the α-phosphate atom is simultaneous with the breaking of a phosphodiester bond on the opposing face (to give $PP_i$ as the leaving group). Consistent with an $S_{N2}$ type mechanism, the bond undergoing formation in the structure disclosed herein is "in-line" or 180 degrees away from the leaving group and thus, the two oxygen atoms bonded to the phosphate invert their geometry upon bond formation. Although the α-phosphate here is not chiral, both the reactant (substrate) and product topologies, as well as the architecture of the active site, clearly suggest that an inversion has occurred.

The present inventors evaluated the $E_p$ steady state kinetics in order to further probe the enzymatic mechanism. The intersecting patterns observed in FIG. 10b and FIG. 10d are consistent with the structural data in support of a single displacement mechanism rather than the previously postulated ping-pong bi bi (double displacement) mechanism. Finally, the $E_p$-dTTP crystals were soaked in a solution containing 2 mM of either Glc-1-P or D-Glc, in addition to the 2 mM dTTP and $Mg^{+2}$ already present. The glucose soaks did not significantly alter the electron density in the active site. On the other hand, Glc-1-P soaks quickly caused deterioration of the crystal diffraction quality. Data collected with crystals soaked for 30 min revealed electron density in the active site that was an average of the density in our EP-dTTP and $E_p$-UDP-Glc crystals. Therefore, the phosphate of Glc-1-P is necessary for binding by $E_p$, and the lack of any observable $E_p$-UMP covalent intermediate in these experiments further supports the single displacement mechanism.

Active-Site Engineering

Two sugar phosphates not utilized by wild-type $E_p$ and two additional sugar phosphates poorly utilized by the enzyme were selected to test rational engineering of $E_p$ substrate promiscuity. Specifically, 6-acetamido-6-deoxy-α-D-glucopyranosyl phosphate (FIG. 11 (86)) is not well-accepted and α-D-glucopyranuronic acid 1-(dihydrogen phosphate) (FIG. 11 (127)) is not accepted by $E_p$, and 2-acetamido-2-deoxy-α-D-glucopyranosyl phosphate (FIG. 11 (108)) and α-D-allopyranosyl phosphate (FIG. 11 (38)) lead to poor conversion. Because a representative "unnatural" sugar phosphate was believed to be efficiently converted only by wild-type $E_p$, 4-amino-4,6-dideoxy-α-D-glucopyranosyl phosphate (FIG. 11 (102)) was also tested with all mutants. Sugar phosphates not utilized by a wild-type enzyme, e.g., $E_p$, and sugar phosphates poorly utilized by the enzyme may be referred to herein as "unnatural" with respect to that enzyme.

Structure-based modeling reveals steric and/or electrostatic infringements may be the limiting factor in the conversion of "unnatural" sugar phosphates. In an attempt to relieve these constraints, three mutants were constructed. In particular, a Thr201Ala mutant and Glu162Asp were believed to decrease the steric interference at the sugar positions C-2 and/or C-3 for compounds (108) and (38), while a Trp224His substitution was designed to decrease steric constraints at C-6 of the substrate (e.g. compound (86)). Furthermore, the glucuronic acid derivative (127) offers the unique challenge of engineering electrostatic balance and the Trp224His variant was predicted to provide a partial positive charge to assist in (127)-binding in addition to steric relief. Alternatively, Asp111 (6 Å from the substrate C-6-OH) was predicted to result in the electrostatic repulsion of substrates containing a negative charge at the C-6 of the sugar phosphate. Thus, an additional mutant (Asp111Asn) was constructed to eliminate this effect.

As a rapid means to assay the entire pool of the four newly constructed mutants, the mutants were combined and the mixture directly tested for ability to convert compounds (2), (108), (89), (102), (38), and (127). FIG. 11 shows that the mutant pool was able to turn over all but one (5) of the sugar phosphates tested. Those substrates turned over include (86) and (127), the two sugar phosphates not accepted or poorly accepted by wild-type $E_p$.

The following nucleotide sugars were produced by the reactions of FIG. 11: (117) Thymidine 5'-(6-acetamido-6-deoxy-α-D-glucopyranosyl diphosphate) (HRMS (FAB): calc for $C_{18}H_{28}O_{16}N_3P_2$ 604.0945. found m/z 604.0953 (M+H)). (118) Uridine 5'-(6-acetamido-6-deoxy-α-D-glucopyranosyl diphosphate) (HRMS (FAB): calc for $C_{17}H_{26}O_{17}N_3P_2$ 606.0737. found m/z 606.0732 (M+H)). (130) Thymidine 5'-(α-D-glucopyran-6-uronic acid diphosphate) (HRMS (FAB): calc for $C_{16}H_{23}O_{17}N_2P_2$ 577.0472. found m/z 577.0465 (M+H)). (131) Uridine 5'-(α-D-glucopyran-6-uronic acid diphosphate) (HRMS (FAB): calc for $C_{15}H_{21}O_{18}N_2P_2$ 579.2774. found m/z 579.2775 (M+H)). (123) Thymidine 5'-(2-acetamido-2-deoxy-α-D-glucopyranosyl diphosphate) (HRMS (FAB): calc for $C_{18}H_{28}O_{16}N_3P_2$ 604.0945. found m/z 604.0951 (M+H)). (124) Uridine 5'-(2-acetamido-2-deoxy-α-D-glucopyranosyl diphosphate) (HRMS (FAB): calc for $C_{17}H_{26}O_{17}N_3P_2$ 606.0737. found m/z 606.0738 (M+H)). (125) Thymidine 5'-(4-amino-4,6-dideoxy-α-D-glucopyranosyl diphosphate) (HRMS (FAB): calc for $C_{16}H_{26}O_{14}N_3P_2$ 546.0889. found m/z 546.0895 (M+H)). (126) Uridine 5'-(4-amino-4,6-dideoxy-α-D-glucopyranosyl diphosphate). HRMS (FAB): calc for $C_{15}H_{24}O_{15}N_3P_2$ 548.0682. found m/z 548.0673 (M+H)) although data is not depicted for all products.

A deconvolution of the mutant pool, by individual mutant analysis, revealed the Trp224His mutation as responsible for converting both (86) and (127). Thr102Ala, on the other hand, was responsible for the 2-fold increase in the conversion of (108). The remaining two mutants (Asp41Asn and Glu162Asp, not shown in FIG. 11) failed to enhance conversion, over wild-type $E_p$, of any of the tested putative substrates. Yet, cumulatively, this small set of directed mutants was able to successfully turn over three of four targeted "unnatural" substrates. Of particular interest is the Trp224His mutant, which displays enhanced promiscuity without affecting wild-type traits. This $E_p$ variant will serve as an excellent foundation for second generation double mutants. Finally, the demonstrated ability to test mutant sets via pooling will rapidly expedite the development of this methodology.

In $E_p$, amino acids that make contacts or near contacts to the sugar in the active site include V173, G147, W224, N112, G175, D111, E162, T201, I200, E199, R195, L89, L89T, L109, Y146 and Y177. These amino acids may be mutated in order to alter the specificity of $E_p$, as demonstrated herein. Any mutation that alters the specificity may be made and tested, as taught herein, to determine its effect on the specificity of $E_p$ for its substrate and the efficiency of conversion of substrate to product.

Thus, the present invention includes a nucleotidylyl-transferase mutated at one or more amino acids selected from the group consisting of V173, G147, W224, N112, G175, D111, E162, T201, I200, E199, R195, L89, L89T, L109, Y146 and Y177. Preferably the nucleotidylyltransferase is $E_p$.

An embodiment of the present invention is directed to a nucleotidylyltransferase mutated such that it is capable of having a different substrate specificity than a non-mutated nucleotidylyltransferase. Examples include nucleotidylyltransferases having a substrate specificity for GTP, ATP, CTP, TTP or UTP. Further provided are methods of altering nucleotidylyltransferase substrate specificity comprising mutating the nucleotidylyltransferase at one or more amino acids selected from the group consisting of V173, G147, W224, N112, G175, D111, E162, T201, I200, E199, R195, L89, L89T, L109, Y146 and Y177. Preferably the nucleotidylyltransferase is $E_p$. Also provided are nucleotidylyl-transferases, so modified.

The present invention also includes purine or pyrimidine triphosphate type nucleotidylyltransferases set forth in FIG. 19, and purine or pyrimidine triphosphate type nucleotidylyltransferases mutated at one or more amino acids selected from the group consisting of V173, G147, W224, N112, G175, D111, E162, T201, I200, E199, R195, L89, L89T, L109, Y146 and Y177.

Further, sequence comparison reveals that many nucleotidyltransferases bear high degrees of sequence identity to $E_p$. The substrate specificity of such enzymes may be altered, using methods described herein for $E_p$, at amino acids that make contacts or near contacts to the sugar in the active site. These amino acids may be located via sequence comparison with $E_p$—the contact sites will often be those at the same relative position as V173, G147, W224, N112, G175, D111, E162, T201, I200, E199, R195, L89, L89T, L109, Y146 and Y177 in $E_p$. FIG. 19 provides a list of nucleotidyltransferases that bear high degrees of sequence identity to $E_p$. FIGS. 12 to 18 show the alignment of the $E_p$ sequence and those of other representative nucleotidyltransferases. Other nucleotidylyltransferases may also be mutated at one or more amino acids in their active sites, divalent cation binding sites and/or auxiliary sites.

Methods for mutating proteins are well-known in the art. For the present invention, it is preferable to perform site-directed mutagenesis on the nucleotide encoding the enzyme of interest. In this manner, and using the guidance provided herein, one of skill in the art can make mutations to the codons encoding the amino acids at the sites of the enzyme desired to be changed. Likewise, the use of site directed mutagenesis allows the worker to ensure that each codon desired to be changed is changed to encode a different amino acid from the wild-type molecule. In contrast, the use of random mutagenesis might result in mutated codons encoding the same amino acids as the wild-type codons, due to the degeneracy of the genetic code. Methods for manipulation and mutation of nucleotides, as well as for the expression of recombinant peptides are well known in the art, as exemplified by Sambrook et al., Molecular Cloning: A Laboratory Manual, Second Edition, Cold Spring Harbor Laboratory Press, 1989

References for nucleotidyltransferases in these Figures, include: AAB31755-Glc-1-P Cytitdylyltransferase from *Yersinia pseudotuberculosis*. See Thorson J S, Lo S F, Ploux O, He X & Liu H W J. Bacteriol. _176:_5483-5493 (1994) [94350832]; AAC39498-Man-1-P Guanylyltransferase from *Hypocrea jecorina*. Kruszewska, J. S., Saloheimo, M., Penttila, M. & Palamarczyk, G. Direct Submission; B72403-Glc-1-P adenylyltransferase from *Thermotoga maritima* (strain MSB8). Nelson K E, Clayton R A, Gill S R, Gwinn M L, Dodson R J, Haft D H, Hickey E K, Peterson J D, Nelson W C, Ketchum K A, McDonald L, Utterback T R, Malek J A, Linher K D, Garrett M M, Stewart A M, Cotton M D, Pratt M S, Phillips C A, Richardson D, Heidelberg J, Sutton G G, Fleischmann R D, Eisen J A, Fraser C M & et al Nature _399:_323-329 (1999) [99287316]; BAA34807-Man-1-P Guanylyltransferase from *Candida albicans*. Ohta, A. & Sudoh, M. Direct Submission; CAA06172-Glc-1-P Uridiylyltransferase from *Streptococcus pneumoniae*. Mollerach M, Lopez R & Garcia E J. Exp. Med. _188:_2047-2056 (1998) [99059828]; D83000-Glc-1-P thymidylyltransferase from *Pseudomonas aeruginosa* (strain PAO1); Stover C K, Pham X Q, Erwin A L, Mizoguchi S D, Warrener P, Hickey M J, Brinkman F S, Hufnagle W O, Kowalik D J, Lagrou M, Garber R L, Goltry L, Tolentino E, Westbrock-Wadman S, Yuan Y, Brody L L, Coulter S N, Folger K R, Kas A, Larbig K, Lim R, Smith K, Spencer D, Wong G K, Wu Z & Paulsen I T Nature _406:_959-964 (19100) [20437337]; E72229-N-acetylglucosamine-1-phosphate (NacGlc-1-P) Uridylyl-transferase from *Thermotoga maritima* (strain MSB8). Nelson K E, Clayton R A, Gill S R, Gwinn M L, Dodson R J, Haft D H, Hickey E K, Peterson J D, Nelson W C, Ketchum K A, McDonald L, Utterback T R, Malek J A, Linher K D, Garrett M M, Stewart A M, Cotton M D, Pratt M S, Phillips C A, Richardson D, Heidelberg J, Sutton G G, Fleischmann R D, Eisen J A, Fraser C M & et al Nature _399:_323-329 (1999) [99287316]; GalU_MY-CGE-Glc-1-P Uridylyltransferase from *Mycoplasma genitalium*. Fraser C M, Gocayne J D, White O, Adams M D, Clayton R A, Fleischmann R D, Bult C J, Kerlavage A R, Sutton G, Kelley J M & et al Science _270:_397-403 (1995) [96026346]; GCAD_BACSU-NacGlc-1-P Uridylyltransferase from *Bacillus subtilis*. Nilsson D, Hove-Jensen B & Arnvig K Mol. Gen. Genet. _218:_565-571 (1989) [90066361]; GLGC_BACSU-Glc-1-P Adenylyltransferase from *Bacillus subtilis*. Kiel J A, Boels J M, Beldman G & Venema G Mol. Microbiol. _11:_203-218 (1994) [94195107]; RFB_SALTY-Glc-1-P Cytidylyltransferase from *Salmonella serovar typhimurium* (strain LT2). Jiang X M, Neal B, Santiago F, Lee S J, Romana L K & Reeves P R Mol. Microbiol. _5:_ 695-713 (1991) [91260454].

According to one embodiment of the present invention mutations at amino acid L89T were tested. Such mutations increased the yield of allo-, altro-, talo-, gulo- and ido-derivatives. Wild-type and/or this mutant also led to the production of the new nucleotide sugar compounds set forth in FIGS. 20(*a*) and (*b*). Methods of production of such compounds and of the mutant nucleotidylyltransferase are as set forth herein with regard to other compounds and mutant nucleotidylyltransferase. In particular, the compounds may be produced by synthesizing the corresponding sugar phosphate followed by $E_p$ catalyzed conversion of the sugar phosphate to the new products.

The present invention includes the nucleotide sugars of FIGS. 20(*a*) and 20(*b*), their corresponding sugar phosphates and nucleotidylyltransferases mutated at L89T, which may convert such sugar phosphates to a nucleotide sugar.

Glycorandomization of Natural Product-Based Metabolites

The wild-type glycosyltransferases in secondary metabolism show significant flexibility with respect to their NDP-sugar donors. Coupled with the presented $E_p$-catalyzed production of NDP-sugar donor libraries and the appropriate aglycon, a diverse library of "glycorandomized" structures based upon a particular natural product scaffold can be rapidly generated.

Accordingly, the present invention is also directed to nucleotide sugar libraries including two or more of the nucleotide sugars described herein. More preferably the nucleotide sugars are nucleotide sugars made by the methods described herein, preferably using a natural or mutated nucleotidylyltransferase as a catalyst. The present invention also includes in vitro glycorandomization using such sugar libraries.

Exploiting the promiscuity of wild type $E_p$ and utilizing the ability conferred by the methods of the present invention to rationally engineer variants able to utilize sugar phosphates not previously usable, libraries of previously unavailable nucleotide sugars may be generated. The ability to generate a set of $E_p$ variants provides the subsequent ability to generate, in a simple one pot reaction, diverse libraries of NDP-sugars. Both sugars that were unknown prior to the present invention and those that could not be synthesized in vitro prior to the present invention may be synthesized using the methods of the present invention. Such libraries of NDP-sugars, in conjunction with downstream glycosyltransferases, form the basis for the in vitro manipulation of metabolite sugar ligands in a combinatorial fashion (or "glycorandomization").

For example, a diverse library of "glycorandomized" structures based upon the known antitumor agent mithramycin (FIG. 5) may be constructed. Beginning with a small pool of sugar phosphates, e.g., 25 different sugar phosphates, the anticipated library size would be the result of combining 25 different sugars at 5 different positions on mithramycin to give $25^5$, or >9.7 million, distinct mithramycin-based variants. Furthermore, as alterations of the carbohydrate ligands of biologically active metabolites can lead to drastically different pharmacological and/or biological properties, this approach has significant potential for drug discovery. As an example of alterations of the carbohydrate ligands of biologically active metabolites producing dramatically different pharmacological properties, the structure of 4-epidoxorubicin differs from that of doxorubicin, which is more toxic, only in carbohydrate ligands. As an example of alterations of the carbohydrate ligands of biologically active metabolites producing dramatically different biological properties, the structure of erythromycin, an antibiotic, differs from that of megalomicin, a compound with antiviral and antiparasitic activity, only in carbohydrate ligands.

An embodiment of the invention includes incubating a glycotransferase with one or more of the sugars of a nucleotide sugar library according to the present invention, and a molecule capable of being glycosylated.

The present inventors have discovered that $E_p$ is pliable in terms of its substrate specificity. The present inventors have also discovered the three dimensional structure of $E_p$ and the molecular details of $E_p$ substrate recognition. The present inventors have invented methods of engineering or modifying $E_p$ to vary its specificity in a directed manner, conferring the ability to rationally engineer variants able to utilize sugar phosphates not previously usable. The present inventors have also invented a method for the synthesis of desired nucleotide sugars using both natural and engineered $E_p$. Thus, the present invention will likely broadly impact efforts to understand and exploit the biosynthesis of glycosylated bioactive natural products, many of which are pharmacologically useful. The ability conferred by the methods of the present invention to alter nucleotidylyltransferase specificity by design allows the creation of promiscuous in vitro systems, which could provide large and diverse libraries of potentially new bioactive metabolites.

The present invention will now be illustrated by the following examples, which show how certain specific representative embodiments of the compounds and methods of the present invention, the compounds, intermediates, process steps, and the like being understood as examples that are intended to be illustrative only. In particular, the invention is not intended to be limited to the conditions, order of the steps and the like specifically recited herein. Rather, the Examples are intended to be illustrative only.

EXAMPLES

General Methods

Infrared spectra were recorded on a Perkin Elmer 1600 series FTIR spectrophotometer. $^1$H NMR spectra were obtained on a Bruker AMX 400 (400 MHz) and are reported in parts per million (δ) relative to either tetramethylsilane (0.00 ppm) or CDCl$_3$ (7.25 ppm) for spectra run in CDCl$_3$ and D$_2$O (4.82 ppm) or CD$_3$OD (3.35 ppm) for spectra run in D$_2$O. Coupling constants (J) are reported in hertz. $^{13}$C NMR are reported in δ relative to CDCl$_3$ (77.00 ppm) or CD$_3$OD (49.05 ppm) as an internal reference and $^{31}$P NMR spectra are reported in δ relative to H$_3$PO$_4$ (0.00 ppm in D$_2$O). Routine mass spectra were recorded on a PE SCIEX API 100 LC/MS mass spectrometer and HRMS was accomplished by the University of California, Riverside Mass Spectrometry Facility. Optical rotations were recorded on a Jasco DIP-370 polarimeter using a 1.0 or 0.5 dm cell at the room temperature (25° C.) and the reported concentrations. Melting points were measured with Electrothermal 1A-9100 digital melting point instrument. Chemicals used were reagent grade and used as supplied except where noted. Analytical TLC was performed on either E. Merck silica gel 60 F$_2$54 plates (0.25 mm) or Whatman AL Sil G/UV silica gel 60 plates. Compounds were visualized by spraying I$_2$/KI/H$_2$SO$_4$ or by dipping the plates in a cerium sulfate-ammonium molybdate solution followed by heating. Liquid column chromatography was performed using forced flow of the indicated solvent on E. Merck silica gel 60 (40-63 μm) and high pressure liquid chromatography was performed on a RAININ Dynamax SD-200 controlled with Dynamax HPLC software.

Although the above methods of IR, NMR, Mass Spec, and HRMS were those used in the examples of the present invention, it would be known to those skilled in the art that other instruments, conditions, types of techniques, and the like may be used to visualize compounds, identify compounds and determine their concentrations and purity.

Methyl 2,3,4-tri-O-acetyl-6-chloro-6-deoxy-α-D-glucopyranoside (7)

Compound 7 was prepared as previously described from methyl α-D-glucopyranoside (5), (7.26 g, 27.7 mmol) in 82% yield (Anisuzzaman, A. K. M.; Whistler, R. L. Carbohydr. Res. 1978, 61, 511-518). R$_f$=0.34 (2:1 hexane/EtOAc); $[α]_D$=147° (c=1, CHCl$_3$); $^1$H NMR (CDCl$_3$) 5.46 (t, 1H, J=9.5 Hz), 4.98 (m, 2H), 4.02 (m, 1H), 3.82 (dd, 1H, J=12.0, 2.5 Hz), 3.73 (dd, 1H, J=12.0, 6.5 Hz), 3.43 (s, 3H), 2.06 (s, 3H), 2.04 (s, 3H), 1.99 (s, 3H); $^{13}$C NMR (CDCl$_3$) 170.45, 170.42, 169.96, 96.98, 77.67, 71.08, 70.46, 70.32, 69.13, 55.85, 43.81, 21.07, 21.05. MS: calcd for C$_{13}$H$_{19}$O$_8$ClNa 360.9. found m/z 360.9 (M+Na).

1,2,3,4-tetra-O-benzoyl-6-deoxy-α,β-D-glucopyranose (8)

Compound 7 (2.9 g, 8.57 mmol) was dissolved in 100 mL dry THF and 1.0 g LiAlH$_4$ slowly added. The corresponding mixture was refluxed for 10 hr under argon and the reaction quenched with 10 mL MeOH and concentrated. The concentrate was then dissolved in a mixture of 40 mL acetic acid and 10 mL 1N HCl and the reaction stirred at 95° C. for 10 hrs. The reaction was neutralized with 1N NaOH and the organics concentrated, dried over MgSO$_4$ and purified by silica gel chromatography (4:1 CHCl$_3$/MeOH). The resulting product was dissolved in 50 mL dry pyridine, 8.0 mL benzoyl chloride (68.9 mmol) was added and the reaction stirred overnight at room temperature. To the reaction mixture was added to 100 mL saturated NaHCO$_3$ solution and the mixture extracted with CHCl$_3$ (3×100 mL). The combined organics were washed with H$_2$O (50 mL), brine (50 mL), dried over Na$_2$SO$_4$, concentrated and purified by silica gel chromatography (2:1 hexane/EtOAc) to give 2.8 g (56.2%) of the desired product 8 (α/β=3:2). This mixture was utilized directly for the next step without further resolution. MS: calcd for C$_{34}$H$_{28}$O$_9$Na 630.2. found m/z 630.2 (M+Na).

Methyl 2,3,6-tri-O-benzoyl-β-D-galactopyranoside (14)

Methyl β-D-galactopyranoside (13), 3.7 g, 19 mmol) gave the desired product 14 (5.2 g, 54%) and 2.3 g (19%) of the corresponding tetra benzoylated derivative as described in Reist, E. J.; Spencer, R. R.; Calkins, D. F.; Baker, B. R.; Goodman, L. J. Org. Chem. 1965, 2312-2317. [α]$_D$=7.3° (c=1, CHCl$_3$); $^1$H NMR (CDCl$_3$) 8.18-7.92 (m, 6H), 7.52-7.38 (m, 8H), 5.77 (dd, 1H, J=8.0, 10.4 Hz), 5.37 (dd, 1H, J=3.2, 10.3 Hz, 1H), 4.72 (dd, 1H, J=6.6, 11.4 Hz), 4.62 (dd, 1H, J=6.4, 11.4 Hz), 4.66 (d, 1H, J=7.9 Hz), 4.36 (m, 1H), 4.08 (t, 1H, J=6.5 Hz), 3.55 (s, 3H), 2.50 (br, 1H, .about.OH); $^{13}$C NMR (CDCl$_3$): 166.9, 166.3, 165.9, 133.9, 133.7, 133.6, 130.4, 130.3, 130.2, 130.1, 130.0, 129.9, 129.4, 129.0, 128.9, 128.8, 128.7, 102.6, 74.6, 72.8, 69.9, 67.7, 63.3, 57.3; MS: calcd for C$_{28}$H$_{26}$O$_9$Na 529.1. found m/z 529.0 (M+Na). (Garegg, P. J.; Oscarson, S. Carbohydr. Res. 1985, 137, 270-275.)

Methyl 2,3,6-tri-O-benzoyl-4-O-pentafluorophenoxythiocarbonyl-β-D-galactopyranoside (15)

Methyl 2,3,6-tri-O-benzoyl-β-D-galactopyranoside (14), (2.3 g, 4.5 mmol) gave 2.88 g (86%) purified product 15 as described in Kanie, O.; Crawley, S. C.; Palcic, M. M.; Hindsgaul, O. Carbohydr. Res. 1993, 243, 139-164. [α]$_D$=9° (c=1, CHCl$_3$); $^1$H NMR (CDCl$_3$) 8.04 (d, 2H, J=7.7 Hz), 7.98 (d, 2H, J=7.6 Hz), 7.93 (d, 2H, J=7.7 Hz), 7.58-7.49 (m, 3H), 7.44-7.34 (m, 6H), 6.23 (d, 1H, J=3.2 Hz), 5.78 (dd, 1H, J=7.9 Hz), 5.70 (dd, 1H, J=3.3, 10.4 Hz), 4.75-4.71 (m, 2H), 4.44 (dd, 1H, J=7.4, 11.0 Hz), 4.37 (t, 1H, J=7.0 Hz), 3.57 (s, 3H); $^{13}$C NMR (CDCl$_3$) 192.5, 166.3, 166.0, 165.5, 134.1, 133.9, 133.7, 130.3, 130.2, 130.1, 129.6, 129.5, 128.9, 128.8, 128.6, 102.7, 79.9, 71.3, 71.1, 69.9, 61.5, 57.6; MS: calcd for C$_{35}$H$_{25}$O$_9$SF$_5$Na 755.1. found m/z 755.1 (M+Na).

Methyl 2,3,6-tri-O-benzoyl-4-deoxy-β-D-galactopyranoside (16)

Methyl 2,3,6-tri-O-benzoyl-4-O-pentafluorophenoxythiocarbonyl-β-D-galactopyranoside (15), (2.65 g, 3.62 mmol) gave 1.53 g (86%) of the desired compound 16 as described in Kanie, O; Crawley, S. C.; Palcic, M. M.; Hindsgaul, O. Carbohydr. Res. 1993, 243, 139-164. [α]$_D$=57.4° (c=1, CHCl$_3$); $^1$H NMR (CDCl$_3$) 8.07 (d, 2H, J=7.3 Hz), 8.00 (d, 2H, J=7.4 Hz), 7.95 (d, 2H, J=7.3 Hz), 7.58 (t, 1H, J=7.4 Hz), 7.53-7.40 (m, 4H), 7.39-7.34 (m, 4H), 5.41 (m, 2H), 4.60 (d, 1H, J=7.5 Hz), 4.51 (dd, 1H, J=5.8, 11.6 Hz), 4.46 (dd, 1H, J=4.4, 11.6 Hz), 4.06 (m, 1H), 2.47 (m, 1H), 1.88 (m, 1H); $^{13}$C NMR (CDCl$_3$) 166.7, 166.3, 165.9, 133.7, 133.6, 133.5, 130.2, 130.1, 130.0, 129.7, 128.9, 128.8, 128.7, 102.6, 72.9, 71.9, 70.0, 66.2, 57.4, 33.4; MS: calcd for C$_{26}$H$_{26}$O$_8$Na 513.1. found m/z 513.0 (M+Na). (Lin, T.-H.; Kovac, P.; Glaudemans, C. P. J. Carbohydr. Res. 1989, 141, 228-238.)

1,2:5,6-Di-O-isopropylidene-3-O-(methylthio)thiocarbonyl-α-D-glucofuranose (22)

Compound 22 was prepared as previously described in 93% yield (see Zhiyuan, Z.; Magnusson, G. Carbohydr. Res. 1994, 262, 79-101). [α]$_D$=-34° (c=1, CHCl$_3$); $^1$H NMR (CDCl$_3$) 5.91 (m, 2H), 4.68 (d, 1H, J=3.77 Hz), 4.31 (m, 1H), 4.10 (dd, 1H, J=5.6, 8.7 Hz), 4.05 (dd, 1H, J=4.6, 8.7 Hz), 2.59 (s, 3H), 1.57 (s, 3H), 1.41 (s, 3H), 1.32 (s, 3H), 1.31 (s, 3H); $^{13}$C NMR (CDCl$_3$) 112.8, 109.7, 105.4, 84.6, 83.1, 80.1, 72.7, 67.3, 27.2, 27.0, 26.6, 25.6, 19.7; MS: calcd for C$_{14}$H$_2$O$_6$S$_2$Na 373.0. found m/z 372.8 (M+Na).

3-Deoxy-1,2:5,6-di-O-isopropylidene-α-D-glucofuranose (23)

To a solution containing 22 (2.6 g, 7.4 mmol) and 120 mg of AIBN (0.73 mmol) in 50 mL dry toluene, 5 mL (n-Bu)$_3$SnH (18.6 mmol) was added and the mixture refluxed for 5 hrs under argon. The reaction was then concentrated and the residue was applied to a silica gel column (10:1-8:1 hexane/EtOAc) to give 1.58 g substantially pure product 23 (87%). [α]$_D$=-9.2° (c=1, CHCl$_3$); $^1$H NMR (CDCl$_3$) 5.82 (d, 1H, J=3.7 Hz), 4.76 (t, 1H, J=4.2 Hz), 4.19-4.07 (m, 3H), 3.84 (m, 1H), 2.18 (dd, 1H, J=3.9, 13.2 Hz), 1.77 (m, 1H), 1.51 (s, 3H), 1.42 (s, 3H), 1.35 (s, 3H), 1.30 (s, 3H); $^{13}$C NMR (CDCl$_3$) 109.6, 107.9, 104.0, 79.4, 77.0, 75.7, 65.6, 33.7, 25.7, 24.9, 24.5, 23.6; MS: calcd for C$_{12}$H$_2$O$_5$Na 267.1. found m/z 266.8 (M+Na). (Barton, D. H. R.; McCombie, S. W. J. Chem. Soc. Perkin Trans. 1 1975, 1574.)[22]

1,2,4,6-tetra-O-benzoyl-3-deoxy-α-D-glucofuranose (24)

Compound 23 (0.59 g, 2.4 mmol) was treated with a mixture of 9 mL CF$_3$CO$_2$H and 1 mL of water for 2 hours at 25° C. The reaction was concentrated under reduced pressure, coevaporated with water (2×5 mL) and further dried under vacuum. This material was dissolved in 20 mL of anhydrous pyridine, to which 2.2 mL (19.3 mmol) of benzoyl chloride was added. The mixture was stirred for 10 hr, pyridine removed in vacuo and the remaining oil diluted with 200 mL EtOAc. The organics washed with saturated NaHCO$_3$ (50 mL), water (40 mL), brine (40 mL), dried over Na$_2$SO$_4$, and purified with silica gel chromatography (3:1 hexanes/EtOAc) to give 0.89 g product which was used directly without further characterization.

General Strategy for Formation of Protected Ethyl 1-thio-β-D-hexopyranosides.

Protected ethyl 1-thio-β-D-hexopyranosides may be formed in accordance with the present invention by the following reaction. A mixture of protected monosaccharide, (ethylthio)-trimethylsilane, and zinc iodide are refluxed for 1½ to 2½ hrs. The reaction is then cooled, diluted, washed, preferably with saturated NaHCO$_3$ solution, water, and then brine. The organics are then dried, and preferably concentrated and resolved to give the desired product. Other conditions, reagents, method steps, solutions and the like of the present method, may be used in accordance with the present invention.

In a typical reaction, a mixture of 3 mmol protected monosaccharide, 1.5 mL (ethylthio)trimethylsilane (9.2 mmol) and 1.95 g zinc iodide (6.1 mmol) in 30 mL dry dichloromethane was refluxed for 2 hrs under argon atmosphere. The reaction was then cooled and diluted with 200 mL CH$_2$Cl$_2$, washed successively with saturated NaHCO$_3$ solution (2×30 mL), water (30 mL) and brine (30 mL). The organics were dried over Na$_2$SO$_4$, concentrated and resolved by silica gel chromatography (8:1 hexanes/EtOAc) to give the desired product.

Ethyl 2,3,4-tri-O-benzoyl-6deoxy-1-thio-β-D-glucopyranoside (9)

Compound 8 (1 g, 1.72 mmol) gave 731 mg (81.5%) of the desired product. R$_f$=0.56 (2:1 hexane/EtOAc); [α]$_D$=7° (c=1.0, CHCl$_3$); $^1$H NMR (CDCl$_3$) 8.00-7.94 (m, 4H), 7.82 (dd, 1H, J=1.4, 7.1 Hz), 7.52 (m, 2H), 7.42-7.37 (m, 5H), 7.23 (m, 2H), 5.85 (t, 1H, J=9.6 Hz), 5.54 (t, 1H, J=9.7 Hz), 5.35 (t, 1H, J=9.6 Hz), 4.80 (d, 1H, J=9.9 Hz), 4.92 (m, 1H), 2.82 (m, 2H), 1.40 (d, 3H, J=6.2 Hz), 1.26 (t, 3H, J=7.4 Hz); $^{13}$C NMR (CDCl$_3$) 164.8, 164.4, 164.2, 132.3, 132.2, 132.1, 128.8, 128.7, 128.6, 128.2, 128.0, 127.9, 127.4, 127.3, 127.2, 82.3, 73.9, 73.1, 72.7, 69.8, 22.9, 16.8, 13.7; MS: calcd for C$_{29}$H$_{28}$O$_7$SNa 543.1. found m/z 542.9 (M+Na).

Ethyl 2,3,6-tri-O-benzoyl-4-deoxy-1-thio-β-D-glucopyranoside (17)

Compound 16 (1.5 g, 3.06 mmol) gave 1.24 g desired product (77.8%). [α]$_D$=56.9° (c=1, CHCl$_3$); $^1$H NMR (CDCl$_3$) 8.08 (d, 2H, J=8.0 Hz), 8.00 (d, 2H, J=8.2 Hz), 7.96 (d, 2H, J=8.0 Hz), 7.60 (t, 1H, J=6.9 Hz), 7.55-7.48 (m, 4H), 7.42-7.36 (m, 4H), 5.50-5.44 (m, 2H), 4.76 (d, 1H, J=9.0 Hz), 4.51 (dd, 1H, J=5.7, 1.9 Hz), 4.46 (dd, 1H, J=4.4, 11.9 Hz), 4.12 (m, 1H), 2.84-2.69 (m, 2H), 2.53 (m, 1H), 1.91 (m, 1H), 1.27 (t, 3H, J=7.6 Hz); $^{13}$C NMR (CDCl$_3$) 166.6, 166.2, 165.9, 133.7, 133.6, 130.2, 130.1, 129.8, 129.7, 128.8, 184.2, 74.0, 73.0, 71.5, 66.3, 33.6, 24.7, 15.4; MS: calcd for C$_{29}$H$_{28}$O$_7$SNa 543.1. found m/z 543.1 (M+Na).

Ethyl 2,4,6-tri-O-benzoyl-3-deoxy-1-thio-β-D-glucopyranoside (25)

Compound 24 (0.89 g, 1.5 mmol) gave 0.79 substantially pure product (90%). $^1$H NMR (CDCl$_3$) 8.14-7.96 (m, 6H), 7.63-7.40 (m, 9H), 5.32-5.21 (m, 2H), 4.79 (d, 1H, J=9.7 Hz), 4.67 (dd, 1H, J=2.9, 12.0 Hz), 4.46 (dd, 1H, J=6.0, 12.0 Hz), 4.09 (m, 1H), 2.96 (m, 1H), 2.78 (m, 2H), 2.00 (m, 1H), 1.27 (t, 3H, J=7.4 Hz); MS: calcd for C$_{29}$H$_{28}$O$_7$SNa 543.1. found m/z 543.1 (M+Na).

Ethyl 3,4,6-tri-O-benzoyl-2-deoxy-1-thio-β-D-glucopyranoside (40)

Compound 39 (1.72 g, 2.96 mmol) gave two products, 0.74 g the desired β isomer (48% yield) and 0.5 g the β isomer (32% yield). β isomer: [α]$_D$=120° (c=1, CHCl$_3$); IR: 2962, 2871, 1723, 1601, 1450, 1314, 1270, 1107, 708, 686 cm$^{-1}$; $^1$H NMR (CDCl$_3$) 8.06-7.93 (m, 6H), 7.51-7.36 (m, 9H), 5.69-5.64 (m, 1H), 5.60-5.56 (m, 2H), 4.80 (m, 1H), 4.57 (dd, 1H, J=2.7, 12.0 Hz), 4.52 (dd, 1H, J=12.0, 5.5 Hz), 2.72-2.54 (m, 3H), 2.41-2.35 (m, 1H), 1.30 (t, 3H, J=7.4 Hz); $^{13}$C NMR (CDCl$_3$): 165.2, 164.6, 164.5, 132.3, 132.1, 132.0, 128.8, 128.7, 128.6, 128.4, 128.1, 127.4, 127.3, 78.5, 69.4, 67.3, 62.4, 34.4, 23.8. MS: calcd for C$_{29}$H$_{28}$O$_7$SNa 543.1. found m/z 543.1 (M+Na). α isomer: [α]$_D$=−46° (c=1, CHCl$_3$) IR: 2961, 2923, 1732, 1717, 1269, 1108, 1099, 708, 685 cm$^{-1}$. $^1$H NMR (CDCl$_3$) 8.12-7.93 (m, 6H), 7.54-7.37 (m, 9H), 5.56 (t, 1H, J=9.7 Hz), 5.46 (m, 1H), 4.87 (dd, 1H, J=11.8, 1.7 Hz), 4.60 (dd, 1H, J=3.1, 12.0 Hz), 4.48 (dd, 1H, J=5.9, 12.0 Hz), 4.06 (m, 1H), 2.83-2.68 (m, 2H), 2.65-2.64 (m, 1H), 2.08 (m, 1H), 1.32 (t, 3H, J=7.4 Hz); $^{13}$C NMR (CDCl$_3$) 166.6, 166.3, 165.9, 134.1, 133.8, 133.7, 133.4, 130.6, 130.1, 130.0, 129.7, 129.5, 128.9, 128.7, 80.3, 77.1, 73.0, 70.5, 64.3, 37.1, 25.5, 15.5. MS: calcd for C$_{29}$H$_{28}$O$_7$SNa 543.1. found: m/z 543.0 (M+Na).

Ethyl 2,3,4,6-tetra-O-benzoyl-1-thio-β-D-gulopyranoside (30)

Compound 29 (0.75 g, 1.07 mmol) gave 0.65 g of the desired compound (94%). $^1$H NMR (CDCl$_3$) 8.18-7.87 (m, 8H), 7.54-7.27 (m, 12H), 5.95 (t, J=3.5 Hz, 1H), 5.67 (dd, J=3.3, 10.3 Hz, 1H), 5.61 (m, 1H), 5.27 (d, J=10.3 Hz, 1H), 4.64 (m, 1H), 4.50 (dd, J=3.8, 9.5 Hz, 1H), 2.84 (m, 2H), 1.34 (t, J=7.4 Hz, 3H); MS: calcd for C$_{36}$H$_{32}$O$_9$SNa 663.2. found m/z 663.1 (M+Na).

Ethyl 2,3,4,6-tetra-O-benzoyl-1-thio-β-D-allopyranoside (35)

Compound 34 (0.97 g, 1.38 mmol) gave 0.85 g desired product (95%). [α]$_D$=12.7° (c=1, CHCl$_3$); $^1$H NMR (CDCl$_3$) 8.07-7.32 (m, 20H), 6.26 (t, J=2.8 Hz, 1H), 5.56 (dd, J=2.8, 10.1 Hz, 1H), 5.51 (dd, J=2.9, 10.1 Hz, 1H), 4.71 (dd, J=2.5, 12.0 Hz, 1H), 4.56 (m, 1H), 4.47 (dd, J=5.3, 12.0 Hz, 1H), 2.80 (m, 2H), 1.29 (t, J=7.5 Hz, 3H); $^{13}$C NMR (CDCl$_3$) 171.6, 166.6, 165.7, 165.2, 134.0, 133.9, 133.8, 133.6, 130.5, 130.3, 130.2, 130.1, 130.0, 129.9, 129.6, 129.3, 129.2, 128.9, 128.8, 81.3, 73.7, 69.7, 68.9, 68.0, 63.9, 24.3, 15.5; MS: calcd for C$_{36}$H$_{32}$O$_9$SNa 663.1. found m/z 663.0 (M+Na).

General Strategy for O-Benzoyl to O-Benzyl Conversion. O-Benzoyl may be converted to O-Benzyl according to the following method or other methods known to those skilled in the art. Protected ethyl 1-thio-β-D-hexopyranoside are dissolved in dry MeOH and toluene to which a sodium methoxide solution is added. The mixture is then stirred, preferably for about 1½ to 2½ hrs at room temperature and optionally neutralized. The organics are preferably concentrated and the corresponding unprotected 1-ethylthio-β-D-glucopyranoside purified, and then dissolved. NaH is then added and the reaction is stirred for about 1½ to 2½ hrs at room temperature followed by the addition of benzyl bromide and stirring, preferably overnight. The mixture may then be diluted, washed with H$_2$O, brine, and organics, dried, concentrated, and purified to give the purified product.

Other conditions, reagents, solutions and the like of the present method, or other methods known to those skilled in the art may be used in accordance with the present invention.

In a typical reaction, 1.4 mmol of protected ethyl 1-thio-β-D-hexopyranoside was dissolved in 10 mL dry MeOH and 3 mL toluene to which 0.25 mL of a sodium methoxide solution (25% NaOMe in methanol) was added. The mixture was stirred for 2 hr at room temperature and neutralized with 1N acetic acid. The organics were concentrated and the corresponding unprotected 1-ethylthio-β-D-glucopyranoside purified by silica gel chromatography (10:1 hexane/EtOAc) which was then dissolved in 10 mL dry DMF and 323 mg 65% NaH (8.0 mmol) was added. The reaction was stirred for 2 hr at room temperature followed by the addition of 1 mL benzyl bromide (8.3 mmol) and continued stirring overnight. The mixture was then diluted with 150 mL EtOAc, washed with H$_2$O (30 mL), brine (30 mL) and the organics dried over Na$_2$SO$_4$, concentrated and purified by silica gel chromatography (10:1 hexane/EtOAc) to give the purified product.

Ethyl 2,3,4-tri-O-benzyl-6-deoxy-1-thio-β-D-glucopyranoside (10)

Compound 9 (0.7 g, 1.35 mmol) gave 480 mg (75%) of purified product. [α]$_D$=5.8° (c=1.0, CHCl$_3$); $^1$H NMR (CDCl$_3$) 7.40-7.29 (m, 15H), 4.95-4.85 (m, 4H), 4.77 (d, 1H, J=10.2 Hz), 4.65 (d, 1H, J=10.5 Hz), 4.48 (d, 1H, J=9.8 Hz), 3.66 (t, 1H, J=8.9 Hz), 3.46-3.38 (m, 2H), 3.23 (t, 1H, J=9.2 Hz), 2.84-2.70 (m, 2H), 1.35-1.27 (m, 2H); $^{13}$C NMR (CDCl$_3$): 138.9, 138.5, 138.4, 128.9, 128.8, 128.7, 128.4, 128.3, 128.2, 128.1, 86.8, 85.2, 83.8, 82.5, 76.2, 75.9, 75.8, 25.4, 18.5, 15.5. MS: calcd for C$_{29}$H$_{34}$O$_4$SNa 501.2. found m/z 501.1 (M+Na).

Ethyl 2,3,6-tri-O-benzyl-4-deoxy-1-thio-β-D-glucopyranoside (18)

Compound 17 (0.85 g, 1.63 mmol) gave 675 mg (86%) purified product. [α]$_D$=40° (c=1, CHCl$_3$), $^1$H NMR (CDCl$_3$) 7.45-7.31 (m, 1SH), 4.92 (d, 1H, J=10.3 Hz), 4.86 (d, 1H, J=10.3 Hz), 4.74 (d, 1H, J=11.7 Hz), 4.69 (d, 1H, J=11.7 Hz), 4.62 (d, 1H, J=12.0 Hz), 4.58 (d, 1H, J=12.0 Hz), 4.49 (d, 1H, J=9.7 Hz), 3.69-3.62 (m, 3H), 3.50 (m, 1H), 3.36 (dd, 1H, J=8.7, 9.4 Hz), 2.82-2.75 (m, 2H), 2.23 (m, 1H), 1.54 (m, 1H), 1.35 (t, 3H, J=7.5 Hz); $^{13}$C NMR (CDCl$_3$) 138.8, 138.7, 138.5, 128.8, 128.7, 128.6, 128.2, 128.1, 128.0, 85.5, 82.3, 80.6, 76.0, 75.4, 73.9, 72.9, 72.3, 34.4, 25.2, 15.6 MS: calcd for C$_{29}$H$_{34}$O$_4$SNa 501.2. found m/z 501.0 (M+Na).

Ethyl 2,4,6-tri-O-benzyl-3-deoxy-1-thio-β-D-glucopyranoside (26)

Compound 25 (608 mg, 1.17 mmol) gave 364 mg substantially pure product (65%). [α]$_D$=-11.8° (c=1, CHCl$_3$); $^1$H NMR (CDCl$_3$) 7.44-7.14 (m, 15H), 4.74 (d, 1H, J=11.6 Hz), 4.66-4.56 (m, 4H), 4.50 (d, 1H, J=9.4 Hz), 4.45 (d, 1H, J=11.4 Hz), 3.83 (d, 1H, J=10.7 Hz), 3.69 (dd, 1H, J=4.4, 10.7 Hz), 3.49 (m, 2H), 3.35 (m, 1H), 2.79 (m, 2H), 2.69 (m, H), 1.54 (m, 1H), 1.35 (t, 3H, J=7.3 Hz); $^{13}$C NMR (CDCl$_3$): 138.8, 138.4, 135.8, 128.9, 128.7, 128.4, 128.2, 128.1, 127.4, 86.9, 81.3, 75.6, 73.8, 73.3, 72.5, 71.6, 69.8, 45.3, 36.7, 25.1, 20.3, 15.5; MS: calcd for C$_{29}$H$_{34}$O$_4$SNa 501.2. found m/z 501.0 (M+Na).

Ethyl 2,3,4,6-tetra-O-benzyl-1-thio-β-D-gulopyranoside (31)

Compound 30 (0.6 g, 0.94 mmol) gave 330 mg substantially pure product (60%). $^1$H NMR (CDCl$_3$) 7.32-7.17 (m, 20H), 4.94 (d, J=9.8 Hz, 1H), 4.55 (m, 2H), 4.40 (m, 4H), 4.22 (m, 2H), 4.00 (t, J=6.4 Hz, 1H), 3.60-3.42 (m, 5H), 2.66 (m, 2H), 1.22 (t, J=7.4 Hz, 3H); MS: calcd for C$_{36}$H$_{40}$O$_5$SNa 607.2. found m/z 607.0 (M+Na).

Ethyl 2,3,4,6-tetra-O-benzyl-1-thio-β-D-allopyranoside (36)

Compound 35 (0.85 g, 1.33 mmol) gave 496 mg substantially pure product (64%). $^1$H NMR (CDCl$_3$) 7.4-7.22 (m, 20H), 5.05 (d, J=9.7 Hz, 1H), 4.86 (d, J=11.8 Hz, 1H), 4.80 (d, J=11.8 Hz, 1H), 4.69-4.40 (m, 6H), 4.13 (m, 1H), 4.03 (dd, J=3.1, 9.7 Hz, 1H), 3.47 (dd, J=2.3, 9.8 Hz, 1H), 3.29 (dd, J=2.3, 9.8 Hz, 1H), 2.75 (m, 2H), 1.32 (t, J=7.5 Hz, 3H); $^{13}$C NMR (CDCl$_3$) 139.4, 138.9, 138.3, 138.2, 128.9, 128.8, 128.7, 128.6, 128.5, 128.3, 128.2, 128.1, 128.0, 127.9, 127.8, 82.0, 79.2, 76.1, 75.4, 74.7, 73.9, 73.8, 72.8, 71.9, 69.9, 25.1, 15.6; MS: calcd for C$_{36}$H$_{40}$O$_5$SNa 607.2. found m/z 607.0 (M+Na).

General Phosphorylation Strategy (Method A: Via Ethyl 1-thio-β-D-hexopyranoside).

Phosphorylation may take place in accordance with the present invention by the following reaction, which involves ethyl 1-thio-β-D-hexopyranoside. The ethyl 1-thio-β-D-hexopyranoside may be ethyl 1-thio-β-D-hexopyranoside prepared according to the methods described herein or ethyl 1-thio-β-D-hexopyranoside prepared by other methods.

According to this method, protected ethyl 1-thio-β-D-hexopyranoside and dibenzyl phosphate are co-evaporated, preferably two times from dry toluene and further dried under high vacuum overnight to which N-iodosuccinamide and dry molecular sieves are preferably added. The mixture is then dissolved, preferably in dry CH$_2$Cl$_2$, cooled to about −40° C. to about −20° C., preferably about −30° C. and trifluoromethane-sulfonic acid is added. The reaction mixture is substantially maintained at the cooled temperature for about 20 to about 40 minutes, preferably about 30 min with stirring. Preferably, the mixture is then diluted, and washed with saturated Na$_2$S$_2$O$_3$ and/or saturated NaHCO$_3$, H$_2$O, and brine. The organics are then preferably dried, filtered, concentrated and purified to give the desired product.

Other conditions, steps, reagents, solutions and the like of the present method may be used in accordance with the present invention.

In a typical reaction, 0.84 mmol protected ethyl 1-thio-β-D-hexopyranoside and 1.44 mmol dibenzyl phosphate were co-evaporated two times from dry toluene and further dried under high vacuum overnight to which 1.24 mmol of N-iodosuccinamide and 300 mg dry molecular sieves were added. The mixture was then dissolved in 10 mL dry CH$_2$Cl$_2$, cooled to −30° C. and 25 μL trifluoromethanesulfonic acid (0.28 mmol) was added. The reaction mixture was maintained at −30° C. for 30 min with stirring and then diluted with 100 mL EtOAc, washed with saturated Na$_2$S$_2$O$_3$ (20 mL) and saturated NaHCO$_3$ (20 mL), H$_2$O (20 mL), and brine (20 mL). The organics were dried over Na$_2$SO$_4$, filtered, concentrated and purified by chromatography on silica gel (3:1 hexane/EtOAc) to give the desired product.

Dibenzyl-(2,3,4-tri-O-benzyl-6-deoxy-α-D-glucopyranosyl) Phosphate (11)

Compound 10 (400 mg, 0.84 mmol) gave 0.44 mg (76%) of the desired product. [α]$_D$=22.8° (c=1, CHCl$_3$); $^1$H NMR (CDCl$_3$) 7.38-7.28 (m, 25H), 5.93 (dd, 1H, J=3.2, 6.6 Hz), 5.30 (m, 4H), 5.18 (m, 3H), 5.09 (m, 2H), 4.67 (m, 2H), 3.94 (m, 1H), 3.64 (m, 1H), 3.18 (m, 1H), 1.21 (d, 3H, J=6.2 Hz); $^{13}$C NMR (CDCl$_3$) 138.9, 138.5, 138.0, 128.9, 128.8, 128.7, 128.4, 128.3, 95.8, 95.7, 94.0, 76.0, 75.7, 73.6, 69.7, 17.3; $^{31}$P NMR (CDCl$_3$) 2.58; MS: calcd for C$_{41}$H$_{43}$O$_8$PNa 717.2. found m/z 717.3 (M+Na).

Dibenzyl-(2,3,6-tri-O-benzyl-4-deoxy-α-D-glucopyranosyl) Phosphate (19)

Compound 18 (512 mg, 1.07 mmol) gave 0.565 g (76%) substantially pure product. [α]$_D$=28.2° (c=1, CHCl$_3$); $^1$H NMR (CDCl$_3$) 7.29-7.10 (m, 25H), 5.91 (dd, 1H, J=3.2, 6.6 Hz), 4.72-4.57 (m, 4H), 4.41 (m, 2H), 4.02 (m, 1H), 3.81 (m, 1H), 3.48 (m, 1H), 3.34 (m, 2H), 2.04-2.00 (m, 1H), 1.60-1.48 (m, 1H); $^{13}$C NMR (CDCl$_3$) 138.6, 138.4, 138.2, 137.8, 137.7, 128.3, 128.2, 128.1, 127.9, 127.8, 127.7, 127.6, 127.5, 127.4, 97.3, 91.9, 83.6, 80.2, 78.1, 74.9, 73.3, 73.0, 72.2, 72.0, 71.9, 70.6, 66.7, 52.7, 33.4; $^{31}$P NMR (CDCl$_3$) 1.25; MS: calcd for C$_{41}$H$_{43}$O$_8$PNa 717.2. found m/z 717.2 (M+Na).

Dibenzyl-(2,4,6-tri-O-benzyl-3-deoxy-α-D-glucopyranosyl) Phosphate (27)

Compound 26 (270 mg, 0.56 mmol) gave 0.31 g substantially pure product (79%, α/β=2:1). $^1$H NMR (CDCl$_3$) 7.32-

7.21 (m, 25H), 5.96 (dd, 1H, J=2.8, 6.6 Hz), 5.06 (m, 4H), 4.66 (d, 1H, J=11.7 Hz), 4.56 (m, 3H), 4.42 (d, 1H, J=12.0 Hz), 4.38 (d, 1H, J=11.3 Hz), 3.82 (m, 1H), 3.66 (m, 3H), 3.49 (m, 1H), 2.54 (m, 0.5H), 2.40 (m, 1H), 1.85 (m, 1H), 1.56 (m, 0.5H); $^{31}$P NMR (CDCl$_3$) 0.54, 0.17; MS: calcd for C$_{41}$H$_{43}$O$_8$PNa 717.2. found m/z 717.2 (M+Na).

Dibenzyl-(3,4,6-tri-O-benzoyl-2-deoxy-α-D-glucopyranosyl) Phosphate (41)

Compound 40 (460 mg, 0.88 mmol) gave 0.49 g of substantially pure product (75%) after silica gel chromatography (3:1-2:1 hexane/EtOAc. [α]$_D$=19° (c=1, CHCl$_3$); $^1$H NMR (CDCl$_3$) 8.05-7.94 (m, 6H), 7.53-7.51 (m, 3H), 7.41-7.34 (m, 16H), 5.96 (dd, 1H, J=1.6, 7.2 Hz), 5.68 (m, 2H), 5.16 (m, 4H), 4.51-4.43 (m, 2H), 4.35 (dd, 1H, J=3.1, 12.0 Hz), 2.56 (m, 1H), 2.04 (m, 1H); $^{13}$C NMR (CDCl$_3$) 166.0, 165.6, 165.3, 135.5, 135.4, 133.3, 133.2, 133.0, 129.8, 129.7, 129.6, 129.3, 128.9, 128.6, 128.4, 128.3, 128.1, 127.9, 95.9, 70.1, 69.5, 69.2, 68.9, 62.6; $^{31}$P NMR (CDCl$_3$) 0.32; MS: calcd for C$_{41}$H$_{37}$O$_{11}$PNa 759.1. found: m/z 759.1 (M+Na).

Dibenzyl-(2,3,4,6-tetra-O-benzyl-α-D-gulopyranosyl) Phosphate (32)

Compound 31 (120 mg, 0.21 mmol) gave 50 mg of the desired compound (30%) and 38 mg of the β isomer (23%). α isomer: $^1$H NMR (CDCl$_3$) 7.30-6.90 (m, 30H), 5.95 (dd, J=3.7, 7.5 Hz, 1H), 4.97 (m, 5H), 4.64 (m, 2H), 4.49-4.30 (m, 8H), 3.80 (m, 2H), 3.60 (d, J=3.4 Hz, 1H), 3.44 (m, 2H); $^{31}$P NMR (CDCl$_3$) 0.8; MS: calcd for C$_{48}$H$_{49}$O$_9$PNa 823.3. found m/z 823.3 (M+Na). β isomer: $^1$H NMR (CDCl$_3$) 7.25-7.15 (m, 30H), 5.61 (t, J=7.2 Hz, 1H), 5.05-4.99 (m, 4H), 4.60 (d, J=12 Hz, 1H), 4.42-4.34 (m, 4H), 4.26 (d, J=6.2 Hz, 1H), 4.17 (t, J=6.3 Hz, 1H), 3.65 (m, 2H), 3.48 (m, 2H), 3.48 (m, 2H), 3.43 (dd, J=1.3, 13.5 Hz, 1H); $^{31}$P NMR (CDCl$_3$) −1.1; MS: calcd for C$_{48}$H$_{49}$O$_9$PNa 823.3. found m/z 823.3 (M+Na).

Dibenzyl-(2,3,4,6-tetra-O-benzyl-α-D-allopyranosyl) Phosphate (37)

Compound 36 (169 mg, 0.29 mmol) gave 70 mg the desired compound (30%) and 64 mg of the β isomer (28%). α isomer: $^1$H NMR (CDCl$_3$) 7.34-7.13 (m, 30H), 6.04 (dd, J=3.6, 7.1 Hz, 1H), 5.11-4.92 (m, 4H), 4.89 (d, J=12.0 Hz, 1H), 4.84 (d, J=12.0 Hz, 1H), 4.75 (d, J=11.8 Hz, 1H), 4.59-4.37 (m, 6H), 4.23 (m, 1H), 3.73 (dd, J=3.0, 10.0 Hz, 1H), 3.66 (dd, J=2.5, 10.0 Hz, 1H), 3.54 (m, 2H); $^{13}$C NMR (CDCl$_3$) 139.4, 138.4, 138.3, 137.9, 136.5, 136.4, 128.9, 128.8, 128.7, 128.7, 128.5, 128.4, 128.3, 128.2, 128.1, 128.0, 127.6, 95.1, 76.2, 74.4, 73.9, 73.3, 71.8, 69.6, 69.2, 68.7, 68.6; $^{31}$P NMR (CDCl$_3$) 0.27; MS: calcd for C$_{48}$H$_{49}$O$_9$PNa 823.3. found m/z 823.3 (M+Na). β isomer: $^1$H NMR (CDCl$_3$) 7.37-7.07 (m, 30H), 5.63 (t, J=7.7 Hz, 1H), 5.00 (m, 4H), 4.79 (d, J=11.9 Hz, 1H), 4.72 (d, J=11.9 Hz, 1H), 4.63 (d, J=11.9 Hz, 1H), 4.51 (d, J=11.9 Hz, 1H), 4.46 (d, J=12.1 Hz, 1H), 4.36 (m, 3H), 4.09 (dd, J=1.4, 9.7 Hz, 1H), 4.02 (s, 1H), 3.64 (dd, J=3.7, 11.0 Hz, 1H), 3.58 (dd, J=1.5, 11.0 Hz, 1H), 3.51 (d, J=2.3, 9.8 Hz, 1H), 3.32 (dd, J=2.3, 7.9 Hz, 1H; $^{31}$P NMR (CDCl$_3$) 0.76; MS: calcd for C$_{48}$H$_{49}$O$_9$PNa 823.3. found m/z 823.3 (M+Na).

General Phosphorylation Strategy (Method B: Via Glycosyl Halide).

According to another embodiment, phosphorylation may take place in accordance with the present invention by the following reaction, which involves glycosyl halide. The glycosyl halide may be glycosyl halide prepared according to the methods described herein or glycosyl halide prepared by other methods.

According to this method, protected D-hexose is dissolved in acetic acid to which HBr in acetic acid was added dropwise at about 0° C. The reaction is allowed to warm to room temperature and stirred for about 1½ to about 2½ hrs. The mixture is then diluted with cold CHCl$_3$, washed successively with cold saturated NaHCO$_3$ solution, H$_2$O and brine, and the organics were dried over anhydrous Na$_2$SO$_4$ and concentrated. The crude protected-α-D-pyranosyl bromide may be used directly without further purification. A mixture of dibenzyl phosphate, silver triflate, 2,4,6-collidine and activated 4 Å molecular sieves in dry CH$_2$Cl$_2$ is stirred at room temperature in the absence of light for about 1 hr. The mixture was then cooled to about −30° C. to about −50° C., preferably about −40° C., to which a solution of the crude protected-α-D-pyranosyl bromide in dry CH$_2$Cl$_2$ is added in dropwise fashion. The reaction mixture is kept at substantially the same cool temperature for about 1½ to about 2½ M hrs, allowed to warm to room temperature and stirred, preferably overnight. The corresponding filtrate is preferably diluted with CH$_2$Cl$_2$, washed with saturated CuSO$_4$, H$_2$O, and brine, and the organics are dried over anhydrous Na$_2$SO$_4$ and concentrated. Purification yields substantially pure product.

Other conditions, steps, reagents, solutions and the like of the present method may be used in accordance with the present invention.

Suitably protected D-hexose (0.64 mmol) was dissolved in 5 mL acetic acid to which 5 mL 33% HBr in acetic acid was added dropwise at 0° C. The reaction was allowed to warm to room temperature and stirred for 2 hr. The mixture was then diluted with 100 mL cold CHCl$_3$, washed successively with cold saturated NaHCO$_3$ solution (×30 mL), H$_2$O (30 mL) and brine (20 mL), and the organics were dried over anhydrous Na$_2$SO$_4$ and concentrated. The crude protected-α-D-pyranosyl bromide was used directly without further purification. A mixture of dibenzyl phosphate (1.80 mmol), silver triflate (1.80 mmol), 2,4,6-collidine (3.0 mmol) and 0.5 g activated 4 Å molecular sieves in 10 mL dry CH$_2$Cl$_2$ was stirred at room temperature under argon atmosphere in the absence of light for 1 hr. The mixture was then cooled to −40° C. to which a solution of the crude protected-α-D-pyranosyl bromide in 10 mL dry CH$_2$Cl$_2$ was added in dropwise fashion. The reaction mixture was kept at −40° C. for 2 hr, allowed to warm to room temperature and stirred overnight. The corresponding filtrate was diluted with 100 mL CH$_2$Cl$_2$, washed with saturated CuSO$_4$ (2×20 mL), H$_2$O (20 mL) and brine (20 mL), and the organics were dried over anhydrous Na$_2$SO$_4$ and concentrated. Purification by silica gel chromatography (1:1 hexanes/EtOAc) gave substantially pure product.

Dibenzyl-(2,3,4,6-tetra-O-benzoyl-α-D-altropyranosyl) Phosphate (45)

Perbenzoylated D-altrose (44), (0.675 g, 0.96 mmol) gave 0.58 g substantially pure product (70% overall). [α]$_D$=40° (c=1, CHCl$_3$); $^1$H NMR (CDCl$_3$) 8.05 (m, 6H), 7.82 (dd, J=1.2, 7.2 Hz, 2H), 7.53-7.22 (m, 22H), 5.87 (m, 3H), 5.38 (d, J=3.1 Hz, 1H), 5.04 (m, 4H), 4.90 (dd, J=3.0, 10.0 Hz, 1H), 4.58 (dd, J=2.4, 12.3 Hz, 1H), 4.38 (dd, J=3.9, 12.3 Hz, 1H); $^{13}$C NMR (CDCl$_3$) 166.4, 165.4, 165.3, 164.8, 135.7, 134.3, 133.9, 133.5, 130.5, 130.4, 130.3, 130.1, 129.6, 129.3, 129.1, 129.0, 128.9, 128.8, 128.4, 128.3, 70.2, 70.1, 70.0, 69.5, 69.4, 67.1, 66.9, 65.5, 63.0; $^{31}$P NMR (CDCl$_3$) −0.02; MS: calcd for C$_{48}$H$_{41}$O$_{13}$NaP 879.2. found m/z 879.2 (M+Na).

Dibenzyl-(2,3,4,6-tetra-O-benzoyl-α-D-idopyranosyl) Phosphate (49)

Perbenzoylated D-idose (48), (0.32 g, 0.46 mmol) gave 270 mg substantially pure product (69% overall). [α]$_D$=11.4° (c=1, CHCl$_3$); $^1$H NMR (CDCl$_3$) 8.11-7.88 (m, 8H), 7.40-7.19 (m, 22H), 6.0 (d, J=6.5 Hz, 1H), 5.68 (m, 1H), 5.46 (m, 1H), 5.22 (m, 1H), 5.07-5.01 (m, 5H), 4.60 (dd, J=7.0, 11.5 Hz, 1H), 4.53 (dd, J=5.8, 11.5 Hz, 1H); $^{13}$C NMR (CDCl$_3$) 166.0, 165.1, 164.7, 164.3, 135.2, 133.6, 133.5, 133.1, 130.1, 130.0, 129.9, 129.7, 129.6, 129.4, 128.9, 128.6, 128.5, 128.4, 128.3, 128.2, 127.9, 127.8, 94.9, 69.7, 69.5, 65.9, 65.7, 62.6; $^{31}$P NMR (CDCl$_3$) 0.1; MS: calcd for C$_{48}$H$_{41}$O$_{13}$NaP 879.2. found m/z 879.1 (M+Na).

Dibenzyl-(2,3,4,6-tetra-O-acetyl-α-D-talopyranosyl) Phosphate (53)

Peracylated D-talose (52), (0.248 g, 0.636 mmol) gave 0.436 g substantially pure product (52% overall) [α]$_D$=40° (c=1, CHCl$_3$); $^1$H NMR (CDCl$_3$) 7.37 (m, 10H), 5.68 (dd, J=1.3, 6.5 Hz, 1H), 5.31 (m, 1H), 5.20 (t, J=3.7 Hz, 1H), 5.11 (m, 4H), 5.04 (d, J=3.0 Hz, 1H), 4.30 (dd, J=1.3, 6.8 Hz, 1H), 4.11 (dd, J=11.3, 6.7 Hz, 1H), 3.99 (dd, J=11.3, 6.7 Hz, 1H), 2.12 (s, 3H), 2.11 (s, 3H), 1.99 (s, 3H), 1.92 (s, 3H); $^{13}$C NMR (CDCl$_3$) 170.7, 170.4, 169.9, 169.8, 135.7, 135.6, 135.5, 129.2, 129.1, 129.0, 128.5, 128.4, 96.3, 70.3, 68.9, 67.0, 65.6, 64.9, 61.7, 21.1, 21.0, 20.9; $^{31}$P NMR (CDCl$_3$) −0.18; HRMS (FAB) calcd for C$_{28}$H$_{34}$O$_{13}$P 609.1737. found m/z 609.1747 (M+H).

General Strategy for Final Deprotection and Conversion to the Sodium Salt.

Final Deprotection and Conversion to sodium salt may take place in accordance with the present invention by the following reaction.

According to this method, protected α-D-pyranosyl phosphate is dissolved in MEOH, NaHCO$_3$ solution and 10% Pd/C are added. The mixture is stirred overnight at room temperature under hydrogen atmosphere after which the catalyst is removed, preferably by filtration and the filtrate concentrated. The aqueous layer is preferably extracted, and then partitioned and submitted to an anion exchange column eluted with water, 0.1M NH$_4$HCO$_3$, 0.2M NH$_4$HCO$_3$ and 0.3M NH$_4$HCO$_3$. The product eluted with 0.2 M NH$_4$HCO$_3$ and these fractions are pooled and co-evaporated with ethanol, preferably several times to remove excess NH$_4$HCO$_3$. The obtained sugar phosphate ammonium salt is subsequently dissolved in water and applied to a cation-exchange column (Na$^-$ type) eluted with mL water. The product containing fractions are collected and lyophilized to give the desired product as the sodium salt.

Other conditions, steps, reagents, solutions and the like of the present method may be used in accordance with the present invention.

In a typical reaction, the protected α-D-pyranosyl phosphate (0.5 mmol) was dissolved in 15 mL MeOH, 1.5 mL 1N NaHCO$_3$ solution and 150 mg 10% Pd/C were added. The mixture was stirred overnight at room temperature under hydrogen atmosphere after which the catalyst was removed by filtration and the filtrate concentrated to approximately a 10 mL volume. The aqueous layer was extracted with 10 mL of EtOAc, and then partitioned and submitted to an anion exchange column (Dowex 1×8, 1.2×12 cm) eluted with 100 mL water, 100 mL 0.1 M NH$_4$HCO$_3$, 100 mL 0.2 M NH$_4$HCO$_3$ and 100 mL 0.3 M NH$_4$HCO$_3$. The product eluted with 0.2M NH$_4$HCO$_3$ and these fractions were pooled and co-evaporated with ethanol several times to remove excess NH$_4$HCO$_3$. The obtained sugar phosphate ammonium salt was subsequently dissolved in 5 mL water and applied to an AG-X8 cation-exchange column (Na$^+$ type) eluted with 100 mL water. The product containing fractions were collected and lyophilized to give the desired product as the sodium salt.

Disodium 6-deoxy-α-D-glucopyranosyl Phosphate (12)

Compound 11 (350 mg, 0.5 mmol) gave 85 mg (58%) of the desired sodium salt. $^1$H NMR (D$_2$O) 5.37 (dd, 1H, J=3.4, 7.2 Hz), 3.98 (m, 1H), 3.70 (t, 1H, J=9.5 Hz), 3.45 (m, 1H), 3.09 (t, 1H, J=9.5 Hz), 1.24 (d, 1H, J=6.2 Hz); $^{13}$C NMR (D$_2$O) 93.74, 75.78, 73.3, 72.9, 68.2, 17.2; $^{31}$P NMR (D$_2$O) 3.02; HRMS (FAB): calcd for C$_6$H$_{12}$O$_8$P 243.0269. found m/z 243.0277 (M+H).

Disodium 4-deoxy-α-D-glucopyranosyl Phosphate (20)

Compound 19 (342 mg, 0.5 mmol) gave 78 mg of the title compound (55%). $^1$H NMR (D$_2$O) 5.49 (dd, 1H, J=3.4, 7.32 Hz), 4.16 (m, 1H), 3.99 (m, 1H), 3.65 (dd, 1H, J=3.2, 12.0 Hz), 3.55 (dd, 1H, J=6.0, 12.0 Hz), 3.41 (m, 1H), 1.99-1.95 (m, 1H), 1.44 (m, 1H); $^{13}$C NMR (D$_2$O) 95.1, 73.8, 69.5, 67.4, 64.0, 34.3; $^{31}$P NMR (D$_2$O) 1.52; HRMS (FAB): calcd for C$_6$H$_{12}$O$_8$P 243.0269. found m/z 243.0260 (M+H).

Disodium 3-deoxy-α-D-glucopyranosyl Phosphate (28)

Compound 27 (270 mg, 0.39 mmol) gave 65 mg title compound (58%) as a 2:1 α/β mixture. $^1$H NMR (D$_2$O) 5.33 (dd, 1H, J=3.2, 7.3 Hz), 3.92-3.50 (m, 5H), 3.46 (m, 1H), 2.33 (m, 0.43H), 2.12 (m, 1H), 1.81 (m, 1H), 1.54 (m, 0.43H); $^{31}$P NMR (D$_2$O) 3.39, 3.12; HRMS (FAB): calcd for C$_6$H$_{12}$O$_8$P 243.0269. found m/z 243.0267 (M+H).

Disodium 2-deoxy-α-D-glucopyranosyl Phosphate (43)

Debenzylation of 41 (329 mg, 0.447 mmol) was accomplished using the general strategy described above. After the filtrate was concentrated to approximately a 10 mL volume, the solution was cooled to 0° C. and 1.5 mL 1N NaOH solution was added in dropwise manner. The mixture was then stirred at room temperature for 4 hr and subsequently neutralized with 1.0 N acetic acid. The final work-up was accomplished as described in the general strategy to give 69 mg title compound (53%). $^1$H NMR (D$_2$O) 5.53 (m, 1H), 4.01 (m, 1H), 3.88-3.84 (m, 3H), 3.72 (dd, 1H, J=6.2, 12.7 Hz), 3.31 (t, 1H, J=9.4 Hz), 2.19 (dd, 1H, J=5.0, 12.9 Hz), 1.66 (m, H); $^{31}$P NMR (D$_2$O) 2.68; HRMS (FAB): calcd for C$_6$H$_{12}$O$_8$P 243.0269. found m/z 243.0268 (M+H).

Disodium α-D-gulopyranosyl Phosphate (33)

Compound 32 (35 mg, 0.044 mmol) gave 7.1 mg of the title compound (55%). $^1$H NMR (D$_2$O) 5.15 (dd, J=3.0, 7.7 Hz, 1H), 4.04 (m, 2H), 3.79 (m, 2H), 3.64 (m, 2H); $^{13}$C NMR (D$_2$O) 96.1, 75.3, 71.6, 70.2, 70.0, 62.2; $^{31}$P NMR (D$_2$O) 2.9; HRMS (FAB): calcd for C$_6$H$_{12}$O$_9$P 259.0218. found m/z 259.0231 (M+H).

Disodium α-D-allopyranosyl Phosphate (38)

Compound 37 (63 mg, 0.079 mmol) gave 18 mg substantially pure product (77%). $^1$H NMR (D$_2$O) 5.44 (dd, J=3.5, 7.5 Hz, 1H), 4.14 (m, 1H), 4.00 (m, 1H), 3.90 (dd, J=1.9, 12.3 Hz, 1H), 3.76 (m, 2H), 3.65 (dd, J=3.0, 10.4 Hz, 1H); $^{13}$C NMR (D$_2$O) 95.8, 75.1, 72.6, 71.8, 68.1, 62.6; $^{31}$P NMR (D$_2$O) 2.39; HRMS (FAB): calcd for C$_6$H$_{12}$O$_9$P 259.0218. found m/z 259.0217 (M+H).

Disodium α-D-altropyranosyl Phosphate (47)

Using the strategy described for 43, compound 45 (260 mg, 0.3 mmol) gave 62 mg of the desired sodium salt (67% overall). $^1$H NMR (D$_2$O) 5.29 (d, J=8.4 Hz, 1H), 4.14 (m, 1H), 3.98 (m, 1H), 3.94 (t, J=3.5 Hz, 1H), 3.90 (dd, J=2.4, 12.3 Hz, 1H), 3.82 (dd, J=3.5, 12.4 Hz, 1H), 3.77 (dd, J=6.5, 12.3 Hz, 1H); $^{13}$C NMR (D$_2$O) 94.9, 70.6, 70.5, 70.0, 64.8, 61.4; $^{31}$P NMR (D$_2$O) 2.05; HRMS (FAB): calcd for C$_6$H$_{12}$O$_9$P 259.0218. found m/z 259.0211 (M+H).

Disodium α-D-idopyranosyl Phosphate (51)

Using the strategy described for 43, compound 49 (213 mg, 0.25 mmol) gave 61 mg of the title compound (62% overall). $^1$H NMR (D$_2$O) 5.14 (dd, J=3.5, 7.7 Hz, 1H), 4.24 (m, 1H), 3.85 (dd, J=8.9, 12.3 Hz, 1H), 3.75 (m, 2H), 3.60 (t, J=5.0 Hz, 1H), 3.32 (m, 1H); $^{13}$C NMR (D$_2$O) 99.1, 75.8, 75.5, 74.1, 63.9, 53.2; $^{31}$P NMR (CDCl$_3$) 2.98; HRMS (FAB): calcd for C$_6$H$_{12}$O$_9$P 259.0218. found m/z 259.0208 (M+H).

Disodium α-D-talopyranosyl Phosphate (55)

Using the strategy described for 43, compound 53 (436 mg, 0.72 mmol) gave 157 mg of the title compound (72%). $^1$H NMR (D$_2$O) 5.48 (d, J=8.2 Hz, 1H), 4.11 (m, 1H), 3.98 (t, J=3.2, 1H), 3.92 (m, 1H), 3.88 (m, 1H), 3.82 (dd, J=11.1, 7.7 Hz, 1H), 3.75 (dd, J=11.7, 4.4 Hz, 1H), 3.19 (q, J=7.3 Hz, 10H), 1.28 (t, J=7.4, 15H); $^{13}$C NMR (D$_2$O): 94.1, 70.2, 68.8, 67.6, 62.8, 59.6; $^{31}$P NMR (D$_2$O) 0.52; HRMS (FAB): calcd for C$_6$H$_{12}$O$_9$P 259.0218. found m/z 259.0209 (M+H).

The following compounds were prepared, preferably according to the methods described herein.

(58) Thymidine 5'-(α-D-glucopyranosyl diphosphate). HRMS (FAB) calc for C$_{16}$H$_{25}$O$_{16}$N$_2$P$_2$ 563.0705. found m/z 563.0679 (M+H).

(59) Uridine 5'-(α-D-glucopyranosyl diphosphate). HRMS (FAB): calc for C$_{14}$H$_{23}$O$_{17}$N$_2$P$_2$ 565.0507. found m/z 565.0472 (M+H).

(60) Thymidine 5'-(2-deoxy-α-D-glucopyranosyl diphosphate). HRMS (FAB) calc for C$_{16}$H$_{25}$O$_{15}$N$_2$P$_2$ 547.0704. found m/z 547.0714 (M+H).

(61) Uridine 5'-(2-deoxy-α-D-glucopyranosyl diphosphate). HRMS (FAB): calc C$_{14}$H$_{23}$O$_{16}$N$_2$P$_2$ 549.0506. found m/z 549.0510 (M+H).

(62) Thymidine 5'-(3-deoxy-α-D-glucopyranosyl diphosphate). HRMS (FAB) calc for C$_{16}$H$_{25}$O$_{15}$N$_2$P$_2$ 547.0704. found m/z 547.0720 (M+H).

(63) Uridine 5'-(3-deoxy-α-D-glucopyranosyl diphosphate). HRMS (FAB): calc C$_{14}$H$_{23}$O$_{16}$N$_2$P$_2$ 549.0506. found m/z 549.0485 (M+H).

(64) Thymidine 5'-(4-deoxy-α-D-glucopyranosyl diphosphate). HRMS (FAB) calc for C$_{16}$H$_{25}$O$_{15}$N$_2$P$_2$ 547.0704. found m/z 547.0693 (M+H).

(65) Uridine 5'-(4-deoxy-α-D-glucopyranosyl diphosphate). HRMS (FAB): calc C$_{14}$H$_{23}$O$_{16}$N$_2$P$_2$ 549.0506. found m/z 549.0500 (M+H).

(66) Thymidine 5'-(6-deoxy-α-D-glucopyranosyl diphosphate). HRMS (FAB) calc for C$_{16}$H$_{25}$O$_{15}$N$_2$P$_2$ 547.0704. found m/z 547.0730 (M+H).

(67) Uridine 5'-(6-deoxy-α-D-glucopyranosyl diphosphate). HRMS (FAB): calc C$_{14}$H$_{23}$O$_{16}$N$_2$P$_2$ 549.0506. found m/z 549.0492 (M+H).

(68) Thymidine 5'-(α-D-mannopyranosyl diphosphate). HRMS (FAB) calc 563.0705. found m/z 563.0701 (M+H).

(69) Uridine 5'-(α-D-mannopyranosyl diphosphate). HRMS (FAB): calc 565.0507. found m/z 565.0503 (M+H).

(70) Thymidine 5'-(α-D-galactopyranosyl diphosphate). HRMS (FAB) calc 563.0705. found m/z 563.0710 (M+H).

(71) Uridine 5'-(α-D-galactopyranosyl diphosphate). HRMS (FAB): calc 565.0507. found m/z 565.0508 (M+H).

(72) Thymidine 5'-(α-D-allopyranosyl diphosphate). HRMS (FAB) calc 563.0705. found m/z 563.0715 (M+H).

(73) Uridine 5'-(α-D-allopyranosyl diphosphate). HRMS (FAB): calc 565.0507. found m/z 565.0507 (M+H).

(74) Thymidine 5'-(α-D-altropyranosyl diphosphate). HRMS (FAB) calc 563.0705. found m/z 563.0699 (M+H).

(75) Uridine 5'-(α-D-altropyranosyl diphosphate). HRMS (FAB): calc 565.0507. found m/z 565.0511 (M+H).

(76) Thymidine 5'-(α-D-gulopyranosyl diphosphate). HRMS (FAB) calc 563.0705. found m/z 563.00712 (M+H).

(77) Uridine 5'-(α-D-gulopyranosyl diphosphate). HRMS (FAB): calc 565.0507. found m/z 565.0512 (M+H).

(78) Thymidine 5'-(α-D-idopyranosyl diphosphate). HRMS (FAB) calc 563.0705. found m/z 563.0708 (M+H).

(79) Uridine 5'-(α-D-idopyranosyl diphosphate). HRMS (FAB): calc 565.0507. found m/z 565.0507 (M+H).

(80) Thymidine 5'-(α-D-talopyranosyl diphosphate). HRMS (FAB) calc 563.0705. found m/z 563.0710 (M+H).

(81) Uridine 5'-(α-D-talopyranosyl diphosphate). HRMS (FAB): calc 565.0507. found m/z 565.0499 (M+H).

Enzyme Purification.

*E. coli*-prfbA-C (from Professor Hung-wen Liu (Dept. of Chem., Univ. of Minnesota)) was grown in 2 L superbroth, 100 μg mL$^{-1}$ ampicillin divided among two 4 L baffled flasks for 18 hours at 37° C. Cells were harvested by centrifugation (5000×g, 20 min, 40° C.), washed twice with buffer A (50 mM potassium phosphate buffer, 1 mM EDTA, pH 7.5), resuspended in buffer A (4× weight) and split into two equal volumes. Each was sonicated by three 40 second bursts at 0° C. followed by centrifugation (4400×g, 20 min, 40° C.) to remove cellular debris and a further 1.3-fold dilution of the supernatant with buffer A. To the combined supernatant (167 mL) was added 31.5 mL 5% streptomycin sulfate in a dropwise fashion followed by gentle stirring (1 hr, 4° C.) and centrifugation (14,000×g, 30 min, 4° C.) to remove precipitate. The supernatant was diluted (0.1-fold 1M potassium phosphate buffer, pH 7.5) followed by the slow addition of ammonium sulfate crystals to 65% saturation, gentle stirring (7.5 hr, 4° C.) and centrifugation (4200×g, 30 min, 4° C.). The precipitated protein was dissolved in a minimum amount of buffer A and dialyzed against buffer B (20 mM Tris.HCl, 1 mM EDTA, pH 7.5). The dialysate was applied to a column of DE52 (3 cm×15 cm) which was washed with 50 mL buffer B and then eluted with a linear gradient (buffer B, 0-500 mM NaCl, 1.0 mL min$^{-1}$). The $E_p$ fractions (which eluted in the range of 35-75 mM NaCl) were combined (24 mL) and concentrated to 1 mL. Aliquots (300 μL) were further resolved by FPLC (S-200, 20×70 cm, 50 mM Tris.HCl, 200 mM NaCl, pH 7.5). The $E_p$ fractions were combined (7 mL), concentrated (64 mg min$^{-1}$) and stored in aliquots (5, 20, and 200 μL) at −80° C. until their use.

General Methods.

Infrared spectra were recorded on a Perkin Elmer 1600 series FTIR spectrophotometer. $^1$H NMR spectra were obtained on a Bruker AMX 400 (400 MHz) and are reported in parts per million (δ) relative to either tetramethylsilane (0.00 ppm) or CDCl$_3$ (7.25 ppm) for spectra run in CDCl$_3$ or relative to D$_2$O (4.82 ppm) or CD$_3$OD (3.35 ppm) for spectra run in D$_2$O. Coupling constants (J) are reported in hertz. $^{13}$C NMR are reported in δ relative to CDCl$_3$ (77.00 ppm) or CD$_3$OD (49.05 ppm) as an internal reference and $^{31}$P NMR spectra are reported in δ relative to H$_3$PO$_4$ (0.00 ppm in D$_2$O). Routine mass spectra were recorded on a PE SCIEX API 100 LC/MS mass spectrometer and HRMS was accomplished by the University of California, Riverside Mass Spectrometry Facility. Optical rotations were recorded on a Jasco DIP-370 polarimeter using a 1.0 dm cell at the room temperature (25° C.) and the reported concentrations. Melting points were measured with Electrothermal 1A-9100 digital melting bpoint instrument. Chemicals used were reagent grade and used as supplied except where noted. Analytical TLC was performed on Whatman AL Sil G/UV silica gel 60 plates. Compounds were visualized by spraying I$_2$/KI/H$_2$SO$_4$ or by dipping the plates in a cerium sulfate-ammonium molybdate solution followed by heating. Liquid column chromatography was performed using forced flow of the indicated solvent on E. Merck silica gel 60 (40-63 μm) and high pressure liquid chromatography was performed on a RAININ Dynamax SD-200 controlled with Dynamax HPLC software.

Although the above methods of IR, NMR, Mass Spec, and HRMS were those used in these examples of the present invention, as indicated above, it would be known to those skilled in the art that other instruments, conditions, types of techniques, and the like may be used for visualization of compounds, to identify compounds and determine their concentrations and purity.

General Strategy for Azide Formation.

Azides in accordance with the present invention may be formed according to the following method. Protected glycoside is dissolved in CH$_2$Cl$_2$. The mixture is cooled to about 0° C. and pyridine and (CF$_3$SO$_2$)$_2$O are added. The reaction was stirred for approximately 30 min at about 0° C. and then diluted with CH$_2$Cl$_2$. The organics were washed with water, dried over Na$_2$SO$_4$ and concentrated. The resulting crude residue was dissolved, preferably in anhydrous DMF, to which was added NaN$_3$. The reaction was subsequently stirred, preferably overnight, at room temperature and then diluted with EtOAc. The organics were washed with water, dried over Na$_2$SO$_4$ and concentrated. Preferably, product purification was accomplished by flash chromatography.

Other conditions, reagents, solutions and the like of the present method, or other methods known to those skilled in the art may be used in accordance with the present invention.

In a typical reaction, the appropriately protected glycoside (2.1 mmol) was dissolved in 10 mL of CH$_2$Cl$_2$. The mixture was cooled to 0° C. to which was added pyridine (6.3 mmol) and (CF$_3$SO$_2$)$_2$O (3.2 mmol). The reaction was stirred 30 min at 0° C. and then diluted with CH$_2$Cl$_2$ (150 mL). The organics were washed with water (30 mL), dried over Na$_2$SO$_4$ and concentrated. The resulting crude residue was dissolved in 10 mL anhydrous DMF, to which was added NaN$_3$ (407 mg, 6.3 mmol). The reaction was subsequently stirred overnight at room temperature and then diluted with EtOAc (250 mL). The organics were washed with water (2×30 mL), dried over Na$_2$SO$_4$ and concentrated. Product purification was accomplished by flash chromatography (4:1 hexane/EtOAc).

Ethyl 4-azide-2,3,6-tri-O-benzyl-4-deoxy-1-thio-β-D-glucopyranoside (FIG. 3(b) (94))

Compound (AGCH) 93 (310 mg, 0.63 mmol)$^8$ gave 285 mg (88%) desired product. $[α]_D$=62.3° (c=1, CHCl$_3$); $^1$H NMR (CDCl$_3$) 7.40-7.31 (m, 15H), 4.94 (d, 1H, J=9.5 Hz), 4.92 (d, 1H, J=10.3 Hz), 4.84 (d, 1H, J=10.6 Hz), 4.73 (d, 1H, J=10.3 Hz), 4.64 (d, 1H, J=12.0 Hz), 4.56 (d, 1H, J=12.0 Hz), 4.44 (d, 1H, J=9.6 Hz), 3.77 (dd, 1H, J=1.8, 10.9 Hz), 3.71-3.62 (m, 2H), 3.54 (t, 1H, J=9.4 Hz), 3.45 (t, 1H, J=9.8 Hz), 3.3 (m, 1H), 2.84-2.69 (m, 2H), 1.33 (t, 3H, J=7.4 Hz); $^{13}$C NMR (CDCl$_3$) 137.8, 137.6, 128.3, 128.2, 128.1, 128.0, 127.8, 127.7, 127.5, 85.0, 84.6, 81.3, 77.8, 75.5, 75.3, 73.3, 69.1, 61.9, 24.8, 15.0; MS: calcd for C$_{29}$H$_{33}$N$_3$O$_4$SNa 542.2. found m/z 542.0 (M+Na).

Ethyl 4-azide-3-O-benzoyl-2-O-benzyl-4,6-dideoxy-1-thio-β-D-glucopyranoside (FIG. 3(b) (106))

Compound (FIG. 3(b) (105)) gave 0.78 g (87.4%) substantially pure product. $[α]_D$=38° (c=1, CHC$_3$); $^1$H NMR (CDCl$_3$) 8.03 (d, 2H, J=8.2 Hz), 7.60 (m, 1H), 7.47 (t, 2H, J=7.5 Hz), 7.30 (s, 2H), 7.12 (m, 3H), 5.43 (t, 1H, J=9.8 Hz), 4.80 (d, 1H, J=10.7 Hz), 4.34 (m, 2H), 3.54 (t, 1H, J=9.5 Hz), 3.44 (m, 1H), 3.32 (t, 1H, J=9.9 Hz), 2.79 (m, 2H), 1.42 (d, 3H, J=6.0 Hz), 1.34 (t, 3H, J=7.4 Hz); $^{13}$C NMR (CDCl$_3$) 165.9, 137.5, 133.8, 130.2, 129.8, 128.9, 128.7, 128.6, 128.2, 85.4, 79.6, 77.7, 76.7, 75.4, 75.1, 66.7, 25.7, 19.0, 15.4; MS: calcd for C$_{22}$H$_{25}$N$_3$O$_4$SNa 450.1. found m/z 450.0 (M+Na).

Ethyl 3-O-benzoyl-2-O-benzyl-6-deoxy-1-thio-β-D-galactopyranoside (FIG. 3(b) (105))

Ethyl 2,3,4-tri-O-acetyl-6-deoxy-1-thio-β-D-galactopyranoside (FIG. 3(b) (104)), 2.72 g, 8.14 mmol) was dissolved in 30 mL MeOH to which 1.2 mL 25% sodium methoxide was added. From this reaction, 1.58 g (93.3%) ethyl 6-deoxy-1-thio-β-D-glactopyranoside was obtained after purification which was combined with TsOH (140 mg, 0.73 mmol) and 2,2-dimethoxypropane (1.9 mL, 15.4 mmol) in 15 mL anhydrous DMF. The reaction was stirred overnight at room temperature, diluted with 200 mL EtOAc and washed successively with saturated NaHCO$_3$ solution (50 mL) and water (30 mL). The organics were dried over Na$_2$SO$_4$ and purified via silica gel chromatography (3:1 hexane/EtOAc) to afford 1.73 g (86%) of purified ethyl 6-deoxy-3,4-O-isopropylidene-1-thio-α-D-galactopyranoside. $[α]_D$=11.9° (c=1, CHCl$_3$); $^1$H NMR (CDCl$_3$) 4.19 (d, 1H, J=10.2 Hz), 4.01 (m, 2H), 3.84 (dq, 1H, J=1.7, 13.1 Hz), 3.50 (dd, 1H, J=6.2, 10.2 Hz), 2.71 (m, 2H), 1.59 (s, 3H), 1.37 (d, 3H, J=6.6 Hz), 1.33 (s, 3H), 1.28 (t, 3H, J=7.5 Hz); $^{13}$C NMR (CDCl$_3$) 110.2, 85.5, 79.5, 76.8, 73.2, 72.3, 28.6, 26.7, 24.6, 17.2, 15.6; MS: calcd for C$_{11}$H$_{20}$O$_4$SNa 271.1. found m/z 270.9 (M+Na).

The obtained ethyl 6-deoxy-3,4-O-isopropylidene-1-thio-α-D-galactopyranoside (1.50 g, 6.0 mmol) was combined with of 60% sodium hydride (0.36 g, 9 mmol) and benzyl bromide (1.44 mL, 12.1 mmol) in 20 mL dry DMF. The reaction was stirred overnight and 1.7 g (83%) ethyl 2-O-benzyl-6-deoxy-3,4-O-isopropylidene-1-thio-α-D-galactopyranoside was obtained after the typical work up and purification. $[α]_D$=−2.8° (c=1, CHCl$_3$); $^1$H NMR (CDCl$_3$) 7.35 (d, 2H, J=7.1 Hz), 7.25 (t, 2H, J=7.1 Hz), 7.09 (m, 1H), 4.77 (d, 1H, J=11.4 Hz), 4.69 (d, 1H, J=11.4 Hz), 4.31 (d, 1H, J=9.8 Hz), 4.11 (m, 1H), 3.96 (dd, 1H, J=2.0, 15.6 Hz), 3.73 (m, 1H), 3.36 (dd, 1H, J=6.7, 19.8 Hz), 2.64 (m, 2H), 1.42 (s, 3H), 1.29 (d, 3H, J=6.6 Hz), 1.27 (s, 3H), 1.22 (t, 3H, J=7.4 Hz); $^{13}$C NMR (CDCl$_3$) 137.9, 128.3, 128.2, 127.6, 109.5, 83.3, 79.7, 78.0, 76.5, 73.4, 72.4, 28.0, 26.4, 24.4, 16.8, 14.8; MS: calcd for $C_{18}H_{26}O_4SNa$ 361.1. found m/z 361.0 (M+Na).

The obtained ethyl 2-O-benzyl-6-deoxy-3,4-O-isopropylidene-1-thio-β-D-galactopyranoside (1.82 g, 5.38 mmol) was dissolved in a mixture solution including 15 mL 0.5M HCl and 45 mL MeOH and the mixture was subsequently refluxed for 30 min. The reaction was cooled to room temperature, neutralized with solid $NaHCO_3$, and the resulting mixture concentrated. The concentrate was diluted with EtOAc (250 mL), washed with water (2×20 mL) and brine (20 mL), dried over $Na_2SO_4$ and purified by flash chromatography (1:1 hexane/EtOAc) to give 1.51 g (94%) substantially pure ethyl 2-O-benzyl-6-deoxy-1-thio-β-D-galactopyranoside. $[\alpha]_D$=8.4° (c=1, $CHCl_3$); $^1H$ NMR ($CDCl_3$) 7.42-7.29 (m, 5H), 4.97 (d, 1H, J=11.0 Hz), 4.67 (d, 1H, J=11.0 Hz), 4.40 (d, 1H, J=9.6 Hz), 3.75 (m, 1H), 3.61 (m, 2H), 3.45 (t, 1H, J=9.3 Hz), 2.78 (m, 2H), 2.48 (d, 1H, J=5.0 Hz), 2.14 (d, 1H, J=5.0 Hz), 1.32 (m, 6H); $^{13}C$ NMR ($CDCl_3$) 138.5, 129.0, 128.7, 128.5, 85.1, 79.3, 77.6, 75.7, 75.6, 74.8, 72.2, 25.4, 16.9, 15.4; MS: calcd for $C_{15}H_{22}O_4SNa$ 321.1. found m/z 321.0 (M+Na).

To a solution of ethyl 2-O-benzyl-6-deoxy-1-thio-β-D-galactopyranoside (1.03 g, 3.45 mmol) and DMAP (126 mg, 1.0 mmol) in 10 mL of dry $CH_2Cl_2$ at −30° C. was added $Et_3N$ (1.92 mL, 13.8 mmol). Benzoyl chloride (0.4 mL, 3.45 mmol) was added to this mixture in a dropwise fashion, and the stirred at −30° C. for 3 hr. The reaction was then quenched by the addition of MeOH (2 mL) and the mixture was gradually warmed to room temperature after which the resulting mixture was diluted with EtOAc (250 mL). The solution was washed with saturated $NaHCO_3$ solution (2×20 mL), water (30 mL), dried over $Na_2SO_4$, concentrated and purified by flash chromatography (3:1 to 1:1 hexane/EtOAc) to give 1.12 g (80%) of the title product. $[\alpha]_D$=−96.9° (c=1, $CHCl_3$); $^1H$ NMR ($CDCl_3$) 8.09-8.03 (m, 2H), 7.56 (t, 1H, J=7.4 Hz), 7.49 (m, 2H), 7.22 (m, 2H), 7.18 (m, 3H), 5.28 (dd, 1H, J=3.0, 9.6 Hz), 4.87 (d, 1H, J=10.6 Hz), 4.67 (d, 1H, J=10.6 Hz), 4.56 (d, 1H, J=9.7 Hz), 4.12 (m, 1H), 3.85 (t, 1H, J=9.8 Hz), 3.80 (m, 1H), 2.81 (m, 2H), 1.93 (d, 1H, J=6.7 Hz), 1.36 (m, 6H); $^{13}C$ NMR ($CDCl_3$) 166.2, 138.0, 133.7, 130.2, 130.1, 128.9, 128.7, 128.6, 128.2, 85.7, 78.1, 77.6, 76.5, 76.0, 74.7, 70.9, 25.6, 16.9, 15.4; MS: calcd for $C_{22}H_{26}O_5SNa$ 425.1. found m/z 425.2 (M+Na).

Strategy for Formation of Protected Ethyl 1-thio-β-D-hexopyranosides.

Ethyl 1-thio-β-D-hexopyranosides may be generally formed as set forth above. The following method is another exemplary embodiment of such method used in accordance with the present invention. In a typical reaction, a mixture of 4.0 mmol protected monosaccharide, 1.5 mL (ethylthio)trimethylsilane (8.0 mmol) and 1.95 g zinc iodide (7.8 mmol) in 30 mL dry dichloromethane was refluxed for 30 min under argon atmosphere. The reaction was then cooled, 50 mL water was added after which the mixture was extracted with chloroform (3×50 mL). The combined organic extracts were washed successively with water (30 mL), saturated $NaHCO_3$ solution (30 mL) and brine (30 mL). The organics were dried over $Na_2SO_4$, concentrated and resolved by silica gel chromatography (2:1 hexanes/EtOAc) to give the desired product.

Again, variations of this method may be made in accordance with the present invention, as would be apparent to one skilled in the art.

Ethyl 2,4,6-tri-O-acetyl-3-azide-3-deoxy-1-thio-β-D-glucopyranoside (FIG. 3(b) (99))

Compound (FIG. 3(b) (99)) (1.5 g, 4.0 mmol) gave 1.26 g (83.5%) title compound. $[\alpha]_D$=−49.4° (c=0.5, $CHCl_3$); $^1H$ NMR ($CDCl_3$) 4.95 (m, 2H), 4.43 (d, 1H, J=9.9 Hz), 4.19 (dd, 1H, J=4.1, 12.4 Hz), 4.09 (m, 1H), 3.65 (m, 2H), 2.68 (m, 2H), 2.12 (s, 3H), 2.10 (s, 3H), 1.24 (t, 3H, J=7.5 Hz), 2.06 (s, 3H); $^{13}C$ NMR ($CDCl_3$) 171.0, 169.6, 169.6, 84.2, 76.8, 70.3, 68.7, 66.1, 62.6, 24.4, 21.2, 21.1, 21.0, 15.1; MS: calcd for $C_{14}H_{21}N_3O_7SNa$ 398.1. found m/z 397.9 (M+Na).

Ethyl 2,3,4-tri-O-acetyl-6-azide-6-deoxy-1-thio-β-D-glucopyranoside (FIG. 3(b) (88))

Compound (FIG. 3(b) (87)) (680 mg, 1.8 mmol)$^6$ gave 590 mg (86%) of the desired title compound. $[\alpha]_D$=−17.5° (c=1, $CHCl_3$); $^1H$ NMR ($CDCl_3$) 5.23 (t, 1H, J=9.4 Hz), 5.02 (m, 2H), 4.54 (d, 1H, J=10.0 Hz), 3.62 (m, 1H), 3.37 (dd, 1H, J=6.5, 13.5 Hz), 3.30 (dd, 1H, J=2.8, 13.5 Hz), 2.73 (m, 2H), 2.07 (s, 3H), 2.04 (s, 3H), 2.02 (s, 3H), 1.28 (t, 3H, J=7.4 Hz); $^{13}C$ NMR ($CDCl_3$) 170.0, 169.4, 169.2, 83.0, 77.2, 73.6, 69.7, 69.3, 51.0, 23.6, 20.6, 20.5, 14.6. MS: calcd for $C_{14}H_{21}N_3O_7SNa$ 398.1. found m/z 397.5 (M+Na).

Ethyl 2,3,4-tri-O-acetyl-6-deoxy-1-thio-β-D-galactopyranoside (FIG. 3(b) (104))

Compound (FIG. 3(b) (103)) (6.1 mmol) gave 1.73 g (83%) of the substantially pure product. $[\alpha]_D$=−17.5° (c=1, $CHCl_3$); $^1H$ NMR ($CDCl_3$) 5.28 (d, 1H, J=3.3 Hz), 5.22 (t, 1H, J=9.9 Hz), 5.05 (dd, 1H, J=3.4, 9.9 Hz), 4.46 (d, 1H, J=9.9 Hz), 3.82 (dd, 1H, J=6.4, 12.8 Hz), 2.74 (m, 2H), 2.17 (s, 3H), 2.06 (s, 3H), 1.98 (s, 3H), 1.28 (t, 3H, J=7.4 Hz), 1.22 (d, 3H, J=6.4 Hz); $^{13}C$ NMR ($CDCl_3$) 171.0, 170.6, 170.1, 83.9, 77.6, 73.6, 72.7, 70.8, 67.7, 24.5, 21.3, 21.1, 21.0, 16.8, 15.1; MS: calcd for $C_{14}H_2O_7SNa$ 357.1. found m/z 356.6 (M+Na).

General Strategy for O-Acetyl to O-Benzyl Conversion.

O-Acetyl may be converted to O-Benzyl according to the following method or other methods known to those skilled in the art. Protected ethyl 1-thio-β-D-hexopyranoside was dissolved in dry MeOH and toluene to which a sodium methoxide solution is added. The mixture was stirred for about 2½ M to about 3½ hrs. at room temperature and neutralized. The organics are then concentrated and the corresponding crude unprotected 1-ethylthio-β-D-glucopyranoside directly dissolved in dry DMF. To this mixture NaH and benzyl bromide is added. The reaction is stirred at room temperature, preferably overnight. The mixture was then diluted with EtOAc, washed with $H_2O$, brine and organics, dried, concentrated, and purified to give the purified product.

Other conditions, reagents, solutions and the like of the present method, or other methods known to those skilled in the art may be used in accordance with the present invention.

In a typical reaction, 2.8 mmol of protected ethyl 1-thio-β-D-hexopyranoside was dissolved in 20 mL dry MeOH and 5 mL toluene to which 0.5 mL of a sodium methoxide solution (25% NaOMe in methanol) was added. The mixture was stirred for 3 hr at room temperature and neutralized with DOWEX 50W X8-100 resin. The organics were concentrated and the corresponding crude unprotected 1-ethylthio-β-D-glucopyranoside directly dissolved in 15 mL dry DMF. To this mixture 330 mg 60% NaH (8.25 mmol) and 1.6 mL benzyl bromide was added. The reaction was stirred at room temperature overnight. The mixture was then diluted with 200 mL EtOAc, washed with $H_2O$ (2×30 mL), brine (30 mL) and the organics dried over $Na_2SO_4$, concentrated and purified by silica gel chromatography (8:1 hexane/EtOAc) to give the purified product.

Ethyl 3-azide-2,4,6-tri-O-benzyl-3-deoxy-1-thio-β-D-glucopyranoside (FIG. 3(b) (100))

Compound (FIG. 3(b) (99)) (1.05 g, 2.8 mmol) gave 1.03 g (71%) of the desired title compound. $[\alpha]_D$=−13.6° (c=1, CHCl$_3$); $^1$H NMR (CDCl$_3$) 7.36-7.28 (m, 15H), 4.90 (d, 1H, J=10.1 Hz), 4.79 (d, 1H, J=10.6 Hz), 4.74 (d, 1H, J=10.1 Hz), 4.60 (d, 1H, J=12.1 Hz), 4.54-4.47 (m, 2H), 4.43 (d, 1H, J=9.6 Hz), 3.70 (m, 1H), 3.57 (t, 1H, J=9.1 Hz), 3.45 (m, 2H), 3.26 (t, 1H, J=9.5 Hz), 2.75 (m, 2H), 1.32 (t, 1H, J=7.3 Hz); $^{13}$C NMR (CDCl$_3$) 138.4, 137.9, 137.8, 129.5, 129.2, 129.1, 128.9, 128.8, 128.7, 128.6, 128.5, 128.4, 128.3, 128.2, 128.1, 128.0, 127.7, 85.7, 80.4, 79.7, 76.7, 75.8, 75.3, 73.9, 72.5, 71.0, 69.1, 25.6, 15.6; MS: calcd for C$_{29}$H$_{33}$N$_3$O$_4$SNa 542.2. found m/z 542.0 (M+Na).

Ethyl 6-azide-2,3,4-tri-O-benzyl-6-deoxy-1-thio-β-D-glucopyranoside (FIG. 3(b) (89))

Compound (FIG. 3(b) (88)) (560 mg, 1.5 mmol) gave 645 mg (85%) of the desired product. [α]$_D$=7.9° (c=1, CHCl$_3$); $^1$H NMR (CDCl$_3$) 7.32-7.16 (m, 15H), 4.87 (d, 1H, J=10.9 Hz), 4.86 (d, 1H, J=10.2 Hz), 4.79 (d, 1H, J=11.2 Hz), 4.76 (d, 1H, J=11.0 Hz), 4.66 (d, 1H, J=10.2 Hz), 4.50 (d, 1H, J=11.0 Hz), 4.43 (d, 1H, J=9.8 Hz), 3.62 (m, 1H), 3.43-3.35 (m, 4H), 3.24 (dd, 1H, J=6.0, 13.1 Hz), 2.72 (m, 2H), 1.26 (t, 3H, J=1.5 Hz); $^{13}$C NMR (CDCl$_3$) 138.2, 137.7, 137.5, 128.5, 128.4, 128.3, 128.2, 128.0, 127.8, 127.7, 86.3, 84.6, 81.5, 78.4, 78.2, 75.7, 75.4, 75.1, 51.3, 24.4, 14.9; MS: calcd for C$_{29}$H$_{33}$N$_3$O$_4$SNa 542.2. found m/z 541.9 (M+Na).

General Strategy for Conversion of Azides to Acetamides.

Azides may be converted to Acetamides according to the following method or other methods known to those skilled in the art. Benzyl-protected ethyl 1-thio-β-D-azidodeoxy-hexopyranoside and SnCl$_2$ are combined in acetonitrile. To this mixture thiophenol and Et$_3$N are added and the reaction is stirred for about ½ to about 1½ hr at room temperature. The mixture is then diluted with EtOAc and washed, preferably with 2N NaOH, water, and brine. The organics are dried, preferably over Na$_2$SO$_4$, concentrated to dryness and the crude residue dissolved in dry pyridine. To this mixture 2 mL acetic anhydride is added and the reaction stirred, preferably overnight, at room temperature. The reaction is concentrated and purified directly by silica gel chromatography (3:2 to 1:1 hexane/EtOAc) to give the purified product.

Other conditions, reagents, solutions and the like of the present method, or other methods known to those skilled in the art may be used in accordance with the present invention.

In a typical reaction, benzyl-protected ethyl 1-thio-β-D-azidodeoxyhexopyranoside (2.8 mmol) and SnCl$_2$ (1.73 mmol) were combined in 10 mL of acetonitrile. To this mixture thiophenol (6.9 mmol) and Et$_3$N (5.2 mmol) were added and the reaction was stirred for 1 hr at room temperature under argon atmosphere. The mixture was then diluted with EtOAc (150 mL) and washed with 2N NaOH (2×2 mL), water (20 mL) and brine (30 mL). The organics were dried over Na$_2$SO$_4$, concentrated to dryness and the crude residue dissolved in 10 mL dry pyridine. To this mixture 2 mL acetic anhydride was added and the reaction stirred overnight at room temperature. The reaction was concentrated and purified directly by silica gel chromatography (3:2 to 1:1 hexane/EtOAc) to give the purified product.

Ethyl 3-acetamido-2,4,6-tri-O-benzyl-3-deoxy-1-thio-β-D-glucopyranoside (FIG. 3(b) (101))

Compound (FIG. 3(b) (100)) (600 mg, 1.15 mmol) gave 523 mg (85%) of the desired product. [α]$_D$=−5.4° (c=1, CHCl$_3$); $^1$H NMR (CDCl$_3$) 7.27-7.17 (m, 15H), 5.57 (d, 1H, J=8.6 Hz), 4.73 (d, 1H, J=11.2 Hz), 4.55-4.39 (m, 5H), 3.97 (dd, 1H, J=8.3, 16.5 Hz), 3.66 (m, 2H), 3.58 (dd, 1H, J=4.1, 10.8 Hz), 3.50 (m, 1H), 3.44 (t, 1H, J=8.4 Hz), 2.71 (m, 2H), 1.60 (s, 3H), 1.24 (t, 3H, J=7.4 Hz); $^{13}$C NMR (CDCl$_3$) 170.0, 137.9, 137.8, 137.7, 128.7, 128.3, 128.2, 128.0, 127.9, 127.7, 127.6, 85.3, 80.1, 78.8, 75.4, 73.7, 73.5, 73.1, 69.4, 55.7, 25.2, 23.4, 15.0; MS: calcd for C$_{31}$H$_{37}$NO$_5$SNa 558.2. found m/z 558.0 (M+Na).

Ethyl 4-acetamido-2,3,6-tri-O-benzyl-4-deoxy-1-thio-β-D-glucopyranoside (FIG. 3(b) (95))

Compound (FIG. 3(b) (94)) (640 mg, 1.23 mmol) gave 530 mg desired product (80%) [α]$_D$=−36.6° (c=0.5, CHCl$_3$); $^1$H NMR (CDCl$_3$) 7.32-7.10 (m, 15H), 5.13 (br, 1H), 4.85 (d, 1H, J=10.2 Hz), 4.75 (d, 1H, J=11.7 Hz), 4.70 (d, 1H, J=10.7 Hz), 4.64 (d, 1H, J=10.2 Hz), 4.43 (m, 3H), 3.64-3.47 (m, 5H), 3.37 (m, 1H), 2.67 (m, 2H), 1.61 (s, 3H), 1.25 (t, 3H, J=7.4 Hz); $^{13}$C NMR (CDCl$_3$) 170.3, 138.3, 138.0, 137.8, 128.5, 128.3, 128.2, 128.1, 127.8, 127.7, 127.6, 84.9, 82.1, 81.7, 78.1, 75.3, 74.7, 73.4, 70.0, 52.6, 24.9, 23.3, 15.1; MS: calcd for C$_{31}$H$_{37}$NO$_5$SNa 558.2. found m/z 557.9 (M+Na).

Ethyl 6-acetamido-2,3,4-tri-O-benzyl-6-deoxy-1-thio-β-D-glucopyranoside (FIG. 3(b) (90))

Compound (FIG. 3(b) (89)) (502 mg, 0.97 mmol) gave 450 mg desired product (87%). [α]$_D$=−20.4° (c=1.0, CHCl$_3$); $^1$H NMR (CDCl$_3$) 7.51-7.23 (m, 15H), 5.87 (d, 1H, J=4.6 Hz), 4.99-4.78 (m, 4H), 4.73 (d, 1H, J=10.2 Hz), 4.63 (d, 1H, J=10.4 Hz), 4.45 (d, 1H, J=9.8 Hz), 3.70-3.60 (m, 2H), 3.52 (m, 1H), 3.41-3.34 (m, 3H), 2.74 (m, 2H), 1.95 (s, 3H), 1.32 (t, 3H, J=7.4 Hz); $^{13}$C NMR (CDCl$_3$) 169.8, 138.1, 137.6, 137.5, 128.4, 128.3, 128.2, 128.1, 127.9, 127.8, 127.6, 86.2, 85.1, 81.5, 78.5, 77.1, 75.6, 75.4, 75.1, 39.9, 25.2, 23.1, 15.1; MS: calcd for C$_{31}$H$_{37}$NO$_5$SNa 558.2. found m/z 558.2 (M+Na).

Phosphorylation Procedure.

As set forth in the methods above, phosphorylation according to the present invention may occur via a protected ethyl 1-thio-β-D-hexopyranoside. The following method is another exemplary embodiment of such method used in accordance with the present invention.

In a typical reaction, 1.13 mmol protected ethyl 1-thio-β-D-hexopyranoside and 1.7 mmol dibenzyl phosphate were co-evaporated two times from dry toluene and further dried under high vacuum for 4 hr to which 1.36 mmol of N-iodosuccinamide and 500 mg of dry molecular sieves were added. The mixture was then dissolved in 10 mL dry dichloromethane, cooled to −30° C. and 30 μL of trifluoromethanesulfonic acid (0.34 mmol) was added. The reaction was maintained at −30° C. for 30 min with stirring and then diluted with EtOAc (150 mL), washed with saturated Na$_2$S$_2$O$_3$ (20 mL), saturated NaHCO$_3$ (20 mL), H$_2$O (20 mL), and brine (30 mL). The organics were dried over Na$_2$SO$_4$, filtered, concentrated and purified by chromatography on silica gel (3:1 hexane/EtOAc) to give the desired product.

Again, variations of this method may be made in accordance with the present invention, as would be apparent to one skilled in the art. Dibenzyl-(3-azide-2,4,6-tri-O-benzyl-3-deoxy-α-D-glucopyranosyl) phosphate (FIG. 3(b) (100a)).

Compound (FIG. 3(b) (100)) (590 mg, 1.55 mmol) gave 700 mg (84%) of the title compound. [α]$_D$=57.8° (c=1, CHCl$_3$); $^1$H NMR (CDCl$_3$) 7.45-7.27 (m, 25H), 5.99 (dd, 1H, J=3.2, 6.8 Hz), 5.11-5.05 (m, 4H), 4.84 (d, 1H, J=10.6 Hz), 4.82 (d, 1H, J=11.4 Hz), 4.72 (d, 1H, J=11.5 Hz), 4.60 (d, 1H, J=12.0 Hz), 4.49 (d, 1H, J=10.7 Hz), 4.46 (d, 1H, J=12.1 Hz), 3.84 (m, 2H), 3.68 (dd, 1H, J=3.0, 10.9 Hz), 3.57 (t, 1H, J=9.8 Hz), 3.48 (m, 2H); $^{13}$C NMR (CDCl$_3$) 137.9, 137.6, 137.4, 136.2, 136.1, 136.0, 129.0, 128.9, 128.7, 128.6, 128.5, 128.4, 128.3, 128.1, 128.0, 94.9, 77.4, 76.1, 75.7, 75.3, 74.0, 73.2, 72.4, 69.9, 69.8, 69.7, 69.6, 67.9, 65.2; $^{31}$P NMR (CDCl$_3$) 0.82; MS: calcd for C$_{41}$H$_{42}$N$_3$O$_8$PNa 758.2. found m/z 758.2 (M+Na).

Dibenzyl-(3-acetamido-2,4,6-tri-O-benzyl-3-deoxy-α-D-glucopyranosyl) Phosphate (FIG. 3(b) (101a))

Compound (FIG. 3(b) (101)) (490 mg, 0.91 mmol) gave 480 mg (70%) of the desired product. [α]$_D$=52° (c=1, CHCl$_3$); $^1$H NMR (CDCl$_3$) 7.40-7.19 (m, 25H), 5.94 (dd, 1H, J=3.2, 6.7 Hz), 5.07 (br, 1H), 4.97 (m, 4H), 4.63 (d, 1H, J=11.7 Hz), 4.56 (d, 1H, J=12.0 Hz), 4.39 (m, 4H), 3.90 (m, 2H), 3.85 (m, 2H), 3.56 (dd, 1H, J=3.3, 11.0 Hz), 3.39 (dd, 1H, J=1.6, 11.0 Hz), 1.76 (s, 3H); $^{13}$C NMR (CDCl$_3$) 170.7, 137.8, 137.5, 137.4, 135.6, 135.5, 128.4, 128.3, 128.2, 127.9, 127.8, 127.7, 127.6, 127.5, 94.9, 77.2, 75.1, 74.0, 73.3, 72.8, 72.3, 69.3, 69.4, 69.0, 67.9, 53.4, 23.4; $^{31}$P NMR (CDCl$_3$) 0.62; MS: calcd for C$_{43}$H$_{46}$NO$_9$PNa 774.3. found m/z 774.3 (M+Na).

Dibenzyl-(4-azide-2,3,6-tri-O-benzyl-4-deoxy-α-D-glucopyranosyl) Phosphate (FIG. 3(b) (94a))

Compound (FIG. 3(b) (94)) (280 mg, 054 mmol) gave 316 mg (80%) of the desired product. [α]$_D$=105.8° (c=1, CHCl$_3$); 7.28-7.14 (m, 25H), 5.85 (dd, 1H, J=3.2, 6.8 Hz), 5.12-4.96 (m, 5H), 4.82 (d, 1H, J=10.6 Hz), 4.71-4.66 (m, 2H), 4.57 (d, 1H, J=11.3 Hz), 4.50 (d, 1H, J=12.1 Hz), 4.37 (d, 1H, J=12.1 Hz), 3.68-3.47 (m, 5H), 3.37 (dd, 1H, J=1.5, 11.0 Hz); $^{13}$C NMR (CDCl$_3$) 137.7, 137.6, 137.5, 135.7, 135.6, 128.5, 128.4, 128.3, 128.2, 128.2, 128.0, 127.9, 127.8, 127.7, 127.6, 127.5, 95.4, 78.9, 78.8, 75.6, 75.5, 73.4, 72.9, 71.5, 69.3, 69.2, 69.2, 67.9, 60.8; $^{31}$P NMR (CDCl$_3$) 0.82; MS: calcd for C$_{41}$H$_{42}$N$_3$O$_8$PNa 758.2. found m/z 758.0 (M+Na).

Dibenzyl-(4-acetamido-2,3,6-tri-O-benzyl-4-deoxy-α-D-glucopyranosyl) Phosphate. (FIG. 3(b) (95))

Compound (FIG. 3(b) (95)) (430 mg, 0.80 mmol) gave 389 mg (65%) of the desired product. [α]$_D$=35° (c=1, CHCl$_3$); $^1$H NMR (CDCl$_3$) 7.23-7.09 (m, 25H), 5.82 (dd, 1H, J=3.2, 6.8 Hz), 5.47 (d, 1H, J=8.5 Hz), 5.01-4.93 (m, 4H), 4.69 (d, 1H, J=11.7 Hz), 4.59 (d, 1H, J=11.1 Hz), 4.54 (m, 2H), 4.35 (d, 1H, J=11.9 Hz), 4.30 (d, 1H, J=11.9 Hz), 3.92 (m, 1H), 3.86 (m, 1H), 3.77 (t, 1H, J=9.7 Hz), 3.55 (m, 1H), 3.39 (m, 2H), 1.65 (s, 3H); $^{13}$C NMR (CDCl$_3$) 170.0, 138.2, 137.7, 137.3 135.7, 135.6, 135.5 128.3, 128.2, 128.1, 128.0, 127.9, 127.8, 127.7, 127.6, 127.4, 95.6, 79.4, 79.3, 77.2, 74.5, 73.3, 72.8, 72.2, 69.2, 50.8, 23.2; $^{31}$P NMR (CDCl$_3$) 0.71; MS: calcd for C$_{43}$H$_{46}$NO$_9$PNa 774.3. found m/z 774.3 (M+Na).

Dibenzyl-(6-azide-2,3,4-tri-O-benzyl-6-deoxy-α-D-glucopyranosyl) Phosphate. (FIG. 3(b) (89a))

Compound (FIG. 3(b) (89)) (430 mg, 0.76 mmol) gave 285 mg (51%) of the desired product and 160 mg the β isomer. [α]$_D$=41.5° (c=1, CHCl$_3$); $^1$H NMR(CDCl$_3$) 7.28-7.16 (m, 25H), 5.87 (dd, 1H, J=3.2, 6.7 Hz), 5.05-4.92 (m, 4H), 4.85 (d, 1H, J=10.9 Hz), 4.81 (d, 1H, J=11.0 Hz), 4.71 (d, 1H, J=11.3 Hz), 4.70 (d, 1H, J=10.9 Hz), 4.60 (d, 1H, J=11.3 Hz), 4.50 (d, 1H, J=11.0 Hz), 3.81 (m, 2H), 3.54 (dt, 1H, J=9.5, 3.1 Hz), 3.47 (t, 1H, J=9.5 Hz), 3.18 (m, 2H); $^{13}$C NMR (CDCl$_3$) 138.2, 137.7, 137.3, 135.7, 135.6, 128.5, 128.4, 128.3, 128.0, 127.9, 127.8, 127.7, 127.6, 95.1, 80.7, 79.3, 79.2, 77.1, 75.5, 75.1, 73.0, 71.9, 69.3, 69.2, 69.2, 69.1, 50.7; $^{31}$P NMR (CDCl$_3$) 0.75; MS: calcd for C$_{41}$H$_{42}$N$_3$O$_8$PNa 758.2. found m/z 758.1 (M+Na).

Dibenzyl-(6-acetamido-2,3,4-tri-O-benzyl-6-deoxy-α-D-glucopyranosyl) Phosphate. (FIG. 3(b) (90a))

Compound (FIG. 3(b) (90)) (430 mg, 0.80 mmol) gave 389 mg (65.0%) of the desired product. $^1$H NMR (CDCl$_3$) 7.27-7.19 (m, 25H), 6.00 (br, 1H), 5.68 (dd, 1H, J=3.4, 5.5 Hz), 4.99-4.93 (m, 4H), 4.85 (d, 1H, J=11.9 Hz), 4.76 (d, 1H, J=10.6 Hz), 4.72 (d, 1H, J=10.5 Hz), 4.65 (d, 1H, J=11.5 Hz), 4.60 (d, 1H, J=11.5 Hz), 4.57 (d, 1H, J=10.5 Hz), 3.81 (m, 2H), 3.49 (dt, 1H, J=3.5, 9.4 Hz), 3.44 (m, 2H), 3.24 (t, 1H, J=9.5 Hz); $^{13}$C NMR (CDCl$_3$) 178.5, 138.3, 138.0, 137.9, 136.2, 136.1, 129.0, 128.9, 128.8, 128.5, 128.4, 128.3, 128.1, 95.5, 75.7, 75.6, 74.6, 73.9, 73.4, 72.9, 70.0, 69.9, 69.6, 69.5, 68.5, 54.0, 29.9; $^{31}$P NMR (CDCl$_3$) 0.53; MS: calcd for C$_{43}$H$_{46}$NO$_9$PNa 774.6. found m/z 774.3 (M+Na).

Dibenzyl-(4-azide-3-O-benzoyl-2-O-benzyl-4,6-dideoxy-α-D-glucopyranosyl) Phosphate. (FIG. 3(b) (106a))

Compound (FIG. 3(b) (106)) (323 mg, 0.76 mmol) gave 350 mg (72%) substantially pure product. [α]$_D$=100.1° (c=1, CHCl$_3$); $^1$H NMR (CDCl$_3$) 8.16 (m, 2H), 7.62 (m, 1H), 7.49 (t, 2H, J=7.9 Hz), 7.34-714 (m, 11H), 5.98 (dd, 1H, J=3.2, 7.1 Hz), 5.68 (t, 1H, J=9.8 Hz), 5.13-5.05 (m, 4H), 4.68 (d, 1H, J=12.1 Hz), 4.50 (d, 1H, J=12.1 Hz), 3.81 (m, 1H), 3.68 (dt, 1H, J=3.0, 9.8 Hz), 3.28 (t, 1H, J=10.0 Hz), 1.24 (d, 3H, J=6.2 Hz); $^{13}$C NMR (CDCl$_3$) 185.8, 137.2, 136.1, 136.0, 133.8, 130.3, 129.9, 129.0, 128.9, 128.8, 128.6, 128.4, 128.1, 95.1, 77.7, 76.5, 72.7, 72.1, 70.1, 70.1, 69.7, 69.7, 68.7, 66.3, 18.6; $^{31}$P NMR (CDCl$_3$) 0.52; MS: calcd for C$_3$H$_3$4N$_3$O$_8$PNa 666.2 found m/z 666.2 (M+Na).

Strategy for Final Deprotection and Conversion to the Sodium Salt.

Set forth above is a general strategy for final deprotection and conversion to the sodium salt according to the present invention. The following method is another exemplary embodiment of such method used in accordance with the present invention.

In a typical reaction, the protected α-D-pyranosyl phosphate (0.5 mmol) was dissolved in 15 mL MeOH, 1.5 mL 1N NaHCO$_3$ solution and 150 mg 10% Pd/C were added. The mixture was stirred overnight at room temperature under hydrogen atmosphere after which the catalyst was removed by filtration and the filtrate concentrated and redissolved 10 mL water. The aqueous layer was extracted with EtOAc (10 mL), and then submitted to an anion exchange column (Dowex 1×8, 1.2×12 cm) eluted with 100 mL water, 100 mL 0.1 M NH$_4$HCO$_3$, 100 mL 0.2 M NH$_4$HCO$_3$ and 100 mL 0.3 M NH$_4$HCO$_3$. The product eluted with 0.2M NH$_4$HCO$_3$ and these fractions were pooled and co-evaporated with ethanol several times to remove excess NH$_4$HCO$_3$. The obtained sugar phosphate ammonium salt was subsequently dissolved in 5 mL water and applied to an AG-X8 cation-exchange column (Na$^+$ type) eluted with 100 mL water. The product containing fractions were collected and lyophilized to give the desired product as the sodium salt.

Again, variations of this method may be made in accordance with the present invention, as would be apparent to one skilled in the art.

Disodium (3-amino-3-deoxy-α-D-glucopyranosyl) Phosphate (FIG. 3(b) (96))

Dibenzyl-(3-azide-2,4,6-tri-O-benzyl-3-deoxy-α-D-glucopyranosyl) phosphate (250 mg, 0.34 mmol) gave 68 mg (66%) of the title compound. $[\alpha]_D$=68.1° (c=1, H$_2$O); $^1$H NMR (D$_2$O) 5.46 (dd, 1H, J=3.0, 7.0 Hz), 3.93 (m, 1H), 3.85 (m, 1H), 3.74 (dd, 1H, J=4.5, 12.5 Hz), 3.69 (m, 1H), 3.58 (m, 1H), 3.45 (t, 1H, J=10.2 Hz); $^{13}$C NMR (D$_2$O) 91.9, 71.2, 68.4, 65.3, 59.3, 54.8; $^{31}$P NMR (D$_2$O) 2.85; HRMS: calcd for C$_6$H$_{13}$NO$_8$P 258.0379. found m/z 258.0372 (M+H).

Disodium-(3-acetamido-3-deoxy-α-D-glucopyranosyl) Phosphate (FIG. 3(b) (97))

Dibenzyl-(3-acetamido-2,4,6-tri-O-benzyl-3-deoxy-α-D-glucopyranosyl) phosphate (280 mg, 0.37 mmol) gave 59 mg (53%) of the desired product. $[\alpha]_D$=93.6° (c=1, H$_2$O); $^1$HNMR (D$_2$O) 5.43 (dd, 1H, J=2.9, 6.5 Hz), 4.07 (t, 1H, J=10.3 Hz), 3.88 (dd, 1H, J=2.5, 9.7 Hz), 3.80 (m, 1H), 3.71 (dd, 1H, J=4.7, 12.3 Hz), 3.57 (m, 1H), 3.40 (t, 1H, 10.1 Hz), 2.01 (s, 3H); $^{13}$C NMR (D$_2$O) 174.4, 92.8, 71.6, 69.5, 67.1, 59.8, 53.3, 21.5; $^{31}$P NMR (D$_2$O) 2.07; HRMS: calcd for C$_8$H$_{15}$NO$_9$P 300.0484. found m/z 300.0478 (M+H).

Disodium-(4-amino-4-deoxy-α-D-glucopyranosyl) Phosphate (FIG. 3(b) (91))

Dibenzyl-(4-azide-2,3,6-tri-O-benzyl-4-deoxy-α-D-glucopyranosyl) phosphate (350 mg, 0.476 mmol) gave 77 mg (54%) the desired product. $^1$H NMR (D$_2$O) 5.46 (dd, 1H, J=3.2, 7.1 Hz), 4.11 (m, 1H), 3.90-3.75 (m, 3H), 3.59 (m, 1H), 3.13 (t, 1H, J=10.2 Hz); $^{13}$C NMR (D$_2$O) 92.9, 71.3, 68.8, 68.2, 59.8, 51.7; $^{31}$P NMR (D$_2$O) 2.80; HRMS: calcd for C$_6$H$_{13}$NO$_8$P 258.0379. found m/z 258.0372 (M+H).

Disodium-(4-acetamido-4-deoxy-α-D-glucopyranosyl) Phosphate (FIG. 3(b) (92))

Dibenzyl-(4-acetamido-2,3,6-tri-O-benzyl-4-deoxy-α-D-glucopyranosyl) phosphate (370 mg, 0.50 mmol) gave 120 mg (71%) of the desired product. $[\alpha]_D$=109.2° (c=1, H$_2$O); $^1$H NMR (D$_2$O) 5.44 (dd, 1H, J=3.3, 7.2 Hz), 3.89 (m, 1H), 3.76 (m, 2H), 3.64 (dd, 1H, J 12.4, 1.2 Hz), 3.53 (m, 2H), 1.99 (s, 3H); $^{13}$C NMR (D$_2$O) 173.8, 93.2, 71.4, 70.4, 69.8, 60.0, 50.6, 21.3; $^{31}$P NMR (D$_2$O) 1.93; HRMS: calcd for C$_8$H$_{15}$NO$_9$P 300.0484. found m/z 300.0499 (M+H).

Disodium-(6-amino-6-deoxy-α-D-glucopyranosyl) Phosphate (FIG. 3(b) (85))

Dibenzyl-(6-azide-2,3,4-tri-O-benzyl-6-deoxy-α-D-glucopyranosyl) phosphate (360 mg, 0.49 mmol) gave 85 mg (57%) of the title compound. $^1$H NMR (D$_2$O) 5.47 (dd, 1H, J=3.5, 6.8 Hz), 4.14 (dt, 1H, J=2.5, 12.6 Hz), 3.78 (t, 1H, J=9.5 Hz), 3.55 (m, 2H), 3.33 (t, 1H, J=9.3 Hz), 3.07 (dd, 1H, J=10.3, 12.9 Hz); $^{13}$C NMR (D$_2$O) 94.1, 73.4, 72.5, 72.4, 72.3, 68.6, 41.0; $^{31}$P NMR (D$_2$O) 2.80; HRMS: calcd for C$_6$H$_{13}$NO$_8$P 258.0379. found m/z 258.0388 (M+H).

Disodium-(6-acetamido-6-deoxy-α-D-glucopyranosyl) Phosphate (FIG. 3(b) (86))

Dibenzyl-(6-acetamido-2,3,4-tri-O-benzyl-6-deoxy-α-D-glucopyranosyl) phosphate (340 mg, 0.45 mmol) gave 124 mg (79.4%) of the desired product. $[\alpha]_D$=60.5° (c=1, H$_2$O); $^1$H NMR (D$_2$O) 5.39 (dd, 1H, J=3.2, 6.5 Hz), 3.95 (m, 1H, J=7.1 Hz), 3.73 (t, 1H, J=9.4 Hz), 3.54 (m, 1H), 3.45 (m, 1H), 3.34 (dd, 1H, J=6.7, 14.1 Hz), 3.25 (t, 1H, J=9.5 Hz), 1.99 (s, 3H); $^{13}$C NMR (D$_2$O) 178.4, 97.4, 76.7, 75.9, 74.8, 73.8, 43.9, 25.6; $^{31}$P NMR (D$_2$O) 2.98; HRMS: calcd for C$_8$H$_{15}$NO$_9$P 300.0484. found m/z 300.0482 (M+H).

Disodium-(4-amino-4,6-dideoxy-α-D-glucopyranosyl) Phosphate (FIG. 3(b) (102))

Dibenzyl-(4-azide-3-O-benzoyl-2-O-benzyl-4,6-dideoxy-α-D-glucopyranosyl) phosphate (300 mg, 0.466 mmol) was dissolved in a mixture of 10 mL of MeOH and 2 mL of toluene. To this solution was added 1.4 mL 1N NaOH and 100 mg of 10% Pd/C and the reaction stirred overnight under hydrogen atmosphere. The catalyst was removed by filtration, the filtrate concentrated to a volume of 4 mL, cooled to 0° C., and 0.7 mL 1N NaOH solution was added in a dropwise fashion. The mixture was stirred for 3 hr at 0° C., neutralized with 1N HOAc and the product purified via anion exchange as described in the general procedure above to give 86 mg (67%) of the substantially pure product. $^1$H NMR (D$_2$O) 5.44 (dd, 1H, J=3.2, 6.7 Hz), 4.24 (m, 1H), 3.88 (t, 1H, J=9.7 Hz), 3.56 (dd, 1H, J=1.3, 9.4 Hz), 2.94 (t, 1H, J=10.3 Hz), 1.32 (d, 3H, J=6.2 Hz); $^{13}$C NMR (D$_2$O) 92.9, 71.5, 68.3, 64.2, 56.6, 16.2; $^{31}$P NMR (D$_2$O) 2.16. HRMS: calcd for C$_6$H$_{13}$NO$_7$P 242.0429. found m/z 242.0441 (M+H).

$E_p$-Catalyzed Conversion.

A reaction containing 2.5 mM NTP, 5.0 mM sugar phosphate, 5.5 mM MgCl$_2$ and 10 U inorganic pyrophosphatase in a total volume of 50 μL 50 mM potassium phosphate buffer, pH 7.5 at 37° C. was initiated by the addition of 3.52 U $E_p$ (1 U=the amount of protein needed to produce 1 μmol TDP-α-D-glucose min$^{-1}$) The reaction was incubated with slow agitation for 30 min at 37° C., quenched with MeOH (50 μL), centrifuged (5 min, 14,000×g) and the supernatant was stored at −20° C. until analysis by HPLC. Samples (30 μL) were resolved on a Sphereclone 5 u SAX column (250×4.6 mm) fitted with a guard column (30×4.6 mm) using a linear gradient (50-200 mM potassium phosphate buffer, pH 5.0, 1.5 mL min$^{-1}$, A$_2$75 nm).

The following compounds were prepared, preferably according to the methods described herein:

(109) Thymidine 5'-(6-amino-6-deoxy-α-D-glucopyranosyl diphosphate). HRMS (FAB): calc for C$_{16}$H$_{26}$O$_{15}$N$_3$P$_2$ 562.0839. found m/z 562.0837 (M+H).

(110) Uridine 5'-(6-amino-6-deoxy-α-D-glucopyranosyl diphosphate). HRMS (FAB): calc for C$_{15}$H$_{24}$O$_{16}$N$_3$P$_2$ 564.0632. found m/z 564.0640 (M+H).

(111) Thymidine 5'-(4-amino-4-deoxy-α-D-glucopyranosyl diphosphate). HRMS (FAB): calc for C$_{16}$H$_{26}$O$_{15}$N$_3$P$_2$ 562.0839. found m/z 562.0848 (M+H).

(112) Uridine 5'-(4-amino-4-deoxy-α-D-glucopyranosyl diphosphate). HRMS (FAB): calc for C$_{15}$H$_{24}$O$_{16}$N$_3$P$_2$ 564.0632. found m/z 564.0638 (M+H).

(113) Thymidine 5'-(3-amino-3-deoxy-α-D-glucopyranosyl diphosphate). HRMS (FAB): calc for C$_{16}$H$_{26}$O$_{15}$N$_3$P$_2$ 562.0839. found m/z 562.0835 (M+H).

(114) Uridine 5'-(3-amino-3-deoxy-α-D-glucopyranosyl diphosphate). HRMS (FAB): calc for C$_{15}$H$_{24}$O$_{16}$N$_3$P$_2$ 564.0632. found m/z 564.0622 (M+H).

(115) Thymidine 5'-(2-amino-2-deoxy-α-D-glucopyranosyl diphosphate). HRMS (FAB): calc for C$_{16}$H$_{26}$O$_{15}$N$_3$P$_2$ 562.0839. found m/z 562.0842 (M+H).

(116) Uridine 5'-(2-amino-2-deoxy-α-D-glucopyranosyl diphosphate). HRMS (FAB): calc for C$_{15}$H$_{24}$O$_{16}$N$_3$P$_2$ 564.0632. found m/z 564.0630 (M+H).

(117) Thymidine 5'-(6-acetamido-6-deoxy-α-D-glucopyranosyl diphosphate). HRMS (FAB): calc for C$_{18}$H$_{28}$O$_{16}$N$_3$P$_2$ 604.0945. found m/z 604.0953 (M+H).

(118) Uridine 5'-(6-acetamido-6-deoxy-α-D-glucopyranosyl diphosphate). HRMS (FAB): calc for $C_{17}H_{26}O_{17}N_3P_2$ 606.0737. found m/z 606.0732 (M+H).

(119) Thymidine 5'-(4-acetamido-4-deoxy-α-D-glucopyranosyl diphosphate). HRMS (FAB): calc for $C_{18}H_{28}O_{16}N_3P_2$ 604.0945. found m/z 604.0940 (M+H).

(120) Uridine 5'-(4-acetamido-4-deoxy-α-D-glucopyranosyl diphosphate). HRMS (FAB): calc for $C_{17}H_{26}O_{17}N_3P_2$ 606.0737. found m/z 606.0730 (M+H).

(121) Thymidine 5'-(3-acetamido-3-deoxy-α-D-glucopyranosyl diphosphate). HRMS (FAB): calc for $C_{18}H_{28}O_{16}N_3P_2$ 604.0945. found m/z 604.0947 (M+H).

(122) Uridine 5'-(3-acetamido-3-deoxy-α-D-glucopyranosyl diphosphate). HRMS (FAB): calc for $C_{17}H_{26}O_{17}N_3P_2$ 606.0737. found m/z 606.0735 (M+H).

(123) Thymidine 5'-(2-acetamido-2-deoxy-α-D-glucopyranosyl diphosphate). HRMS (FAB): calc for $C_{18}H_{28}O_{16}N_3P_2$ 604.0945. found m/z 604.0951 (M+H).

(124) Uridine 5'-(2-acetamido-2-deoxy-α-D-glucopyranosyl diphosphate). HRMS (FAB): calc for $C_{17}H_{26}O_{17}N_3P_2$ 606.0737. found m/z 606.0738 (M+H).

(125) Thymidine 5'-(4-amino-4,6-dideoxy-α-D-glucopyranosyl diphosphate). HRMS (FAB): calc for $C_{16}H_{26}O_{14}N_3P_2$ 546.0889. found m/z 546.0895 (M+H).

(126) Uridine 5'-(4-amino-4,6-dideoxy-α-D-glucopyranosyl diphosphate). HRMS (FAB): calc for $C_{15}H_{24}O_{15}N_3P_2$ 548.0682. found m/z 548.0673 (M+H).

Structure-Based Engineering of $E_p$

Expression, Purification and Mutagenesis of $E_p$.

$E_p$ may be modified in accordance with the present invention according to the following method: $E_p$ and $E_p$ mutants are expressed and purified by methods known in the art. For seleno-methionine-labeled protein, the expression vector was transformed into the methionine auxotroph E. coli B834 and grown, preferably overnight at a temperature of about 25° C. to about 35° C., preferably about 30° C. in the presence of seleno-methionine. Seleno-methionine-labeled $E_p$ is purified using the standard protocol but in the presence of DTT. All $E_p$ mutant gene cassettes are generated by a two-step PCR approach. Mutant genes are subsequently characterized by dsDNA sequencing of both strands.

According to a preferred method, expression and purification and $E_p$ and $E_p$ mutants were accomplished as described in Jiang, J., Biggins, J. B. & Thorson, J. S. A General Enzymatic Method for the Synthesis of Natural and "Unnatural" UDP- and TDP-Nucleotide Sugars. J. Am. Chem. Soc. 122, 6803-6804 (2000). For seleno-methionine-labeled protein, the expression vector was transformed into the methionine auxotroph E. coli B834 and grown overnight at 30° C. in the presence of 50 mg $L^{-1}$ seleno-methionine. Seleno-methionine-labeled $E_p$ was purified using the standard protocol but in the presence of 5 mM DTT. No additional proteolysis or modifications during this process were observed by mass spectrometry. All $E_p$ mutant gene cassettes were generated by a two-step PCR approach. Mutant genes were subsequently characterized by dsDNA sequencing of both strands.

Crystallization. A general crystallization technique that may be used in accordance with the present invention, is as follows: Purified $E_p$ is concentrated in a buffer, and crystallized in a hanging drop by vapor diffusion at approximately room temperature (20° C.). $E_p$-dTTP crystals are obtained against reservoir containing TTP, 2.0 M ammonium phosphate, 0.1 M Tris.HCl, pH 8.5, and 20 mM $MgCl_2$. Crystals grow with two monomers (half of the Ep tetramer) in the asymmetric unit. The $E_p$-UDP-Glc crystals were obtained against a reservoir containing 2 mM UDP-Glc, 1.9 M ammonium sulfate, isopropanol.

According to an exemplary method, the purified $E_p$ was concentrated to 20 mg $mL^{-1}$ in a buffer containing 10 mM KCl, 2 mM $MgCl_2$ and 10 mM HEPES, pH 7.2, and crystallized in a hanging drop by vapor diffusion at room temperature (20° C.). The $E_p$-dTTP crystals were obtained against reservoir containing 2 mM TTP, 2.0 M ammonium phosphate, 0.1 M Tris.HCl, pH 8.5, and 20 mM $MgCl_2$. Crystals grow in the tetragonal space group $P4_32_12$ (a=b=120 Å, c=94 Å) with two monomers (half of the $E_p$ tetramer) in the asymmetric unit. The $E_p$-UDP-Glc crystals were obtained against a reservoir containing 2 mM UDP-Glc, 1.9 M ammonium sulfate, and 7.5% isopropanol. These crystals grow in the orthorhombic space group $P2_12_12_1$ (a=93 Å, b=112 Å, c=132 Å) with four monomers (one tetramer) in the asymmetric unit.

Data Collection and Structure Determination.

Data may be collected and structure determination made according to methods that would be known to those skilled in the art, including, for example, x-ray crystallography.

According to an exemplary embodiment, crystals were harvested and flash frozen in the cold stream of an X-Stream cooling system (Rigaku) in the mother liquor with added 20-25% glycerol as a cryoprotectant. Data was collected either in house using a Rigaku RAXIS-IV imaging plate area detector, or at the NSLS Brookhaven beamline X9B. Oscillation photographs were integrated, scaled and merged using DENZO and SCALEPACK. (Otwinowski, Z. & Minor, W. Data Collection and Processing., Sawyer, L., Isaacs, N. & Bailey, S. Ed. SERC Daresbury Laboratory: Warrington, UK. 556-562 (1993).) Subsequent calculations were performed with the CCP4 program suite. (CCP4, The CCP4 suite: programs for X-ray crystallography. Acta Crystallogr. D, 50, 760-763 (1994).) The $E_p$-UDP-Glc structure was determined using the single wavelength anomalous diffraction phasing method. (Hendrickson, W. A., Determination of Macromolecular Structures from Anomalous Diffraction of Synchrotron Radiation. Science, 254, 51-58 (1991).) Only the dataset collected at the wavelength of the selenium absorption peak was processed. Peak wavelength anomalous data were input to the program SnB to identify the location of the Se atoms. Twenty peaks from the best solution were refined using MLPHARE (CCP4) employing only the peak wavelength anomalous differences in the resolution range 35 to 2 A. Additional Se sites were located using anomalous-difference fourier maps. The final round of MLPHARE consisted of 47 Se sites. Seven of these sites correspond to Se-methionines with dual sidechain conformation. The phases calculated from MLPHARE had a figure of merit of 0.34 which was improved to 0.72 by density modification with the program DM (CCP4). The resulting electron density map was clearly interpretable, indicating also the correct handedness of the Se substructure. The map was further improved using free atom refinement and the automatic chain tracing procedure of the wARP program. Out of the 1156 residues, the main chain of 1003 were automatically traced and very clear density could be seen for the rest of the structure. The unambiguous tracing and sequence assignment of the $E_p$ tetramer was completed using the 0 program. (Jones, T. A., et al., Improved Methods for Building Protein Models in Electron Density Maps and the Location of Errors in these Models. Acta Crystallogr., A47, 110-119 (1991).) Refinement of the model by conventional least-squares algorithm was done with XPLOR. (Brunger, A. T., X-PLOR v. 3.1 Manual. New Haven: Yale University (1993).) The final refined $E_p$ tetramer model at 2.0 A resolution had a free R-value (Brunger, A. T., Free R Value: A Novel Statistical Quantity for Assessing the Accuracy of Crystal Structures. Nature, 355, 472-475 (1992)) of 22.3% and included 9938 non-hydrogen atoms in 1156 well-ordered residues (1-289 in each monomer) and 762 water molecules. In our determination, electron density was lacking for only the 3 C-terminal residues of each monomer. Restrained refinement of temperature factors was monitored throughout by the free R-factor criterion as set forth in Liu, H.-w. & Thorson, J. S. Pathways and Mechanisms in the Biogenesis of Novel Deoxysugars by Bacteria. Ann. Rev. Microbiol. 48, 223-256 (1994) and Johnson, D. A. & Liu, H.-w. Mechanisms and Pathways from Recent Deoxysugar Biosynthesis Research. Curr. Opin. Chem. Biol. 2, 642-649 (1998)). Stereochemical analysis of the refined model using PROCHECK (CCP4 suite) revealed main-chain and side-chain parameters better than, or within, the typical range of values for protein structures determined at 2.0 Å resolution (overall G-factor, 2.2). None of the $E_p$ residues fell in the disallowed region of the Ramachandran plot. (Ramachandran, G. N., Ramakrishnan, C. & Sasisekharan, V. Stereochemistry of Polypeptide Chain Configuration. J. Molec. Biol., 7, 95-99 (1963).) The $E_p$-dTTP structure was determined using the Molecular Replacement (MR) method, with our $E_p$-UDP-Glc structure as a search model and the program XPLOR. The final refined model (half of the $E_p$ tetramer) at 2.1 Å resolution had a free R value[35] of 23.5% and included 5017 non-hydrogen atoms in 578 well defined in the electron density map amino acids (1-289 for each monomer), and 387 water molecules. The PROCHECK overall G-factor is 2.5, and none of the $E_p$ residues fell in the disallowed region of the Ramachandran plot.

Enzyme Assays and Determination of Steady State Kinetic Parameters.

Assays for product formation and steady state kinetics were accomplished using conditions similar to those described. in Jiang, J., Biggins, J. B. & Thorson, J. S. A General Enzymatic Method for the Synthesis of Natural and "Unnatural" UDP- and TDP-Nucleotide Sugars. J. Am. Chem. Soc. 122, 6803-6804 (2000). For the mutant pool assays, an aliquot which contained an eqimolar ratio of each mutant (60 µg) was utilized.

While the present invention is described with respect to particular examples and preferred embodiments, it is understood that the present invention is not limited to these examples and embodiments. The present invention as claimed therefore, includes variations from the particular examples and preferred embodiments described herein, as will be apparent to one of skill in the art.

What is claimed is:

1. A nucleotide sugar library comprising two or more nucleotide sugars produced by (a) combining α-D-hexopyranosyl phosphate and NTP in the presence of at least one mutant Ep nucleotidylyltransferase, wherein the at least one mutant Ep nucleotidylyltransferase is mutated at one or more amino acids of SEQ ID NO:1 selected from the group consisting of V173, G147, W224, N122, G175, D111, E162, T201, I200, E199, R195, L89, L109, Y146, and Y177, and (b) recovering the resulting nucleotide sugars.

2. A nucleotide sugar library comprising two or more nucleotide sugars produced by (a) combining α-D-hexopyranosyl phosphate other than Glc1P and NTP in the presence of at least one mutant Ep nucleotidylyltransferase, wherein the at least one mutant Ep nucleotidylyltransferase is mutated at one or more amino acids of SEQ ID NO:1 selected from the group consisting of V173, G147, W224, N122, G175, D111, E162, T201, I200, E199, R195, L89, L109, Y146, and Y177, and (b) recovering the resulting nucleotide sugars.

3. A nucleotide sugar library comprising two or more nucleotide sugars produced by (a) combining α-D-hexopyranosyl phosphate and NTP other than TTP in the presence of at least one mutant Ep nucleotidylyltransferase, wherein the at least one mutant Ep nucleotidylyltransferase is mutated at one or more amino acids of SEQ ID NO:1 selected from the group consisting of V173, G147, W224, N122, G175, D111, E162, T201, I200, E199, R195, L89, L109, Y146, and Y177, and (b) recovering the resulting nucleotide sugars.

4. A nucleotide sugar library comprising two or more nucleotide sugars selected from the group consisting of Thymidine 5'-(α-D-glucopyranosyl diphosphate) (58);
Uridine 5'-(α-D-glucopyranosyl diphosphate) (59);
Thymidine 5'-(2-deoxy-α-D-glucopyranosyl diphosphate) (60);
Uridine 5'-(2-deoxy-α-D-glucopyranosyl diphosphate) (61);
Thymidine 5'-(3-deoxy-α-D-glucopyranosyl diphosphate) (62);
Uridine 5'-(3-deoxy-α-D-glucopyranosyl diphosphate) (63);
Thymidine 5'-(4-deoxy-α-D-glucopyranosyl diphosphate) (64);
Uridine 5'-(4-deoxy-α-D-glucopyranosyl diphosphate) (65);
Thymidine 5'-(6-deoxy-α-D-glucopyranosyl diphosphate) (66);
Uridine 5'-(6-deoxy-α-D-glucopyranosyl diphosphate) (67);
Thymidine 5'-(α-D-mannopyranosyl diphosphate) (68);
Uridine 5'-(α-D-mannopyranosyl diphosphate) (69);
Thymidine 5'-(α-D-galactopyranosyl diphosphate) (70);
Uridine 5'-(α-D-galactopyranosyl diphosphate) (71);
Thymidine 5'-(α-D-allopyranosyl diphosphate) (72);
Uridine 5'-(α-D-allopyranosyl diphosphate) (73);
Thymidine 5'-(α-D-altropyranosyl diphosphate) (74);
Uridine 5'-(α-D-altropyranosyl diphosphate) (75);
Thymidine 5'-(α-D-gulopyranosyl diphosphate) (76);
Uridine 5'-(α-D-gulopyranosyl diphosphate) (77);
Thymidine 5'-(α-D-idopyranosyl diphosphate) (78);
Uridine 5'-(α-D-idopyranosyl diphosphate) (79);
Thymidine 5'-(α-D-talopyranosyl diphosphate) (80);
Uridine 5'-(α-D-talopyranosyl diphosphate) (81);
Thymidine 5'-(6-amino-6-deoxy-α-D-glucopyranosyl diphosphate) (109);

Uridine 5'-(6-amino-6-deoxy-α-D-glucopyranosyl diphosphate) (110);
Thymidine 5'-(4-amino-4-deoxy-α-D-glucopyranosyl diphosphate) (111);
Uridine 5'-(4-amino-4-deoxy-α-D-glucopyranosyl diphosphate) (112);
Thymidine 5'-(3-amino-3-deoxy-α-D-glucopyranosyl diphosphate) (113);
Uridine 5'-(3-amino-3-deoxy-α-D-glucopyranosyl diphosphate) (114);
Thymidine 5'-(2-amino-2-deoxy-α-D-glucopyranosyl diphosphate) (115);
Uridine 5'-(2-amino-2-deoxy-α-D-glucopyranosyl diphosphate) (116);
Thymidine 5'-(6-acetamido-6-deoxy-α-D-glucopyranosyl diphosphate) (117);
Uridine 5'-(6-acetamido-6-deoxy-α-D-glucopyranosyl diphosphate) (118);
Thymidine 5'-(4-acetamido-4-deoxy-α-D-glucopyranosyl diphosphate) (119);
Uridine 5'-(4-acetamido-4-deoxy-α-D-glucopyranosyl diphosphate) (120);
Thymidine 5'-(3-acetamido-3-deoxy-α-D-glucopyranosyl diphosphate) (121);
Uridine 5'-(3-acetamido-3-deoxy-α-D-glucopyranosyl diphosphate) (122);
Thymidine 5'-(2-acetamido-2-deoxy-α-D-glucopyranosyl diphosphate) (123);
Uridine 5'-(2-acetamido-2-deoxy-α-D-glucopyranosyl diphosphate) (124);
Thymidine 5'-(4-amino-4,6-dideoxy-α-D-glucopyranosyl diphosphate) (125);
Uridine 5'-(4-amino-4,6-dideoxy-α-D-glucopyranosyl diphosphate) (126);

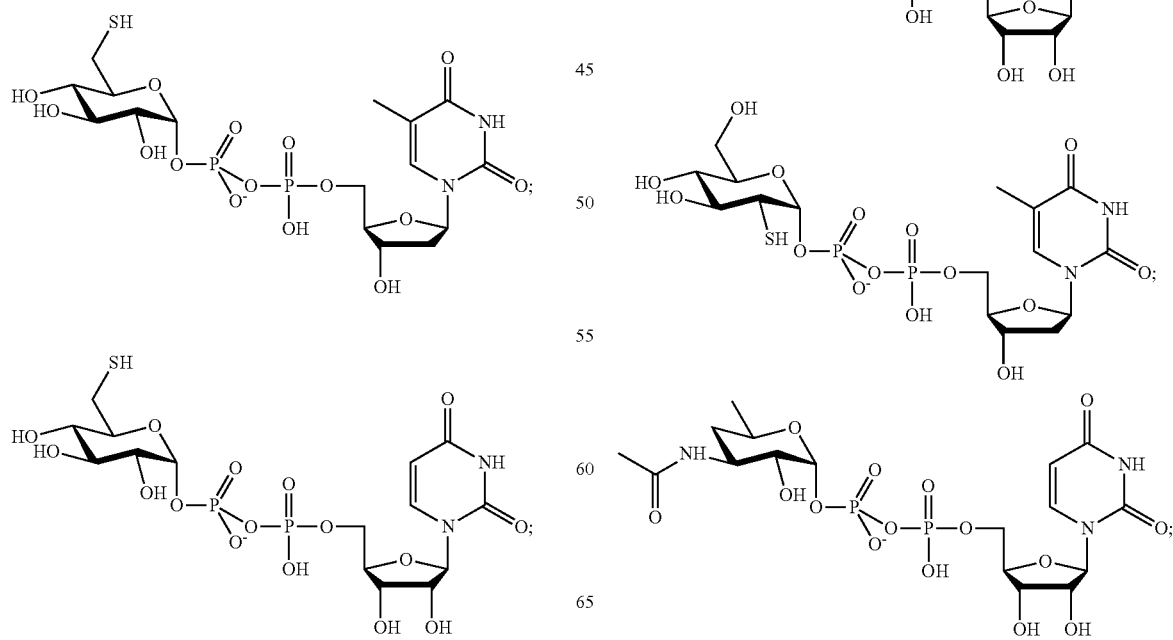

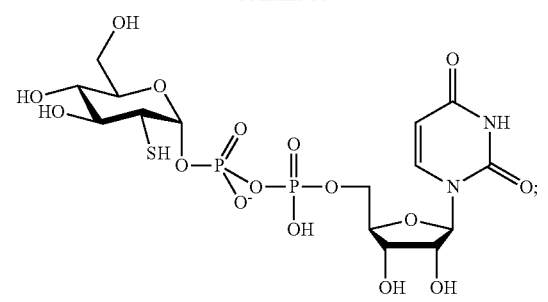
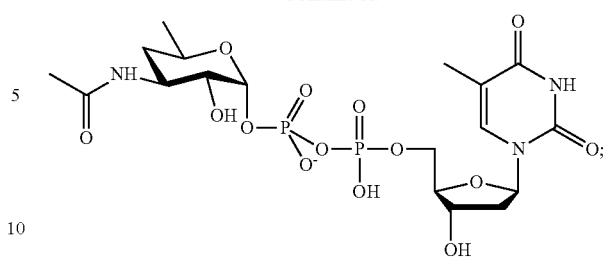
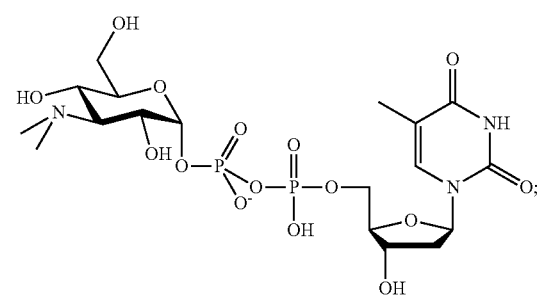
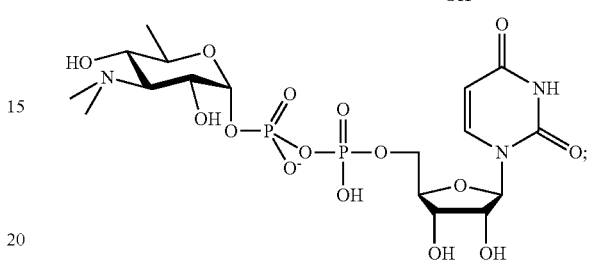
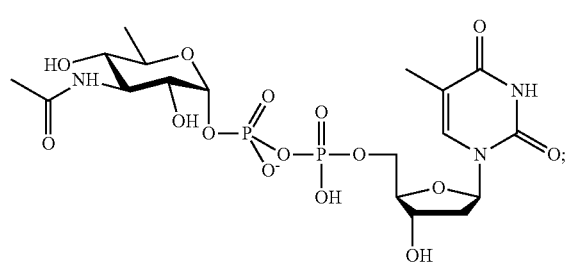
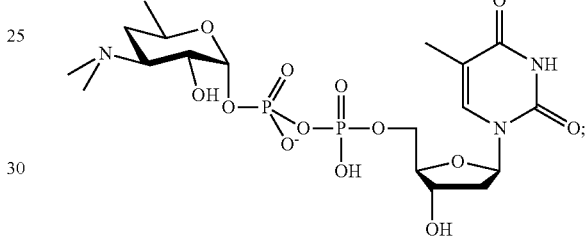
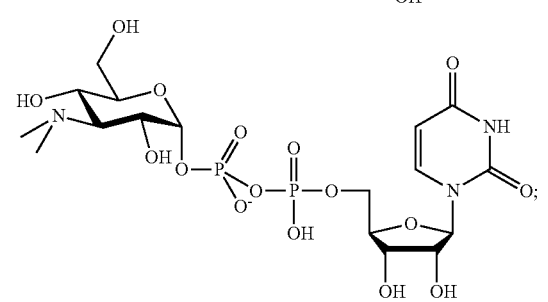
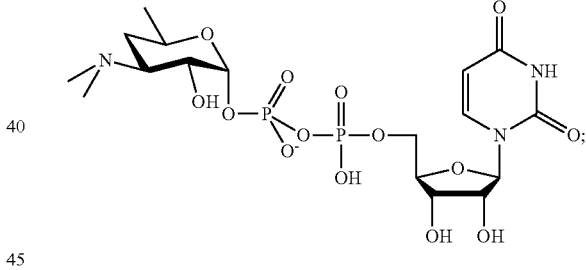
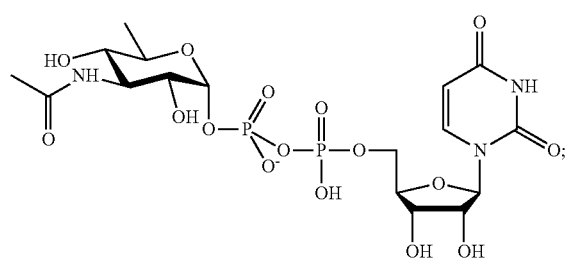
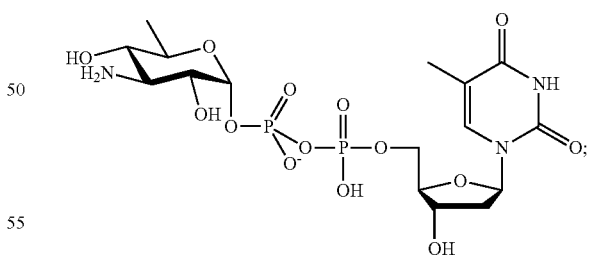
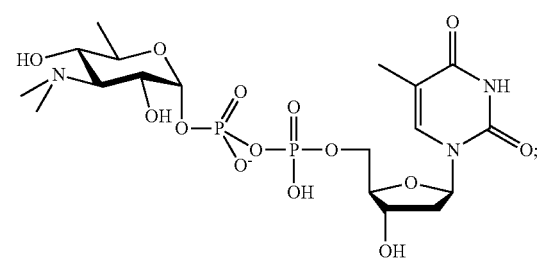
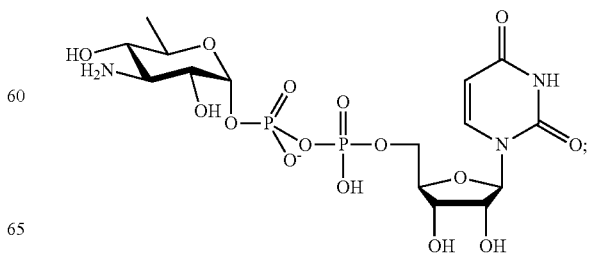

81
-continued
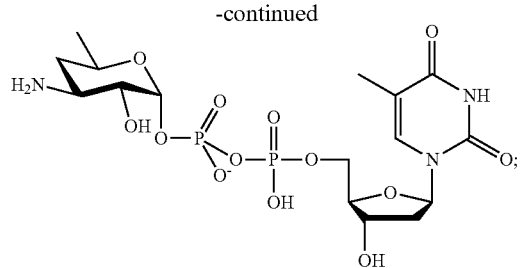
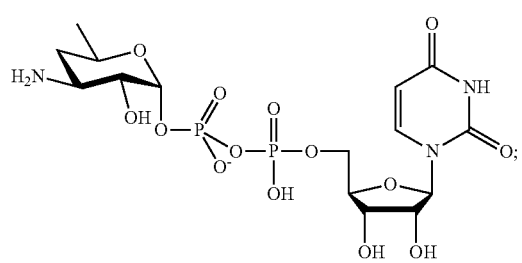
82
-continued
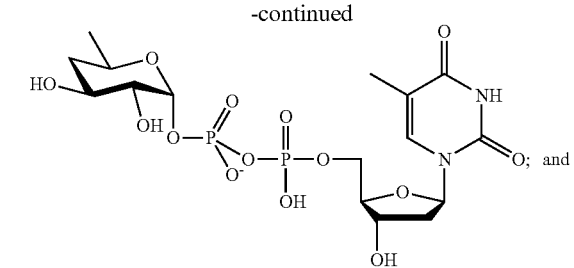; and
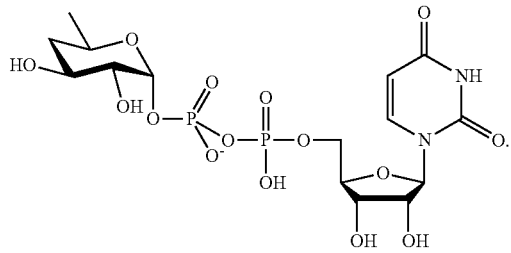.
* * * * *